(12) United States Patent
Zhang et al.

(10) Patent No.: US 7,417,142 B2
(45) Date of Patent: Aug. 26, 2008

(54) CHIRAL PORPHYRINS, CHIRAL METALLOPORPHYRINS, AND METHODS FOR SYNTHESIS OF THE SAME

(75) Inventors: X. Peter Zhang, Knoxville, TN (US); Ying Chen, Knoxville, TN (US); Guang-yao Gao, Knoxville, TN (US)

(73) Assignee: The University of Tennessee Research Foundation, Inc., Knoxville, TN (US)

( * ) Notice: Subject to any disclaimer, the term of this patent is extended or adjusted under 35 U.S.C. 154(b) by 194 days.

(21) Appl. No.: 10/967,601

(22) Filed: Oct. 18, 2004

(65) Prior Publication Data

US 2005/0124596 A1    Jun. 9, 2005

Related U.S. Application Data

(63) Continuation-in-part of application No. 10/401,211, filed on Mar. 27, 2003, now Pat. No. 6,951,935.

(60) Provisional application No. 60/368,295, filed on Mar. 28, 2002.

(51) Int. Cl.
*C07D 487/22* (2006.01)
*C07B 47/00* (2006.01)
(52) U.S. Cl. .................................... 540/145
(58) Field of Classification Search ................ 540/145; 514/185, 410; 424/9.362, 9.61
See application file for complete search history.

(56) References Cited

U.S. PATENT DOCUMENTS 6,951,935 B2 * 10/2005 Zhang et al. ................ 540/145

OTHER PUBLICATIONS

Huang et al. Diastereoselective and enantioselective cyclopropanation of alkenes catalyzed by cobalt porphyrins *Journal of Organic Chemistry*, vol. 68, (2003), pp. 8179-8184.

Collman et al. Threitol-strapped manganese porphyrins as enantioselective epoxidation catalysts of unfunctionalized olefins *Journal of Americal Chemical Society*, vol. 117, (1995), pp. 692-703.

Gao et al. Versatile synthesis of meso-aryloxy-and alkoxy-substituted porphyrins via palladium-catalyzed C—O cross-coupling reactions *Organics Letters*, vol. 5, No. 18, (2003), pp. 3261-3264.

Gao et al. General and efficient synthesis of arylamino- and alkylamino-sybstituted diphenylportphyrins and tetraphenylporthyrins via palladium-catalyzed multiple amination reactions *Journal of Organic Chemistry*, vol. 68, (2003), 6215-6221.

Chen et al. Facile and efficient synthesis of meso-arylamino- and alkylamino-substituted porphyrins via palladium-catalyzed amination *Journal of Organic Chemistry*, vol. 68, (2003), pp. 4432-4438.

(Continued)

*Primary Examiner*—James O. Wilson
*Assistant Examiner*—Paul V. Ward
(74) *Attorney, Agent, or Firm*—Jenkins, Wilson, Taylor & Hunt, P.A.

(57) ABSTRACT

Novel methods of synthesizing heteroatom-containing chiral porphyrins and chiral metalloporphyrins and the novel chiral porphyrins and chiral metalloporphyrins themselves are disclosed. Metal complexes of the chiral porphyrins are prepared in high yields and shown to be active catalysts for highly enantioselective and diastereoselective cyclopropanation, aziridination, and epoxidation of alkenes under a practical one-pot protocol.

28 Claims, 29 Drawing Sheets

Facile and General Synthesis of Porphyrins with Nitrogen, Oxygen and Other Heteroatom-Based Substituents via Metal-Catalyzed Cross-Coupling Reactions

OTHER PUBLICATIONS

Chen et al. Iron(III) and ruthenium(II) porphyrin complex-catalyzed selective olefinationof aldehydes with ethyl diazoacetate *Journal of Organic Chemistry*, vol. 68, (2003), pp. 3714-3717.

Chen et al. Efficient and stereoselective synthesis of β-trifluoromethyl α, β-unsaturated esters via iron(III) porphyrin-catalyzed olefination of ketones *Journal of Organic Chemistry*, vol. 68, (2003), pp. 5925-5929.

Chen et al. Acid-promoted olefination of ketones by an iron(III) porphyrin complex *Organic Letters*, vol. 5, No. 14, (2493-2496).

Johnson et al. meso-substitution products of Aetoporphyrin I *Journal of Chemical Society*, (1966), pp. 794-798.

Evans et al. Orientation of nucleophilic substitution in µ-cation radicals or µ-dication from meso-substituted metalloporphyrins *Tetrahedron*, vol. 33, (1977), pp. 629-633.

Fuhrhop et al. Reactions of oxophlorines and their µ radicals *Journal of the Americal Chemical Society*, vol. 97, No. 24, (1975), pp. 7141-7152.

Callot et al. N-aminoporthyrins. Preparation and metal complexes. Structure of N-tosylamino-5, 10, 15, 20-tetraphenylporphinatonickel(II) *Journal of the American Chemical Society*, vol. 100, No. 15, (1978), pp. 4733-4741.

Chen et al. Acid-promoted olefination of ketones by an iron(III) porphyrin complex *Organic Letters*, vol. 5, No. 14, (2003), pp. 2493-2496.

* cited by examiner

Ligand:

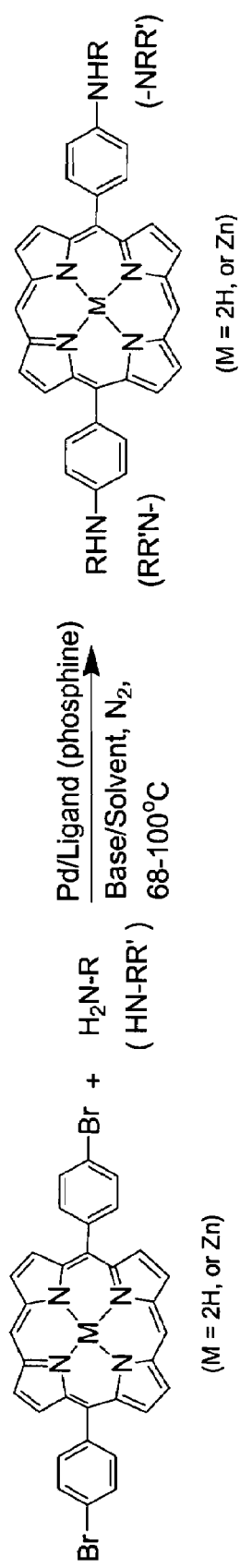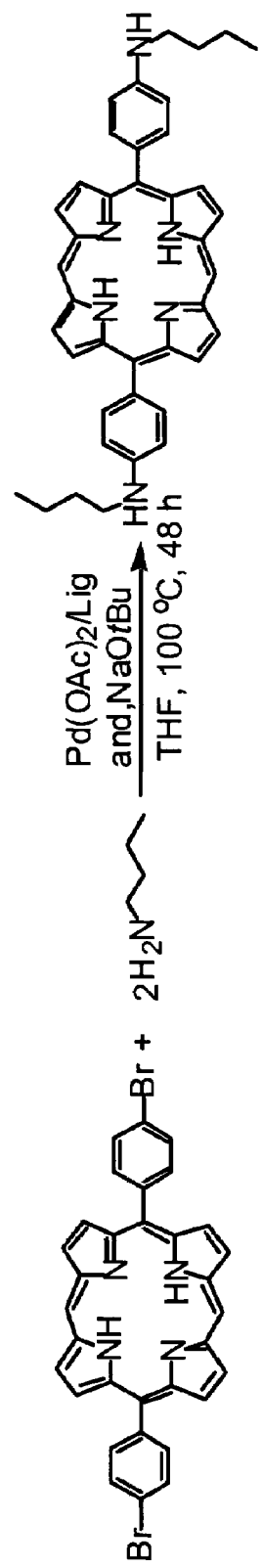
FIG. 5A
FIG. 5B

US 7,417,142 B2

CHIRAL PORPHYRINS, CHIRAL METALLOPORPHYRINS, AND METHODS FOR SYNTHESIS OF THE SAME

CROSS REFERENCE TO RELATED APPLICATIONS

This application is a continuation-in-part of U.S. patent application Ser. No. 10/401,211, filed Mar. 27, 2003, now U.S. pat No. 6,951,935, the disclosure of which is incorporated herein by reference in its entirety and which claims the benefit of and priority to U.S. Provisional Patent Application Ser. No. 60/368,295, filed Mar. 28, 2002, the disclosure of which is incorporated herein by reference in its entirety.

TECHNICAL FIELD

The presently disclosed subject matter relates to methods of synthesizing heteroatom-substituted chiral porphyrins, and to the novel heteroatom-substituted chiral porphyrins themselves. Further, the presently disclosed subject matter relates to methods of using the chiral porphyrins as catalysts in cyclopropanation reactions, aziridination reactions, and epoxidation reactions.

| ABBREVIATIONS | |
|---|---|
| Ac | acetyl |
| t-BDA | t-butyl diazoacetate |
| BINAP | 2,2'-bis(diphenylphosphino)-1,1'-binaphthyl |
| Bu | butyl |
| BT | bromamine-T |
| calc'd | calculated |
| CT | chloramine-T |
| dba | dibenzylidieneacetone |
| DDQ | 2,3-dichloro-5,6-dicyano-1,4-Benzoquinone |
| DMAP | 4-dimethylaminopyridine |
| DMF | dimethyl formamide |
| DMSO | dimethyl sulfoxide |
| DPEphos | bis(2-diphenylphosphinophenyl) ether |
| dppf | 1,1'-bis(diphenylphosphino) ferrocene] |
| EDA | ethyl diazoacetate |
| ee | enantiomeric excess |
| EI | electron impact |
| Et | ethyl |
| eV | electron volt |
| FT-IR | Fourier transform infrared |
| KOt-Bu | potassium tertiary butoxide |
| LDA | lithium diisopropyl amide |
| Me | methyl |
| Mg | milligram |
| MHz | megahertz |
| ML | milliliter |
| [M(Por)] | metalloporphyrin complex |
| [M(Por*)] | chiral metalloporphyrin complex |
| NaOt-Bu | sodium tertiary butoxide |
| NMR | nuclear magnetic resonance |
| Nu | nucleophile |
| Nu* | chiral nucleophile |
| OAc | acetate |
| OEP | octaethylporphyrin |
| OTf | trifluoromethanesulfonate |
| PDT | photodynamic therapy |
| Ph | phenyl |
| Por | porphyrin |
| Por* | chiral porphyrin |
| Pr | propyl |
| rt | room temperature |
| TFA | trifluoroacetatic acid |
| THF | tetrahydrofuran |

| -continued ABBREVIATIONS | |
|---|---|
| TLC | thin layer chromatography |
| TOF | turnover frequency |
| TON | turnover number |
| TPFPP | tetrakis(pentafluorophenyl)porphyrin |
| TPP | 5,10,15,20-Tetraphenyl-21H,23H-Porphine |
| UV-Vis | ultraviolet-visible |
| vis | visible |

BACKGROUND

Synthetic porphyrins and metalloporphyrins have become increasingly important in numerous and diverse technical fields. Their several practical applications include their use as sensitizers in photodynamic therapy (PDT) (Mody, (2000) *J. Porphyrins Phthalocyanines* 4: 362); in electron transfer (Lippard and Berg, (1994) *Principles of Bioinorganic Chemistry*, University Science Book: Mill Valley, Calif.); in DNA strand cleavage (Bennett et al., (2000) *Proc. Natl. Acad. Sci.* 97: 9476; Hashimoto et al., (1983) *Tetrahedron Letters*, 24: 1523); as carriers of cytotoxic anticancer drugs such as platinum (Song et al., (2002) *Inorganic Biochemistry* 83: 83; and Lottner et al., (2002) *J. Med. Chem.*, 45, 2064); as components of synthetic receptors (Jain and Hamilton, (2002) *Org. Lett.* 2: 1721); and as oxidation catalysts (Guo et al., (2001) *J. Mol. Catal. A Chem.* 170: 43). Additionally, functionalized porphyrins have become important leads in current drug discovery techniques (See Mody, supra, and Priola et al., (2002) *Science* 287: 1503). Accordingly, the development of new methodologies and strategies to improve the synthesis of functionalized porphyrins has become highly desirable.

Numerous methods for the synthesis of porphyrins are known. The classical methods for porphyrin synthesis typically require harsh reaction conditions and can provide disappointingly low yields (Rothemund, (1935) *J. Am. Chem. Soc.*, 57: 2010; Adler et al., (1967) *J. Org. Chem.* 32: 476). Newer methodologies, such as those developed by Lindsey and colleagues, have resolved certain issues regarding reaction conditions and yields (Lindsey et al., (1987) *J. Org. Chem.* 52: 827). More recently, transition metal-catalyzed organic synthesis methodologies (e.g., Suzuki coupling, Heck-type coupling, and Stille cross coupling), have been successfully employed with porphyrin systems, providing versatile and general synthetic approaches for the preparation of a variety of functionalized porphyrins and porphyrin analogs. See, e.g., DiMagno et al., (1993) *J. Org. Chem.*, 58: 5983; DiMagno et al., (1993) *J. Am. Chem. Soc.* 115: 2513; Chan et al., (1995) *Tetrahedron* 51: 3129; Zhou et al., (1996) *J. Org. Chem.* 61: 3590; Risch and Rainer, (1997) *Tetrahedron Letters* 38: 223; Hyslop et al., (1998) *J. Am. Chem. Soc.* 120:12676; Boyle and Shi, (2002) *J. Chem. Soc. Perkin Trans.*, 1: 1397; and Pereira et al., (2002) *J. Chem. Soc. Perkin Trans.*, 2: 1583. See also, Suzuki, (1998) *Metal-Catalyzed Cross-Couplinq Reactions*, pp. 49-97, Wiley-VCH, Weinheim, Germany; Liu et al., (1998) *J. Chem. Soc., Dalton Trans.* 1805; Shi et al., (2000) *J. Org. Chem.* 65: 1650; Shanmugathasan et al., (2000) *Porphyrins Phthalocyanines* 4: 228; Lovine et al., (2000) *J. Am. Chem. Soc.* 122: 8717; Deng et al., (2000) *Angew. Chem. Int. Ed.* 39: 1066; and Chang et al., (2003) *J. Org. Chem.* 68: 4075; U.S. Pat. No. 5,550,236 and U.S. Pat. No. 5,756,804, which references are incorporated herein by reference. Further, porphyrin synthesis via palladium-catalyzed C—N bond formation, see Khan et al., (2001) *Tetrahedron Lett.* 42: 1615; Takanami et al., (2003) *Tetrahedron Lett.* 44: 7353, and metal-mediated C—C bond formation, see Sharman et al., (2000) *Porphyr. Phthalocyanines* 4: 441, has been reported.

Each of these foregoing methods, however, possesses undesirable aspects that should be mitigated, including incompatibilities between catalysts and reaction compounds, low turnover number (TON) and low turnover frequency (TOF). Thus, despite recent advances in porphyrin chemistry, a need still exists for facile and general syntheses for, in particular, heteroatom-substituted porphyrins and metalloporphyrins.

More particularly, a need exists for facile and general syntheses for heteroatom-substituted chiral porphyrins. Chiral porphyrins have found a range of applications in many areas, such as asymmetric catalysis, chiral recognition/sensing, and enzymatic mimicry. Of particular interest is the use of chiral porphyrins in asymmetric catalysis.

Biologically relevant porphyrins are among the most versatile ligands for transition metal complexes. See Brothers, (2001) *Adv. Organometallic Chem.* 46:223; Brothers, (2001) *Adv. Organometallic Chem.* 48: 289. Metalloporphyrins have found a diverse array of applications in areas ranging from chemistry to biology and from materials to medicine. Metalloporphyrins are known to catalyze a range of fundamentally and practically important chemical transformations, including an array of atom/group transfer reactions, such as oxene (epoxidation and hydroxylation), nitrene (aziridination and amination), and carbene (cyclopropanation and carbene insertion) transfers, that allow the direct conversion of abundant and inexpensive alkenes and alkanes into functional molecules. See *The Porphyrin Handbook;* Kadish, K. M., Smith, K. M., Guilard, R., Eds., Academic Press: San Diego, 2000-2003; *Metalloporphyrins in Catalytic Oxidations*; Sheldon, R. A., Ed.; Marcel Dekker: New York, 1994; *Metalloporphyrins Catalyzed Oxidations: Montanari, F., Casella, L., Eds., Kluwer Academic Publishers: Boston,* 1994. Due to the unique ligand environment and metal coordination mode of metalloporphyrins, unusual reaction selectivities and excellent catalyst turnovers have been observed for metalloporphyrin-based catalysts. Thus, there is a significant interest in designing and synthesizing chiral porphyrins for developing asymmetric versions of the abovementioned catalytic processes.

Since the first application of a chiral iron porphyrin complex for catalytic asymmetric epoxidation, see Groves et al., (1983) *J. Am. Chem. Soc.* 105: 5791, a number of chiral porphyrins have been synthesized as potential asymmetric catalysts. See Marchon, (2003) in *The Porphyrin Handbook*; supra, Vol. 11, pp 75-132; Simonneaux et al., (2002) *Coord. Chem. Rev.* 228: 43; Rose et al., (2000) *Polyhedron* 19: 581; Collman et al., (1999) *Chemtracts* 12: 299; Rose et al., (1998) *Coord. Chem. Rev.* 178-180: 1407; Collman et al., (1993) *Science* 261: 1404; Rose et al., (2004) *Chem. Eur. J.* 10: 224. Although significant progress has been made in this area, catalytic reactions based on metalloporphyrins have not been developed into practical methodologies that can be used in asymmetric synthesis. This lack of development can be attributed mainly to the expense and difficulty associated with chiral porphyrin synthesis.

Several approaches have been applied to chiral porphyrin synthesis. See Marchon, supra, Rose et al., (2000), supra, and Collman et al., (1993), supra. The most general and chirally economic scheme for synthesizing chiral porphyrins is to covalently attach suitable chiral building blocks to a preformed porphyrin synthon comprising peripheral functional groups. See Tani et al., (2002) *Coord. Chem. Rev.* 226: 219; Simonneaux et al., supra; Collman et al., (1999), supra; Rose et al., (1998), supra; Boschi, in *Metalloporphyrins Catalyzed Oxidations*: Montanari, F., Casella, L., Eds., Kluwer Academic Publishers: Boston, 1994; pp 239-267; and Naruta, (1994) in *Metalloporphyrins in Catalytic Oxidations; Sheldon, R. A., Ed.; Marcel Dekker: New York, pp 241-259.*

Representative porphyrin synthons that have been found to be useful for synthesizing chiral porphyrins include meso-tetrakis(o-aminophenyl)porphyrin (See Collman et al., (1975) *J. Am. Chem. Soc.* 97: 1427 and Leondiadis et al., (1989) *J. Org. Chem.* 54: 6135), meso-tetrakis(2,6-diaminophenyl)porphyrin (see Rose et al., (1996) *J. Am. Chem. Soc.* 118: 1567), meso-tetrakis (2,6-dihydroxyphenyl)porphyrin (see Collman et al., (1997) *Inorg. Synth.* 31: 117 and Tsuchida et al., (1990) *J. Chem. Soc.-Dalton Trans.* 2713), and meso-tetrakis(2,6-dicarboxyphenyl)porphyrin (ee Nakagawa et al., (2001) *Org. Lett.* 3: 1805). These synthons allow the attachment of chiral acids, chiral amines, or chiral alcohols through amide or ester bond formation. To enhance the synthetic utility and flexibility of metalloporphyrin-based asymmetric catalysis, it is desirable to develop alternative synthons for the versatile construction of chiral porphyrins that could be employed in practical asymmetric catalysis.

Within this context, halogenated porphyrins, e.g., bromoporphyrins, have been shown to be versatile precursors for the synthesis of heteroatom-functionalized porphyrins via metal-catalyzed carbon-heteroatom cross-coupling reactions with soft, non-organometallic nucleophiles. See Chen et al., (2003) *J. Org. Chem.* 68: 4432; Gao et al., (2003) *J. Org. Chem.* 68: 6215; Gao et al., (2003) *Org. Lett.* 5: 3261; and Gao et al., (2004) *Org. Lett.* 6: 1837. These methods are based on metal-catalyzed carbon-heteroatom bond formations. See Lev et al., (2003) *Angew. Chem.-Int. Edit.* 42: 5400; Prim et al., (2002) *Tetrahedron,* 58: 2041; Muci et al., (2002) *Top. Curr. Chem.* 219: 131; Hartwig, (2002) in *Handbook of Organopalladium Chemistry for Organic Synthesis;* Negishi, E., Ed.; Wiley-Interscience: New York, pp 1051; Yang et al., (1999) *J. Organomet. Chem.* 576: 125; Wolfe et al., (1998) *Acc. Chem. Res.* 31: 805; Hartwig, (1998) *Angew. Chem.-Int. Edit.* 37: 2047; and Hartwig, (1997) *Synlett,* 329. Such syntheses can be performed under mild conditions with a wide range of nucleophiles, including amines, amides, alcohols, and thiols, leading to a family of novel porphyrins comprising otherwise inaccessible heteroatom functionalities in high yields.

For example, a general and efficient method has been developed for the synthesis of meso-arylamino- and meso-alkylamino-substituted porphyrins from reactions of meso-bromoporphyrins with amines. See Chen et al., (2003) *J. Org. Chem.* 68: 4432. Similar methodology also can be effectively applied to brominated diphenylporphyrins and tetraphenylporphyrins, leading to the versatile synthesis of porphyrin derivatives bearing multiple arylamino and alkylamino groups. See Gao et al., (2003) *J. Org. Chem.* 68: 6215. In addition, a convenient and general approach has been developed for the synthesis of meso-aryloxy- and meso-alkoxy-substituted porphyrins from reactions with alcohols via palladium-catalyzed etheration. See Gao et al., (2003) *Org. Lett.* 5: 3261. A general synthetic method for meso-amidoporphyrins from reactions with amides via palladium-catalyzed amidation also has been developed. See Gao et al., (2004) *Org. Lett.* 6: 1837. Expanding the synthetic strategy to palladium-mediated carbon-sulfur bond formation, a versatile procedure also has been developed for the synthesis of meso-arylsulfanyl- and mesoalkylsulfanyl-substituted porphyrins from reactions of the corresponding bromoporphyrin precursors and thiols. See Gao et al., (2004), submitted for publication.

There exists, however, a need in the art for improved methods for the synthesis of heteroatom-substituted chiral porphyrins.

Accordingly, the presently disclosed subject matter describes the use of haloporphyrins as a new class of synthons for the versatile syntheses of chiral porphyrins via metal catalyst-mediated carbon-heteroatom bond formation reactions with chiral nucleophiles, such as chiral amines, chiral amides, chiral alcohols, and chiral thiols, and the use of these chiral porphyrins as catalysts in asymmetric cyclopropanation, asymmetric aziridination, and asymmetric epoxidation reactions.

SUMMARY

In some embodiments, the presently disclosed subject matter provides novel heteroatom-substituted porphyrin compounds. Novel compounds of the presently disclosed subject matter have the structure of Formula I, as follows:

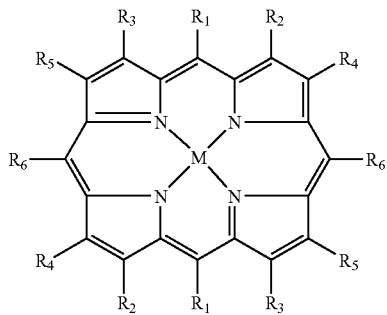

(I)

In Formula I, M is $H_2$ or a transition metal; each $R_1$, $R_2$, $R_3$, $R_4$, $R_5$ and $R_6$ are each independently selected from the group consisting of Y, H, alkyl, substituted alkyl, arylalkyl, aryl, and substituted aryl; Y is a heteroatom-containing moiety; and at least one of $R_1$, $R_2$, $R_3$, $R_4$, $R_5$ and $R_6$ is Y. In some embodiments, M is selected from the group consisting of $H_2$, Fe, Zn and Ni, although numerous other transition metals are useful in the presently disclosed subject matter. In some embodiments, Y is a heteroatom-containing moiety selected from the group consisting of $NR_7R_8$, $NR_{10}$, $OR_{10}$, $PR_7R_8$, $SR_{10}$, $SiR_7R_8R_9$, $BR_7R_8$, $GeR_7R_8R_9$, $SnR_7R_8R_9$ and $SeR_{10}$, wherein $R_7$, $R_8$, $R_9$, and $R_{10}$ are each independently selected from the group consisting of H, alkyl, substituted alkyl, arylalkyl, aryl, and substituted aryl. In some embodiments, Y is a selected from the group consisting of amino, substituted amino, imino, substituted imino, and phenoxy groups.

In some embodiments, the presently disclosed subject matter describes a method of synthesizing a heteroatom-substituted porphyrin compound, whereby a porphyrin precursor and a heteroatom reagent is reacted in the presence of a ligand, a metal compound, and a base to yield the substituted porphyrin. In some embodiments, the porphyrin precursor has the same general structure of Formula I, wherein M is $H_2$ or a transition metal; each $R_1$, $R_2$, $R_3$, $R_4$, $R_5$ and $R_6$ are each independently selected from the group consisting of X, H, alkyl, substituted alkyls, arylalkyls, aryls, and substituted aryls, and X is selected from the group consisting of halogen, trifluoromethanesulfonate (OTf), haloaryl and haloalkyl. In this embodiment, at least one of $R_1$, $R_2$, $R_3$, $R_4$, $R_5$ and $R_6$ is X. In some embodiments, M is selected from the group consisting of $H_2$, Zn, Fe and Ni. In some embodiments, the heteroatom reagents comprise moieties in which the heteroatom is selected from the group consisting of N, O, P, S, Si, B, Ge, Sn, and Se. In some embodiments, the heteroatom reagent is selected from one of N and O.

Accordingly, the presently disclosed subject matter provides a novel heteroatom-substituted porphyrin compound and a novel method of synthesizing a heteroatom-substituted porphyrin compound.

Certain objects of the presently disclosed subject matter having been stated hereinabove, which are addressed in whole or in part by the presently disclosed subject matter, other aspects and objects will become evident as the description proceeds when taken in connection with the accompanying Drawings and Examples as best described herein below.

BRIEF DESCRIPTION OF THE DRAWINGS

In FIG. 1, "M" represents $H_2$, or a transition metal; "X" represents a reactive group such as, for example a halide, trifluoromethanesulfonate (OTf), haloalkyl or haloaryl; and "Y" is heteroatom moiety such as, for example, $NR_7R_8$, $NR_{10}$, $OR_{10}$, $PR_7R_8$, $SR_{10}$, $SiR_7R_8R_9$, $BR_7R_8$, $GeR_7R_8R_9$, $SnR_7R_8R_9$ and $SeR_{10}$, where $R_7$, $R_8$, $R_9$, and $R_{10}$ are each independently, for example, H, alkyl, substituted alkyl, arylalkyl, aryl, or substituted aryl.

FIG. 3A shows two generalized schemes of palladium-catalyzed amination reactions of meso-monobromoporphyrins (left-hand scheme) and meso-dibromoporphyrins (right-hand scheme). FIG. 3B shows the same two amination reactions with specific reaction components and conditions indicated. In FIG. 3B, the upper reaction scheme represents the amination of a meso-monobromoporphyrin, while the lower scheme represents the amination of a meso-dibromoporphyrin.

FIGS. 5A-5D are schemes of particular embodiments of the presently disclosed subject matter. FIG. 5A is a general scheme of the synthesis of aminophenylporphyrins by a palladium-catalyzed amination reaction of p-bromophenyl porphyrin and its zinc complex. FIG. 5B illustrates a particular embodiment of the general scheme of FIG. 5A, wherein specific reaction conditions and components are indicated. FIG. 5C illustrates yet another particular embodiment of the general reaction shown in FIG. 5A, wherein specific reaction conditions and components are indicated. FIG. 5D illustrates a generalized scheme of a palladium-catalyzed reaction of a tetrakis-p-bromophenyl porphyrin that yields a tetrakis-aminophenyl porphyrin.

FIG. 8A shows a generalized scheme of a palladium-catalyzed amination reaction of a meso-dibromoporphyrin to form meso-arylamino and meso-alkylamino substituted porphyrins. FIG. 8B shows a generalized scheme of a palladium-catalyzed amidation reaction of a meso-dibromoporphyrin to form meso-amido substituted porphyrins. FIG. 8C shows a generalized scheme of a palladium-catalyzed C—O cross coupling reaction of a meso-dibromoporphyrin and an alcohol to form meso-aryloxy- and meso-alkoxy-substituted porphyrins. FIG. 8D shows a generalized scheme of a palladium-catalyzed C—S bond formation reaction between a meso-dibromoporphyrin and a thiol to form meso-arylsulfanyl- and meso-alkylsulfanyl-substituted porphyrins. FIG. 8E shows a generalized scheme of a palladium-catalyzed amination reaction of a di(p-bromophenyl) porphyrin to form aminophenylporphyrins. FIG. 8F shows a generalized scheme of a palladium-catalyzed nucleophilic substitution reaction between a brominated porphyrin and a heteroatom nucleophile (H-Nu) to form a heteroatom-substituted porphyrin.

FIG. 14a represents the X-ray structure of a meso-aminoporphyrin comprising an N-methylaniline group. FIG. 14b represents the X-ray structure of a meso-aminoporphyrin comprising a diphenylamine group.

FIG. 17 illustrates the conversion of chiral porphyrins comprising hydrogen atoms at meso-positions (A) to meso-dibromoporphyrins (B) by selective bromination, followed by the conversion of meso-dibromoporphyrins B to the desired meso heteroatom-substituted ortho-chiral porphyrins C.

DETAILED DESCRIPTION

Figure 1:
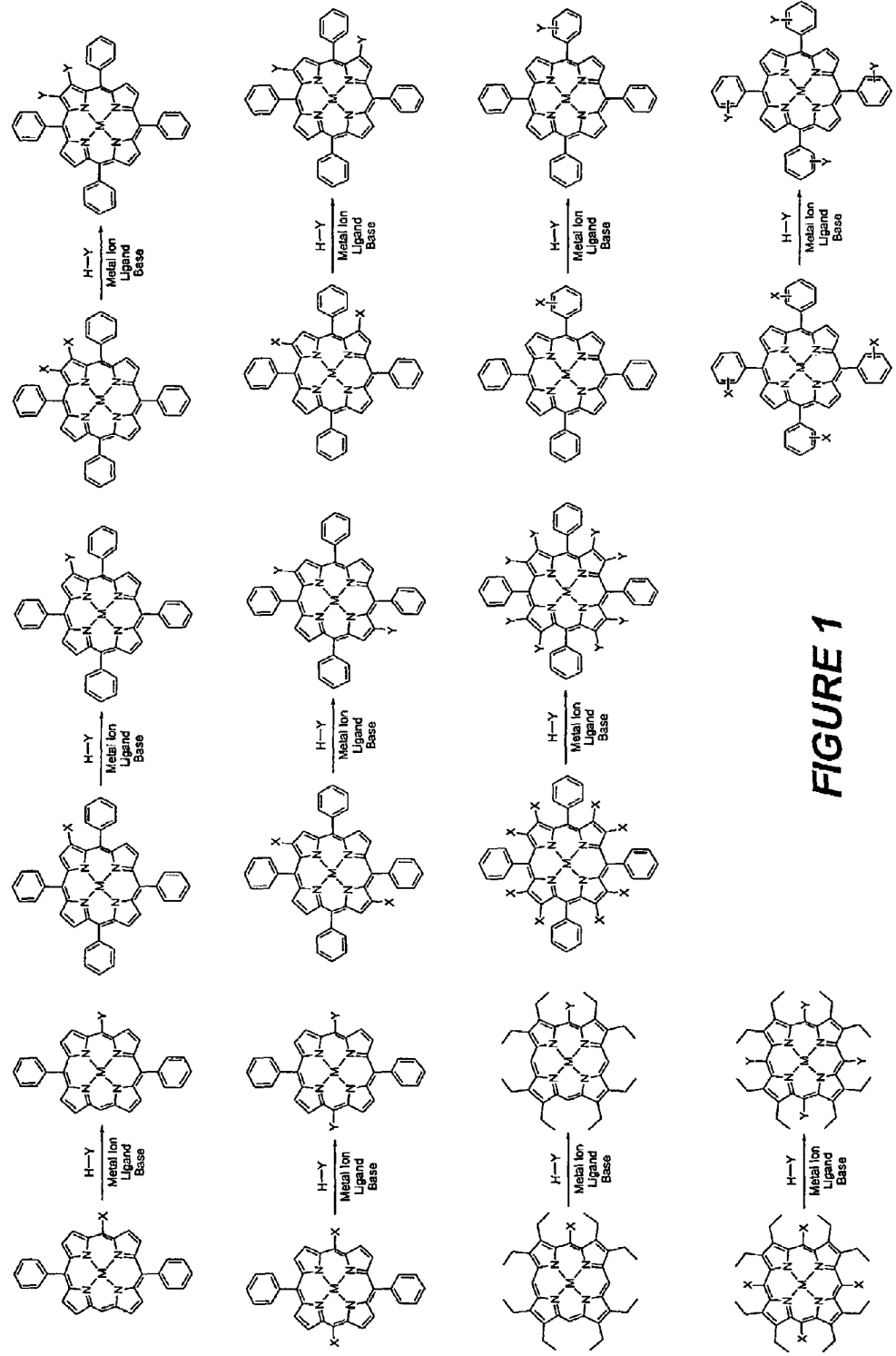
FIG. 1 illustrates several schemes by which heteroatom substituents (e.g., nitrogen, oxygen, etc.) can be substituted into porphyrins by metal/ligand-catalyzed cross-coupling or amination reactions.

In some embodiments the presently disclosed subject matter describes a modular approach for the versatile syntheses of chiral porphyrins which can be utilized as supporting ligands for metal-based asymmetric catalysis. In some embodiments the approach employs haloporphyrins as a new class of synthons to react with chiral nucleophiles via metal catalyst (e.g. palladium)-mediated carbon-heteroatom bond formation reactions, thereby providing a diverse family of chiral porphyrins.

Chiral porphyrin synthesis can play a role in the development of metalloporphyrin-based asymmetric catalysis. The synthetic approach described by the presently disclosed subject matter is modular and in some embodiments includes at least one of several attractive characteristics: (1) the haloporphyrin synthons are stable and readily accessible in large quantities from haloaldehydes or through selective halogenation; (2) the position and number of halide atoms can be varied, leading to chiral porphyrins with different symmetries; (3) the metal (e.g. palladium)-catalyzed crosscoupling reactions have high yields, are reliable, and can be performed under mild conditions for which functional and sensitive groups are well tolerated; and (4) a wide range of readily available, optically pure building blocks, such as chiral amines, chiral amides, chiral alcohols, and chiral thiols, can be coupled to form porphyrins with diverse chiral environments to create a chemical library or "toolbox" of chiral porphyrins.

Recognizing the usefulness of the "toolbox" approach in asymmetric catalysis, in some embodiments the presently disclosed subject matter couples various haloporphyrins with a diverse assortment of chiral building blocks to construct a family of new chiral porphyrins with tunable electronic, steric, geometric, and chiral environments. Accordingly, the presently disclosed subject matter can provide a "toolbox" of effective chiral porphyrins for a variety of metal-based asymmetric catalytic processes. Further, the presently disclosed subject matter can provide a class of "privileged chiral catalysts" that can be used for practical asymmetric syntheses of pharmaceutically and agriculturally important compounds. See Yoon et al., (2003) *Science* 299: 1691.

Accordingly, in some embodiments the presently disclosed subject matter describes the use of metal complexes of these chiral porphyrins as catalysts for asymmetric catalytic processes including a number of important atom/group transfer reactions. For example, the presently disclosed subject matter describes the use of chiral cobalt porphyrins as a catalyst for novel asymmetric cyclopropanation, asymmetric aziridination reactions, and asymmetric epoxidation reactions. The presently disclosed subject matter demonstrates in some embodiments that both high diastereoselectivity and high enantioselectivity, as well as high chemical yields, can be achieved under practical conditions for each of the possible isomers by using chiral porphyrins under conditions comprising different environments.

Further, in some embodiments the presently disclosed subject matter describes the use of chiral porphyrins as a catalyst for asymmetric aziridination reactions with nitrene sources that are convenient and environmentally benign. For example, the presently disclosed subject matter describes the use of the easily accessible and highly stable bromamine-T and diphenylphosphoryl azide as nitrene sources for the catalytic aziridination by chiral porphyrins.

In sum, the presently disclosed subject matter can provide at least one of: (1) haloporphyrins as a new class of versatile synthons for modular construction of chiral porphyrins via palladium-catalyzed cross-coupling reactions with optically active nucleophiles as chiral building blocks; (2) the synthesis of a family of new chiral porphyrins with tunable electronic, steric, geometric, and chiral environments; (3) efficient catalytic systems for asymmetric cyclopropanation under practical conditions with both high diastereoselectivity and high enantioselectivity; (4) convenient and environmentally benign catalytic systems for asymmetric aziridination using alternative nitrene sources; and (5) catalytic systems for asymmetric epoxidation reactions.

The presently disclosed subject matter will now be described more fully hereinafter with reference to the accompanying Drawings and Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all stereoisomers.

I. Definitions

The term "independently selected" is used herein to indicate that the R groups, e.g., $R_1$, $R_2$, $R_3$ or $R_4$, can be identical or different (e.g., $R_1$, $R_2$ and $R_3$ can all be substituted alkyls, or $R_1$ and $R_4$ can be a substituted alkyl and $R_3$ can be an aryl, etc.). Moreover, "independently selected" means that in a multiplicity of R groups with the same name, each group can be identical to or different from each other (e.g., one $R_1$ can be an alkyl, while another $R_1$ group in the same compound can be aryl; one $R_2$ group can be H, while another $R_2$ group in the same compound can be alkyl, etc.).

A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

As used herein, the term "alkyl" means $C_{1-20}$ inclusive, linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups.

The alkyl group can be optionally substituted with one or more alkyl group substituents which can be the same or different, where "alkyl group substituent" includes alkyl, halo, arylamino, acyl, hydroxy, aryloxy, alkoxyl, alkylthio, arylthio, aralkyloxy, aralkylthio, carboxy, alkoxycarbonyl, oxo and cycloalkyl. Suitable substituted alkyls include, for example, benzyl, trifluoromethyl and the like. There can be optionally inserted along the alkyl chain one or more oxygen, sulfur or substituted or unsubstituted nitrogen atoms, wherein the nitrogen substituent is hydrogen, alkyl (also referred to herein as "alkylaminoalkyl"), or aryl. "Branched" refers to an alkyl group in which an alkyl group, such as methyl, ethyl or propyl, is attached to a linear alkyl chain.

The term "aryl" is used herein to refer to an aromatic substituent which can be a single aromatic ring or multiple aromatic rings which are fused together, linked covalently, or linked to a common group such as a methylene or ethylene moiety. The common linking group can also be a carbonyl as in benzophenone or oxygen as in diphenylether or nitrogen in diphenylamine. The aromatic ring(s) can include phenyl, naphthyl, biphenyl, diphenylether, diphenylamine and benzophenone among others. In particular embodiments, the term "aryl" means a cyclic aromatic comprising about 5 to about 10 carbon atoms, including 5- and 6-membered hydrocarbon and heterocyclic aromatic rings.

The aryl group can be optionally substituted with one or more aryl group substituents which can be the same or different, where "aryl group substituent" includes alkyl, aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NR'R", where R' and R" can be each independently hydrogen, alkyl, aryl and aralkyl.

Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like.

The term "alkoxy" is used herein to refer to the —$OZ_1$ radical, where $Z_1$ is selected from the group consisting of alkyl, substituted alkyl, cycloalkyl, substituted cycloalkyl, heterocycloalkyl, substituted heterocycloalkyl, silyl groups and combinations thereof as described herein. Suitable alkoxy radicals include, for example, methoxy, ethoxy, benzyloxy, t-butoxy, and the like. A related term is "aryloxy" where $Z_1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

The term "amino" is used herein to refer to the group —$NZ_1Z_2$, where each of $Z_1$ and $Z_2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof. Additionally, the amino group can be represented as $N^+Z_1Z_2Z_3$, with the previous definitions applying and $Z_3$ being either H or alkyl.

A "heteroatom," as used herein, is an atom other than carbon. In some embodiments, the heteroatoms are selected from the group consisting of N, O, P, S, Si, B, Ge, Sn, and Se. In some embodiments of the presently disclosed subject matter, the heteroatoms are selected from one of N and O. "Halide" or "halo" is defined as being selected from the group consisting of Br, Cl, I and F. In the some embodiments, the halo groups are selected from one of Br and I.

The term "stereoisomer" refers to molecules that are made up of the same atoms connected by the same sequence of bonds, but have different three dimensional structures. The term stereoisomer includes enantiomers, i.e., mirror image stereoisomers, cis-trans isomers, and diastereomers.

The term "chiral" refers to the stereochemical property of a molecule of being non-superimposible on its mirror image. A chiral molecule has no symmetry elements of the second kind, e.g., a mirror plane, a center of inversion, and a rotation-reflection axis. The two forms of a chiral molecule are known as enantiomers. A collection containing equal amounts of the two enantiomeric forms of a chiral molecule is referred to as a racemic mixture or racemate. In some embodiments, a chiral "R" group is represented by "R*."

The term "diastereomer" refers to non-enantiomeric isomers which arise when more than one stereocenter is present in a molecule.

A collection of molecules containing only one enantiomeric form of a chiral molecule is referred to as "enantiopure," "enantiomerically pure," or "optically pure." A mixture containing predominantly one enantiomer is referred to as enantiomerically enriched or enantioenriched. Enantiopurity is usually reported in terms of "enantiomeric excess" (e.e.), which is determined as:

% e.e.=(major−minor)*100/(major+minor)

wherein the term "major" refers to the more abundant enantiomer and the term "minor" refers to the less abundant enantiomer. For example, in some embodiments of the presently disclosed subject matter, an optically active compound can have an enantiopurity of greater than 50%; of greater than 75%; of greater than 90%; or of greater than 95%.

The term "nucleophile" or "nucleophilic reagent" refers to a reagent that forms a bond to its reaction partner, e.g., an "electrophile" by donating both bonding electrons.

The term "porphyrin" refers to a compound comprising a fundamental skeleton of four pyrrole nuclei united through the α-positions by four methane groups to form the following macrocyclic structure:

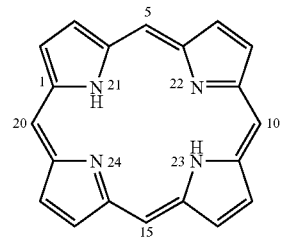

The term "meso" refers to the position on the porphyrin structure adjacent to the reduced pyrrole ring, i.e., positions 5, 10, 15, and 20. Said another way, a "meso-porphyrin" is a porphyrin compound comprising substitutent groups at the 5, 10, 15, and 20 position, or combinations thereof.

II. Synthesis of Hetero-substituted Porphyrins

Heteroatom-substituted porphyrins and/or heteroatom-substituted chiral porphyrins of the presently disclosed subject matter are synthesized by reacting a porphyrin precursor and a heteroatom reagent and/or heteroatom chiral reagent in the presence of a metal compound, ligand and a base. Although applicants do not wish to be bound to any particular theory of the presently disclosed subject matter, it appears that the metal and ligand together (e.g., as a metal-ligand complex, or metal/ligand composition) function as a catalyst for the reaction, by which a heteroatom-substituted porphyrin and/or heteroatom-substituted chiral porphyrin is produced.

Depending on the heteroatom reagent, reactions of the presently disclosed subject matter can be, for example, cross-coupling reactions, amination reactions, or arylamination reactions. For example, in one embodiment, the metal compound and ligand together (in the configuration of a metal complex) catalyze the cross coupling reaction between the porphyrin precursor and the heteroatom reagent to yield the heteroatom-substituted porphyrin. Representative methods of the presently disclosed subject matter are generally illustrated in the several schemes shown in FIG. 1.

Porphyrin precursors of the presently disclosed subject matter have the structure of Formula I:

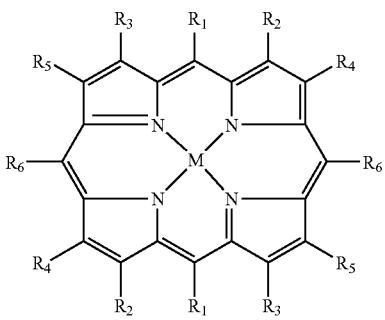

(I)

wherein:
M is $H_2$ or a transitional metal;
each $R_1$, $R_2$, $R_3$, $R_4$, $R_5$ and $R_6$ are each independently selected from the group consisting of X, H, alkyl, substituted alkyls, arylalkyls, aryls and substituted aryls;
X is selected from the group consisting of halogen, trifluoromethanesulfonate (OTf), haloaryl and haloalkyl, and at least one of $R_1$, $R_2$, $R_3$, $R_4$, $R_5$ and $R_6$ is X.

Transitional metals of the presently disclosed subject matter include any of the 30 metals in the 3d, 4d and 5d transition metal series of the Periodic Table of the Elements, including the 3d series that includes Sc, Ti, V, Cr, Mn, Fe, Co, Ni, Cu, and Zn; the 4d series that includes Y, Zr, Nb, Mo, Tc, Ru, Rh, Pd, Ag and Cd; and the 5d series that includes Lu, Hf, Ta, W, Re, Os, Ir, Pt, Au and Hg. In some embodiments, M is $H_2$ or a transition metal from the 3d series. In some embodiments, M is selected from the group consisting of $H_2$, Zn, Fe, and Ni. In some embodiments, M is selected from the group consisting of $H_2$ and Zn.

In some embodiments, the porphyrin precursor compound is halogenated, that is, at least one of $R_1$, $R_2$, $R_3$, $R_4$, $R_5$ and $R_6$ is halogen. In some embodiments, at least one meso-position of the porphyrin precursor compound is halogenated. In some embodiments, more than one meso-position of the porphyrin precursor compound is halogenated. When a porphyrin precursor compound of the presently disclosed subject matter is halogenated, one such halogen group is Br, although other halogen groups also are useful in the practice of the presently disclosed subject matter.

In some embodiments of the presently disclosed subject matter, the heteroatom reagent has the chemical structure Y—H, where Y is heteroatom-containing moiety comprising at least one of N, O, P, S, Si, B, Ge, Sn, and Se. Exemplary heteroatom-containing moieties include, but are not limited to, $NR_7R_8$, $NR_{10}$, $OR_{10}$, $PR_7R_8$, $SR_{10}$, $SiR_7R_8R_9$, $BR_7R_8$, $GeR_7R_8R_9$, $SnR_7R_8R_9$ and $SeR_{10}$, wherein $R_7$, $R_8$, $R_9$, and $R_{10}$ are each independently selected from the group consisting of H, alkyl, substituted alkyl, arylalkyl, aryl, and substituted aryl. In some embodiments, the heteroatom-containing moiety comprises one of N or O.

In some embodiments, the heteroatom reagent comprises at least one amino group. Suitable amino groups include, but are not limited to, primary amines, secondary amines, anilines, substituted aniline derivatives, aromatic amines, primary aliphatic amines, secondary aliphatic amines and cycloaliphatic amines. Specific amino groups useful in the presently disclosed subject matter include, but are not limited to, aniline, 4-nitroaniline, N-methylaniline, 4-trifluoromethylaniline, p-anisidine, 3,5-di-tert-butylaniline, n-hexylamine, benzylamine, diphenylamine, n-butylamine, 4-aminomethylpyridine, and o-toluidine. In some embodiments, the heteroatom reagent comprises an imino group. Suitable imino groups include but are not limited to benzophenone imino groups.

In some embodiments, the heteroatom reagent comprises an aryl or aryl halide group, which groups are sometimes referred to herein as phenyl or substituted phenyl groups. Suitable aryl groups include phenyl, 4-methoxyphenyl, 4-t-butylphenyl, 4-fluorophenyl, 2-isopropylphenyl, 3-cresol, 4-cresol, and 4-methoxyphenyl.

Reactions of the presently disclosed subject matter involve a catalyst, which catalyst generally has the form of a metal complex. The metal complex comprises a metal compound of the presently disclosed subject matter complexed with a ligand. In some embodiments, the ligand comprises a phosphine ligand. Metal compounds of the presently disclosed subject matter can optionally be provided as metal precursors. Thus, as used herein, a "metal compound" can also be referred to as a "metal precursor," a "metal precursor compound," a "metal salt," or a "metal ion."

The metal precursor compounds can be characterized by the general formula $M'(L)_n$ (also referred to as $M'L_n$ or $M'-L_n$) where M' is a metal selected from the group consisting of Groups 5, 6, 7, 8, 9 and 10 of the Periodic Table of Elements, L is independently each occurrence, a neutral or charged ligand, and n is a number 0, 1, 2, 3, 4, or 5, depending on M'. In some embodiments, M' is selected from the group consisting of Ni, Pd, Fe, Pt, Ru, Rh, Co and Ir. In some embodiments, M' is selected from the group consisting of Pd, Ni, Cu or Pt; in some embodiments, M' is Pd. L is a compound chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is charged, L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When L is neutral, L can be selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino.

Specific examples of suitable metal precursor compounds include $Pd(dba)_2$, $Pd_2(dba)_3$, $Pd(OAc)_2$, $PdCl_2$, $Pd(TFA)_2$, $(CH_3CN)_2PdCl_2$, and the like. In some embodiments, the metal precursor compounds of the presently disclosed subject matter include $Pd(OAc)_2$ and $Pd_2(dba)_3$, where "Ac" means acetyl and "dba" means dibenzylidieneacetone.

In the practice of the presently disclosed subject matter, ligands of the presently disclosed subject matter can be combined with such a metal compound in order to provide a catalyst for the heteroatom-substitution reaction. For example, the ligand can be added to a reaction vessel at the same time as metal precursor compound along with the reactants. In other applications, the ligand will be mixed with a suitable metal precursor compound prior to or simultaneous with allowing the mixture to be contacted to the reactants. When the ligand is mixed with the metal precursor compound, a metal-ligand complex can be formed, which can be a catalyst.

Figure 2:
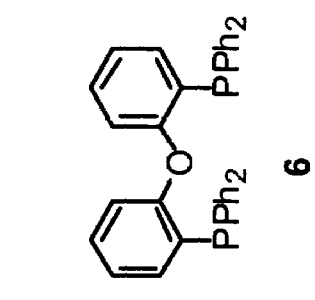
FIG. 2 illustrates the chemical structures of eleven compounds that are representative, although not inclusive, of phosphine ligands useful in the presently disclosed subject matter.
Figure 2:
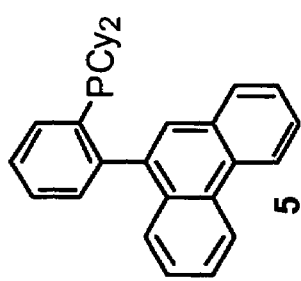
Figure 2:
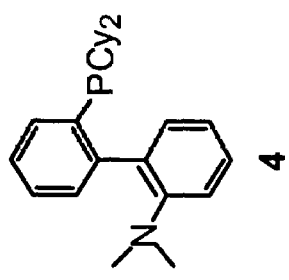
Figure 2:
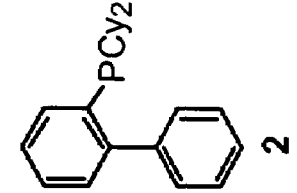
Figure 2:
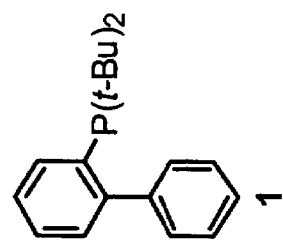
Figure 2:
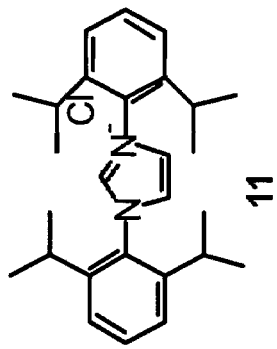
Figure 2:
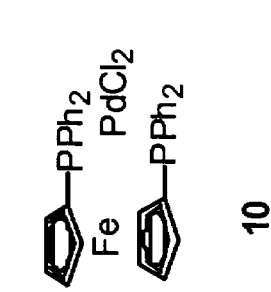
Figure 2:
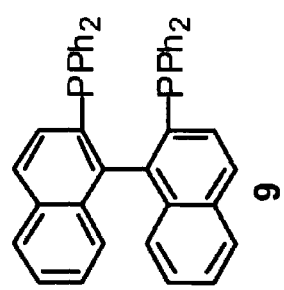
Figure 2:
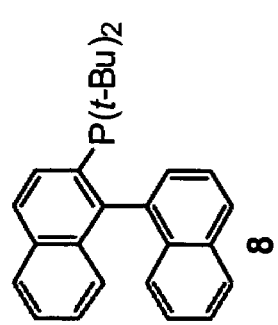
Figure 2:
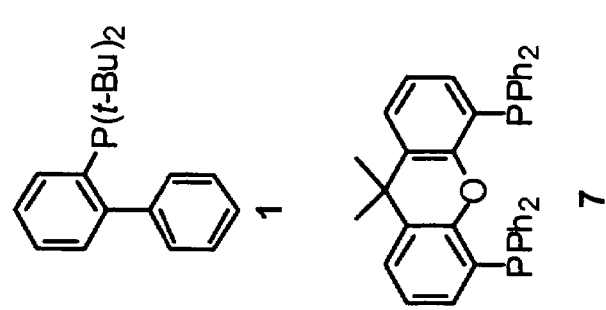

Generally, the ligands useful in the presently disclosed subject matter can be purchased or prepared by methods known to those of skill in the art. In some embodiments, the ligand comprises a phosphine ligand. Suitable phosphine ligand-metal complexes are disclosed in U.S. Pat. No. 6,268,513 to Guram et al., which patent is incorporated herein by reference in its entirety. Phosphine ligands can comprise dicycloalkylphenyl phosphine ligand or dialkylphenyl phosphine ligand, which can be in the form of a metal-ligand complex or a metal precursor/ligand composition. In some embodiments, the phosphine ligands useful in the presently disclosed subject matter comprise a cyclopentadienyl ring. Specific ligands that are useful in the practice of the presently disclosed subject matter include, but are not limited to, those whose structures are shown in FIG. 2. In some embodiments, the ligand is selected from the group consisting of DPEphos (FIG. 2, Ligand 6), BINAP (FIG. 2, Ligand 9) and 2-(Di-t-butylphosphino)-1,1-binaphthyl (FIG. 2, Ligand 8).

To carry out the process of the presently disclosed subject matter for one type of reaction, the porphyrin precursor, the heteroatom reagent, a base, a catalytic amount of metal precursor compound and a catalytic amount of the ligand are added to an inert solvent or inert solvent mixture. In a batch methodology, this mixture is stirred in some embodiments at a temperature of from 0° C. to 200° C., in some embodiments from 30° C. to 170° C., in some embodiments from 50° C. to 150° C., and in some embodiments from 60° C. to 120° C. In some embodiments, the mixture is strirred at 68° C. The mixture is stirred in some embodiments for a period of from 5 minutes to 100 hours, in some embodiments from 15 minutes to 70 hours, in some embodiments from ½ hour to 50 hours, and in some embodiments from 1 hour to 30 hours. After the reaction is complete, the catalyst can be obtained as solid and separated off by filtration. The crude product is freed of the solvent or the solvents and is subsequently purified by methods known to those skilled in the art and matched to the respective product, e.g. by recrystallization, distillation, sublimation, zone melting, melt crystallization or chromatography.

Solvents suitable for the process of the presently disclosed subject matter are, for example, ethers (e.g., diethyl ether, dimethoxymethane, diethylene glycol, dimethyl ether, tetrahydrofuran (THF), dioxane, diisopropyl ether, tert-butyl methyl ether), hydrocarbons (e.g., hexane, iso-hexane, heptane, cyclohexane, benzene, toluene, xylene), alcohols (e.g., methanol, ethanol, 1-propanol, 2-propanol, ethylene glycol, 1-butanol, 2-butanol, tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), water and mixtures thereof. In some embodiments, the solvents are selected from one of ethers (e.g., dimethoxyethane, THF), and hydrocarbons (e.g., cyclohexane, benzene, toluene, xylene). In some embodiments, the solvents are selected from one of toluene and THF.

Bases which are useful in the process of the presently disclosed subject matter are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, alkali metal and alkaline earth metal phosphates, primary, secondary and tertiary amines, alkali metal and alkaline earth fluorides, and ammonium fluorides. In some embodiments, the bases include but are not limited to n-BuLi, LDA, $NaNH_2$, NaOH, $Et_3N$, NaOAc, KOt-Bu, NaOt-Bu, $Cs_2CO_3$, $K_2CO_3$, $K_3PO_4$, carbonate-containing compounds, and phosphate-containing compounds. In some embodiments, the bases include, but are not limited to, $Cs_2CO_3$ and NaOt-Bu. In some embodiments, the base is used in the process of the presently disclosed subject matter in an amount of from about 0.1 to about 100 equivalents, in some embodiments from about 0.5 to about 50 equivalents, in some embodiments from about 1.0 to about 10 equivalents, and in some embodiments from about 1.0 to about 1.5 equivalents.

The metal precursor compound used in this reaction is as described above and can be added to the process along with the other reactants. The metal portion of the catalyst (i.e., the metal precursor compound) is used in the process of the presently disclosed subject matter in some embodiments in a proportion of from about 0.01 to about 100 mol %, in some embodiments from about 0.1 to about 50 mol %, in some embodiments from about 0.5 to about 10 mol %, and in some embodiments from about 1 to about 5 mol %. The ligand component of the catalyst, which in some embodiments is complexed to the metal precursor compounds and in some embodiments is not complexed to the metal precursor compound, is used in the reaction in some embodiments in a proportion of from about 0.01 to about 100 mol %, in some embodiments from 0.1 to about 50 mol %, in some embodiments from about 0.5 to about 10 mol %, and in some embodiments from about 1 to about 5 mol %. These amounts can be combined to give metal precursor to ligand ratios useful in the process. It is also possible, if desired, to use mixtures of two or more different ligands.

Figure 3A:
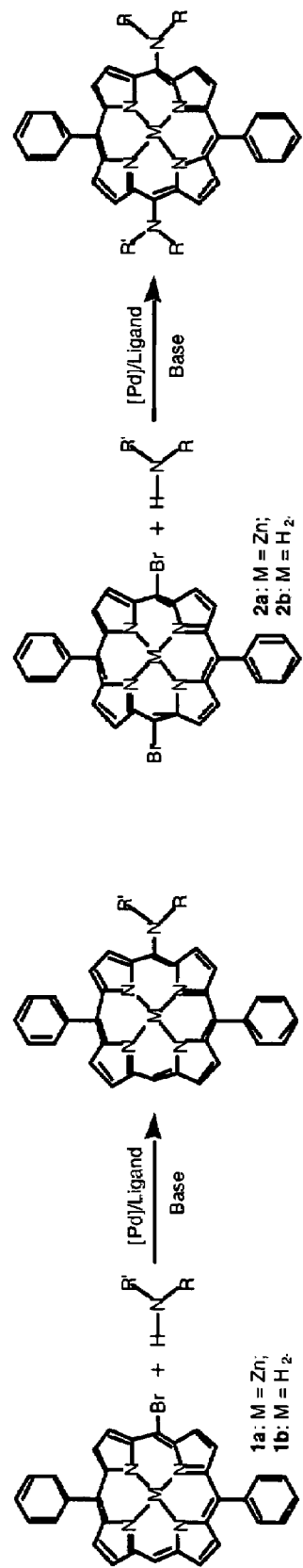
FIGS. 3A and 3B are schemes of particular embodiments of the presently disclosed subject matter.
Figure 3B:
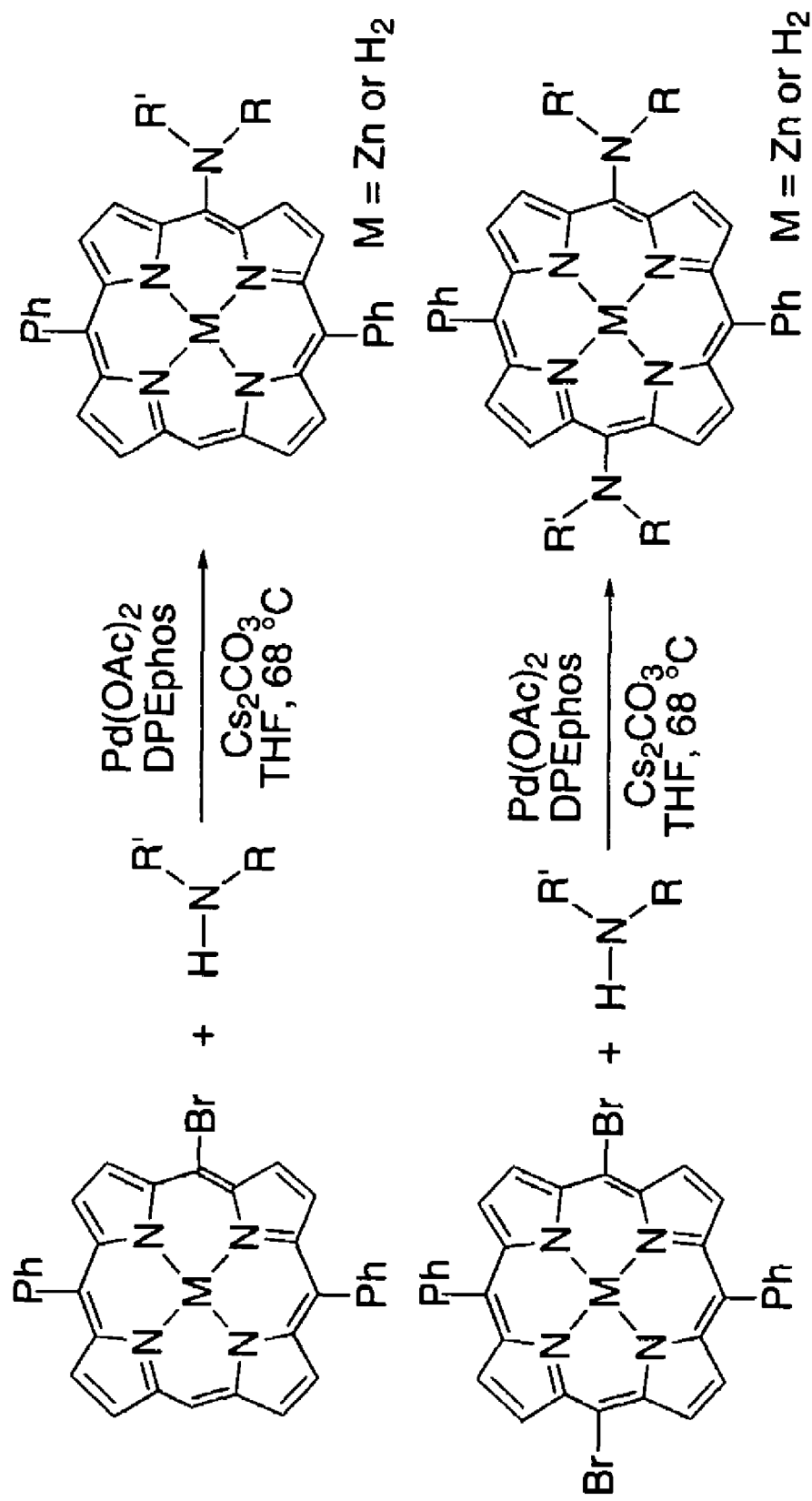

In some embodiments of the presently disclosed subject matter, at least one meso-position of the synthesized heteroatom-substituted porphyrin is substituted; that is, the heteroatom-substituted porphyrin is a meso-substituted porphyrin. In some embodiments of the presently disclosed subject matter, amino-substituted porphyrins are obtained from halogenated porphyrin precursors via palladium-catalyzed amination. Specifically, meso-arylamino- and alkylamino-substituted porphyrins are efficiently synthesized by reacting meso-halogenated porphyrins with amines via palladium-catalyzed amination. A general schematic of this embodiment is illustrated in FIG. 3A. FIG. 3B illustrates two particular embodiments of the presently disclosed subject matter. In the schematic on the left side of the figure, the porphyrin precursors 5-bromo-10,20-diphenylporphyrine and its corresponding zinc complex [5-bromo-10,20-diphenyl porphyrino]zinc(II) are each reacted with an amino group to yield the illustrated amino-substituted porphyrin. In the schematic on the right side of the picture, [5,15-dibromo-10,20-diphenylporphyrino]zinc(II) and its corresponding zinc complex [5,15-dibromo-10,20-diphenylporphyrino]zinc(II) are each reacted with an amino group to provide the indicated amino-substituted porphyrin. The precursors and amine reagents are reacted in the presence of palladium acetate and the commercially available phosphine ligand bis(2-diphenylphosphinophenyl) ether, or "DPEphos".

Figure 4:
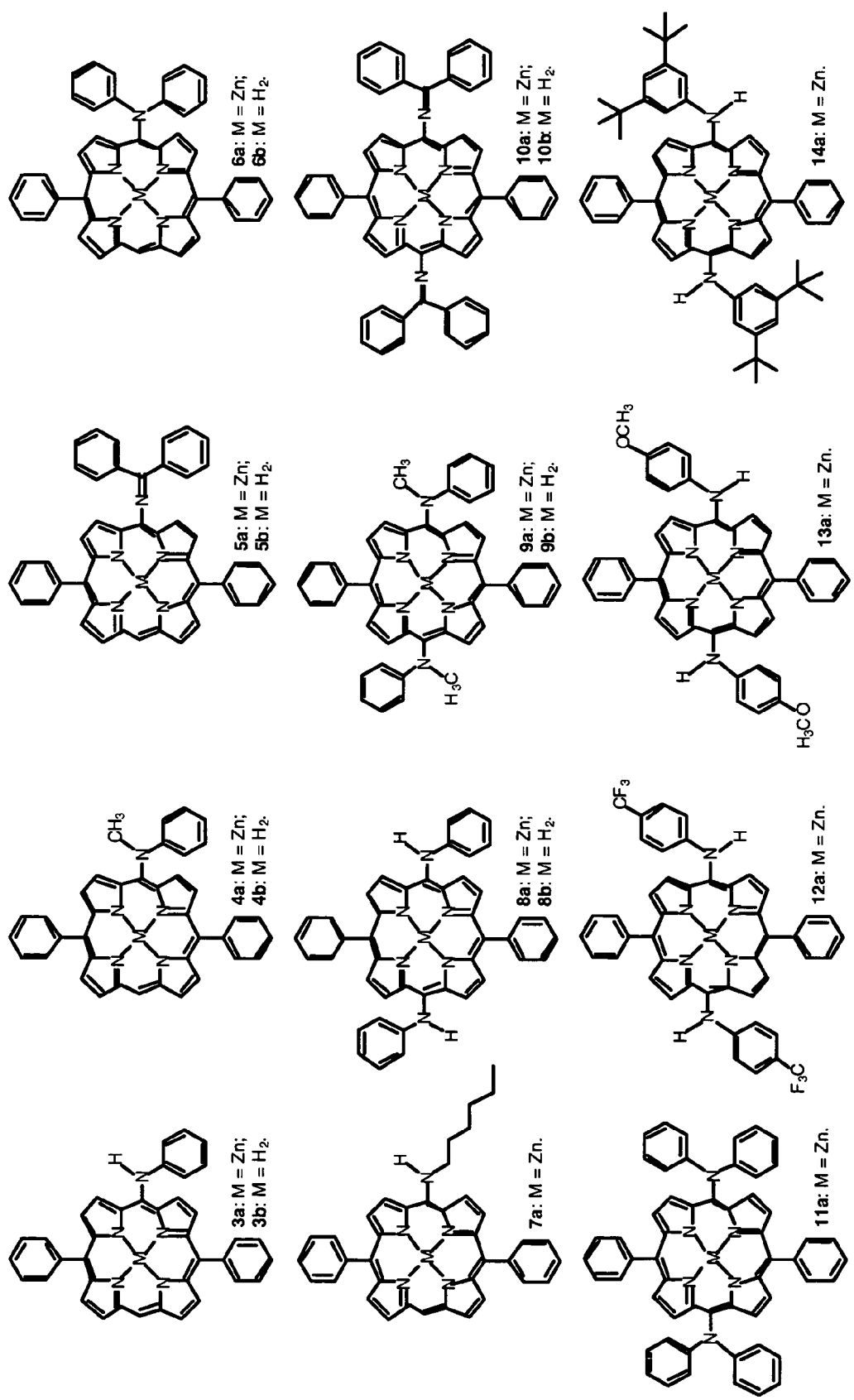
FIG. 4 illustrates the chemical structures of several compounds of the presently disclosed subject matter, which compounds are synthesized by the presently disclosed methods. The compound numbers shown in FIG. 4 (e.g., 3a, 3b, 4a, 4b, etc.) correspond to the compound numbers indicated in Table 1, below.
Figure 5C:
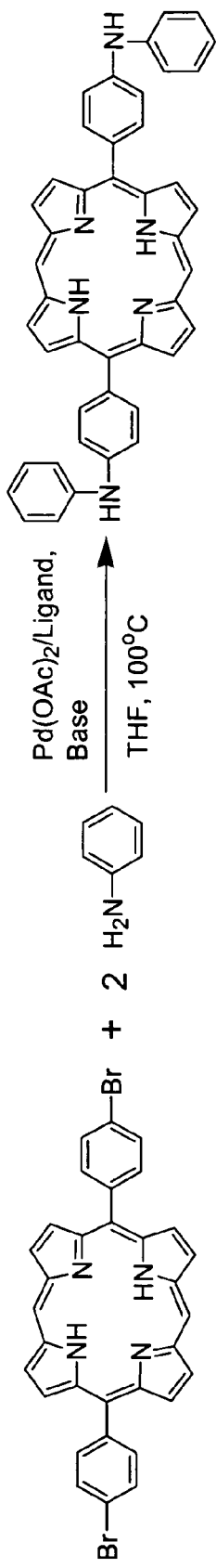
Figure 5D:
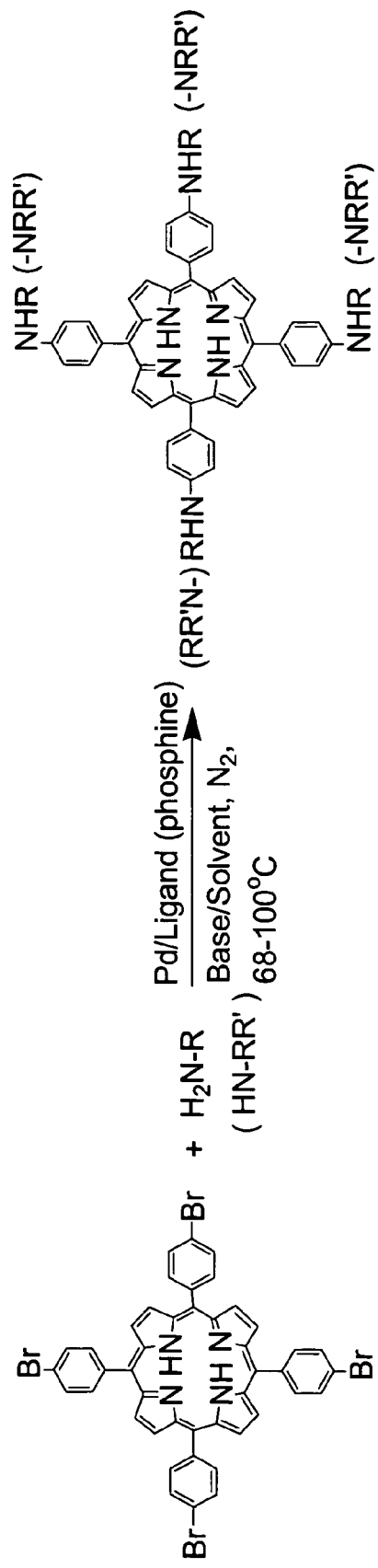

In some embodiments of the presently disclosed subject matter, a variety of different amines are efficiently coupled with the meso-brominated 10,20-diphenylporphyrins 5-bromo-10,20-diphenylporphyrine and 5,15-dibromo-10,20-diphenylporphyrine (compounds 1b and 2b in Table 1) as well as their corresponding zinc complexes [5-bromo-10,20-diphenylporphyrino]zinc(II) and [5,15-dibromo-10,20-diphenylporphyrino]zinc(II) (compounds 1a and 2a in Table 1). The meso-arylamino- and alkylamino-substituted porphyrins that are obtained are summarized in Table 1, below, with the structures of the resulting compound being shown in FIG. 4. Specifically, both the primary aniline (Table 1, entry 1) and the secondary N-methylaniline (Table 1, entry 3) can be effectively coupled with 1a to give monoamino-substituted porphyrins 3a and 4a, respectively. When 2a is used, the corresponding diamino-substituted porphyrins 8a (Table 1, entry 10) and 9a (Table 1, entry 12) are synthesized via double amination reactions. Substituted aniline derivatives such as 4-trifluoromethylaniline (Table 1, entry 17), p-anisidine (Table 1, entry 18) and 3,5-di-tert-butylaniline (Table 1, entry 19) also give high yields of double amination products when reacted with 2a. Primary aliphatic amines can also be well-coupled, as demonstrated in the case of n-hexylamine with 1a (Table 1, entry 9).

In addition to primary and secondary amines, imines are also suitable coupling partners under similar reaction conditions. When benzophenone imine was employed, monoimino-substituted porphyrin 5a (Table 1, entry 5) and diimino-substituted porphyrin 10a (Table 1, entry 14) are obtained from its reactions with 1a and 2a, respectively.

TABLE 1

Palladium-Catalyzed Amination of meso-bromoporphyrins with amines

| entry | reactant[b] | amine | time (h)[c] | product[d] | yield (%)[e] |
|---|---|---|---|---|---|
| 1 | 1a | PhNH$_2$ | 13 | 3a | 95 |
| 2 | 1b | PhNH$_2$ | 19 | 3b | 98 |
| 3 | 1a | Ph(Me)NH | 13 | 4a | 99 |
| 4 | 1b | Ph(Me)NH | 16 | 4b | 94 |
| 5 | 1a | Ph$_2$C=NH | 22 | 5a | 94 |
| 6 | 1b | Ph$_2$C=NH | 24 | 5b | 84 |
| 7 | 1a | Ph$_2$NH | 25 | 6a | 61[f] |
| 8 | 1b | Ph$_2$NH | 40 | 6b | 66 |
| 9 | 1a | n-HexNH$_2$ | 50 | 7a | 80 |
| 10 | 2a | PhNH$_2$ | 13 | 8a | 82 |
| 11 | 2b | PhNH$_2$ | 20 | 8b | 65 |
| 12 | 2a | Ph(Me)NH | 17 | 9a | 82 |
| 13 | 2b | Ph(Me)NH | 15 | 9b | 71 |
| 14 | 2a | Ph$_2$C=NH | 16 | 10a | 84 |
| 15 | 2b | Ph$_2$C=NH | 15 | 10b | 95 |
| 16 | 2a | Ph$_2$NH | 50 | 11a | 30 |
| 17 | 2a | (4-CF$_3$Ph)NH$_2$ | 17 | 12a | 90 |
| 18 | 2a | (4-CH$_3$OPh)NH$_2$ | 16 | 13a | 94 |
| 19 | 2a | (3,5-di-t-BuPh)NH$_2$ | 62 | 14a | 95 |

Reactions were carried out at 68° C. in THF under N$_2$ with 1.0 equiv of bromoporphyrin, 3.6 equiv of amine for 1b and 2b or 4.8 equiv of amine for 1a and 2a, 5 mol % Pd(OAc)$_2$ and 7.5 mol % DPEphos in the presence of 1.4 equiv of Cs$_2$CO$_3$ per Br. Concentration: 0.05 mmol bromoporphyrin/5 mL THF. Yields represent isolated yields of >95% purity as determined by $^1$H NMR. The reaction was conducted using 10 mol % Pd(OAc)$_2$ and 15 mol% DPEphos in the presence of 2.8 equiv of NaOt-Bu.

In embodiments of the presently disclosed subject matter, the methods of the presently disclosed subject matter are carried out to produce aminophenylporphyrins. In one such embodiment, the porphyrin precursors are p-bromophenyl porphyrin and its zinc complex, and the amination reaction is catalyzed by palladium. Schemes for this reaction are illustrated in FIGS. 5A-5D, with exemplary aminophenylporphyrins obtained in the presently disclosed subject matter being described in Tables 2 and 3, below.

TABLE 2

5,15-di-aminophenylporphyrin and zinc complex synthesized via Pd catalyzed amination reaction

| Entry | Amine (8.0 equiv) | Ligand (10%) equiv | Base (8.0) equiv | Solvent | Time | Isolated yield (%) A M = 2H | B M = Zn(II) |
|---|---|---|---|---|---|---|---|
| 1 | H$_2$N—Ph | 9 | Cs$_2$CO$_3$ | Toluene | 48 h | 70 | 66 |
|  |  | 9 | NaOtBu | Toluene | 48 h | 88 | — |
|  |  | 9 | NaOtBu | THF | 24 h | 95 | — |
|  |  | 9 | NaOtBu | THF | 13 h | 83 | — |
|  |  | 9 | Cs$_2$CO$_3$ | THF | 48 h | 92 | — |
|  |  | 9 | Cs$_2$CO$_3$ | THF | 48 h | 85[a] | — |
|  |  | 9 | NaOtBu | THF | 48 h | 92 | — |
|  |  | 9 | NaOtBu | THF | 48 h | — | — |
| 2 | H$_2$N—Ph—NO$_2$ | 9 | Cs$_2$CO$_3$ | Toluene | 48 h | 76 | — |
| 3 | H$_2$N—Ph—OCH$_3$ | 3 | NaOtBu | THF | 48 h | 93 | 68 |
| 4 | H$_2$N—CH$_2$—Ph | 3 | NaOtBu | THF | 48 h | — | 83 |

TABLE 2-continued 5,15-di-aminophenylporphyrin and zinc complex synthesized via Pd catalyzed amination reaction

| Entry | Amine (8.0 equiv) | Ligand (10%) equiv | Base (8.0) equiv | Solvent | Time | Isolated yield (%) A M = 2H | B M = Zn(II) |
|---|---|---|---|---|---|---|---|
| 5 | 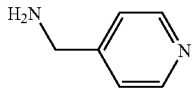 | 9 | NaOtBu | THF | 48 h | 88 | — |
|   |   | 8 | NaOtBu | THF | 48 h | 80 | — |
|   |   | 9 | Cs₂CO₃ | Toluene | 66.5 h | 45 | — |
| 6 | 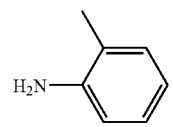 | 3 | NaOtBu | THF | 48 h | 87 | 73 |
| 7 | 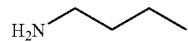 | 8 | NaOtBu | THF | 48 h | 83 | 93 |
|   |   | 8 | NaOtBu | THF | 24 h | 63 | — |
|   |   | 8 | NaOtBu | THF | 13 h | 76 | — |
|   |   | 8 | NaOtBu | THF | 48 h | 69ᵃ | — |
|   |   | 1 | Cs₂CO₃ | THF | 48 h | 79 | — |
|   |   | 2 | NaOtBu | THF | 48 h | 66ᵇ | — |
|   |   | 2 | NaOtBu | THF | 48 h | 99 | — |
|   |   | 3 | NaOtBu | THF | 48 h | 92 | — |
|   |   | 3 | NaOtBu | THF | 48 h | 93 | — |
| 8 | 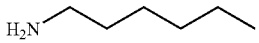 | 3 | NaOtBu | THF | 48 h | 90 | 53ᶜ |
| 9 | 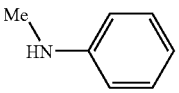 | 3 | NaOtBu | THF | 48 h | 88 | 73 |
| 10 | 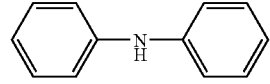 | 3 | NaOtBu | THF | 48 h | 81 | 57 |
|   |   | 9 | NaOtBu | THF | 48 h | 57 | — |
| 11 | 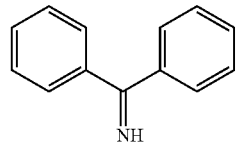 | 1 | NaOtBu | THF | 48 h | 52 | — |
| 12 | 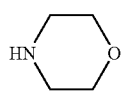 | 8 | Cs₂CO₃ | THF | 48 h | 76 | — |
|   |   | 8 | NaOtBu | THF | 48 h | 70 | — |

Note
ᵃ4.0 equiv aniline;
ᵇPd(OAc)₂/Ligand = 10%/20%,
ᶜligand 7

TABLE 3

Tetrakis-aminophenylporphyrins synthesized from
tetrakis-p-bromophenylporphyrin through
Pd catalyzed amination reaction

| Entry | Amine 16.0 equiv | Pd (5%) equiv | Ligand (10%) equiv | Base (16.0) equiv | Solvent | °C. | Time | Isolated yield |
|---|---|---|---|---|---|---|---|---|
| 1 | H₂N-phenyl | Pd(OAc)₂ | 9 | NaOtBu | THF | 100 | 72 h | 91% |
| 2 | H₂N-propyl | Pd(OAc)₂ | 8 | NaOtBu | THF | 100 | 72 h | 86% |
| 3 | Me-HN-phenyl | Pd(OAc)₂ | 9 | NaOtBu | THF | 100 | 72 h | 82% |
| 4 | diphenylamine | Pd(OAc)₂ | 9 | NaOtBu | THF | 100 | 72 h | 81% |

Figure 6:
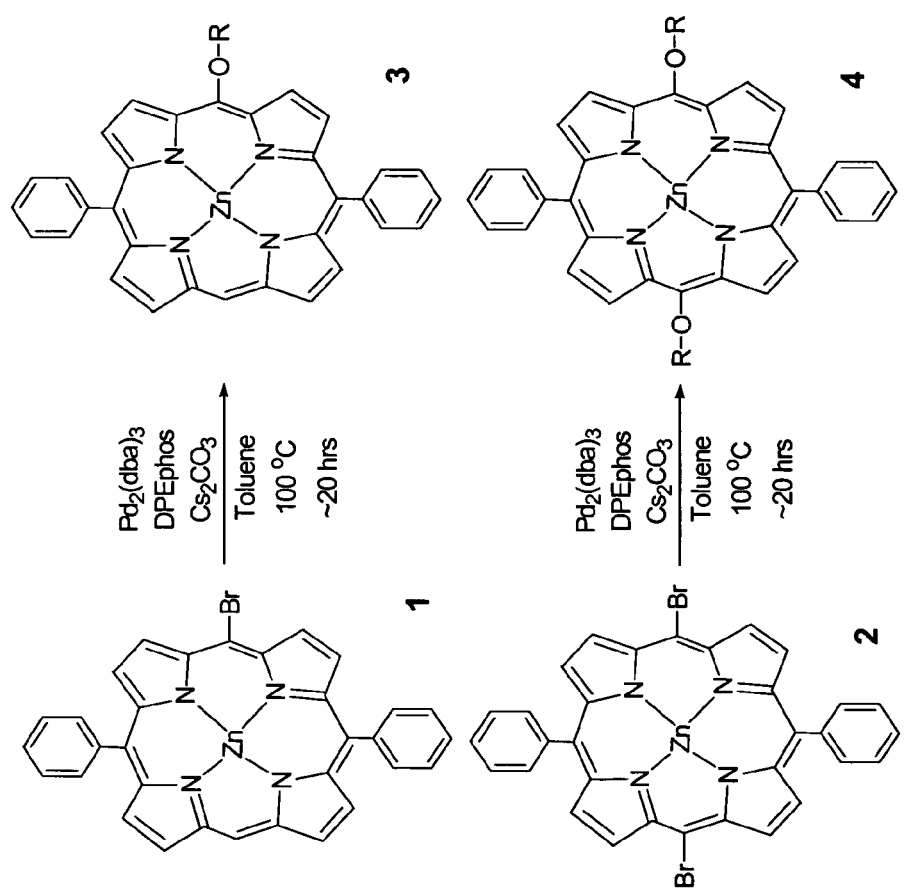
FIG. 6 illustrates a general reaction scheme whereby [5-bromo-10,20-diphenylporphyrino]zinc(II) (indicated in the Figure as compound 1) and [5,15-dibromo-10,20-diphenylporphyrino]zinc(II) (indicated in the Figure as compound 2) undergo a palladium-catalyzed cross-coupling reaction to yield the corresponding meso-substituted phenoxyporphyrins (indicated in the Figure as compounds 3 and 4, respectively).
Figure 7:
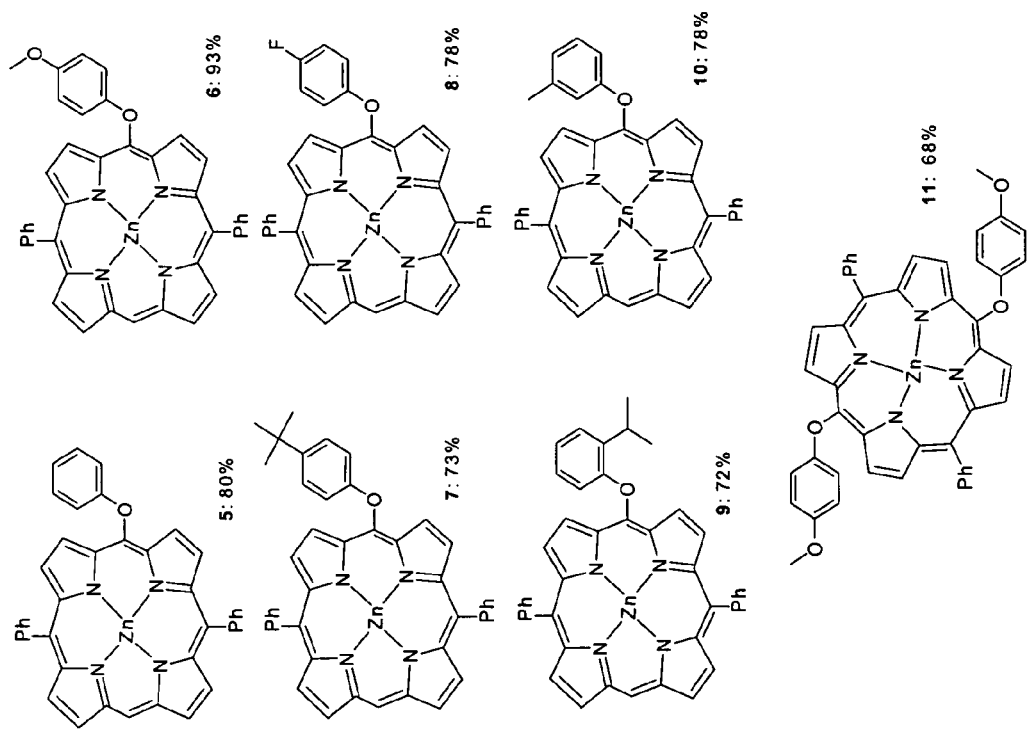
FIG. 7 shows the chemical structures of several heteroatom-substituted phenoxyporphyrin compounds of the presently disclosed subject matter, which compounds are synthesized via the methods described herein.

In some embodiments of the presently disclosed subject matter, monobromo-porphyrin [5-bromo-10,20-diphenylporphyrino]zinc(II) and the dibromoporphyrin [5,15-dibromo-10,20-diphenylporphyrino]zinc(II) can undergo efficient cross-coupling reactions with various phenyls under mild conditions to yield desired phenoxy- and diphenoxy-substituted porphyrins. FIG. 6 illustrates the etheration of monobromo-porphyrin [5-bromo-10,20-diphenylporphyrino]zinc(II) and the dibromoporphyrin [5,15-dibromo-10,20-diphenylporphyrino]zinc(II) using a combination of Pd(OAc)₂ or Pd₂(dba)₃ and a phosphine ligand as the catalyst. FIG. 7 illustrates the chemical structures of a variety of phenoxy- and diphenoxy-substituted porphyrins that are obtained in the practice of the presently disclosed subject matter.

Figure 8:
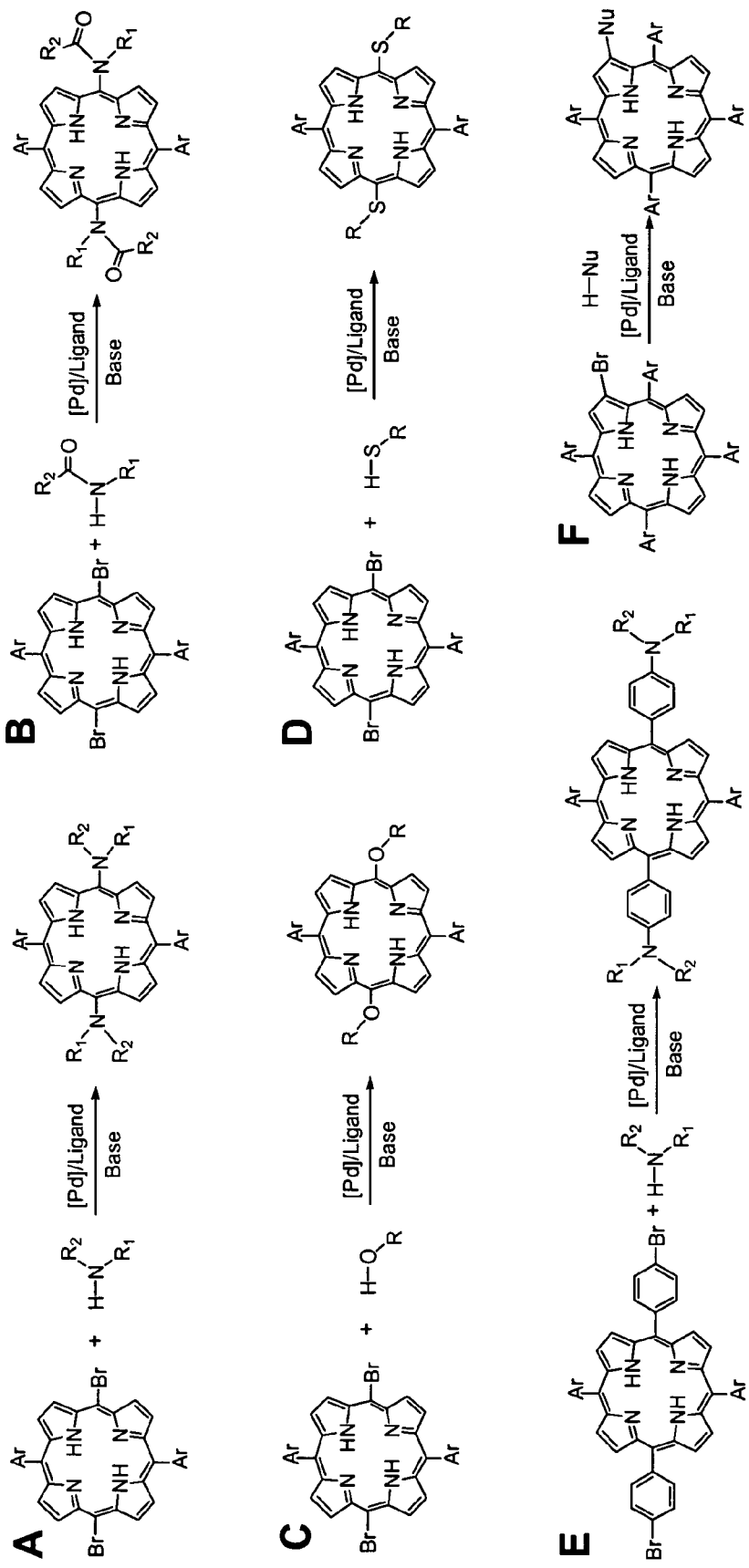
FIG. 8 provides general reaction schemes of the presently disclosed subject matter for the synthesis of heteroatom-substituted porphyrins via palladium-catalyzed cross-coupling reactions.

In summary, and as provided in FIG. 8, the presently disclosed subject matter demonstrates that halogenated porphyrins, e.g., bromoporphyrins, are versatile precursors for the synthesis of heteroatom-functionalized porphyrins via metal-catalyzed carbon-heteroatom cross-coupling reactions with soft, non-organometallic nucleophiles. See also Chen et al., (2003) *J. Org. Chem.* 68: 4432; Gao et al., (2003) *J. Org. Chem.* 68: 6215; Gao et al., (2003) *Org. Lett.* 5: 3261; and Gao et al., (2004) *Org. Lett.* 6: 1837, each of which is incorporated herein by reference in their entirety. As provided herein below, these methods also can be used to synthesize heteroatom chiral porphyrins.

III. Chiral Porphyrins

In some embodiments, the presently disclosed subject matter describes a chiral porphyrin compound having the structure of Formula (I):

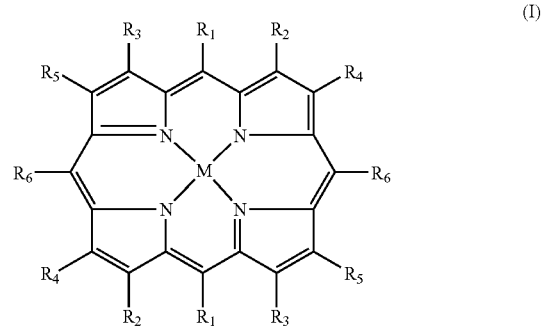

(I)

wherein: M is present or absent and when present is $H_2$ or a transition metal; $R_1$, $R_2$, $R_3$, $R_4$, $R_5$ and $R_6$ are each independently selected from the group consisting of Y, H, alkyl, substituted alkyl, arylalkyl, aryl, and substituted aryl, wherein Y is a heteroatom-containing chiral moiety; and at least one of $R_1$, $R_2$, $R_3$, $R_4$, $R_5$ and $R_6$ comprises Y. Representative chiral porphyrins of the presently disclosed subject matter and methods for preparing the same are provided herein below in Examples 59-148.

In some embodiments, M is present and is selected from the group consisting of $H_2$, Zn, Fe, Ni, Co, Mn, Ru, and Rh. In some embodiments, M is Co.

In some embodiments, Y comprises a heteroatom-containing chiral moiety selected from the group consisting of $NR_7R_8$, $OR_9$, $SR_{10}$, and $BR_{10}$ wherein $R_7$, $R_8$, $R_9$, and $R_{10}$ are each independently selected from the group consisting of H, alkyl, substituted alkyl, arylalkyl, alkoxyl, carboxyl, aryl, and substituted aryl. In some embodiments, Y is a selected from the group consisting of chiral amino, substituted chiral amino, chiral amido, substituted chiral amido, chiral alkoxy, substituted chiral alkoxy, chiral thio, substituted chiral thio, and chiral borate ester moieties. In some embodiments, Y is selected from the group consisting of (±)-estrone; (±)-dihydrocholesterol; R-(±)-1,1'-bi-2-naphthol; (R)-(±)-4-benzyl-2-oxazolidinone; (L)-phenylalanine methyl ester; 1-[1'-(R)-α-methylbenzyl]-aziridine-2(R)-carboxamide; (R)-(−)-2-methoxypropionamide; (S)-(+)-2-methoxypropionamide; (S)-(+)-2,2-dimethylcyclopropanecarboxamide; and L-(R)-lactamide.

In some embodiments, at least one of $R_1$ and $R_6$ is substituted aryl, further wherein at least one sunstituted of the substituted aryl group is a heteroatom-containing chiral moiety Y. In some embodiments, the substituted aryl group has the structure:

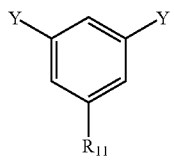

wherein $R_{11}$ is selected from the group consisting of H, alkyl, substituted alkyl, alkoxy, substituted alkoxy, halogen, arylalkyl, aryl, and substituted aryl.

In some embodiments, at least one of $R_1$ and $R_6$ is H. In some embodiments, at least one of $R_1$ and $R_6$ is alkyl. In some embodiments, at least one of $R_1$ and $R_6$ is n-heptyl. In some embodiments, at least one of $R_1$ and $R_6$ is aryl. In some embodiments, at least one of $R_1$ and $R_6$ is phenyl. In some embodiments, at least one of $R_1$ and $R_6$ is substituted aryl. In some embodiments, at least one of $R_1$ and $R_6$ is selected from the group consisting of 2,6-dimethylphenyl, 2,4,6-trimethylphenyl, 3,5-di-tert-butylphenyl, 2,6-dimethoxyphenyl, 3,5-dimethoxyphenyl, 4-t-butylphenyl, 4-acetylphenyl, 4-trifluoromethylphenyl, and pentafluorophenyl. In some embodiments, at least one of $R_1$ and $R_6$ is Y. In some embodiments, each $R_6$ is Y.

IV. Method of Synthesizing a Heteroatom-Substituted Chiral Prophyrin

Based on the methods of synthesizing heteroatom-substituted porphyrins as provided hereinabove and as summarized in FIG. 8, in some embodiments, the presently disclosed subject matter describes the use of haloporphyrins as a new class of synthons for the modular construction of chiral porphyrins via palladium-mediated carbon-heteroatom bond formation reactions with chiral amines, chiral amides, chiral alcohols, and chiral thiols.

Accordingly, in some embodiments, a method of synthesizing a heteroatom-substituted chiral porphyrin compound is disclosed, the method comprising reacting a porphyrin precursor with a chiral reagent comprising a heteroatom, the porphyrin precursor having a structure of Formula II:

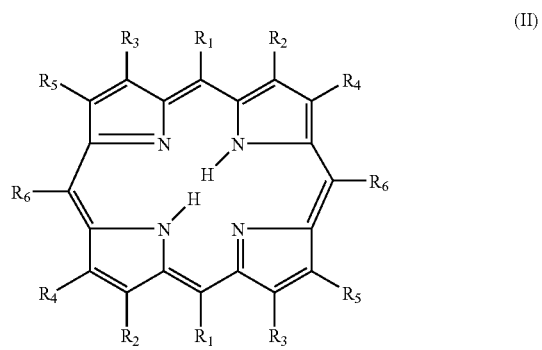

wherein $R_1$, $R_2$, $R_3$, $R_4$, $R_5$ and $R_6$ are each independently selected from the group consisting of X, H, alkyl, substituted alkyl, arylalkyl, aryl, and substituted aryl; X is selected from the group consisting of halogen, trifluoromethanesulfonate (OTf), OTf-substituted aryl, haloaryl and haloalkyl, and at least one of $R_1$, $R_2$, $R_3$, $R_4$, $R_5$ and $R_6$ is X; wherein the chiral reagent comprising a heteroatom has the structure H—Y and Y is a heteroatom-containing chiral moiety comprising at least one of N, O, and S; and wherein the porphyrin precursor and chiral reagent comprising a heteroatom are reacted in the presence of a metal compound, a ligand, and a base to produce a heteroatom-substituted chiral porphyrin.

In some embodiments, X is a halogen selected from the group consisting of Br, Cl, I and F. In some embodiments, X is Br. In some embodiments, at least one meso-position of the porphyrin precursor of Formula II is halogenated. In some embodiments, X is haloaryl. In some embodiments, the haloaryl is 2,6-dibromophenyl.

In some embodiments, the metal compound comprises a metal selected from the group consisting of Pd, Pt, Ni, or Cu. In some embodiments, the metal compound is a metal precursor compound selected from the group consisting of Pd(dba)$_2$, Pd$_2$(dba)$_3$, Pd(OAc)$_2$, PdCl$_2$, Pd(TFA)$_2$, and (CH$_3$CN)$_2$PdCl$_2$. In some embodiments, the base is selected from the group consisting of n-BuLi, LDA, NaNH$_2$, NaOH, Et$_3$N, NaOAc, KOt-Bu, NaOt-Bu, Cs$_2$CO$_3$, K$_2$CO$_3$, and K$_3$PO$_4$.

In some embodiments, the ligand is selected from the group of ligands provided in FIG. 2.

In some embodiments, Y comprises a heteroatom-containing chiral moiety selected from the group consisting of NR$_7$R$_8$, OR$_9$, and SR$_{10}$ wherein R$_7$, R$_8$, R$_9$, and R$_{10}$ are each independently selected from the group consisting of H, alkyl, substituted alkyl, arylalkyl, alkoxyl, carboxyl, aryl, and substituted aryl.

In some embodiments, Y is a selected from the group consisting of chiral amino, substituted chiral amino, chiral amido, substituted chiral amido, chiral alkoxy, substituted chiral alkoxy, chiral thio, and substituted chiral thio moieties. In some embodiments, Y is selected from the group consisting of (+)-estrone; (+)-dihydrocholesterol; R-(+)-1,1'-bi-2-naphthol; (R)-(+)-4-benzyl-2-oxazolidinone; (L)-phenylalanine methyl ester; 1-[1'-(R)-α-methylbenzyl]-aziridine-2(R)-carboxamide; (R)-(−)-2-methoxypropionamide; (S)-(+)-

2-methoxypropionamide; (S)-(+)-2,2-dimethylcyclopropanecarboxamide; and L-(R)-lactamide.

V. Method of Synthesizing a Cyclopropane Compound

Transition metal complex-mediated cyclopropanation of alkenes with diazo compounds as shown in Equation 1 is an efficient and selective method for constructing synthetically and biologically important cyclopropanes.

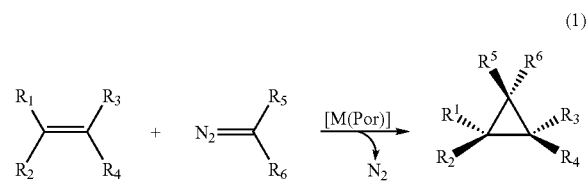
(1)

Among the various catalysts used in cyclopropanation reactions, metalloporphyrins are unique in their unusual selectivity and high catalytic turnover. The family of chiral porphyrins described by the presently disclosed subject matter provides improved metal-based, catalytic systems for cyclopropanation.

Accordingly, in some embodiments, the presently disclosed subject matter discloses a method of synthesizing a cyclopropane compound, the method comprising reacting an alkene with a diazo compound in the presence of a chiral porphyrin metal complex, wherein the chiral porphyrin metal complex has the structure of Formula (I):

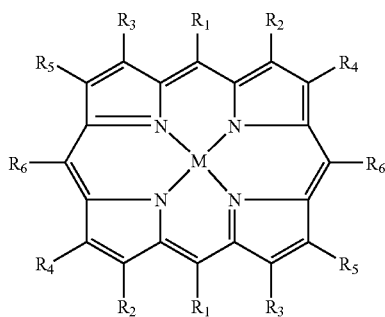
(I)

wherein: M is a transition metal; $R_1$, $R_2$, $R_3$, $R_4$, $R_5$ and $R_6$ are each independently selected from the group consisting of Y, H, alkyl, substituted alkyl, arylalkyl, aryl, and substituted aryl, wherein Y is a heteroatom-containing chiral moiety; and at least one of $R_1$, $R_2$, $R_3$, $R_4$, $R_5$ and $R_6$ comprises Y.

In some embodiments, M is selected from the group consisting of Zn, Fe, Ni, Co, Mn, Ru, and Rh. In some embodiments, M is Co.

In some embodiments, the diazo compound is selected from the group consisting of diazo ethylacetate, diazo-t-butylacetate, 2,6-di-tert-butyl-4-methylphenyl diazoacetate, methyl phenyldiazoacetate, ethyl diazoacetacetate, diethyl diazomalonate, and trimethylsilyldiazomethane. In some embodiments, the diazo compound is selected from one of diazo ethylacetate and diazo t-butylacetate.

In some embodiments, the alkene is selected from the group consisting of aromatic alkene, non-aromatic alkene, di-substituted alkene, tri-substituted alkene, tetra-substituted alkene, cis-alkene, trans-alkene, cyclic-alkene, and non-cyclic alkene. In some embodiments, the alkene is styrene.

In some embodiments, the method comprises an additive. In some embodiments, the additive is selected from the group consisting of 4-dimethylaminopyridine, nitrogen, phosphine, and sulfur coordinating ligands.

In some embodiments, the cyclopropane compound has an enantiomeric purity ranging from about 30% enantiomeric excess to about 99% enantiomeric excess. In some embodiments, the cyclopropane compound has an enantiomeric purity ranging from about 50% enantiomeric excess to about 99% enantiomeric excess. In some embodiments, the cyclopropane compound has an enantiomeric purity ranging from about 80% enantiomeric excess to about 99% enantiomeric excess. In some embodiments, the cyclopropane compound has an enantiomeric purity ranging from about 90% enantiomeric excess to about 99% enantiomeric excess.

VI. Method of Synthesizing an Aziridine Compound

Aziridines are a class of synthetically and biologically important compounds that have found many applications. Among synthetic methodologies, transition metal complex-mediated aziridination represents a direct and powerful approach for the construction of the aziridine rings. An example of a metalloporphyrin mediated aziridination of an alkene is illustrated in Equation 2.

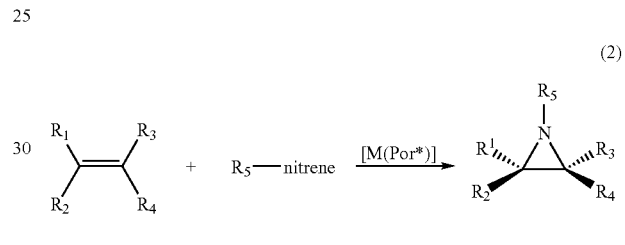
(2)

Accordingly, in some embodiments, the presently disclosed subject matter describes a method of synthesizing an aziridine compound, the method comprising reacting an alkene with a nitrene source in the presence of a chiral porphyrin metal complex, wherein the chiral porphyrin metal complex has the structure of Formula (I):

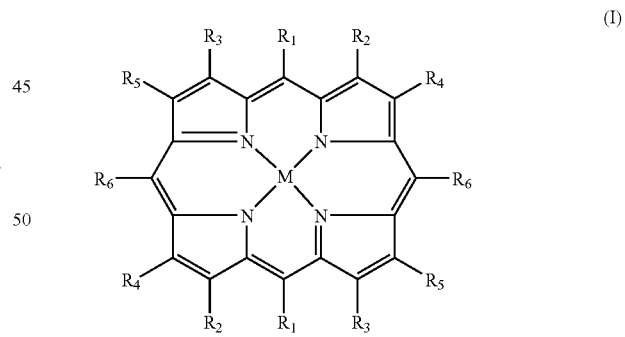
(I)

wherein: M is a transition metal; $R_1$, $R_2$, $R_3$, $R_4$, $R_5$ and $R_6$ are each independently selected from the group consisting of Y, H, alkyl, substituted alkyl, arylalkyl, aryl, and substituted aryl, wherein Y is a heteroatom-containing chiral moiety; and at least one of $R_1$, $R_2$, $R_3$, $R_4$, $R_5$ and $R_6$ comprises Y.

In some embodiments, M is selected from the group consisting of Zn, Fe, Ni, Co, Mn, Ru, and Rh. In some embodiments, M is Co.

In some embodiments, the nitrene source is selected from the group consisting of bromamine-T, a phosphoryl azide, a phosphinyl azide, and a phosphorodiamidic azide. In some embodiments, the nitrene source is bromamine-T. In some embodiments, the nitrene source is diazo diphenylphosphoryl azide.

In some embodiments, the alkene is selected from the group consisting of aromatic alkene, non-aromatic alkene, di-substituted alkene, tri-substituted alkene, tetra-substituted alkene, cis-alkene, trans-alkene, cyclic-alkene, and non-cyclic alkene.

VII. Method of Synthesizing an Epoxide Compound

The chiral porphyrins of the presently disclosed subject matter also can be used as catalysts in asymmetric epoxidation reactions as illustrated in Equation 3.

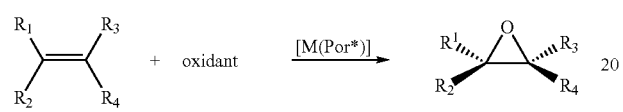

(3)

In some embodiments, the presently disclosed subject matter describes a method of synthesizing an epoxide compound, the method comprising reacting an alkene with a oxidant in the presence of a chiral porphyrin metal complex, wherein the chiral porphyrin metal complex has the structure of Formula (I):

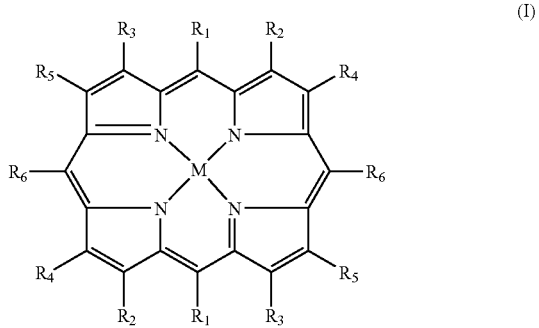

(I)

wherein: M is a transition metal; $R_1$, $R_2$, $R_3$, $R_4$, $R_5$ and $R_6$ are each independently selected from the group consisting of Y, H, alkyl, substituted alkyl, arylalkyl, aryl, and substituted aryl, wherein Y is a heteroatom-containing chiral moiety; and at least one of $R_1$, $R_2$, $R_3$, $R_4$, $R_5$ and $R_6$ comprises Y.

In some embodiments, M is selected from the group consisting of Zn, Fe, Ni, Co, Mn, Ru, and Rh. In some embodiments, M is Co.

In some embodiments, the oxidant is selected from the group consisting of sodium hypochlorite, potassium monopersulfate, hydrogen peroxide, alkylhydroperoxides, m-chloroperbenzoic acid, amines, N-oxides, iodosylbenzene, peroxycarboxylic acids, dioxiranes, hypochlorite, and oxygen. In some embodiments, the oxidant is oxygen.

In some embodiments, the alkene is selected from the group consisting of aromatic alkene, non-aromatic alkene, di-substituted alkene, tri-substituted alkene, tetra-substituted alkene, cis-alkene, trans-alkene, cyclic-alkene, and non-cyclic alkene.

VIII. Chemical Library of Chiral Metalloporphyrins and Methods of Use Thereof In some embodiments, the presently disclosed subject matter describes a chemical library comprising a plurality of chiral metalloporphyrin compounds having the structure of Formula (I):

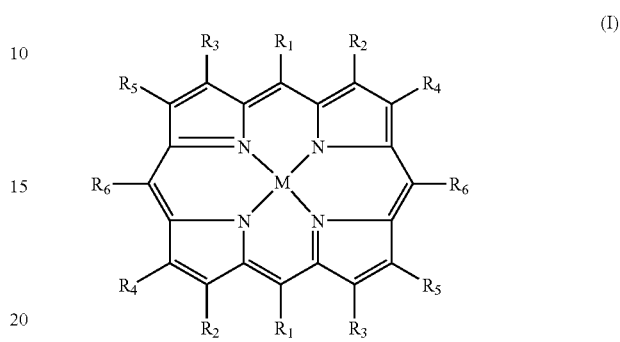

(I)

wherein M is a transition metal; $R_1$, $R_2$, $R_3$, $R_4$, $R_5$ and $R_6$ are each independently selected from the group consisting of Y, H, alkyl, substituted alkyl, arylalkyl, aryl, and substituted aryl, wherein Y is a heteroatom-containing chiral moiety; and at least one of $R_1$, $R_2$, $R_3$, $R_4$, $R_5$ and $R_6$ comprises Y.

In some embodiments, M is selected from the group consisting of Zn, Fe, Ni, Co, Mn, Ru, and Rh. In some embodiments, M is Co.

In some embodiments, the chiral metalloporphyrins are attached to a substrate. In some embodiments, the substrate comprises a microfluidic device.

In some embodiments, the presently disclosed subject matter describes a method of screening a chiral metalloporphyrin for catalytic activity, the method comprising: (a) providing a chemical library comprising a plurality of chiral metalloporphyrin compounds having the structure of Formula (I):

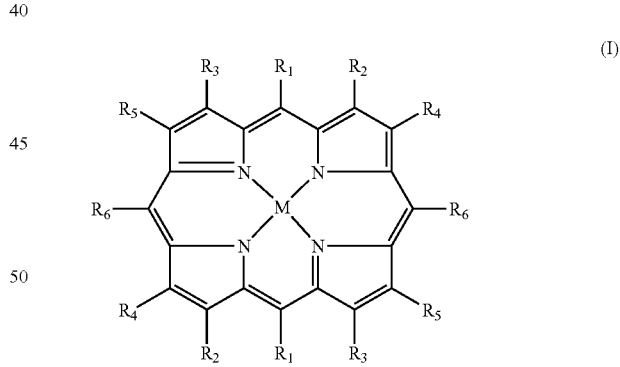

(I)

wherein: M is a transition metal; $R_1$, $R_2$, $R_3$, $R_4$, $R_5$ and $_6$ are each independently selected from the group consisting of Y, H, alkyl, substituted alkyl, arylalkyl, aryl, and substituted aryl, wherein Y is a heteroatom-containing chiral moiety; and at least one of $R_1$, $R_2$, $R_3$, $R_4$, $R_5$ and $R_6$ comprises Y;(b) providing at least one target chemical reagent; (c) contacting the plurality of chiral metalloporphyrins with the target chemical reagent; and (d) detecting an interaction between the plurality of chiral metalloporphyrins and the target chemical reagent, wherein the presence or the absence of the interaction is indicative of the catalytic activity of the chiral metalloporphyrin.

In some embodiments, M is selected from the group consisting of Zn, Fe, Ni, Co, Mn, Ru, and Rh. In some embodiments, M is Co.

EXAMPLES

The following Examples have been included to illustrate modes of the presently disclosed subject matter. Certain aspects of the following Examples are described in terms of techniques and procedures found or contemplated to work well in the practice of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Examples 1-148 relate to methods of the presently disclosed subject matter for the synthesis of porphyrins, metalloporphyrins, chiral porphyrins, and chiral metalloporphyrins.

Example 1

General Considerations

All reactions were carried out under a nitrogen atmosphere in oven-dried glassware using standard Schlenk techniques. Tetrahydrofuran was distilled under nitrogen from sodium benzophenone ketyl. 5-Bromo-10,20-diphenylporphyrine and 5,15-dibromo-10,20-diphenylporphyrine as well as their corresponding zinc complexes [5-bromo-10,20-diphenylporphyrino]zinc(II) and [5,15-dibromo-10,20-diphenylporphyrino]zinc(II) were synthesized by literature methods. Bis(2-diphenylphosphinophenyl)ether (DPEphos), palladium(II) acetate and tris(dibenzylideneacetone) dipalladium(0) were purchased from Strem Chemical Co. Cesium carbonate was obtained as a gift from Chemetall Chemical Products, Inc. Proton and carbon nuclear magnetic resonance spectra ($^1$H NMR and $^{13}$C NMR) were recorded on a Varian Mercury 300 spectrometer and referenced with respect to residual solvent. Infrared spectra were obtained using a Bomen B100 Series FT-IR spectrometer. Samples were prepared as films on a NaCl plate by evaporating THF solutions. UV-Vis spectra were obtained using a Hewlett-Packard 8452A diode array spectrophotometer. High-resolution mass spectroscopy was performed by the Mass Spectrometry Center located in the Chemistry Department of the University of Tennessee on a VG Analytical hybrid high performance ZAB-EQ (B-E-Q geometry) instrument using electron impact (EI) ionization technique with a 70 eV electron beam. Thin layer chromatography was carried out on E. Merck Silica Gel 60 F-254 TLC plates.

Example 2

General Procedures for Amination of Bromoporphyrin

The bromoporphyrin, palladium precursor, phosphine ligand and base were placed in an oven-dried, resealable Schlenk tube. The tube was capped with a Teflon screwcap, evacuated, and backfilled with nitrogen. The screwcap was replaced with a rubber septum, and amine was added via syringe, followed by solvent. The tube was purged with nitrogen for 2 min, and then the septum was replaced with the Teflon screwcap. The tube was sealed, and its contents were heated with stirring until the starting bromoporphyrin had been completely consumed as indicated by TLC analysis. The resulting mixture was cooled to room temperature, taken up in ethyl acetate (60 mL) and transferred to a separatory funnel. The mixture was washed with water (×2), dried over anhydrous sodium sulfate, filtered and concentrated in vacuo. The crude product was then purified.

Example 3

Synthesis Of [5-(N-Phenylamino)-10,20-diphenylporphyrino]zinc(II) (Table 1, Product 3a)

The general procedure was used to couple [5-bromo-10, 20-diphenylporphyrino]zinc(II) (30 mg, 0.050 mmol) with aniline (17 µL, 0.18 mmol), using palladium acetate (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 13 h. The title compound was isolated by flash column chromatography (silica gel, ethyl acetate:hexanes (v)=1:4) as purple solids (29 mg, 95%). $^1$H NMR (300 MHz, THF-d$_8$): δ 10.08 (s, 1H), 9.48 (d, J=4.8 Hz, 2H), 9.31 (s, 1H), 9.29 (d, J=4.8 Hz, 2H), 8.92 (d, J=4.8 Hz, 2H), 8.81 (d, J=4.8 Hz, 2H), 8.22 (m, 4H), 7.75 (m, 6H), 7.04 (t, J=7.2 Hz, 2H), 6.87 (d, J=7.5 Hz, 2H), 6.65 (t, J=7.2 Hz, 1H). $^{13}$C NMR (75 MHz, THF-d$_8$): δ 164.8, 161.0, 160.8, 160.4, 160.2, 154.0, 145.1, 142.4, 141.7, 139.4, 139.2, 137.6, 136.8, 130.3, 130.2, 127.9, 124.6, 115.4. IR (film, cm$^{-1}$): 3383, 3050, 2953, 1599, 1493, 1307, 1061, 996, 793, 748. UV-vis (THF, λ$_{max}$, nm): 422, 554, 602. HRMS-EI ([M]$^+$): calcd for C$_{38}$H$_{25}$N$_5$Zn, 615.1401; found: 615.1382 with an isotope distribution pattern that is same as the calculated one.

Example 4

Synthesis of 5-(N-Phenylamino)-10.20-diphenylporphyrin (Table 1, Product 3b)

The general procedure was used to couple 5-bromo-10,20-diphenylporphyrin (27 mg, 0.05 mmol) with aniline (17 µL, 0.18 mmol), using palladium acetate (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 19 h. The title compound was isolated by flash chromatography (silica gel, ethyl acetate:hexanes (v)=1:4) as red solids (27 mg, 98%). $^1$H NMR (300 MHz, THF-d$_8$): δ 10.14 (s, 1H), 9.44 (d, J=4.8 Hz, 2H), 9.42 (s, 1H), 9.30 (d, J=4.8 Hz, 2H), 8.90 (d, J=4.8 Hz, 2H), 8.77 (d, J=4.8 Hz, 2H), 8.21 (m, 4H), 7.78 (m, 6H), 7.06 (t, J=7.4, 2H), 6.86 (d, J=7.4 Hz, 2H), 6.69 (J=7.4 Hz, 1H), −2.54 (s, 2H). $^{13}$C NMR (75 MHz, THF-d$_8$): δ 154.8, 147.7, 142.7, 135.5, 132.1, 131.9, 131.1, 129.7, 128.5, 127.7, 120.6, 120.1, 119.0, 115.5, 105.1. IR (film, cm$^{-1}$): 3302, 3043, 1599, 1495, 1476, 1338, 1309, 1255, 1064, 973, 958, 797, 748. UV-vis(THF, λ$_{max}$, nm): 412, 512, 582, 660. HRMS-EI ([M]$^+$): calcd for C$_{38}$H$_{27}$N$_5$, 553.2266; found: 553.2274 with an isotope distribution pattern that is same as the calculated one.

Example 5

Synthesis of [5-(N-Methyl-N-phenylamino)-10,20-diphenylporphyrino]zinc(II) (Table 1, Product 4a)

The general procedure was used to couple [5-bromo-10, 20-diphenylporphyrino]zinc(II) (30 mg, 0.050 mmol) with N-methylaniline (20 µL, 0.18 mmol), using palladium acetate (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 13 h. The title compound was isolated by flash column chromatography (silica gel, THF:hexanes (v)=1:8) as purple solids (31 mg, 99%). $^1$H NMR (300 MHz, THF-$d_8$): δ 10.20 (s, 1H), 9.36 (d, J=4.8 Hz, 2H), 9.19 (d, J=4.8 Hz, 2H), 8.97 (d, J=4.8 Hz, 2H), 8.87 (d, J=4.8 Hz, 2H), 8.23 (m, 4H), 7.77 (m, 6H), 7.05 (broad, 2H), 6.69 (broad, 2H), 6.61 (t, J=7.2 Hz, 1H), 4.28 (s, 3H). $^{13}$C NMR (75 MHz, THF-$d_8$): δ 156.0, 152.0, 151.2, 150.9, 150.7, 144.2, 135.5, 133.0, 132.8, 132.4, 130.0, 129.3, 128.1, 127.2, 125.3, 120.8, 116.7, 114.1, 106.9, 45.7. IR (film, cm$^{-1}$): 3054, 3023, 2978, 2876, 2807, 1596, 1498, 1341, 1120, 994, 793, 747. UV-vis (THF, $\lambda_{max}$, nm): 416, 552, 598. HRMS-EI ([M]$^+$): calcd for $C_{39}H_{27}N_5Zn$, 629.1558; found: 629.1549 with an isotope distribution pattern that is same as the calculated one.

Example 6

Synthesis Of
5-(N-Methyl-N-phenylamino)-10,20-diphenylporphyrin
(Table 1, Product 4b)

The general procedure was used to couple 5-bromo-10,20-diphenylporphyrin (54 mg, 0.10 mmol) with N-methylaniline (40 µL, 0.36 mmol), using palladium acetate (1.1 mg, 0.005 mmol) as the palladium precursor, DPEphos (4.0 mg, 0.0075 mmol) as the phosphine ligand and cesium carbonate (45.6 mg, 0.014 mmol) as the base. The reaction was conducted in THF (5 mL) at 68° C. for 16 h. The title compound was isolated by flash column chromatography (silica gel, ethyl acetate:hexanes (v)=1:4) as purple solids (53 mg, 94%). $^1$H NMR (300 MHz, CDCl$_3$): δ 10.18 (s, 1H), 9.30 (d, J=4.8 Hz, 2H), 9.19 (d, J=4.8 Hz, 2H), 9.00 (d, J=4.8 Hz, 2H), 8.90 (d, J=4.8 Hz, 2H), 8.23 (m, 4H), 7.78 (m, 6H), 7.19 (broad, 2H), 6.73 (broad, 3H), 4.26 (s, 3H), −2.82 (s, 2H). $^{13}$C NMR (75 MHz, CDCl$_3$): δ 154.9, 141.6, 134.9, 131.9, 131.7, 131.6, 129.6, 129.1, 128.0, 127.2, 124.2, 119.8, 116.9, 113.9, 105.8, 45.5. IR (film, cm$^{-1}$): 3303, 3055, 3026, 2875, 2810, 1596, 1498, 1351, 1113, 971, 796, 731. UV-vis (CHCl$_3$, $\lambda_{max}$, nm): 410, 512, 548, 592. HRMS-EI ([M]$^+$): $C_{39}H_{29}N_5$, 567.2423; found: 567.2419 with an isotope distribution pattern that is same as the calculated one.

Example 7

Synthesis of [5-Benzophenoeimino-10,20-diphenylporphyrino]zinc(II) (Table 1, Product 5a)

The general procedure was used to couple [5-bromo-10,20-diphenylporphyrino]zinc(II) (30 mg, 0.050 mmol) with benzophenone imine (31 µL, 0.18 mmol), using palladium acetate (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 22 h. The title compound was isolated by flash column chromatography (silica gel, ethyl acetate:hexanes (v)=1:4) as purple solids (33 mg, 94%). $^1$H NMR (300 MHz, THF-$d_8$): δ 9.80 (s, 1H), 9.23 (d, J=4.8 Hz, 2H), 9.13 (d, J=4.8 Hz, 2H), 8.79 (d, J=4.8 Hz, 2H), 8.71 (d, J=4.8 Hz, 2H), 8.19 (broad, 6H), 7.73 (m, 6H), 7.66 (broad, 3H), 7.36 (broad, 2H), 6.65 (broad, 3H). $^{13}$C NMR (75 MHz, THF-$d_8$): δ 170.8, 152.0, 150.3, 149.9, 144.5, 142.5, 135, 4, 133.0, 131.6, 131.1, 130.9, 130.0, 129.4, 128.8, 127.9, 127.2, 120.6, 103.7. IR (film, cm$^{-1}$): 3056, 3023, 2962, 1618, 1596, 1578, 1490, 1439, 1124, 1061, 994, 794. UV-vis (THF, $\lambda_{max}$, nm): 428, 562, 610. HRMS-EI ([M]$^+$): calcd for $C_{45}H_{29}N_5Zn$, 703.1714; found: 703.1699 with an isotope distribution pattern that is same as the calculated one.

Example 8

Synthesis of
5-Benzophenoeimino-10,20-diphenylporphyrin
(Table 1, Product 5b)

The general procedure was used to couple 5-bromo-10,20-diphenylporphyrin (27 mg, 0.05 mmol) with benzophenone imine (31 µL, 0.18 mmol), using palladium acetace (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 24 h. The title compound was isolated by flash column chromatography (silica gel, ethyl acetate:hexanes (v)=1:8) as purple solids (27 mg, 84%). $^1$H NMR (300 MHz, CDCl$_3$): δ 9.78 (s, 1H), 9.23 (d, J=4.8 Hz, 2H), 9.08 (d, J=4.8 Hz, 2H), 8.85 (d, J=4.8 Hz, 2H), 8.75 (d, J=4.8 Hz, 2H), 8.26 (broad, 6H), 7.76 (broad, 9H), 7.18 (broad, 2H), 6.61 (broad, 3H), −2.34 (s, 2H). $^{13}$C NMR (75 MHz, CDCl$_3$): δ 171.6, 146.0, 141.7, 134.6, 133.6, 131.6, 130.7, 129.8, 127.9, 127.5, 126.8, 119.4, 102.4. IR (film, cm$^{-1}$): 3306, 3057, 3026, 1808, 1616, 1595, 1576, 1476, 1442, 1405, 1316, 1241, 1097, 976, 954, 845, 797, 745. UV-vis (CHCl$_3$, $\lambda_{max}$, nm): 424, 526, 564, 604, 658. HRMS-EI ([M]$^+$): calcd for $C_{45}H_{31}N_5$, 641.2579; found: 641.2591 with an isotope distribution pattern that is same as the calculated one.

Example 9

Synthesis of [5-(N-Diphenylamino)-10,20-diphenylporphyrino]zinc(II) (Table 1, Product 6a)

The general procedure was used to couple [5-bromo-10,20-diphenylporphyrino]zinc(II) (30 mg, 0.05 mmol) with diphenylamine (0.031 g, 0.18 mmol), using palladium acetate (1.1 mg, 0.005 mmol) as the palladium precursor, DPEphos (4.0 mg, 0.0075 mmol) as the phosphine ligand and sodium tert-butoxide (13.5 mg, 0.14 mmol) as the base. The reaction was conducted in THF (5 mL) at 68° C. for 25 h. The title compound was isolated by flash column chromatography (silica gel, THF: hexanes (v)=1:6) as purple solids (21 mg, 61%). $^1$H NMR (300 MHz, THF-$d_8$): δ 10.17 (s, 1H), 9.33 (m, 4H), 8.93 (d, J=4.8 Hz, 2H), 8.80 (d, J=4.8 Hz, 2H), 8.20 (m, 4H), 7.75 (m, 6H), 7.33 (m, 8H), 7.12 (t, J=7.8 Hz, 8H), 6.80 (t, J=7.2 Hz, 4H). $^{13}$C NMR (75 MHz, CDCl$_3$): δ 153.7, 153.0, 151.3, 151.0, 150.1, 144.1, 135.4, 133.3, 132.8, 132.4, 130.9, 129.8, 129.6, 128.1, 127.2, 122.9, 121.1, 120.9, 107.0. IR (film, cm$^{-1}$): 3055, 2961, 2361, 1598, 1587, 1490, 1293, 1273, 1062, 1003, 994, 794, 752. UV-vis (THF, $\lambda_{max}$, nm): 412, 558, 604. HRMS-EI ([M]$^+$): calcd for $C_{44}H_{29}N_5Zn$, 691.1714; found: 691.1712 with an isotope distribution pattern that is same as the calculated one.

Example 10

Synthesis of
5-(N-Diphenylamino)-10,20-diphenylporphyrin
(Table 1, Product 6b)

The general procedure was used to couple 5-bromo-10,20-diphenylporphyrin (54 mg, 0.1 mmol) with diphenylamine (0.061 g, 0.36 mmol), using palladium acetate (1.1 mg, 0.005 mmol) as the palladium precursor, DPEphos (4.0 mg, 0.0075 mmol) as the phosphine ligand and cesium carbonate (45.6 mg, 0.014 mmol) as the base. The reaction was conducted in THF (5 mL) at 68° C. for 40 h. The title compound was isolated by flash column chromatography (silica gel, THF: hexanes (v)=1:8) as purple solids (41 mg, 66%). $^1$H NMR (300 MHz, CDCl$_3$): δ 10.13 (s, 1H), 9.33 (d, J=4.8 Hz, 2H), 9.26 (d, J=4.8 Hz, 2H), 8.96 (d, J=4.8 Hz, 2H), 8.83 (d, J=4.8 Hz, 2H), 8.20 (m, 4H), 7.76 (m, 6H), 7.35 (m, 4H), 7.20 (t, J=7.2 Hz, 4H), 6.89 (t, J=7.2 Hz, 2H), −2.69 (s, 2H). $^{13}$C NMR (75 MHz, CDCl$_3$): δ 152.5, 141.3, 134.8, 134.6, 132.0, 131.4, 130.1, 129.1, 127.8, 126.8, 122.3, 120.8, 119.6, 105.6. IR (film, cm$^{-1}$): 3307, 3055, 3029, 1591, 1491, 1342, 1184, 973, 796, 750, 731, 695. UV-vis (CHCl$_3$, λ$_{max}$, nm): 407, 523, 577, 656. HRMS-EI ([M]$^+$): calcd for C$_{44}$H$_{31}$N$_5$, 629.2579; found: 629.2576 with an isotope distribution pattern that is same as the calculated one.

Example 11

Synthesis of [5-(N-Hexylamino)-10,20-diphenylporphyrino]zinc(I) (Table 1, Product 7a)

The general procedure was used to couple [5-bromo-10,20-diphenylporphyrino]zinc(II) (30 mg, 0.05 mmol) with hexylamine (0.024 mL, 0.18 mmol), using palladium acetate (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 50 h. The title compound was isolated by flash column chromatography (silica gel, THF: hexanes (v)=1:8) as purple solids (25 mg, 80%). $^1$H NMR (300 MHz, THF-d$_8$): δ 9.63 (s, 1H), 9.43 (d, J=4.8 Hz, 2H), 9.05 (d, J=4.8 Hz, 2H), 8.76 (d, J=4.8 Hz, 2H), 8,65 (d, J=4.8 Hz, 2H), 8.18 (m, 4H), 7.75 (m, 6H), 7.33 (m, 8H), 6.78 (s, 1H), 4.38 (m, 2H), 2.04 (m, 2H), 1.58 (m, 2H), 1.37 (m, 4H), 0.87 (t, J=7.2 Hz, 3H). $^{13}$C NMR (75 MHz, THF-d$_8$): δ 152.7, 149.9, 149.5, 147.0, 144.7, 135.3, 133.0, 131.4, 130.2, 127.8, 127.2, 126.9, 120.5, 102.4, 60.2, 32.8, 32.5, 28.0, 23.5, 14.4. IR (film, cm$^{-1}$): 3330, 3053, 2954, 2925, 2854, 1584, 1542, 1489, 1440, 1213, 1062, 1010, 1002, 992, 836, 789, 780, 750. UV-vis (THF, λ$_{max}$, nm): 428, 606. HRMS-EI ([M]$^+$): calcd for C$_{38}$H$_{33}$N$_5$Zn, 623.2027; found: 623.2009 with an isotope distribution pattern that is same as the calculated one.

Example 12

Synthesis of [5.15-Bis(N-phenylamino)-10,20-diphenylporphyrino]zinc(II) (Table 1, Product 8a)

The general procedure was used to couple [5,15-dibromo-10,20-diphenylporphyrino]zinc(II) (34 mg, 0.050 mmol) with aniline (22 μL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 13 h. The title compound was isolated by flash column chromatography (silica gel, THF:hexanes (v)=1:4) as purple solids (29 mg, 82%). $^1$H NMR (300 MHz, THF-d$_8$): δ 9.36 (d, J=4.8 Hz, 4H), 9.17 (s, 2H), 8.69 (d, J=4.8 Hz, 4H), 8.16 (m, 4H), 7.72 (m, 6H), 7.03 (t, J=6.9, 7.2 Hz, 4H), 6.84 (d, J=8.4 Hz, 4H), 6.64 (t, J=7.2 Hz, 2H). $^{13}$C NMR (75 MHz, THF-d$_8$): δ 155.1, 152.0, 150.5, 144.4, 135.3, 132.2, 129.7, 129.6, 128.0, 127.2, 121.0, 119.9, 118.2, 115.0. IR (film, cm$^{-1}$): 3380, 3047, 3020, 2953, 1599, 1492, 1339, 1308, 1063, 1003, 795, 747. UV-vis (THF, μ$_{max}$, nm): 440, 564, 620. HRMS-EI ([M]$^+$): calcd for C$_{44}$H$_{30}$N$_6$Zn, 706.1823; found: 706.1840 with an isotope distribution pattern that is same as the calculated one.

Example 13

Synthesis of 5,15-Bis(N-phenylamino)-10,20-diphenylporphyrin (Table 1, Product 8b)

The general procedure was used to couple 5,15-dibromo-10,20-diphenylporphyrin (31 mg, 0.05 mmol) with aniline (22 μL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 20 h. The title compound was isolated by flash column chromatography (silica gel, ethyl acetate:hexanes (v)=1:4) as purple solids (21 mg, 65%). $^1$H NMR (300 MHz, THF-d$_8$): δ 9.32 (d, J=4.8 Hz, 4H), 9.29 (s, 2H), 8.65 (d, J=4.8 Hz, 4H), 8.17 (m, 4H), 7.75 (m, 6H), 7.07 (t, J=8.1 Hz, 4H), 6.86 (d, J=8.1 Hz, 4H), 6.69 (t, J=7.4 Hz, 2H), −2.03 (s, 2H). $^{13}$C NMR (75 MHz, THF-d$_8$): δ 154.5, 142.9, 137.1, 135.3, 129.7, 128.5, 127.6, 120.5, 119.7, 118.9, 115.4. IR (film, cm$^{-1}$): 3307, 1599, 1496, 1474, 1340, 1306, 1258, 1071, 974, 797, 732. UV-vis (THF, λ$_{max}$, nm): 438, 526, 592, 680. HRMS-EI ([M]$^+$): calcd for C$_{44}$H$_{32}$N$_6$, 644.2688; found: 644.2704 with an isotope distribution pattern that is same as the calculated one.

Example 14

Synthesis of [5,15-Bis(N-methyl-N-phenylamino)-10,20-diphenylporphyrino]zinc(II) (Table 1, Product 9a)

The general procedure was used to couple [5,15-dibromo-10,20-diphenylporphyrino]zinc(II) (34 mg, 0.050 mmol) with N-methylaniline (26 μL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 17 h. The title compound was isolated by flash column chromatography (silica gel, THF:hexanes (v)=1:8) as purple solids (30 mg, 82%). $^1$H NMR (300 MHz, THF-d$_8$): δ 9.10 (d, J=4.8 Hz, 4H), 8.75 (d, J=4.8 Hz, 4H), 8.15 (m, 4H), 7.73 (m, 6H), 7.04 (broad, 4H), 6.69 (broad, 4H), 6.59 (t, J=7.2 Hz, 2H), 4.25 (s, 6H). $^{13}$C NMR (75 MHz, THF-d$_8$): δ 155.8, 152.4, 150.9, 144.0, 135.2, 133.1, 130.1, 129.3, 128.2, 127.2, 125.7, 121.2, 116.8, 114.2, 45.6. IR (film, cm$^{-1}$): 3054, 2985, 2883, 2807, 1597, 1496, 1346, 1118, 1000, 796, 747. UV-vis (THF, λ$_{max}$, nm): 422, 562, 608. HRMS-EI ([M]$^+$): calcd for C$_{46}$H$_{34}$N$_6$Zn, 734.2136; found: 734.2128 with an isotope distribution pattern that is same as the calculated one.

Example 15

Synthesis of 5,15-Bis(N-methyl-N-phenylamino)-10.20-diphenylporphyrin (Table 1, Product 9b)

The general procedure was used to couple 5,15-dibromo-10,20-diphenylporphyrin (31 mg, 0.05 mmol) with N-methylaniline (26 μL, 0.24 mmol), using palladium acetate (1.1 mg, 0.0050 mmol) as the palladium precursor, DPEphos (4.0 mg, 0.0075 mmol) as the phosphine ligand and the cesium carbonate (45.6 mg, 0.14 mmol) as the base. The reaction was conducted in THF (5 mL) at 68° C. for 15 h. The title compound was isolated by flash column chromatography (silica gel, ethyl acetate:hexanes (v)=1:4) as red solids (24 mg, 71%). $^1$H NMR (300 MHz, CDCl$_3$): δ 9.08 (d, J=4.8 Hz, 4H), 8.77 (d, J=4.8 Hz, 4H), 8.16 (m, 4H), 7.72 (m, 6H), 7.14 (m, 4H), 6.72 (m, 6H), 4.23 (s, 6H), −2.54 (s, 2H). $^{13}$C NMR (75 MHz, CDCl$_3$): δ 154.4, 141.3, 134.5, 131.9, 128.9, 128, 127.8, 126.8, 124.3, 119.9, 116.7, 113.8, 45.1. IR (film, cm$^{-1}$): 3315, 3026, 2359, 1596, 1498, 1475, 1354, 1114, 972, 798. UV-vis (CHCl$_3$, λ$_{max}$, nm): 412, 522, 562, 596, 608. HRMS-EI ([M]$^+$): calcd for C$_{46}$H$_{36}$N$_6$, 672.3001; found: 672.3003 with an isotope distribution pattern that is same as the calculated one.

Example 16

Synthesis of [5,15-Bis(benzophenoeimino)-10,20-diphenylporphyrino]zinc(II) (Table 1, Product 10a)

The general procedure was used to couple [5,15-dibromo-10,20-diphenylporphyrino]zinc(II) (34 mg, 0.050 mmol) with benzophenoe imine (41 µL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 16 h. The title compound was isolated by flash column chromatography (silica gel, ethyl acetate:hexanes (v)=1:4) as purple solids (37 mg, 84%). $^1$H NMR (300 MHz, CDCl$_3$): δ 9.06 (d, J=4.8 Hz, 4H), 8.57 (d, J=4.8 Hz, 4H), 8.19 (m, 4H), 8.07 (m, 4H), 7.68 (m, 6H), 7.61 (m, 6H), 7.33 (m, 4H), 6.62 (m, 6H). $^{13}$C NMR (75 MHz, CDCl$_3$): δ 170.8, 149.4, 144.7, 143.8, 135.4, 135.2, 132.7, 131.9, 131.5, 130.8, 129.9, 129.3, 128.4, 128.0, 127.7, 127.2, 127.1, 126.9, 120.9. IR (film, cm$^{-1}$): 3054, 3027, 2976, 1618, 1597, 1485, 1442, 1338, 1212, 1118, 1004, 793, 753. UV-vis (THF, λ$_{max}$, nm): 438, 652. HRMS-EI ([M]$^+$): calcd for C$_{58}$H$_{38}$N$_6$Zn, 882.2449, found: 882.2464 with an isotope distribution pattern that is same as the calculated one.

Example 17

Synthesis of 5,15-Bis(benzophenoeimino)-10,20-diphenylporphyrin (Table 1, Product 1b)

The general procedure was used to couple 5,15-dibromo-10,20-diphenylporphyrin (31 mg, 0.05 mmol) with benzophenoe imine (41 µL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 15 h. The title compound was isolated by flash column chromatography (silica gel, ethyl acetate:hexanes (v)=1:4) as purple solids (39 mg, 95%). $^1$H NMR(300 MHz, THF-d$_8$): δ 9.09 (d, J=4.8 Hz, 4H), 8.57 (d, J=4.8 Hz, 4H), 8.10 (m, 8H), 7.64 (m, 12H), 7.23 (broad, 4H), 6.62 (broad, 6H), −1.87 (s, 2H). $^{13}$C NMR (75 MHz, THF-d$_8$): δ 172.3, 143.2, 140.8, 137.9, 135.4, 135.1, 132.1, 131.0, 129.3, 128.9, 128.3, 128.2, 127.5, 120.3, 108.4. IR (film, cm$^{-1}$) 3316, 3056, 3022, 1614, 1596, 1575, 1465, 1443, 1351, 1316, 1278, 1244, 1105, 1066, 976, 950, 798, 725. UV-vis (THF, λ$_{max}$, nm): 434, 592, 700. HRMS-EI ([M]$^+$): calcd for C$_{58}$H$_{40}$N$_6$, 820.3314; found: 820.3308 with an isotope distribution pattern that is same as the calculated one.

Example 18

Synthesis of [5,15-Bis(N-diphenylamino)-10,20-diphenylporphyrino]zinc(II) (Table 1, Product 11a)

The general procedure was used to couple [5,15-dibromo-10,20-diphenylporphyrino]zinc(II) (34 mg, 0.05 mmol) with diphenylamine (0.041 g, 0.24 mmol), using palladium acetate (1.1 mg, 0.0050 mmol) as the palladium precursor, DPEphos (4.0 mg, 0.0075 mmol) as the phosphine ligand and sodium tert-butoxide (13.5 mg, 0.14 mmol) as the base. The reaction was conducted in THF (5 mL) at 68° C. for 50 h. The title compound was isolated by flash column chromatography (silica gel, THF: hexanes (v)=1:6) as purple solids (13 mg, 30%). $^1$H NMR (300 MHz, CDCl$_3$): δ 9.25 (d, J=4.8 Hz, 4H), 8.75 (d, J=4.8 Hz, 4H), 8.09 (m, 4H), 7.66 (m, 6H), 7.29 (m, 8H), 7.15 (t, J=7.8 Hz, 8H), 6.85 (t, J=7.4 Hz, 4H). $^{13}$C NMR (75 MHz, CDCl$_3$): δ 152.6, 152.3, 149.7, 142.1, 134.3, 133.3, 130.5, 129.1, 127.6, 126.5, 122.8, 122.1, 121.0, 120.7. IR (film, cm$^{-1}$): 3056, 2360, 1595, 1590, 1490, 1341, 1294, 1249, 1002, 794, 750. UV-vis (CHCl$_3$, λ$_{max}$, nm): 406, 460, 572, 628. HRMS-EI ([M]$^+$): calcd for C$_{56}$H$_{38}$N$_6$Zn, 858.2449; found: 858.2436 with an isotope distribution pattern that is same as the calculated one.

Example 19

Synthesis of [5,15-Bis(N-4-trifluoromethylphenylamino)-10,20-diphenylporphyrino]zinc(II) (Table 1, Product 12a)

The general procedure was used to couple [5,15-dibromo-10,20-diphenylporphyrino]zinc(II) (34 mg, 0.05 mmol) with 4-trifluoromethyllaniline (0.030 mL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 17 h. The title compound was isolated by flash column chromatography (silica gel, ethyl acetate:hexanes (v)=1:2) as purple solids (38 mg, 90%). $^1$H NMR (300 MHz, THF-d$_8$): δ 9.84 (s, 2H), 9.43 (d, J=4.8 Hz, 4H), 8.84 (d, J=4.8 Hz, 4H), 8.22(m, 4H), 7.78 (m, 6H), 7.41 (d, J=8.2 Hz, 4H), 6.93 (d, J=8.2 Hz, 4H). $^{13}$C NMR (75 MHz, THF-d$_8$): δ 157.5, 151.7, 151.0, 144.1, 135.4, 132.9, 129.7, 128.2, 127.3, 127.2, 127.1, 121.6, 119.3, 118.1, 114.1. IR (film, cm$^{-1}$): 3376, 1614, 1522, 1322, 1110, 1065, 1003, 828, 797. UV-vis (THF, λ$_{max}$, mm): 435, 562, 612. HRMS-EI ([M]$^+$): calcd for C$_{46}$H$_{28}$N$_6$F$_6$Zn, 842.1571; found: 842.1590 with an isotope distribution pattern that is same as the calculated one.

Example 20

[5,15-Bis(N-4-methoxyphenylamino)-10,20-diphenylporphyrino]zinc(II) (Table 1, Product 13a)

The general procedure was used to couple [5,15-dibromo-10,20-diphenylporphyrino]zinc(II) (34 mg, 0.05 mmol) with p-anisidine (30 mg, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 16 h. The title compound was isolated by flash column chromatography (silica gel, ethyl acetate:hexanes (v)=1:3 as purple solids (36 g, 94%). $^1$H NMR (300 MHz, THF-d$_8$): δ 9.34 (d, J=4.8 Hz, 4H), 8.88 (s, 2H), 8.66 (d, J=4.8 Hz, 4H), 8.17 (m, 4H), 7.73

(m, 6H), 6.87 (d, J=9.0 Hz, 4H), 6.69 (d, J=9.0 Hz, 4H), 3.65 (s, 6H). $^{13}$C NMR (75 MHz, THF-d$_8$): δ 153.5, 151.9, 150.2, 149.6, 144.6, 135.3, 131.9, 129.3, 127.8, 127.1, 121.2, 120.7, 116.6, 115.0, 55.6. IR (film, cm$^{-1}$): 3372, 1597, 1507, 1489, 1339, 1234, 1036, 1002, 797. UV-vis (THF, $\lambda_{max}$, nm): 447, 571, 629.

Example 21

Synthesis of [5,15-Bis(N-3.5-di-tert-butylphenylamino)-10,20-diphenylporphyrino]zinc(II) (Table 1, Product 14a)

The general procedure was used to couple [5,15-dibromo-10,20-diphenylporphyrino]zinc(II) (34 mg, 0.05 mmol) with 3,5-di-tert-butylaniline (0.050 g, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 62 h. The title compound was isolated by flash column chromatography (silica gel, ethyl acetate:hexanes (v)=1:4) as purple solids (44 mg, 95%). $^1$H NMR (300 MHz, CDCl$_3$): δ 9.28 (d, J=4.8 Hz, 4H), 8.68 (d, J=4.8 Hz, 4H), 8.14 (m, 4H), 7.71 (m, 8H), 6.87 (m, 6H), 1.21 (s, 36H). $^{13}$C NMR (75 MHz, CDCl$_3$): δ 152.1, 151.5, 150.6, 149.4, 143.0, 134.8, 131.7, 128.5, 127.1, 126.4, 120.4, 118.8, 113.4, 109.6, 34.7, 31.3. IR (film, cm$^{-1}$): 3383, 3055, 2961, 2902, 2867, 1595, 1488, 1436, 1340, 1064, 1004, 796. UV-vis (THF, $\lambda_{max}$, nm): 448, 576, 634. HRMS-EI ([M]$^+$): calcd for C$_{60}$H$_{62}$N$_6$Zn, 930.4327; found: 930.4354 with an isotope distribution pattern that is same as the calculated one.

Examples 22 through 47 relate to methods of synthesizing aminophenylporphyrins, and novel aminophenylporphyrins, according to the presently disclosed subject matter. In Example 22-47, ligands referred to by number refer to the numbered ligands shown in FIG. 2.

Example 22

General Considerations

All reactions were carried out under a nitrogen atmosphere in oven-dried Schlenk tube. All amines were purchased from Acros Organics or Aldrich Chemical Co. and used without further purification. Tetrahydrofuran and toluene were continuously refluxed and freshly distilled from sodium benzophenone ketyl under nitrogen. Sodium tert-butoxide was purchased from Aldrich Chemical Co.; Cesium carbonate was obtained as a gift from Chemetall Chemical Products, Inc.

Potassium phosphate, potassium carbonate, palladium(II) acetate, tris(dibenzylideneacetone)dipalladium(0), 2-(di-t-butylphosphino)biphenyl (FIG. 2, Ligand 1), 2-(dicyclohexylphosphino)biphenyl (FIG. 2, Ligand 2), 2-dicyclohexylphosphino-2'-(N,N-di-methylamino)biphenyl (FIG. 2, Ligand 4), bis(2-diphenylphosphinophenyl)ether (DPEphos, FIG. 2, Ligand 6), Xantphos (FIG. 2, Ligand 7), racemic-2-(di-t-butylphosphino)-1,1'-binaphthyl (FIG. 2, Ligand 8), (i)BINAP (FIG. 2, Ligand 9), dichloro[1,1'-bis(diphenylphosphino)ferrocene]palladium(II) dichloride ((dppf)PdCl$_2$, FIG. 2, Ligand 0.10) and 1,3-bis(2,6-di-1-propylphenyl)imidazolium chloride (FIG. 2, Ligand 11) were purchased from Strem Chemical Co.; 2-(dicyclohexylphosphino)-2'6'dimethyl-biphenyl (FIG. 2, Ligand 3) and the ligand shown in FIG. 2 as Ligand 5 were synthesized according to literature methods. All ligands and palladium precursors and bases were stored in desiccators filled with anhydrous calcium sulfate, and weighed in the air. 5,15-di-p-bromophenylporphyrin as well as its zinc complex, and tetrakis-p-bromophenylporphyrin were prepared according to the method described in literatures. $^1$H NMR and $^{13}$C NMR were recorded on Varian Mercury 300 spectrometer with TMS as an internal standard. UV-Vis spectra were measured on Hewlett-Packard 8452 diode array spectrometer. High resolution mass spectroscopy was determined on a VG analytical hybrid high performance ZAB-EQ(B-E-Q geometry) instrument by the Mass Spectrometry Center (Department of Chemistry, University of Tennessee). All solvents were supplied by Fisher Scientific, Inc. with HPLC grade and used as received. Thin layer chromatography was performed on Silica Gel 60F-254 precasted aluminum TLC plate.

Example 23

General Procedures for Amination of Bromophenylporphyrin

An oven-dried Schlenk tube equipped with stirring bar was degassed on vacuum line and purged with nitrogen. The tube was charged with Pd(OAc)$_2$ or Pd$_2$(dba)$_3$ (5 mole %), phosphine ligand (10 mole %), bromophenylporphyrin or zinc complex (0.05 mmole), base (NaOtBu or Cs$_2$CO$_3$, 4.0 equiv for 1.0 equiv Br) and solid amine, if any. The tube was capped with a Teflon screw cap, evacuated on vacuum line for 40-50 min and backfilled with nitrogen. The Teflon screw cap was then replaced with a rubber septum, 2-3 mL of freshly redistilled and dried solvent, and amine (4.0 equiv for 1.0 equiv Br) was added via syringe successively. Additional 2-3 mL of solvent was added against the wall of the tube to wash down the possible reactants on the wall. The tube was purged with nitrogen for 1-2 min, and the septum was then replaced by Teflon screw cap. The tube was tightly sealed and immersed in a 100° C. oil bath. The reaction was preceded under this condition with stirring for 48 h (72 h for tetra-bromophenylporphyrin), and cooled to room temperature. The aliquot of the solution was detected on TLC (methylene chloride:hexanes=8:2 or ethyl acetate:hexanes=5:5) to monitor the result.

Example 24

General Workup Procedures for Amination of Bromophenylporphyrin

The reaction solution was transferred with a long glass pipet to a small round-bottom flask, the residue was washed with acetone or chloroform and pooled to the flask as well. The solution was concentrated on rotavapor to remove the solvent. The residue was redissolved in ethyl acetate and transferred to a separatory funnel, washed with deioned water three times to remove the base and salts. The organic layer was concentrated on rotavapor to dryness. The residue was dissolved in minimal acetone (or methylene chloride, or THF), and small amount of hexanes was added to recrystallize the product. The product gradually precipitated or crystallized from the solution, filtered on funnel, washed with small amount of hexanes to afford the pure product (purity 98-99%). Extra pure compound can be obtained through flash chromatography on silica gel column. (methylene chloride:hexanes (8:2 to 10:0) as elute).

Example 25

Synthesis of 5,15-di-p-(N-phenylamino)phenylporphyrin (Table 2, entry 1, A)

The general procedure using 5,15-di-p-bromophenylporphyrin (31.0 mg, 0.05 mmol), Pd(OAc)$_2$ (1.12 mg, 0.005 mmol), (±) BINAP (6.2 mg, 0.01 mmol, 9), Cs$_2$CO$_3$ (130.33 mg, 0.4 mmol), aniline (36.5 μL, 0.4 mmol) and toluene, the reaction proceeded at 100° C. for 48 h. After workup with general procedure, the title compound was obtained as dark-purple solid (22.6 mg, 70%). $^1$H NMR (CDCl$_3$, 300 MHz) δ 10.29 (s, meso-2H), 9.39 (d, J=4.5 Hz, β-4H), 9.17 (d, J=4.8 Hz, β-4H), 8.14 (d, J=8.7 Hz, 4H), 7.50 (d, J=8.4 Hz, 4H), 7.38-7.46 (m, 8H), 7.06 (m, 2H), 6.13 (s, 2H), −3.05 (s, 2H). $^{13}$C NMR (CDCl$_3$, 75 MHz) δ 142.9, 142.6, 135.9, 131.5, 131.0, 129.6, 121.6, 118.6, 115.7, 105.1. UV-vis (μ$_{max}$, nm) 421, 508, 548, 580, 637. HRMS-EI ([M+1]$^+$): calc'd for C$_{44}$H$_{33}$N$_6$, 645.2767; found 645.2734.

Example 26

Synthesis of 5,15-di-p-(N-phenylamino)phenylporphyrin (Zn II) (Table 2, entry 1, B)

The reactants were as the same as entry 1 A except 5,15-di-p-bromophenylporphyrin was replaced by its zinc complex (34.5 mg, 0.05 mmol). After workup with general procedure, the title compound was obtained as brown solid (23.5 mg, 66%). $^1$H NMR (CDCl$_3$, 300 MHz) δ 10.31 (s, meso-2H), 9.45 (d, J=4.2 Hz, β-4H), 9.24 (d, J=4.5 Hz, β-4H), 8.14 (d, J=8.1 Hz, 4H), 7.50 (d, J=8.4 Hz, 4H), 7.40-7.47 (m, 8H), 7.06 (m, 2H), 6.11 (s, 2H). $^{13}$C NMR (CDCl$_3$, 75 MHz) δ 150.4, 149.3, 135.7, 132.5, 131.6, 129.5, 121.5, 118.4, 115.5, 106.1. UV-vis (λ$_{max}$, nm) 419, 542, 583. HRMS-EI ([M]$^+$): calc'd for C$_{44}$H$_{30}$N$_6$Zn, 706.1823; found 706.1845.

Example 27

Synthesis of 5,15-di-p-[N-(4-nitrophenyl)amino]phenylporphyrin (Table 2, entry 2, A)

The general procedure using 5,15-di-p-bromophenylporphyrin (31.0 mg, 0.05 mmol), Pd(OAc)$_2$ (1.12 mg, 0.005 mmol), (±) BINAP (6.2 mg, 0.01 mmol, 9), Cs$_2$CO$_3$ (130.33 mg, 0.4 mmol), 4-nitroaniline (55.3 mg, 0.4 mmol) and toluene, the reaction proceeded at 100° C. for 48 h. After workup with general procedure, the title compound was obtained as brown solid (28.0 mg, 76%). $^1$H NMR (DMSO-d$_6$, 300 MHz) δ 10.64 (s, meso-2H), 9.82 (s, 2H), 9.67 (d, J=4.2 Hz, β-4H), 9.15 (d, J=4.2 Hz, β-4H), 8.24-8.29 (m, 8H), 7.75 (d, J=7.5 Hz, 4H), 7.45 (d, J=9.0 Hz, 4H), −3.19 (s, 2H). $^{13}$C NMR (DMSO-d$_6$, 75 MHz) δ 150.5, 146.7, 144.7, 140.2, 138.4, 135.9, 134.9, 132.7, 130.9, 126.4, 118.9, 114.3, 105.8. UV-vis (λ$_{max}$, nm) 413, 506, 542, 579, 635. HRMS-EI ([M+1]$^+$): calc'd for C$_{44}$H$_{31}$N$_8$O$_4$, 735.2463; found 725.2436.

Example 28

Synthesis of 5,15-di-p-[N-(4-methoxyphenyl)amino]phenylporphyrin (Table 2, entry 3, A)

The general procedure using 5,15-di-p-bromophenylporphyrin (31.0 mg, 0.05 mmol), Pd(OAc)$_2$ (1.12 mg, 0.005 mmol), ligand 3 (3.8 mg, 0.01 mmol), NaOtBu (38.22 mg, 0.4 mmol), p-anisidine (49.3 mg, 0.4 mmol) and THF, the reaction proceeded at 100° C. for 48 h. After workup with general procedure, the title compound was obtained (32.6 mg, 93%). $^1$H NMR (DMSO-d$_6$, 300 MHz) δ 10.56 (s, meso-2H), 9.62 (d, J=4.2 Hz, β-4H), 9.15 (d, J=4.8 Hz, β-4H), 8.44 (s, 2H), 8.07 (d, J=7.8 Hz, 4H), 7.37 (d, J=9.0 Hz, 4H), 7.41 (d, J=8.7 Hz, 4H), 7.02 (d, J=8.4 Hz, 4H), 3.78 (s, 6H), −3.09 (s, 2H). $^{13}$C NMR (DMSO-d$_6$, 75 MHz) δ 154.3, 147.0, 145.2, 144.4, 136.1, 135.7, 134.7, 134.6, 132.3, 129.9, 121.4, 119.3, 114.7, 113.3, 55.3. UV-vis (λ$_{max}$, nm) 418, 510, 552, 583, 640. HRMS-EI ([M+1]$^+$): calc'd for, C$_{46}$H$_{37}$N$_6$O$_2$, 705.2978; found 705.3018.

Example 29

Synthesis of 5,15-di-p-[N-(4-methoxyphenyl)amino]phenylporphyrin (Zn II) (Table 2, entry 3, B)

The general procedure using 5,15-di-p-bromophenylporphyrin (Zn II)(34.5 mg, 0.05 mmol), Pd(OAc)$_2$ (1.12 mg, 0.005 mmol), ligand 8 (3.98 mg, 0.01 mmol), NaOtBu (38.22 mg, 0.4 mmol), p-anisidine (49.3 mg, 0.4 mmol) and THF, the reaction proceeded at 100° C. for 48 h. After workup with general procedure, the title compound was obtained (26 mg, 68%). $^1$H NMR (DMSO-d$_6$, 300 MHz) δ 10.29 (s, meso-2H), 9.47 (d, J=4.5 Hz, β-4H), 9.07 (d, J=4.2 Hz, β-4H), 8.36 (s, 2H), 8.02 (d, J=8.1 Hz, 4H), 7.39 (d, J=8.1 Hz, 4H), 7.37 (d, J=8.1 Hz, 4H), 7.01 (d, J=8.1 Hz, 4H), 3.78 (s, 6H). $^{13}$C NMR (DMSO-d$_6$, 75 MHz) δ 154.1, 149.8, 148.7, 144.6, 136.1, 135.7, 134.7, 132.3, 131.9, 131.8, 121.0, 119.5, 114.7, 113.0, 105.8, 55.3. UV-vis (λ$_{max}$, nm) 419, 545, 585.

Example 30

Synthesis of 5,15-di-p-(N-benzylamino)phenylporphyrin (Zn II) (Table 2, entry 4, B)

The general procedure using 5,15-di-p-bromophenylporphyrin (Zn II) (34.2 mg, 0.05 mmol), Pd(OAc)$_2$ (1.12 mg, 0.005 mmol), ligand 8 (3.98 mg, 0.01 mmol), NaOtBu (38.22 mg, 0.4 mmol), benzylamine (43.7 μL, 0.4 mmol) and THF, the reaction proceeded at 100° C. for 48 h. After workup with general procedure, the title compound was obtained (30.7 mg, 83%). $^1$H NMR (CDCl$_3$, 300 MHz) δ 10.17 (s, meso-2H), 9.35 (d, J=4.2 Hz, β-4H), 9.17 (d, J=4.8 Hz, β-4H), 8.04 (d, J=7.2 Hz, 4H), 7.58 (d, J=7.5 Hz, 4H), 7.35-7.49 (m, 6H), 7.02 (d, J=7.5 Hz, 4H), 5.5 (s, 2H). UV-vis (λ$_{max}$, nm) 419, 543, 584.

Example 31

Synthesis of 5,15-di-β-[N-(4-methylpyridyl)amino]phenylporphyrin (Table 2, entry 5, A)

The general procedure using 5,15-di-p-bromophenylporphyrin (31.0 mg, 0.05 mmol), Pd(OAc)$_2$ (1.12 mg, 0.005 mmol), (±) BINAP (6.2 mg, 0.01 mmol, 9), NaOtBu (38.22 mg, 0.4 mmol), 4-aminomethylpyridine (41 μL, 0.4 mmol) and THF, the reaction proceeded at 100° C. for 48 h. After workup with general procedure, the title compound was obtained (29.6 mg, 88%). Different yield was observed by using other conditions (table 1). $^1$H NMR (DMSO-d$_6$, 300 MHz) δ 10.52 (s, meso-2H), 9.58 (d, J=4.5 Hz, β-4H), 9.07 (d, J=4.2 Hz, β-4H), 8.63 (d, J=5.7 Hz, 4H), 7.98 (d, J=8.4 Hz, 4H), 7.58 (d, J=5.7 Hz, 4H), 7.05 (d, J=8.7 Hz, 4H), 6.97 (t, 2H), 4.61 (d, J=5.7, 4H), −3.10 (s, 2H). $^{13}$C NMR (DMSO-d$_6$, 75 MHz) δ 149.8, 148.2, 147.1, 144.6, 136.0, 134.6, 134.4, 134.3, 132.2, 130.8, 128.1, 122.5, 111.4, 105.4, 45.6. UV-vis (λ$_{max}$, nm) 416, 508, 548, 581, 638.

Example 32

Synthesis of 5,15-di-o-[N-(o-methylphenyl)amino]phenylporphyrin (Table 2, entry 6, A)

The general procedure using 5,15-di-p-bromophenylporphyrin (31.0 mg, 0.05 mmol), Pd(OAc)$_2$ (1.12 mg, 0.005 mmol), ligand 3 (3.8 mg, 0.01 mmol), NaOtBu (38.22 mg, 0.4 mmol), o-toluidine (43 μL, 0.4 mmol) and THF, the reaction proceeded at 100° C. for 48 h. After workup with general procedure, the title compound was obtained (29.1 mg, 87%). $^1$H NMR (DMSO-d$_6$, 300 MHz) δ 10.56 (s, meso-2H), 9.62 (d, J=4.8 Hz, β-4H), 9.16 (d, J=4.8 Hz, β-4H), 8.08 (d, J=8.7 Hz, 4H), 7.98 (s, 2H), 7.59 (d, J=7.5 Hz, 2H), 7.38 (d, J=8.7 Hz, 4H), 7.27-7.38 (m, 4H), 7.04 (m, 2H), 2.44 (s, 6H), −3.10 (s, 2H). $^{13}$C NMR (DMSO-d$_6$, 75 MHz) δ 147.5, 144.9, 142.6, 140.9, 135.9, 131.4, 131.2, 131.0, 128.9, 126.9, 122.6, 119.6, 115.5, 105.1, 18.0. UV-vis (λ$_{max}$, nm) 419, 510, 552, 583, 640. HRMS-EI ([M+1]$^+$): calc'd for, C$_{46}$H$_{37}$N$_6$, 673.3080; found 673.3107.

Example 33

Synthesis of 5,15-di-p-[N-(o-methylphenyl)amino]phenylporphyrin(Zn(II)) (Table 2, entry 6, B)

The general procedure using 5,15-di-p-bromophenylporphyrin(Zn(II)) (34.2 mg, 0.05 mmol), Pd(OAc)$_2$ (1.12 mg, 0.005 mmol), ligand 3 (3.8 mg, 0.01 mmol), NaOtBu (38.22 mg, 0.4 mmol), o-toluidine (43 μL, 0.4 mmol) and THF, the reaction proceeded at 100° C. for 48 h. After workup with general procedure, the title compound (29.1 mg, 87%) was obtained. $^1$H NMR (DMSO-d$_6$, 300 MHz) δ 10.23 (s, meso-2H), 9.39 (d, J=4.8 Hz, β-4H), 9.20 (d, J=4.8 Hz, β-4H), 8.11 (d, J=8.1 Hz, 4H), 7.63 (d, J=7.5 Hz, 2H), 7.36 (d, J=8.4 Hz, 4H), 7.27-7.35 (m, 4H), 7.04 (dd, J=7.8 Hz 2H), 5.76 (s, 2H), 2.48 (s, 6H). $^{13}$C NMR (CDCl$_3$, 75 MHz) δ 150.3, 149.3, 139.7, 135.8, 132.3, 131.4, 131.1, 122.2, 115.4, 105.8, 18.2. UV-vis (λ$_{max}$, nm) 421, 542, 583. HRMS-EI ([M-Zn+1]$^+$): calc'd for, C$_{46}$H$_{35}$N$_6$, 673.3080; found 673.3075.

Example 34

Synthesis of 5,15-di-n-butylaminophenylporphyrin (Table 2, entry 7, A)

The general procedure using 5,15-di-p-bromophenylporphyrin (31.0 mg, 0.05 mmol), Pd(OAc)$_2$ (1.12 mg, 0.005 mmol), ligand 3 (3.78 mg, 0.01 mmol), NaOtBu (38.22 mg, 0.4 mmol), n-butylamine (40 μL, 0.4 mmol) and THF (4-6 mL), the reaction proceeded at 100° C. for 48 h. After workup with general procedure, the title compound (27.7 mg, 92%) was obtained. By using other ligand or other condition, the same product with different yield was obtained (table 1, entry 7). $^1$H NMR (CDCl$_3$, 300 MHz) δ 10.25 (s, meso-2H), 9.35 (d, J=4.6 Hz, β-4H), 9.16 (d, J=4.5 Hz, β-4H), 8.06 (d, J=8.4 Hz, 4H), 7.03 (d, J=8.4 Hz, 4H), 3.40 (t, J=6.6, 7.2 Hz, 4H), 1.83 (m, 4H), 1.59 (m, 4H), 1.08 (m, 6H), −3.00 (s, 2H). $^{13}$C NMR (CDCl$_3$, 75 MHz) δ 148.1, 147.8, 144.8, 136.1, 131.2, 131.1, 130.0, 119.7, 111.3, 104.9, 44.9, 31.8, 20.5, 14.1. UV-vis (λ$_{max}$, nm) 419, 511, 553, 586, 641. HRMS-EI ([M+1]$^+$): calc'd for, C$_{40}$H$_{41}$N$_6$, 605.3393; found 605.3395.

Example 35

Synthesis of 5,15-di-n-butylaminophenylporphyrin (Zn II) (Table 2, entry 7, B)

The general procedure using 5,15-di-p-bromophenylporphyrin (Zn II) (34.2 mg, 0.05 mmol), Pd(OAc)$_2$ (1.12 mg, 0.005 mmol), ligand 8 (3.98 mg, 0.01 mmol), NaOtBu (38.22 mg, 0.4 mmol), n-butylamine (40 μL, 0.4 mmol) and THF (4-6 mL), the reaction proceeded at 100° C. for 48 h. After workup with general procedure, the title compound (31.1 mg, 93%) was obtained. $^1$H NMR (DMSO-d$_6$, 300 MHz) δ 10.26 (s, meso-2H), 9.44 (d, J=4.8 Hz, β-4H), 9.04 (d, J=4.8 Hz, #4H), 7.92 (d, J=8.1 Hz, 4H), 7.01 (d, J=8.1 Hz, 4H), 6.04 (t, 2H), 3.28 (m, 4H), 1.76 (m, 4H), 1.55 (m, 4H), 1.05 (m, 6H). $^{13}$C NMR (DMSO-d$_6$, 75 MHz) δ 149.9, 148.5, 135.6, 134.5, 134.3, 131.6, 129.5, 110.4, 42.8, 31.2, 20.1, 14.0. UV-vis (λ$_{max}$, nm 419, 545, 586. HRMS-EI ([(M-Zn)+1]$^+$): calc'd for, C$_{40}$H$_{41}$N$_6$, 605.3393; found 605.3360.

Example 36

Synthesis of 5,15-di-n-hexylaminophenylporphyrin (Table 2, entry 8, A)

The general procedure using 5,15-di-p-bromophenylporphyrin (31.0 mg, 0.05 mmol), Pd(OAc)$_2$ (1.12 mg, 0.005 mmol), ligand 3 (3.78 mg, 0.01 mmol), NaOtBu (38.22 mg, 0.4 mmol), n-hexylamine (52.8 μL, 0.4 mmol) and THF (4-6 mL), the reaction proceeded at 100° C. for 48 h. After workup with general procedure, the title compound (29.7 mg, 90%) was obtained. $^1$H NMR (CDCl$_3$, 300 MHz) δ 10.25 (s, meso-2H), 9.35 (d, J=4.8 Hz, β-4H), 9.16 (d, J=4.2 Hz, β-4H), 8.05 (d, J=8.4 Hz, 4H), 7.03 (d, J=8.4 Hz, 4H), 4.05 (br, s, 2H), 3.40 (t, J=7.2 Hz, 4H), 1.84 (m, 4H), 1.54 (m, 4H), 1.43 (m, 4H), 0.97 (m, 6H), −3.00 (s, 2H). $^{13}$C NMR (CDCl$_3$, 75 MHz) δ 148.1, 147.8, 144.8, 136.1, 131.2, 131.1, 130.0, 119.7, 111.4, 104.9, 44.3, 31.8, 29.7, 27.0, 22.7, 14.1. UV-vis (λ$_{max}$, nm) 421, 509, 549, 583, 638.

Example 37

5,15-di-n-hexylaminophenylporphyrin (Zn II) (Table 2, entry 8, B)

The general procedure using 5,15-di-p-bromophenylporphyrin (Zn II) (34.2 mg, 0.05 mmol), Pd(OAc)$_2$ (1.12 mg, 0.005 mmol), ligand 7 (5.78 mg, 0.01 mmol), NaOtBu (38.22 mg, 0.4 mmol), n-hexylamine (52.8 μL, 0.4 mmol) and THF (4-6 mL), the reaction proceeded at 100° C. for 48 h. After workup with general procedure, the title compound (17 mg, 53%) was obtained. $^1$H NMR (CDCl$_3$, 300 MHz) δ 10.22 (s, meso-2H), 9.38 (d, J=4.8 Hz, β-4H), 9.18 (d, J=4.2 Hz, β-4H), 7.95 (d, J=8.1 Hz, 4H), 6.70 (d, J=8.1 Hz, 4H), 3.44 (m, 4H), 2.95 (m, 4H), 1.76 (m, 4H), 1.61 (m, 4H), 1.36 (m, 8H), 0.94 (m, 6H). $^{13}$C NMR (DMSO-d$_6$, 75 MHz) δ 150.5, 149.2, 139.4, 135.4, 132.5, 131.1, 111.4, 104.9, 44.1, 31.5, 28.0, 26.6, 22.7, 14.1. UV-vis (λ$_{max}$, nm) 419, 543, 584.

Example 38

5,15-di-p-(N-methyl,N-phenylamino)phenylporphyrin (Table 2, entry 9, A)

The general procedure using 5,15-di-p-bromophenylporphyrin (31.0 mg, 0.05 mmol), Pd(OAc)$_2$ (1.12 mg, 0.005 mmol), ligand 3 (3.78 mg, 0.01 mmol), NaOtBu (38.22 mg, 0.4 mmol), N-methylaniline (43.7 µL, 0.4 mmol) and THF (4-6 mL), the reaction proceeded at 100° C. for 48 h. After workup with general procedure, the title compound (29.5 mg, 88%) was obtained. $^1$H NMR (CDCl$_3$, 300 MHz) δ 10.28 (s, meso-2H), 9.39 (d, J=4.8 Hz, β-4H), 9.20 (d, J=4.8 Hz, β-4H), 8.14 (d, J=8.7 Hz, 4H), 7.37-7.50 (m, 12H), 7.13 (dd, J=2.1, 6.6 Hz, 2H), 3.62 (s, 6H), −3.02 (s, 2H). $^{13}$C NMR (CDCl$_3$, 75 MHz) δ 148.9, 148.5, 147.6, 144.9, 135.8, 133.0, 131.4, 131.1, 129.6, 122.8, 122.7, 119.2, 116.9, 105.1, 40.6. UV-vis (λ$_{max}$, nm) 413, 510, 552, 583, 640. HRMS-EI ([M]$^+$): calc'd for C$_{46}$H$_{36}$N$_6$, 672.3001; found 672.3010.

Example 39

Synthesis of 5,15-di-p-(N-methyl, N-phenylamino) phenylporphyrin (Zn II) (Table 2, entry 9, B)

The general procedure using 5,15-di-p-bromophenylporphyrin (Zn II) (34.2 mg, 0.05 mmol), Pd(OAc)$_2$ (1.12 mg, 0.005 mmol), ligand 3 (3.78 mg, 0.01 mmol), NaOtBu (38.22 mg, 0.4 mmol), N-methylaniline (43.7 µL, 0.4 mmol) and THF (4-6 mL), the reaction proceeded at 100° C. for 48 h. After workup with general procedure, the title compound (27 mg, 73%) was obtained. $^1$H NMR (CDCl$_3$, 300 MHz) δ 10.24 (s, meso-2H), 9.39 (d, J=4.2 Hz, β-4H), 9.22 (d, J=4.8 Hz, β-4H), 8.12 (d, J=8.1 Hz, 4H), 7.37-7.49 (m, 12H), 7.13 (m, 2H), 3.63 (s, 6H). $^{13}$C NMR (CDCl$_3$, 75 MHz) δ 150.4, 149.2, 148.3, 135.6, 134.5, 132.6, 131.5, 129.5, 122.4, 122.2, 117.0, 106.0, 40.6. UV-vis (λ$_{max}$, nm) 413, 544, 587. HRMS-EI ([M-Zn+1]$^+$): calc'd for C$_{46}$H$_{35}$N$_6$, 673.3080; found 673.3104.

Example 40

Synthesis of 5,15-di-p-diphenylaminophenylporphyrin (Table 2, entry 10, A)

The general procedure using 5,15-di-p-bromophenylporphyrin (31.0 mg, 0.05 mmol), Pd(OAc)$_2$ (1.12 mg, 0.005 mmol), ligand 3 (3.78 mg, 0.01 mmol), NaOtBu (38.22 mg, 0.4 mmol), diphenylamine (67.7 mg, 0.4 mmol) and THF (4-6 mL), the reaction proceeded at 100° C. for 48 h. After workup with general procedure, the title compound (32.4 mg, 81%) was obtained. $^1$H NMR (CDCl$_3$, 300 MHz) δ 10.28 (s, meso-2H), 9.39 (d, J=4.8 Hz, β-4H), 9.20 (d, J=4.8 Hz, β-4H), 8.14 (d, J=8.7 Hz, 4H), 7.37-7.50 (m, 12H), 7.13 (dd, J=2.1, 6.6 Hz, 2H), 3.62 (s, 6H), −3.04 (s, 2H). $^{13}$C NMR (CDCl$_3$, 75 MHz) δ 147.8, 135.8, 131.5, 131.0, 129.5, 124.9, 123.3, 121.6, 105.2. UV-vis (λ$_{max}$, nm) 410, 510, 552, 583, 640. HRMS-EI ([M+1]$^+$): calc'd for C$_{56}$H$_{41}$N$_6$, 797.3393; found 797.3398.

Example 41

Synthesis of 5,15-di-p-diphenylaminophenylporphyrin (Zn II) (Table 2, entry 10, B)

The general procedure using 5,15-di-p-bromophenylporphyrin (Zn II) (34.2 mg, 0.05 mmol), Pd(OAc)$_2$ (1.12 mg, 0.005 mmol), ligand 8 (3.98 mg, 0.01 mmol), NaOtBu (38.22 mg, 0.4 mmol), diphenylamine (67.7 mg, 0.4 mmol) and THF (4-6 mL), the reaction proceeded at 100° C. for 48 h. After workup with general procedure, the title compound (24.5 mg, 57%) was obtained. $^1$H NMR (DMSO-d$_6$, 300 MHz) δ 10.35 (s, meso-2H), 9.52 (d, J=4.8 Hz, β-4H), 9.08 (d, J=4.5 Hz, β-4H), 8.12 (d, J=8.1 Hz, 4H), 7.37-7.51 (m, 12H), 7.17 (m, 4H). $^{13}$C NMR (DMSO-d$_6$, 75 MHz) δ 149.4, 148.9, 147.4, 146.6, 136.6, 135.6, 132.1, 129.9, 124.5, 123.4, 121.1, 118.8, 116.7, 106.1. UV-vis (λ$_{max}$, nm) 416, 543, 584. HRMS-EI ([M-Zn+1]$^+$): calc'd for C$_{56}$H$_{41}$N$_6$Zn, 797.3393; found 797.3408.

Example 42

Synthesis of 5,15-di-β-benzophenone iminophenylporphyrin (Table 2, entry 11, A)

The general procedure using 5,15-di-p-bromophenylporphyrin (31.0 mg, 0.05 mmol), Pd$_2$(dba)$_3$ (4.58 mg, 0.005 mmol), ligand 1 (2.98 mg, 0.01 mmol), NaOtBu (38.22 mg, 0.4 mmol), benzophenone imine (67.1 µL, 0.4 mmol) and THF (4-6 mL), the reaction proceeded at 100° C. for 48 h. After workup with general procedure, the title compound (21.4 mg, 81%) was obtained. $^1$H NMR (CDCl$_3$, 300 MHz) δ 10.27 (s, meso-2H), 9.36 (d, J=4.8 Hz, β-4H), 9.95 (d, J=4.8 Hz, β-4H), 8.0 (d, J=7.5 Hz, 4H), 7.95 (d, J=8.7 Hz, 4H), 7.52 (m, 12H), 7.43 (m, 4H), 7.13 (d, J=7.5 Hz, 4H), −3.18 (s, 2H). $^{13}$C NMR (CDCl$_3$, 75 MHz) δ 142.9, 142.6, 135.9, 131.5, 131.0, 129.6, 121.6, 118.6, 115.7, 105.1. UV-vis (λ$_{max}$, nm) 412, 506, 541, 578, 634. HRMS-EI ([M+1]$^+$): calc'd for C$_{58}$H$_{41}$N$_6$, 821.3393; found 821.3370.

Example 43

Synthesis of 5,15-di-p-morpholinophenylporphyrin (Table 2, entry 12, A)

The general procedure using 5,15-di-p-bromophenylporphyrin (31.0 mg, 0.05 mmol), Pd(OAc)$_2$ (1.12 mg, 0.005 mmol), ligand 8 (3.98 mg, 0.01 mmol), Cs$_2$CO$_3$ (130.33 mg, 0.4 mmol), morpholine (35 µL, 0.4 mmol) and THF (4-6 mL), the reaction proceeded at 100° C. for 48 h. After workup with general procedure, the title compound (25 mg, 76%) was obtained.

Example 44

Synthesis Of Tetrakis-p-(N-phenylamino)phenylporphyrin (Table 3, entry 1)

The general procedure using tetrakis-p-bromophenylporphyrin (46.5 mg, 0.05 mmol), Pd(OAc)$_2$ (2.24 mg, 0.01 mmol), (±) BINAP (12.4 mg, 0.02 mmol, 9), NaOtBu (76.44 mg, 0.8 mmol), aniline (73 µL, 0.8 mmol) and THF (4-6 mL), the reaction proceeded at 100° C. for 72 h. After workup with general procedure, the title compound (44.6 mg, 91%) was obtained. $^1$H NMR (CDCl$_3$, 300 MHz) $^1$H NMR (CDCl$_3$, 300 MHz) δ 8.95 (s, β-8H), 8.08 (d, J=8.1 Hz, 8H), 7.34-7.42 (m, 24H), 7.04 (t, J=6.6, 7.2 Hz, 4H), 6.05 (s, 4H), −2.66 (s, 2H). $^{13}$C NMR (CDCl$_3$, 75 MHz) δ 142.9, 142.7, 135.7, 134.6, 129.5, 121.5, 119.9, 118.5, 115.3. UV-vis (λ$_{max}$, nm) 433, 524, 566, 657. HRMS-EI ([M+1]$^+$): calc'd for C$_{68}$H$_{51}$N$_8$, 979.4237; found 979.4218.

Example 45

Synthesis Of Tetrakis-p-(n-butylamino)phenylporphyrin (Table 3, entry 2)

The general procedure using tetrakis-p-bromophenylporphyrin (46.5 mg, 0.05 mmol), Pd(OAc)$_2$ (2.24 mg, 0.01 mmol), ligand 8 (7.96 mg, 0.02 mmol), NaOtBu (76.44 mg, 0.8 mmol), n-butylamine (80 µL, 0.8 mmol) and THF (4-6 mL), the reaction proceeded at 100° C. for 72 h. After workup with general procedure, the title compound (38.5 mg, 86%) was obtained. $^1$H NMR (CDCl$_3$, 300 MHz) δ 8.91 (s, β-8H), 8.01 (d, J=8.1 Hz, 8H), 6.95 (d, J=8.1 Hz, 8H), 3.95 (s, 4H), 3.60 (t, J=7.2, 8.4 Hz, 8H), 1.79 (m, 8H), 1.59 (m, 8H), 1.06 (t, J=6.9, 7.2 Hz, 12H), −2.64 (s, 2H). $^{13}$C NMR (CDCl$_3$, 75 MHz) δ 147.9, 135.8, 131.3, 120.3, 110.9, 43.9, 31.9, 20.5, 14.0. UV-vis ($\lambda_{max}$, nm) 434, 527, 571, 661. HRMS-EI ([M+1]$^+$): calc'd for C$_{60}$H$_{67}$N$_8$, 899.5489; found 899.5507.

Example 46

Synthesis of Tetrakis-p-(N-methyl, N-phenylamino)phenylporphyrin (Table 3, entry 3)

The general procedure using tetrakis-p-bromophenylporphyrin (46.5 mg, 0.05 mmol), Pd(OAc)$_2$ (2.24 mg, 0.01 mmol), (±) BINAP (12.4 mg, 0.02 mmol, 9), NaOtBu (76.44 mg, 0.8 mmol), N-methylaniline (87.4 µL, 0.8 mmol) and THF (4-6 mL), the reaction proceeded at 100° C. for 72 h. After workup with general procedure, the title compound (42.4 mg, 82%) was obtained. $^1$H NMR (CDCl$_3$, 300 MHz) δ 8.78 (s, β-8H), 7.92 (d, J=7.8 Hz, 8H), 7.21-7.30 (m, 16H), 7.16 (d, J=8.1 Hz, 8H), 7.05 (s, 2H), 6.95(t, 4H), 3.42 (s, 12H), −2.81 (s, 2H). $^{13}$C NMR (CDCl$_3$, 75 MHz) δ 148.9, 148.4, 135.6, 134.1, 129.5, 122.7, 122.6, 122.5, 120.1, 116.6, 116.5, 40.5. UV-vis ($\lambda_{max}$, nm) 435, 525, 567, 657. HRMS-EI ([M+1]$^+$): Calc'd for C$_{72}$H$_{59}$N$_8$, 1035.4863; found 1035.4836.

Example 47

Synthesis Of Tetrakis-p-(diphenylamino)phenylporphyrin (Table 3, entry 4)

The general procedure using tetrakis-p-bromophenylporphyrin (46.5 mg, 0.05 mmol), Pd(OAc)$_2$ (2.24 mg, 0.01 mmol), ligand 3 (7.56 mg, 0.02 mmol), NaOtBu (76.44 mg, 0.8 mmol), diphenylamine (135.4 mg, 0.8 mmol) and THF (4-6 mL), the reaction proceeded at 100° C. for 72 h. After workup with general procedure, the title compound (52.2 mg, 81%) was obtained. $^1$H NMR (CDCl$_3$, 300 MHz) δ 9.02 (s, β-8H), 8.12 (d, J=8.7 Hz, 8H), 7.47 (d, J=8.4 Hz, 8H), 7.43 (s, 16H), 7.41 (m, 4H), 7.15 (s, 8H), −2.66 (s, 2H). $^{13}$C NMR (CDCl$_3$, 75 MHz) δ 147.8, 147.4, 135.9, 135.7, 129.5, 124.8, 123.3, 121.3, 119.9, 117.7. UV-vis ($\lambda_{max}$, nm) 439, 526, 570, 659. HRMS-EI ([M+1]$^+$): calc'd for C$_{92}$H$_{67}$N$_8$, 1283.5489; found 1283.5478.

Example 48 through 58 relate to methods for synthesizing meso-substituted phenoxyporphyrins, and the phenoxyporphyrin compounds so made, according to the presently disclosed subject matter.

Example 48

General Procedure

All reactions were carried out under a nitrogen atmosphere in oven-dried glassware using standard Schlenk techniques. Toluene was distilled under nitrogen from sodium benzophenone ketyl. Deuterated solvents were purchased from Cambridge Isotope Laboratories and were used as supplied. All other solvents were of liquid chromatography grade, which were purchased from Fisher Scientific and used as supplied. Phenyls were purchased from Acros Organics or Aldrich Chemical Co. and used without further purification. [5-bromo-10,20-diphenylporphyrino]zinc(II) and [5,15-dibromo-10,20-diphenylporphyrino]zinc(II) were synthesized according to the literature. Phosphine ligands notably, bis(2-diphenylphosphinophenyl)ether (DPEphos), were purchased from Strem along with the metal precursors; palladium(II) acetate and tris(dibenzylideneacetone)dipalladium(0). Cesium carbonate was obtained as a gift from Chemetall Chemical Products, Inc. Proton and carbon nuclear magnetic resonance spectra ($^1$H NMR and $^{13}$C NMR) were recorded on a Varian Mercury 300 spectrometer and referenced with respect to residual solvent. Infrared spectra were obtained using a Bomen B100 Series FT-IR spectrometer. Samples were prepared as films on a NaCl plate by evaporating THF solutions. UV-Vis spectra were obtained using a Hewlett-Packard 8452A diode array spectrophotometer. High-resolution mass spectroscopy was performed by the Mass Spectrometry Center located in the Chemistry Department of the University of Tennessee on a VG Analytical hybrid high performance ZAB-EQ (B-E-Q geometry) instrument using electron impact (EI) ionization technique with a 70 eV electron beam. Thin layer chromatography was carried out on E. Merck Silica Gel 60 F-254 TLC plates.

Example 49

General Procedures for Catalytic C—O Coupling of Bromoporphyrin

The bromoporphyrin, palladium precursor, phosphine ligand and base were placed in an oven-dried, resealable Schlenk tube. The tube was sealed with a Teflon screw cap, evacuated, and backfilled with nitrogen. The screw cap was replaced with a rubber septum; the phenyl was then added via syringe, followed by solvent. The tube was purged with nitrogen for 2 min, and then the septum was replaced with the Teflon screw cap. The tube was sealed, and its contents were placed in a heated oil-bath with constant stirring until the starting bromoporphyrin had been completely consumed as indicated by TLC analysis. The resulting mixture was cooled to room temperature, taken up in ethyl acetate (60 mL) and transferred to a separatory funnel. The mixture was then washed with water (×2), dried over anhydrous sodium sulfate, filtered and dried in vacuo. The crude product was then purified.

Example 50

Synthesis of 5-phenoxy-10,20-diphenylporphinato zinc(II)

The general procedure was used to couple 5-bromo-10,20-diphenylporphinato zinc(II) (30 mg, 0.05 mmol) with phenyl (17 mg, 0.018 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 23 hours. Isolated via flash chromatography (silica gel, THF:hexanes (v)=1:8 as a red solid (24 mg, 80%). $^1$H NMR (300 MHz, CDCl$_3$): δ 10.13 (s, 1H), 9.39 (d, J=4.5 Hz, 2H), 9.31 (d, J=4.8 Hz, 2H), 9.09 (d J=4.5 Hz, 2H), 8.92 (d, J=4.8 Hz, 2H), 8.19 (m, 4H), 7.74 (m, 6H), 7.23 (m, 2H), 7.02 (m, 3H). $^{13}$C NMR (75 MHz, CDCl$_3$): δ 165.9, 150.3, 150.1, 149.7, 145.8, 142.3, 134.5, 132.9, 132.2, 131.8, 129.6, 128.0, 127.5, 126.6, 121.5, 120.7, 116.6, 107.7, 105.6. UV-vis (CHCl$_3$, $\lambda_{max}$, nm): 218, 418. IR (film, cm$^{-1}$): 3609, 3583, 3047, 2362, 1591, 1544, 1486, 1440, 1384, 1361, 1319, 1295, 1214, 1163, 1147, 1062, 996, 851, 790, 750, 721, 701. HRMS-EI ([M]$^+$): $C_{38}H_{24}N_4OZn$, 616.124; found: 616.125.

Example 51

Synthesis of 5-(4-methoxyphenoxy)-10,20-diphenylporphinato zinc(II)

The general procedure was used to couple 5-bromo-10,20-diphenylporphinato zinc(II) (30 mg, 0.05 mmol) with 4-methoxyphenyl (22 mg, 0.18 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 17 hours. Isolated via flash chromatography (silica gel, THF:hexanes (v)=1:8 as a red solid (29.9 mg, 93%). $^1$H NMR (300 MHz, CDCl$_3$): δ 10.02 (s, 1H), 9.35 (d, J=4.2 Hz, 2H), 9.24 (d, J=3.9 Hz, 2H), 8.98 (d, J=4.2 Hz, 2H), 8.8 (d, J=3.9 Hz, 2H), 8.18 (m, 4H), 7.75 (m, 6H), 6.92 (d, J=8.4 Hz, 2H), 6.67 (d, J=8.4 Hz, 2H), 3.60 (S, 3H). $^{13}$C NMR (75 MHz, CDCl$_3$): δ 160.8, 153.9, 150.2, 150.0, 149.5, 145.9, 142.6, 134.6, 132.7, 132.1, 132.0, 131.6, 127.9, 127.4, 126.5, 120.4, 117.1, 114.6, 105.2, 55.6. UV-vis (CHCl$_3$, λ$_{max}$, nm): 418, 548. IR (film, cm$^{-1}$): 3291, 3054, 2973, 2954, 2877, 2833, 2738, 1808, 1721, 1595, 1538, 1502, 1459, 1440, 1385, 1360, 1322, 1294, 1243, 1147, 1103, 1061, 1037, 994, 881, 846, 827, 793, 751, 724, 701. HRMS-EI ([M]$^+$): $C_{39}H_{26}N_4O_2Zn$, 646.135; found: 646.137.

Example 52

Synthesis of 5-(4-t-butylphenoxy)-10,20-diphenylporphinato zinc(II)

The general procedure was used to couple 5-bromo-10,20-diphenylporphinato zinc(II) (30 mg, 0.05 mmol) with 4-t-butylphenyl (27 mg, 0.18 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 18 hours. Isolated via flash chromatography (silica gel, THF:hexanes (v)=1:8 as a red solid (23.8 mg, 73%). $^1$H NMR (300 MHz, CDCl$_3$): δ 10.16 (s, 1H), 9.45 (d, J=4.8 Hz, 2H), 9.34 (d, J=4.2 Hz, 2H), 9.06 (d, J=4.5 Hz, 2H), 8.93 (d, J=4.8 Hz, 2H), 8.22 (m, 4H), 7.77 (m, 6H), 7.24 (d, J=9.9 Hz, 2H), 6.96 (d, J=8.7 Hz, 2H), 1.26 (S, 9H). $^{13}$C NMR (75 MHz, CDCl$_3$): δ 164.0, 159.9, 150.4, 150.1, 149.7, 146.0, 144.1, 142.4, 134.5, 132.9, 132.1, 131.7, 128.1, 127.5, 126.7, 126.3, 120.66, 115.9, 105.5, 31.5, 29.7. UV-vis (CHCl$_3$, λ$_{max}$, nm): 418, 548. IR (film, cm$^{-1}$): 3297, 3054, 3027, 2961, 2872, 1806, 1599, 1542, 1505, 1488, 1460, 1386, 1362, 1322, 1295, 1266, 1220, 1173, 1150, 1110, 1062, 1041, 995, 883, 846, 832, 792, 750, 723, 701. HRMS-EI ([M]$^+$): $C_{42}H_{32}N_4OZn$, 672.187; found: 672.186.

Example 53

Synthesis of 5-(4-fluorophenoxy)-10,20-diphenylporphinato zinc(II)

The general procedure was used to couple 5-bromo-10,20-diphenylporphinato zinc(II) (30 mg, 0.05 mmol) with 4-fluorophenyl (20 mg, 0.18 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 17 hours. Isolated via flash chromatography (silica gel, THF:hexanes (v)=1:8 as a red solid (25.4 mg, 78%). $^1$H NMR (300 MHz, CDCl$_3$): δ 10.10 (s, 1H), 9.35 (d, J=4.5 Hz, 2H), 9.29 (d, J=4.2 Hz, 2H), 9.02 (d, J=4.8 Hz, 2H), 8.91 (d, J=4.8 Hz, 2H), 8.19 (m, 4H), 7.76 (m, 6H), 6.93 (m, 4H). $^{13}$C NMR (75 MHz, CDCl$_3$): δ 150.4, 150.2, 149.70, 145.4, 134.5, 132.9, 132.2, 131.8, 127.7, 127.5, 126.6, 120.6, 117.4, 117.2, 116.1, 115.8, 105.6. UV-vis (CHCl$_3$, λ$_{max}$, nm): 418, 546. IR (film, cm$^{-1}$): 3273, 3101, 3073, 3054, 3023, 2974, 2933, 2875, 2740, 2951, 2582, 2552, 1807, 1719, 1597, 1541, 1520, 1498, 1459, 1440, 1386, 1360, 1322, 1295, 1260, 1195, 1145, 1091, 1062, 1041, 995, 885, 847, 832, 793, 751, 724, 701. HRMS-EI ([M]$^+$): $C_{38}H_{23}N_4OFZn$, 634.115; found: 634.113.

Example 54

Synthesis of 5-(2-isopropylphenoxy)-10,20-diphenylporphinato zinc(II)

The general procedure was used to couple 5-bromo-10,20-diphenylporphinato zinc(II) (30 mg, 0.05 mmol) with 2-isopropylphenyl (25 μL, 0.018 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 17 hours. Isolated via flash chromatography (silica gel, THF:hexanes (v)=1:8 as a red solid (23 mg, 72%). $^1$H NMR (300 MHz, CDCl$_3$): δ 10.05 (s, 1H), 9.33 (d, J=4.8 Hz, 2H), 9.26 (d, J=4.5 Hz, 2H), 9.01 (d, J=4.8 Hz, 2H), 8.90 (d, J=4.5 Hz, 2H), 8.19 (m, 4H), 7.75 (m, 6H), 7.60 (d, J=7.8 Hz, 1H), 6.96 (t, J=7.5 Hz, 1H), 6.67 (t, J=7.2 Hz, 1H), 6.02 (d, J=8.1 Hz, 1H), 4.40 (m, 1H), 1.82 (d, J=6.9 Hz, 6H). $^{13}$C NMR (75 MHz, CDCl$_3$): δ 163.86, 150.3, 150.0, 149.6, 145.8, 142.5, 135.8, 134.5, 132.8, 132.1, 131.6, 127.9, 127.4, 126.6, 126.5, 121.3, 120.4, 116.4, 105.2, 28.0, 23.3. UV-vis (CHCl$_3$, λ$_{max}$, nm): 418, 546. IR (film, cm$^{-1}$): 3293, 3055, 3026, 2961, 2873, 1805, 1596, 1542, 1483, 1441, 1385, 1360, 1322, 1294, 1261, 1218, 1191, 1154, 1061, 1039, 994, 885, 847, 824, 793, 750, 723, 701. HRMS-EI ([M]$^+$): $C_{41}H_{30}N_4OZn$, 658.171; found: 658.168.

Example 55

Synthesis of 5-(3-methylphenoxy)-10,20-diphenylporphinato zinc(II)

The general procedure was used to couple 5-bromo-10,20-diphenylporphinato zinc(II) (30 mg, 0.05 mmol) with 3-cresol (20 μL, 0.018 mmol), using palladium DBA (1.5 mg, 0.0075 mmol) as the palladium precursor, DPEphos (9.6 mg, 0.036 mmol) as the phosphine ligand and cesium carbonate (34 mg, 0.1 mmol) as the base. The reaction was conducted in toluene (5 mL) at 100° C. for 16 hours. Isolated via flash chromatography (silica gel, THF:hexanes (v)=1:8 as a red solid (25 mg, 78%). $^1$H NMR (300 MHz, CDCl$_3$): δ 10.03 (s, 1H), 9.36 (d, J=4.5 Hz, 2H), 9.25 (d, J=4.5 Hz, 2H), 9.00 (d, J=4.2 Hz, 2H), 8.89 (d, J=4.5 Hz, 2H), 8.2 (m, 4H), 7.76 (m, 6H), 7.10 (t, J=7.5 Hz, 1H), 6.80 (m, 3H), 2.15 (S, 3H). $^{13}$C NMR (75 MHz, CDCl$_3$): δ 166.1, 150.0, 150.2, 149.6, 145.8, 142.7, 139.7, 134.6, 132.7, 132.0, 131.6, 127.9, 127.4, 126.5, 122.2, 120.3, 117.3, 113.7, 105.2, 21.4. UV-vis (CHCl₃, $\lambda_{max}$, nm): 418, 546. IR (film, cm$^{-1}$): 3053, 3024, 2922, 2877, 1587, 1542, 1484, 1458, 1440, 1384, 1360, 1321, 1294, 1248, 1217, 1188, 1158, 1061, 1039, 995, 911, 881, 848, 793, 781, 752, 723, 700. HRMS-EI ([M]$^+$): $C_{39}H_{26}N_4OZn$, 630.140; found: 630.139.

Example 56

Synthesis of 5-(4-methylphenoxy)-10,20-diphenylporphinato zinc(II)

The general procedure was used to couple 5-bromo-10,20-diphenylporphinato zinc(II) (30 mg, 0.05 mmol) with 4-cresol (20 mg, 0.018 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 16 hours. Isolated via flash chromatography (silica gel, toluene:hexanes (v)=3:1 as a red solid (21 mg, 65%). $^1$H NMR (300 MHz, CDCl₃): δ 9.97 (s, 1H), 9.30 (d, J=4.5 Hz, 2H), 9.21 (d, J=4.5 Hz, 2H), 8.92 (d, J=4.5 Hz, 2H), 8.8 (d, J=4.5 Hz, 2H), 8.13 (m, 4H), 8.13 (m, 6H), 6.97 (d, J=9.0 Hz, 2H), 6.86 (d, J=8.7 Hz, 2H), 2.2 (S, 3H). $^{13}$C NMR (75 MHz, CDCl₃): δ 150.3, 145.8, 143.4, 142.7, 134.6, 132.7, 132.0, 131.6, 130.4, 130.0, 128.9, 128.4, 127.9, 127.4, 126.5, 125.2, 120.3, 116.3, 105.2, 24.9. UV-vis (CHCl₃, $\lambda_{max}$, nm): 416, 546. IR (film, cm$^{-1}$): 3324, 2988, 1557, 1505, 1453, 1440, 1384, 1358, 1321, 1294, 1215, 1167, 1145, 1060, 993, 846, 820, 793, 753, 723. HRMS-EI ([M]$^+$): $C_{39}H_{26}N_4OZn$, 630.140; found: 630.141.

Example 57

Synthesis of 5-(2-methylphenoxy)-10.20-diphenylporphinato zinc(II)

The general procedure was used to couple 5-bromo-10,20-diphenylporphinato zinc(II) (30 mg, 0.05 mmol) with 2-cresol (20 mg, 0.018 mmol), using palladium DBA (1.5 mg, 0.0075 mmol) as the palladium precursor, DPEphos (9.6 mg, 0.036 mmol) as the phosphine ligand and cesium carbonate (24 mg, 0.07 mmol) as the base. The reaction was conducted in toluene (5 mL) at 100° C. for 17 hours. Isolated via flash chromatography (silica gel, toluene:hexanes (v)=3:1 as a red solid (27.8 mg, 89%). $^1$H NMR (300 MHz, CDCl₃): δ 9.94 (s, 1H), 9.33 (d, J=4.8 Hz, 2H), 9.19 (d, J=4.5 Hz, 2H), 8.97 (d, J=4.2 Hz, 2H), 8.90 (d, J=4.8 Hz, 2H), 8.18 (m, 4H), 7.74 (m, 6H), 7.47 (d, J=6.9 Hz, 1H), 6.90 (t, J=7.2 Hz, 7.5 Hz 1H), 6.68 (t, J=7.5 Hz, 7.2 Hz 1H), 6.02 (d, J=8.4 Hz, 1H), 3.10 (S, 3H). $^{13}$C NMR (75 MHz, CDCl₃): δ 150.1, 149.9, 149.6, 145.7, 142.3, 140.7, 140.6, 140.6, 140.5, 134.5, 132.8, 132.1, 131.6, 131.0, 127.8, 127.5, 126.8, 126.6, 121.1, 116.2, 105.3, 17.0. UV-vis (CHCl₃, $\lambda_{max}$, nm): 415, 546. IR (film, cm$^{-1}$): 3047, 3024, 2922, 2877, 1587, 1542, 1484, 1458, 1440, 1384, 1359, 1321, 1294, 1217, 1188, 1158, 1061, 991, 908, 877, 851, 793, 779, 751, 723. HRMS-EI ([M]$^+$): $C_{39}H_{26}N_4OZn$, 630.140; found: 630.139.

Example 58

Synthesis of bis-5,15-(4-methoxyphenoxy)-10,20-diphenylporphinato zinc(II)

The general procedure was used to couple 5,15-dibromo-10,20-diphenylporphinato zinc(II) (34 mg, 0.05 mmol) with 4-methoxyphenyl (22 mg, 0.018 mmol), using palladium DBA (1.5 mg, 0.0075 mmol) as the palladium precursor, DPEphos (9.6 mg, 0.036 mmol) as the phosphine ligand and cesium carbonate (47 mg, 0.14 mmol) as the base. The reaction was conducted in toluene (5 mL) at 100° C. for 18 hours. Isolated via flash chromatography (silica gel, THF:hexanes (v)=1:8 as a purple solid (26 mg, 68%). $^1$H NMR (300 MHz, THF-d₈): δ 9.28 (m, 4H), 8.77 (m, 4H), 8.17 (m, 4H), 7.73 (m, 6H), 8.8 (d, J=4.5 Hz, 2H), 8.13 (m, 4H), 7.73 (m, 6H), 6.95 (d, J=9.3 Hz, 4H), 6.77 (d, J=9.6 Hz, 4H), 3.67 (s, 6H). $^{13}$C NMR (75 MHz, CDCl₃): δ 155.4, 150.4, 147.8, 144.0, 135.3, 132.7, 128.4, 128.2, 127.2, 117.8, 115.3, 55.7. UV-vis (CHCl₃, $\lambda_{max}$, nm):426, 554. IR (film, cm$^{-1}$): 3056, 2950, 2903, 2833, 2353, 1812, 1722, 1596, 1502, 1490, 1461, 1439, 1332, 1302, 1243, 1198, 1166, 1144, 1103, 1063, 1035, 1003, 920, 884, 827, 796, 751, 735, 722, 702. HRMS-EI ([M]$^+$): $C_{46}H_{32}N_4O_4Zn$, 768.162; found: 768.164.

Example 59

General Considerations for the Synthesis of meso-Chiral Porphyrins via Palladium-Mediated C—N and C—O Bond Formations All reactions were carried out under a nitrogen atmosphere in oven-dried glassware following standard Schlenk techniques. Tetrahydrofuran and toluene were distilled under nitrogen from sodium benzophenone ketyl. 5,15-dibromo-10,20-diphenylporphyrin, 5,15-dibromo-10,20-di(3',5'-di-tert-butylphenyl)porphyrin, 5,15-dibromo-10,20-di(2',6'-dimethylphenyl)porphyrin and 5,15-dibromo-10,20-di(2',4',6'-trimethylphenyl)porphyrin were synthesized by literature methods. See Lindsey et al., (1987) 52: 827; DiMagno et al., (1993) *J. Org. Chem.* 58: 5983. Thin-layer chromatography was carried out on E. Merck Silica Gel 60 F-254 TLC plates.

Example 60

General Procedures for the Etheration and the Amidation of a Bromoporphyrin

The general procedures for the etheration and amidation of bromoporphyrin follow those described by Gao et al., (2003) *Org. Lett.* 5: 3261; and Gao et al., (2004) *Org. Lett.* 6: 1837. The bromoporphyrin, chiral alcohol or amide, palladium precursor, phosphine ligand, and base were placed in an oven-dried, resealable Schlenk tube. The tube was capped with a Teflon screwcap, evacuated, and backfilled with nitrogen. The screwcap was replaced with a rubber septum, and solvent was added via syringe. The tube was purged with nitrogen for 2 min, and then the septum was replaced with the Teflon screwcap. The tube was sealed, and its contents were heated with stirring until the starting bromoporphyrin had been completely consumed as indicated by TLC analysis. The resulting mixture was cooled to room temperature, taken up in ethyl acetate, and transferred to a separatory funnel. The mixture was washed with water and concentrated in vacuo. The crude product was then purified by flash chromatography.

Example 61

General Procedures for the Synthesis of a Cobalt Porphyrin Complex

The general procedures for the synthesis of cobalt porphyrin follow those described by Tsuchida et al., (1990) *Chem. Lett.* 3: 389; Tsuchida et al., (1990) *J. Chem. Soc.-Dalton Trans.* 2713; and Komatsu et al., (1990) *J. Chem. Soc.-Chem. Commun.* 66. Free base porphyrin and anhydrous $CoCl_2$ were placed in an oven-dried, resealable Schlenk tube. The tube was capped with a Teflon screwcap, evacuated, and backfilled with nitrogen. The screwcap was replaced with a rubber septum, 2,6-lutidine and dry THF were added via syringe. The tube was purged with nitrogen for 2 minutes, and then the septum was replaced with the Teflon screwcap. The tube was sealed, and its contents were heated with stirring. The resulting mixture was cooled to room temperature, taken up in ethyl acetate and transferred to a separatory funnel. The mixture was washed with water 3 times and concentrated in vacuo.

Example 62 meso-Chiral Porphyrin 15a

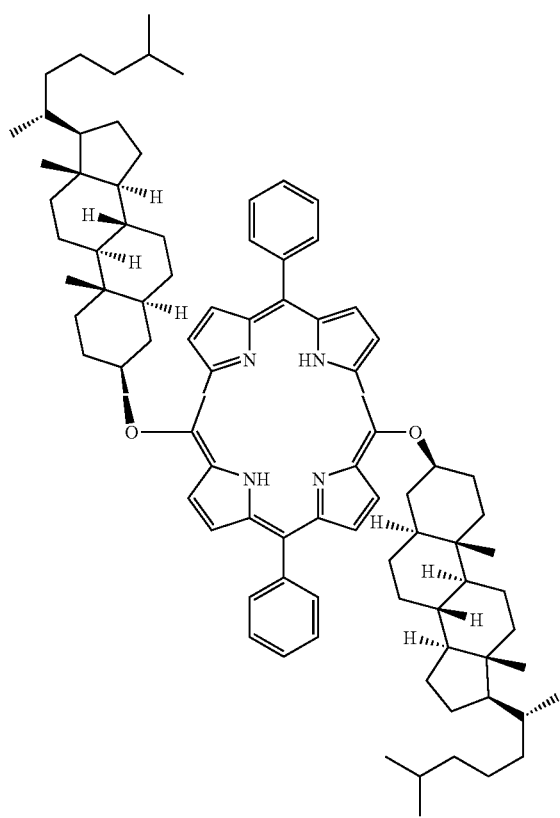

The general procedure was used to couple 5,15-dibromo-10,20-diphenylporphyrin (31.0 mg, 0.05 mmol) with (+)-dihydrocholesterol (77.8 mg, 0.2 mmol), using $Pd_2(dba)_3$ (4.6 mg, 0.005 mmol) and DPEphos (10.7 mg, 0.02 mmol) in the presence of $Cs_2CO_3$ (65.2 mg, 0.2 mmol). The reaction was conducted in toluene at 100° C. for 17 h. The title compound was isolated by flash chromatography (silica gel, methylene chloride: hexanes (v/v)=8:2) as a purple solid (27.5 mg, 45%). $^1$H NMR (300 MHz, $CDCl_3$): δ 9.43 (d, J=4.8 Hz, 4H), 8.78 (d, J=4.8 Hz, 4H), 8.18 (m, 4H), 7.74 (m, 6H), 4.95 (s, 2H), 0.62-2.3 (m, 92H), −2.59 (s, 2H). UV-vis ($CH_2Cl_2$, $\lambda_{max}$, nm): 418, 520, 557, 602, 660. HRMS-MALDI ($[M+H]^+$): calcd for $C_{86}H_{115}N_4O_2$, 1235.9015, found 1235.90110 with an isotope distribution pattern that is the same as calculated one.

Example 63

Cobalt Complex 16a

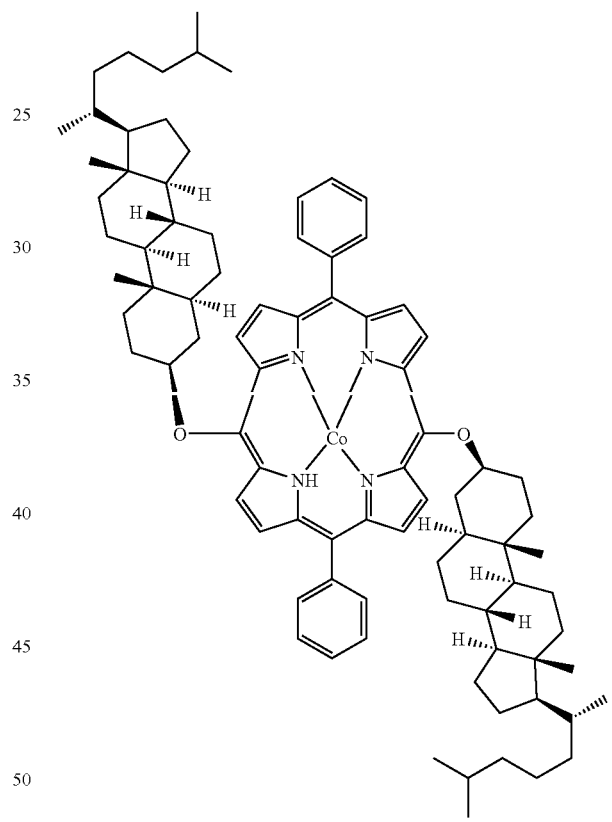

The general procedure was used for cobalt ion insertion. meso-Chiral porphyrin 15a (0.040 g), anhydrous $CoCl_2$ (0.030 g), 2,6-lutidine (0.012 mL), and dry THF (8 mL) were heated at 70° C. under $N_2$ for 15 hours. The resulting mixture was cooled to room temperature, taken up in ethyl acetate and transferred to a separatory funnel. The mixture was washed with water 3 times and concentrated in vacuo. The title compound was obtained as a red solid (0.030 g, 71%). UV-vis ($CHCl_3$, $\lambda_{max}$, nm): 412, 535, 577. HRMS-EI ($[M-1$ Cholestane+$H]^+$): calcd for $C_{59}H_{66}CoN_4O_2$, 921.4518, found 921.4487 with an isotope distribution pattern that is the same as calculated one.

Example 64 meso-Chiral Porphyrin 15b

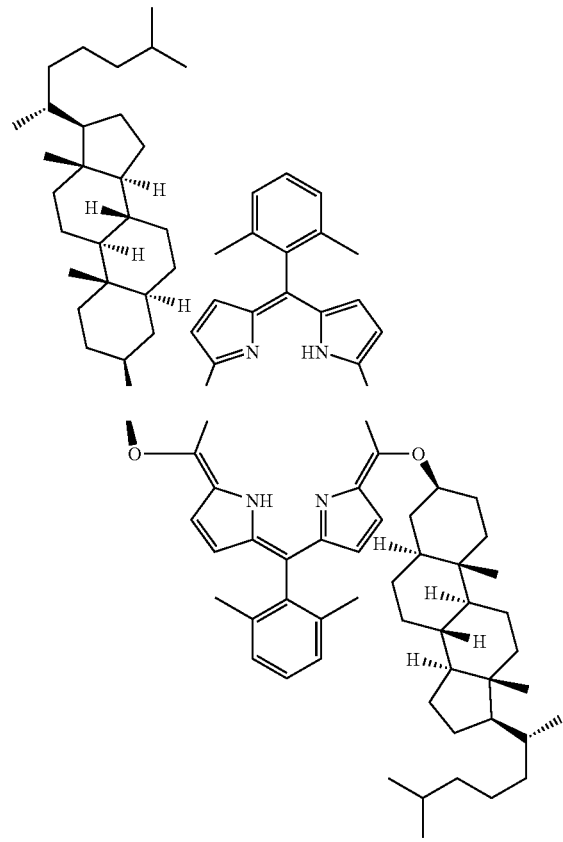

The general procedure was used to couple 5,15-dibromo-10,20-di(2',6'-dimethylphenyl)porphyrin (0.034 g, 0.05 mmol) with (+)-dihydrocholesterol (0.1556 g, 0.4 mmol), using $Pd_2(dba)_3$ (0.0046 g, 0.005 mmol) and DPEphos (0.0107 g, 0.02 mmol) in the presence of $Cs_2CO_3$ (0.0652 g, 0.2 mmol). The reaction was conducted in toluene (5 mL) at 100° C. for 20 h. The title compound was isolated by flash column chromatography (silica gel, ethyl acetate:hexanes (v/v)=1:10) as purple solids (0.053 g, 82%). $^1$H NMR (300 MHz, $CDCl_3$): δ 9.43 (d, J=4.8 Hz, 4H), 8.65 (d, J=4.8 Hz, 4H), 7.63 (t, J=7.5 Hz, 2H), 7.49 (d, J=7.5 Hz, 4H), 5.02 (m, 2H), 2.32-0.55 (m, 92H), 1.93 (s, 12H), -2.42 (s, 2H). $^{13}$C NMR (75 MHz, $CDCl_3$): δ 141.0, 139.6, 135.6, 128.2, 127.0, 117.5, 91.8, 56.4, 56.2, 54.3, 45.0, 42.5, 39.9, 39.5, 37.1, 36.1, 35.8, 35.7, 35.4, 32.0, 29.4, 28.7, 28.2, 28.0, 24.2, 23.8, 22.8, 22.6, 21.8, 21.2, 18.6, 12.6, 12.1. UV-vis ($CHCl_3$, $\lambda_{max}$, nm): 418, 518, 555, 600, 659. HRMS-MALDI ($[M+H]^+$): calcd for $C_{90}H_{123}N_4O_2$, 1291.9641; found: 1291.9650 with an isotope distribution pattern that is the same as calculated one.

Example 65

Cobalt Complex 16b

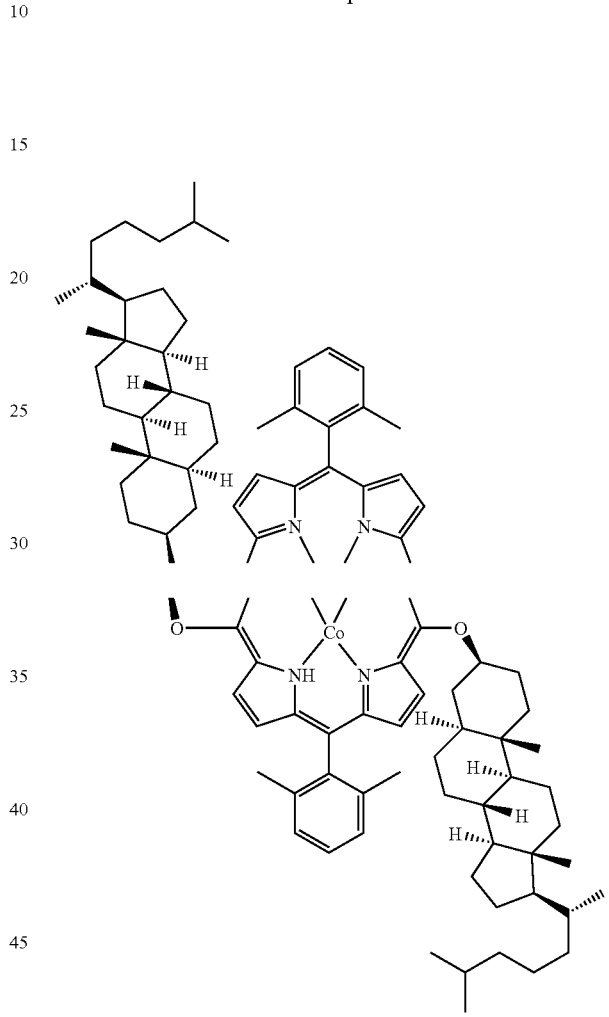

The general procedure was used for cobalt ion insertion. meso-Chiral porphyrin 15b (0.030 g), anhydrous $CoCl_2$ (0.020 g), 2,6-lutidine (0.008 mL) and dry THF (5 mL) were heated at 70° C. under $N_2$ for 14 hours. The resulting mixture was cooled to room temperature, taken up in ethyl acetate and transferred to a separatory funnel. The mixture was washed with water 3 times and concentrated in vacuo. The title compound was obtained as a red solid (0.030 g, 96%). UV-vis ($CHCl_3$, $\lambda_{max}$, nm): 411, 533, 571. HRMS-MALDI ($[M-2Cholestane+2H]^+$): calcd for $C_{36}H_{28}CoN_4O_2$, 607.1539, found 607.1570 with an isotope distribution pattern that is the same as calculated one.

Example 66 meso-Chiral Porphyrin 15c

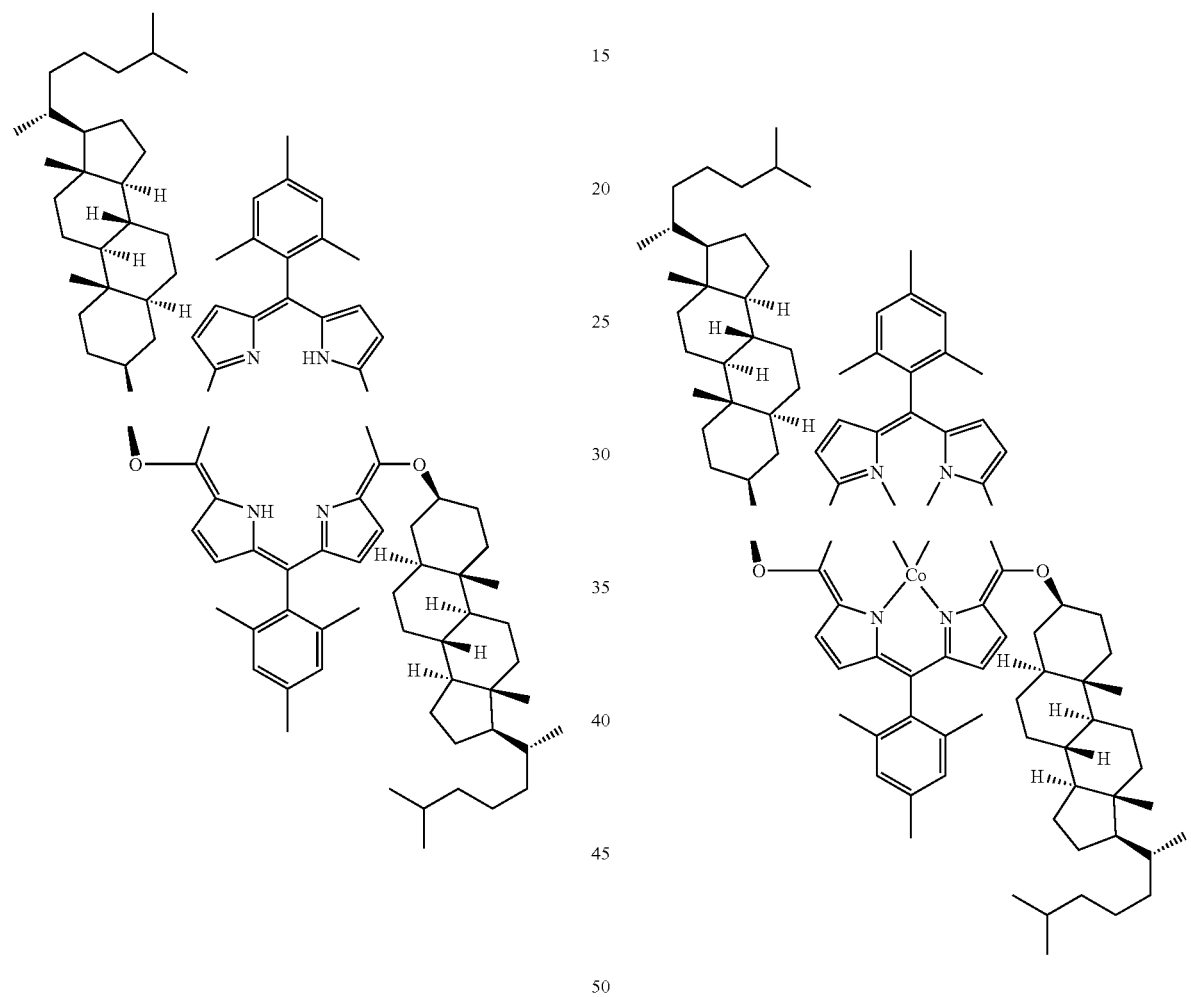

The general procedure was used to couple 5,15-dibromo-10,20-di(2',4',6'-trimethylphenyl)porphyrin (0.035 g, 0.05 mmol) with (+)-dihydrocholesterol (0.1556 g, 0.4 mmol), using $Pd_2(dba)_3$ (0.0046 g, 0.005 mmol) and DPEphos (0.0107 g, 0.02 mmol) in the presence of $Cs_2CO_3$ (0.0652 g, 0.2 mmol). The reaction was conducted in toluene (5 mL) at 100° C. for 20 h. The title compound was isolated by flash column chromatography (silica gel, ethyl acetate:hexanes (v/v)=1:10) as purple solids (0.052 g, 80%). $^1H$ NMR (300 MHz, $CDCl_3$): δ 9.42 (d, J=4.8 Hz, 4H), 8.67 (d, J=4.8 Hz, 4H), 7.32 (s, 4H), 5.02 (m, 2H), 2.31-0.55 (m, 92H), 2.67 (s, 6H) 1.90 (s, 12H), −2.43 (s, 2H). $^{13}C$ NMR (75 MHz, $CDCl_3$): δ 139.4, 138.1, 137.6, 135.5, 127.8, 117.6, 91.7, 56.4, 56.2, 54.3, 45.0, 42.5, 40.0, 39.5, 37.1, 36.1, 35.8, 35.4, 32.0, 29.4, 28.7, 28.2, 28.0, 24.2, 23.8, 22.8, 22.6, 21.7, 18.6, 12.6, 12.1. UV-vis ($CHCl_3$, $\lambda_{max}$, nm): 418, 519, 557, 601, 659. HRMS-MALDI ([M+H]$^+$): calcd for $C_{92}H_{127}N_4O_2$, 1319.9954; found: 1320.0008 with an isotope distribution pattern that is the same as calculated one.

Example 67

Cobalt Complex 16c

The general procedure was used for cobalt ion insertion. meso-Chiral porphyrin 15c (0.023 g), anhydrous $CoCl_2$ (0.020 g), 2,6-lutidine (0.008 mL) and dry THF (5 mL) were heated at 70° C. under $N_2$ for 14 hours. The resulting mixture was cooled to room temperature, taken up in ethyl acetate and transferred to a separatory funnel. The mixture was washed with water 3 times and concentrated in vacuo. The title compound was obtained as a red solid (0.021 g, 88%). UV-vis ($CHCl_3$, $\lambda_{max}$, nm): 412, 534, 574. HRMS-MALDI ([M-2Cholestane+2H]$^+$): calcd for $C_{38}H_{32}CoN_4O_2$, 635.1852, found 635.1844 with an isotope distribution pattern that is the same as calculated one.

Example 68 meso-Chiral Porphyrin 15d

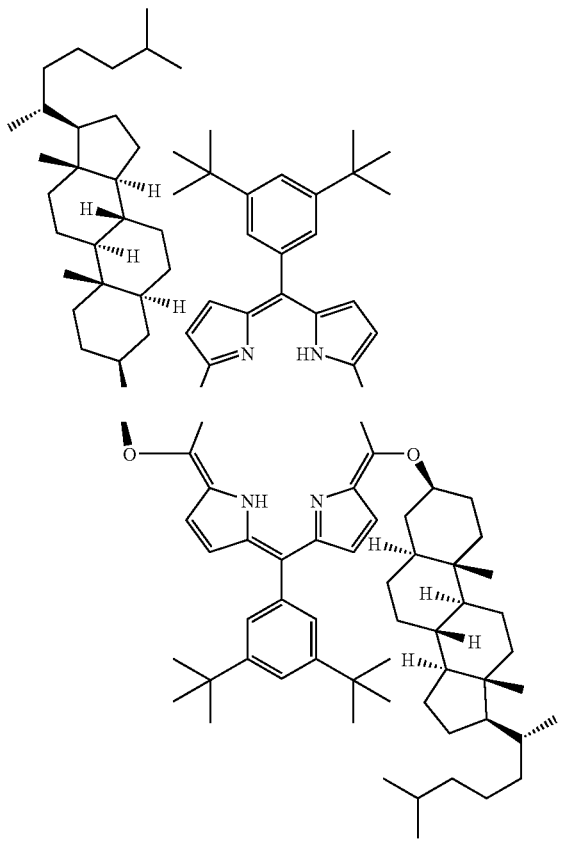

The general procedure was used to couple 5,15-dibromo-10,20-di(3,5-di-tert-butylphenyl)porphyrin (0.043 g, 0.05 mmol) with (+)-dihydrocholesterol (0.1556 g, 0.4 mmol), using $Pd_2(dba)_3$ (0.0046 g, 0.005 mmol) and DPEphos (0.0107 g, 0.02 mmol) in the presence of $Cs_2CO_3$ (0.0652 g, 0.2 mmol). The reaction was conducted in toluene (5 mL) at 100° C. for 18 h. The title compound was isolated by flash column chromatography (silica gel, ethyl acetate:hexanes (v/v)=1:20) as purple solids (0.059 g, 79%). $^1H$ NMR (300 MHz, $CDCl_3$): δ 9.46 (d, J=4.8 Hz, 4H), 8.87 (d, J=4.8 Hz, 4H), 8.09 (d, J=2.1 Hz, 4H), 7.81 (t, J=1.8 Hz, 2H), 5.01 (m, 2H), 2.26-0.61 (m, 92H), 1.57 (s, 36H), −2.48 (s, 2H). $^{13}C$ NMR (75 MHz, $CDCl_3$): δ 148.9, 140.8, 135.8, 130.6, 129.9, 127.4, 121.0, 120.8, 91.6, 56.3, 56.1, 54.2, 44.9, 42.5, 39.9, 39.5, 37.0, 36.1, 35.8, 35.7, 35.4, 35.0, 31.8, 29.3, 28.7, 28.2, 28.0, 24.1, 23.8, 22.8, 22.5, 21.9, 18.6, 12.6, 12.0. UV-vis ($CHCl_3$, $\lambda_{max}$, nm): 420, 521, 560, 604, 661. HRMS-MALDI ([M+H]$^+$): calcd for $C_{102}H_{147}N_4O_2$, 1460.1519, found 1460.1522 with an isotope distribution pattern that is the same as calculated one.

Example 69

Cobalt Complex 16d

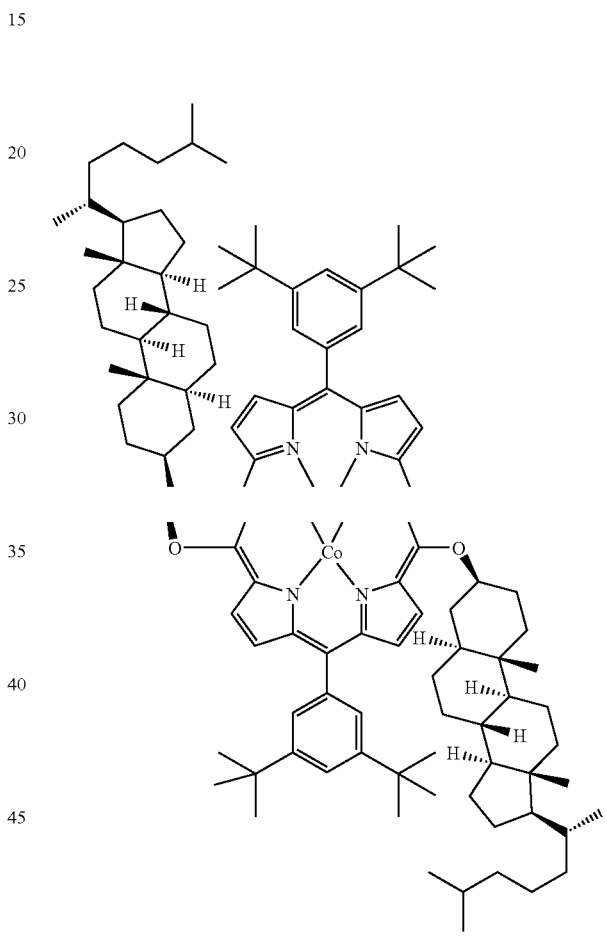

The general procedure was used for cobalt ion insertion. meso-Chiral porphyrin 15d (0.027 g), anhydrous $CoCl_2$ (0.020 g), 2,6-lutidine (0.008 mL) and dry THF (5 mL) were heated at 70° C. under $N_2$ for 14 hours. The resulting mixture was cooled to room temperature, taken up in ethyl acetate and transferred to a separatory funnel. The mixture was washed with water 3 times and concentrated in vacuo. The title compound was obtained after flash chromatography (silica gel, ethyl acetate:hexanes (v/v)=1:8) as a red solid (0.025 g, 89%). UV-vis ($CHCl_3$, $\lambda_{max}$, nm): 413, 534, 578. HRMS-MALDI ([M-2Cholestane+2H]$^+$): calcd for $C_{48}H_{52}CoN_4O_2$, 775.3422, found 775.3425 with an isotope distribution pattern that is the same as calculated one.

Example 70 meso-Chiral Porphyrin 15e

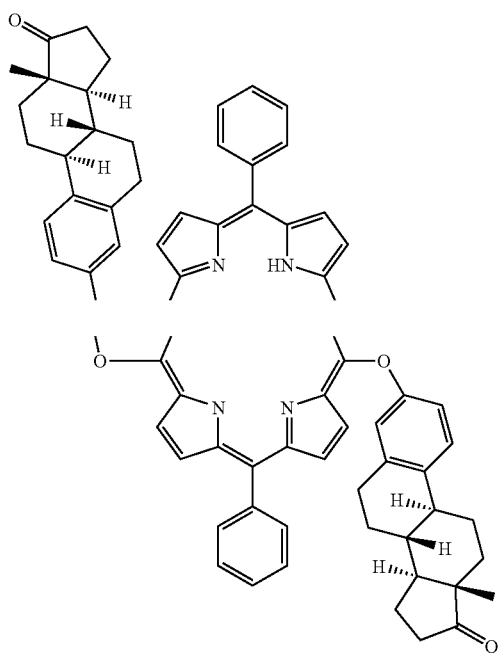

The general procedure was used to couple 5,15-dibromo-10,20-diphenylporphyrin (31.0 mg, 0.05 mmol) with (+)-estrone (108 mg, 0.2 mmol), using $Pd_2(dba)_3$ (4.6 mg, 0.005 mmol) and DPEphos (10.7 mg, 0.02 mmol) in the presence of $Cs_2CO_3$ (65.2 mg, 0.2 mmol). The reaction was conducted in toluene at 100° C. for 40 h. The title compound was isolated by flash chromatography (silica gel, methylene choloride: ethyl acetate (v/v)=9:1) as a purple solid (49.1 mg, 98%). $^1$H NMR (300 MHz, $CDCl_3$): δ 9.30 (d, J=4.5 Hz, 4H), 8.78 (d, J=4.8 Hz, 4H), 8.16 (m, 4H), 7.74 (m, 6H), 7.16 (d, J=8.4 Hz, 1H), 7.13 (d, J=8.4 Hz, 1H), 6.89 (d, J=8.4, 2.7 Hz, 1H), 6.86 (d, J=8.4, 3.0 Hz, 1H), 6.65 (d, J=3.0 Hz, 2H), 1.20-2.8 (m, 30H), 0.88 (s, 3H), 0.86 (s, 3H), −2.47 (s, 2H). $^{13}$C NMR (75 MHz, $CDCl_3$): δ 141.1, 138.1, 134.6, 133.1, 132.0, 131.3, 131.0, 127.8, 126.9, 120.2, 116.3, 114.0, 50.3, 47.9, 44.0, 38.3, 38.1, 35.9, 31.5, 29.4, 26.3, 25.8, 21.5, 13.8. UV-vis ($CH_2Cl_2$, $\lambda_{max}$, nm): 420, 517, 555, 598, 655. HRMS-EI ([M]$^+$): calcd for $C_{68}H_{62}N_4O_4$, 998.4771, found 998.4773 with an isotope distribution pattern that is the same as calculated one.

Example 71

Cobalt Complex 16e

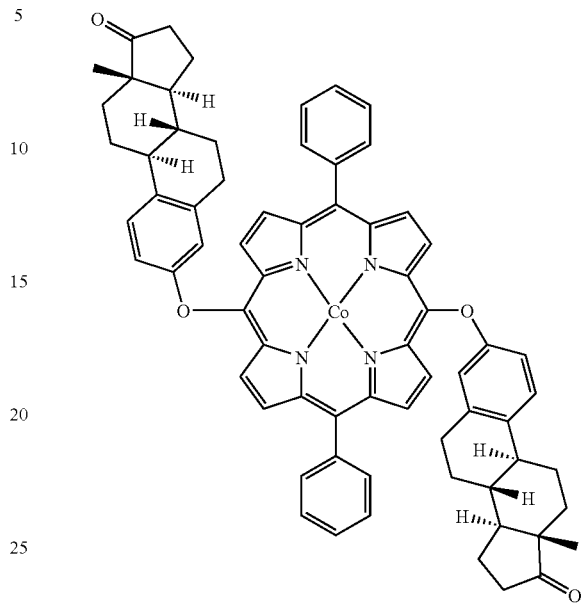

To 100 mg meso-Chiral porphyrin 15e in DMF (40 mL) was added cobalt acetate tetrahydrate (150 mg, 0.8 mmol). The solution was purged with nitrogen and heated at 160° C. for 2 h, cooled to room temperature, and poured into water. The crude product was extracted with ethyl acetate and concentrated to dry. The pure compound obtained after flash chromatography (silica gel, methylene chloride: hexanes (v/v)=8:2) as a red solid (81 mg, 77%). UV-vis ($CH_2Cl_2$, $\lambda_{max}$, nm): 413, 436, 531. HRMS-EI ([M]$^+$): calcd for $C_{68}H_{60}CoN_4O_4$, 1055.3947, found 1055.3937 with an isotope distribution pattern that is the same as calculated one.

Example 72 meso-Chiral Porphyrin 15f (Mixture of α,α and α,β)

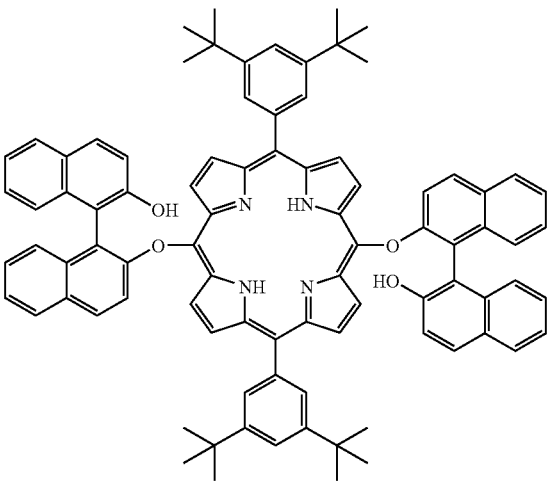

The general procedure was used to couple 5,15-dibromo-10,20-di(3,5-di-tert-butylphenyl)porphyrin (0.043 g, 0.05 mmol) with R-(+)-1,1'-bi-2-naphthol (0.167 g, 0.58 mmol), using $Pd_2(dba)_3$ (0.0046 g, 0.005 mmol) and DPEphos (0.0107 g, 0.02 mmol) in the presence of $Cs_2CO_3$ (0.0652 g, 0.2 mmol). The reaction was conducted in toluene (5 mL) at 100° C. for 20 h. The title compound was isolated by flash column chromatography (silica gel, ethyl acetate:hexanes (v/v)=1:5) as purple solids (0.022 g, 35%). $^1$H NMR (300 MHz, $CDCl_3$): δ 9.21 (d, J=4.8 Hz, 4H), 8.77 (d, J=4.8 Hz, 4H), 7.37-8.05 (m, 26H), 7.07 (d, J=16.2 Hz, 2H), 6.49 (d, J=9.6 Hz, 2H), 5.66 (s, 2H), 1.51 (m, 36H), −2.45 (s, 2H). $^{13}$C NMR (75 MHz, $CDCl_3$): δ 161.2, 151.9, 149.0, 140.0, 134.4, 133.9, 131.7, 130.8, 130.3, 129.7, 129.6, 128.9, 128.6, 128.4, 127.9, 127.4, 127.0, 125.2, 125.0, 123.7, 121.3, 117.8, 117.2, 114.5, 35.0, 31.7. UV-vis ($CHCl_3$, $\lambda_{max}$, nm): 425, 521, 558, 598, 655. HRMS-MALDI ($[M+H]^+$): calcd for $C_{88}H_{79}N_4O_4$, 1255.6096, found 1255.6045 with an isotope distribution pattern that is the same as calculated one.

Example 73

Cobalt Complex 16f

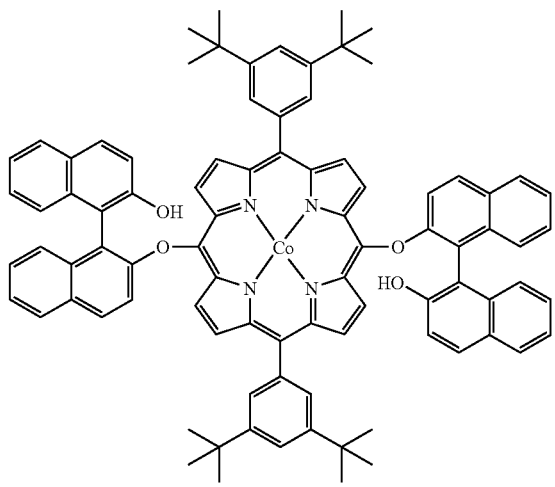

The general procedure was used for cobalt ion insertion. meso-Chiral porphyrin 15f (0.020 g), anhydrous $CoCl_2$ (0.017 g), 2,6-lutidine (0.006 mL) and dry THF (4 mL) were heated at 70° C. under $N_2$ for 14 hours. The resulting mixture was cooled to room temperature, taken up in ethyl acetate and transferred to a separatory funnel. The mixture was washed with water 3 times and concentrated in vacuo. The title compound was obtained as a red solid (0.020 g, 96%). UV-vis ($CHCl_3$, $\lambda_{max}$, nm): 417, 532, 564. HRMS-MALDI ($[M]^+$): calcd for $C_{88}H_{76}CoN_4O_4$ 1311.5199, found 1311.5225 with an isotope distribution pattern that is the same as calculated one.

Example 74

Meso-Chiral Porphyrin 17a (mixture of α,α and α,β)

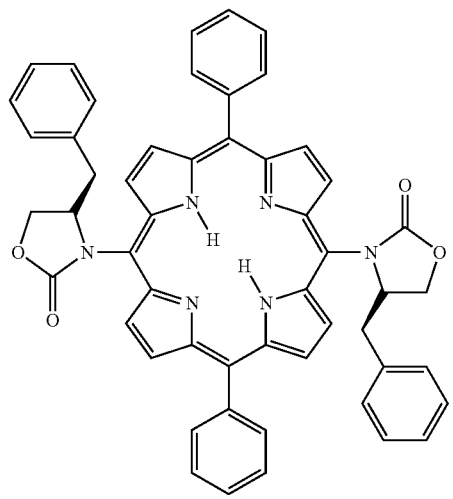

The general procedure described by Gao et al., (2004) Org. Lett., 6:1837, was used to couple 5,15-dibromo-10,20-diphenylporphyrin (31.0 mg, 0.05 mmol) with (R)-(+)-4-benzyl-2-oxazolidinone (70.8 mg, 0.4 mmol), using $Pd_2(dba)_3$ (2.3 mg, 0.0025 mmol) and Xantphos (5.78 mg, 0.01 mmol) in the presence of $Cs_2CO_3$ (65.2 mg, 0.2 mmol). The reaction was conducted in THF at 68° C. for 22 h., The title compound was isolated by flash chromatography (silica gel, methylene chloride:ethyl acetate (v/v)=9:1) as a purple mixture of two atropic isomers (25 mg, 62%, α,α/α,β=50%/50%). $^1$H NMR (300 MHz, $CDCl_3$): δ 9.46 (d, J=5.1 Hz, 4H), 9.42 (d, J=4.8 Hz, 4H), 9.24 (t, J=4.2 Hz, 4H), 9.00 (d, J=4.8 Hz, 2H), 8.96 (d, J=4.2 Hz, 4H), 8.93 (d, J=4.8 Hz, 2H), 8.32 (d, J=4.8 Hz, 2H), 8.20 (t, J=7.2 Hz, 4H), 8.06 (d, J=4.8 Hz, 2H), 7.79 (m, 12H), 7.07 (m, 6H), 7.02 (m, 6H), 6.83 (m, 8H), 5.35 (m, 2H), 5.23 (m, 2H), 5.00 (dd, J=9.0 Hz, 4H), 4.82 (dd, J=9.0 Hz, 4H), 3.13-3.30 (m, 4H), 2.94 (dd, J=13.2, 3.3 Hz, 2H), 2.70 (dd, J=13.2, 3.3 Hz, 2H), −2.84 (s, 2H), −2.89 (s, 2H); $^{13}$C NMR (75 MHz, $CDCl_3$): δ 147.1, 140.1, 140.9, 135.0, 134.6, 128.8, 128.7, 128.2, 127.1, 126.9, 126.8, 121.4, 111.5, 68.3, 66.4, 40.4, 40.3. UV-vis ($CH_2Cl_2$, $\lambda_{max}$, nm): 412, 526, 558. HRMS-MALDI ($[M+H]^+$): calcd for $C_{52}H_{41}N_6O_4$, 813.3184, found 813.3194 with an isotope distribution pattern that is the same as calculated one.

Example 75

Cobalt Complex 18a

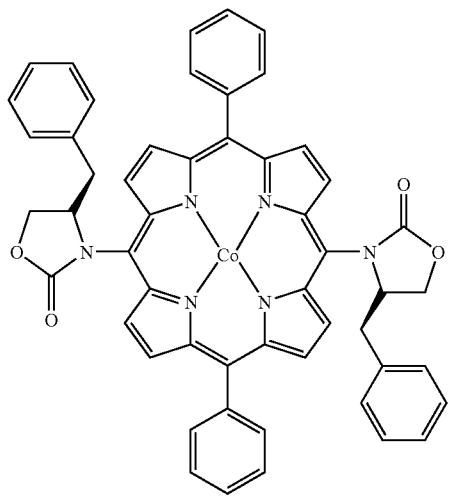

The general procedure was used for cobalt ion insertion. meso-Chiral porphyrin 17a (0.030 g), anhydrous $CoCl_2$ (0.038 g), 2,6-lutidine (0.015 mL) and dry THF (5 mL) were heated at 70° C. under $N_2$ for 14 hours. The resulting mixture was cooled to room temperature, taken up in ethyl acetate and transferred to a separatory funnel. The mixture was washed with water for 3 times and concentrated in vacuo. The title compound was obtained as a red solid (0.028 g, 87%). UV-vis ($CHCl_3$, $\lambda_{max}$, nm): 408, 528, 560. HRMS-MALDI ([M+H]$^+$): calcd for $C_{52}H_{39}CoN_6O_4$ 870.2359, found 870.2332 with an isotope distribution pattern that is the same as calculated one.

Example 76 meso-Chiral Porphyrin 17b (Mixture of α,α and α,β)

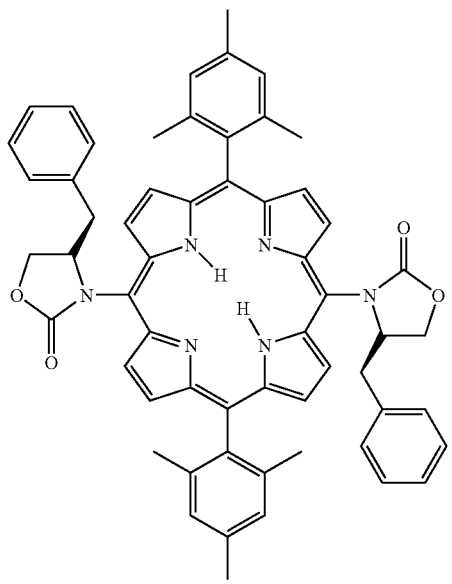

The general procedure was used to couple 5,15-dibromo-10,20-di(2',4',6'-trimethylphenyl)porphyrin (0.035 g, 0.05 mmol) with (R)-(+)$_4$-benzyl-2-oxazolidinone (0.0708 g, 0.4 mmol), using $Pd_2(dba)_3$ (0.0046 g, 0.005 mmol) and Xantphos (0.0116 g, 0.02 mmol) in the presence of $Cs_2CO_3$ (0.0652 g, 0.2 mmol). The reaction was conducted in THF (5 mL) at 80° C. for 20 h. The title compound was isolated by flash column chromatography (silica gel, ethyl acetate:hexanes (v/v)=1:2) as purple mixture of two atropic isomers (0.032 g, 72%, α,α and αβ, =50%/50%). $^1$H NMR (300 MHz, $CDCl_3$): δ 9.45 (d, J=4.8 Hz, 2H), 9.41 (d, J=4.8 Hz, 2H), 9.22 (m, 4H), 8.88 (d, J=4.8 Hz, 2H), 8.82 (m, 6H), 7.35 (m, 8H), 7.10 (m, 8H), 6.95 (m, 4H), 6.86 (m, 8H), 5.36 (m, 2H), 5.20 (m, 2H), 5.03 (m, 4H), 4.86 (m, 4H), 3.28 (m, 4H), 3.07 (dd, J=13.2, 3.6 Hz, 2H), 2.75 (dd, J=13.2, 3.3 Hz, 2H), 2.67 (s, 12H), 2.04 (s, 6H), 1.89 (s, 6H), 1.86 (s, 6H), 1.73 (s, 6H), −2.67 (s, 2H), −2.76 (s, 2H). $^{13}$C NMR (75 MHz, $CDCl_3$): δ 159.5, 139.5, 139.3, 139.1, 138.2, 137.3, 137.2, 135.0, 128.8, 128.6, 128.5, 128.1, 127.9, 127.7, 127.1, 126.9, 119.9, 111.1, 110.8, 68.8, 66.3, 40.4, 21.9, 21.7, 21.6, 21.5. UV-vis ($CHCl_3$, $\lambda_{max}$, nm): 416, 512, 544, 590, 646. HRMS-MALDI ([M+H]$^+$): calcd for $C_{58}H_{53}N_6O_4$, 897.4123, found 897.4109 with an isotope distribution pattern that is the same as calculated one.

Example 77

Cobalt Complex 18b

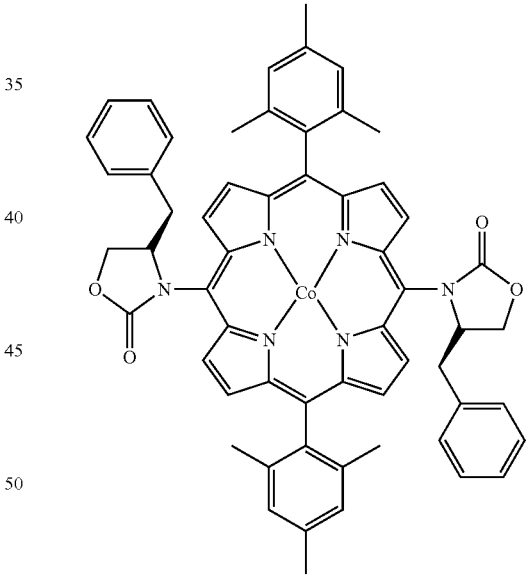

The general procedure was used for cobalt ion insertion. meso-Chiral porphyrin 17b (0.020 g), anhydrous $CoCl_2$ (0.020 g), 2,6-lutidine (0.008 mL) and dry THF (4 mL) were heated at 70° C. under $N_2$ for 14 hours. The resulting mixture was cooled to room temperature, taken up in ethyl acetate and transferred to a separatory funnel. The mixture was washed with water for 3 times and concentrated in vacuo. The title compound was obtained as a red solid (0.020 g, 94%). UV-vis ($CHCl_3$, $\lambda_{max}$, nm): 409, 528, 559. HRMS-EI ([M]$^+$): calcd for $C_{58}H_{50}CoN_6O_4$ 953.3226, found: 953.3254 with an isotope distribution pattern that is the same as calculated one.

Example 78 meso-Chiral Porphyrin 17c (Mixture of α,α and α,β)

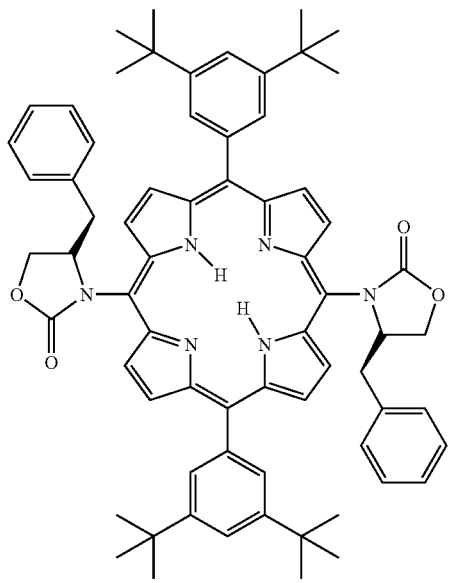

The general procedure was used to couple 5,15-dibromo-10,20-di(3',5'-di-tert-butylphenyl)porphyrin (0.043 g, 0.05 mmol) with (R)-(+)-4-benzyl-2-oxazolidinone (0.0708 g, 0.4 mmol), using $Pd_2(dba)_3$ (0.0023 g, 0.0025 mmol) and Xantphos (0.0058 g, 0.01 mmol) in the presence of $Cs_2CO_3$ (0.0652 g, 0.2 mmol). The reaction was conducted in THF (5 mL) at 80° C. for 22 h. The title compound was isolated by flash column chromatography (silica gel, ethyl acetate:hexanes (v/v)=1:3) as purple mixture of two atropic isomers (0.039 g, 79%, α,α/α,β=50%/50%). $^1$H NMR (300 MHz, $CDCl_3$): δ 9.48 (d, J=4.8 Hz, 2H), 9.46 (d, J=4.8 Hz, 2H), 9.27 (d, J=4.8 Hz, 2H), 9.25 (d, J=4.8 Hz, 2H), 9.08 (d, J=4.8 Hz, 2H), 9.04 (d, J=4.8 Hz, 2H), 9.02 (d, J=4.8 Hz, 2H), 9.00 (d, J=4.8 Hz, 2H), 8.24 (s, 2H), 8.12 (d, J=0.9 Hz, 2H), 8.07 (d, J=0.9 Hz, 2H), 7.93 (s, 2H), 7.86 (s, 4H), 7.08 (m, 12H), 6.88 (m, 8H), 5.40 (m, 2H), 5.27 (m, 2H), 5.03 (q, J=9.0 Hz, 4H), 4.84 (q, J=7.8 Hz, 4H), 3.27 (m, 4H), 3.00 (m, 2H), 2.77 (m, 2H), 1.61 (s, 18H), 1.59 (s, 18H), 1.56 (s, 18H), 1.53 (s, 18H), −2.76 (s, 2H), −2.81 (s, 2H). $^{13}$C NMR (75 MHz, $CDCl_3$): δ 159.5, 159.4, 149.3, 149.1, 149.0, 140.2, 140.0, 135.1, 130.1, 130.1, 129.8, 129.8, 128.8, 128.7, 127.1, 127.0, 122.9, 121.5, 111.4, 111.2, 68.9, 68.8, 66.3, 40.5, 40.4, 35.1, 31.8, 31.7. UV-vis ($CHCl_3$, $\lambda_{max}$, nm): 419, 514, 549, 591, 646. HRMS-MALDI ([M+H]$^+$): calcd for $C_{68}H_{73}N_6O_4$, 1037.5688; found: 1037.5677 with an isotope distribution pattern that is the same as calculated one.

Example 79

Cobalt Complex 18c

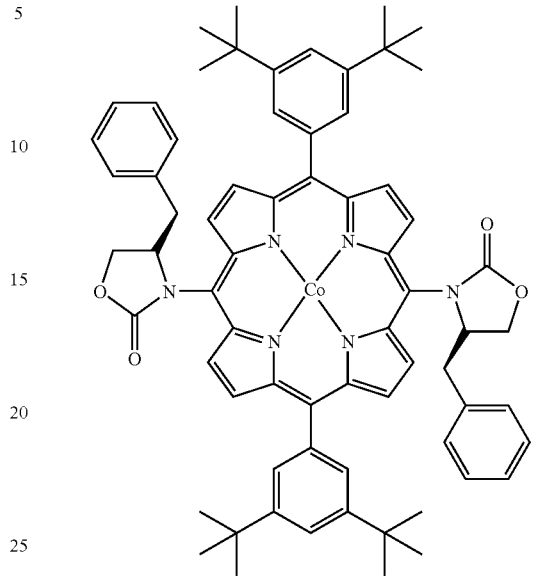

The general procedure was used for cobalt ion insertion. meso-Chiral porphyrin 17c (0.029 g), anhydrous $CoCl_2$ (0.029 g), 2,6-lutidine (0.010 mL) and dry THF (4 mL) were heated at 70° C. under $N_2$ for 14 hours. The resulting mixture was cooled to room temperature, taken up in ethyl acetate and transferred to a separatory funnel. The mixture was washed with water 3 times and concentrated in vacuo. The title compound was obtained as a red solid (0.029 g, 95%). UV-vis ($CHCl_3$, $\lambda_{max}$, nm): 409, 530, 561. HRMS-MALDI ([M+H]$^+$): calcd for $C_{68}H_{71}CoN_6O_4$, 1094.4863, found: 1094.4838 with an isotope distribution pattern that is the same as calculated one.

Example 80

General Considerations for the Synthesis of Chiralporphyrins via Palladium-catalyzed C—O and C—N Bond Formation All reactions were carried out under a nitrogen atmosphere in oven-dried glassware following standard Schlenk techniques. Toluene and THF were distilled under nitrogen from sodium benzophenone ketyl. All chiral building blocks and chemicals were purchased from Acros Organics or Aldrich Chemical Co. and used without further purification. Cesium carbonate was obtained as a gift from Chemetall Chemical Products, Inc. Palladium(II) acetate, tris(dibenzylideneacetone)dipalladium(0), bis(2-diphenylphosphinophenyl)ether (DPEphos) and 9,9-dimethyl-4,5-bis(diphenylphosphino) xanthene (Xantphos) were purchased from Strem Chemical Co. All ligands, palladium precursors and bases were stored in desiccators filled with anhydrous calcium sulfate, and weighed in the air. All bromoporphyrins were prepared according to the method described in the literature. See Lindsey et al., (1987) *J. Org. Chem.* 52: 827; DiMagno et al., (1993) *J. Org. Chem.* 58: 5983; Shi et al., (2000) *J. Org. Chem.* 65: 1650; Shanmugathasan et al., (2000) *Porphyrins Phthalocyanines* 4: 228. Porphyrin triflate was synthesized based on the procedure described below.

Example 81

General Procedure for the Synthesis of Porphyrin Triflates (22-1a, 22-1b, 22-1c and 22-2a, 22-2b, 22-2c)

Figure 9:
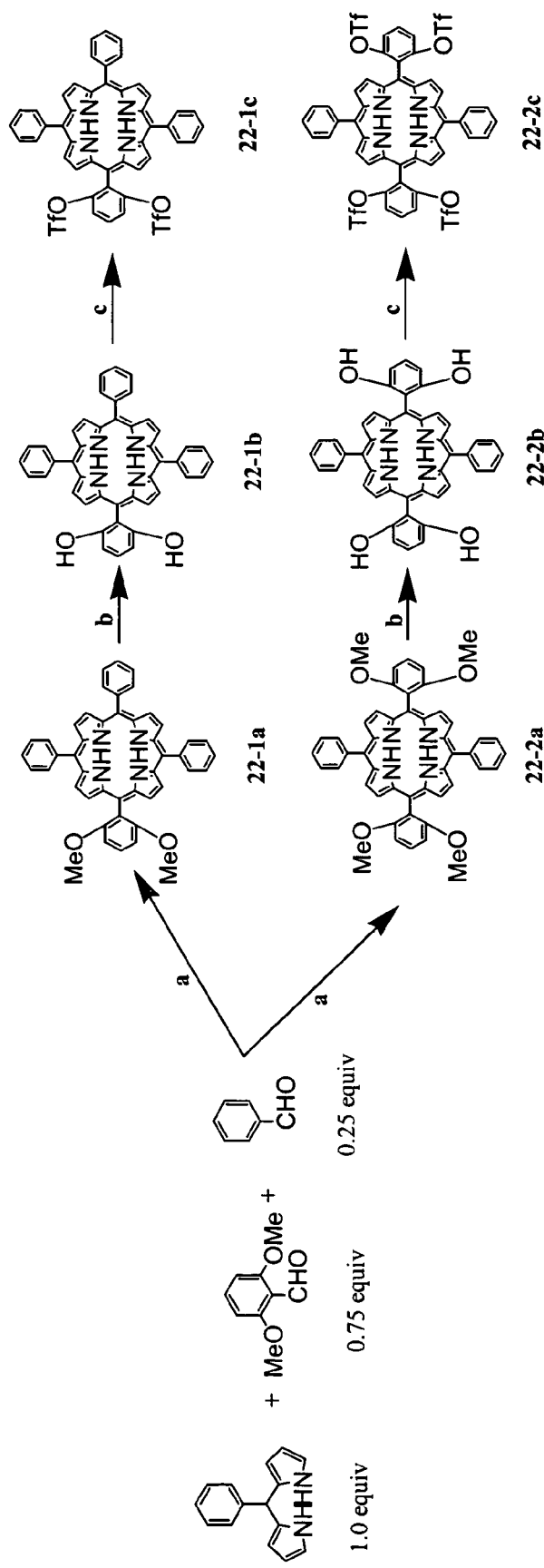
FIG. 9 provides reaction schemes for the synthesis of porphyrin triflates, e.g., compounds 22-1a, 22-1b, 22-1c and compounds 22-2a, 22-2b, 22-2c, which are representative, of the presently disclosed subject matter.

The general procedure for the synthesis of porphyrin triflates following Lindsey's method is provided in FIG. 9. See Lindsey et al., (1987) *J. Org. Chem.* 52: 827; DiMagno et al., (1993) *J. Org. Chem.* 58:5983; Shi et al., (2000) *J. Org. Chem.* 65: 1650; and Shanmugathasan et al., (2000) *J. Porphyrins Phthalocyanines* 4: 228.

Example 82

5-(2,6-Dimethoxy-phenyl)-10,15,20-triphenylporphyrin (22-1a) and 5,15-bis(2,6-Dimethoxy-phenyl)-10,20-diphenylporphyrin (22-2a)

Compounds 22-1a and 22-2a were prepared based on Lindsey's method as provided in FIG. 9. Both 22-1a (12.2% yield) and 22-2a (12.2% yield) were obtained after flash chromatography (silica gel: methylene chloride). For 22-1a, $^1$H NMR (300 MHz, CDCl$_3$) δ 8.80 (d, J=5.4 Hz, 8H), 8.20 (m, 6H), 7.72 (m, 10H), 7.01 (d, J=8.4 Hz, 2H), 3.51 (s, 6H), −2.71 (s, 2H); $^{13}$C NMR (CDCl$_3$, 75 MHz) δ 160.5, 142.3, 134.5, 130.2, 127.5, 126.6, 119.5, 104.1, 56.0. UV-vis (CH$_2$Cl$_2$, λ$_{max}$, nm): 417, 514, 546, 590, 645. HRMS-EI ([M]$^+$): calcd for C$_{46}$H$_{34}$N$_4$O$_2$, 674.2682; found: 674.2690. For 22-2a, $^1$H NMR (300 MHz, CDCl$_3$) δ 8.76 (s, 8H), 8.20 (m, 4H), 7.71 (m, 8H), 6.98 (dd, J=8.1, 1.8 Hz, 4H), 3.49 (s, 12H), −2.65 (s, 2H); $^{13}$C NMR (CDCl$_3$, 75 MHz) δ 160.5, 142.4, 134.5, 130.1, 127.4, 126.5, 119.9, 118.8, 112.1, 104.1, 56.1. UV-vis (CH$_2$Cl$_2$, λ$_{max}$, nm): 417, 513, 547, 590, 643. HRMS-EI ([M]$^+$): calcd for C$_{48}$H$_{38}$N$_4$O$_4$, 734.2893; found: 734.2906.

Example 83

5-(2,6-Dihydroxy-phenyl)-10,15,20-triphenylporphyrin (22-1b) and 5,15-bis(2,6-Dihydroxy-phenyl)-10,20-diphenylporphyrin (22-2b)

To a solution of 22-1a (or 22-2a) in anhydrous methylene, BBr$_3$ was added dropwise slowly under N$_2$ until the concentration of BBr$_3$ reached 2M. The mixture was stirred under N$_2$ in room temperature for 4-5 h. A small amount of water was then added carefully. The product was extracted with ethyl acetate and washed with water to neutral. The ethyl acetate solution was concentrated to dry and the residue was recrystallized in hexanes to give pure title compound as a purple solid (90-95% yield, in general). For 22-1b, $^1$H NMR (300 MHz, CDCl$_3$) δ 8.91 (m, 4H), 8.87 (m, 4H), 8.20 (m, 6H), 7.77 (m, 9H), 7.59 (t, J=8.1 Hz, 1H), 6.96 (d, J=8.1 Hz, 2H), 4.72 (s, 2H), −2.74 (s, 2H); $^{13}$C NMR (CDCl$_3$, 75 MHz) δ 156.2, 141.8, 141.5, 134.5, 130.9, 127.9, 126.8, 126.7, 122.0, 120.8, 115.5, 107.7, 103.2. UV-vis (CH$_2$Cl$_2$, λ$_{max}$, nm): 417, 514, 549, 588, 642. HRMS-EI ([M]$^+$): calcd for C$_{44}$H$_{30}$N$_4$O$_2$, 646.2369; found: 646.2362. For 22-2b, $^1$H NMR (300 MHz, CDCl$_3$) δ 8.95 (d, J=4.8 Hz, 4H), 8.92 (d, J=4.8 Hz, 4H), 8.17 (m, 4H), 7.78 (m, 6H), 7.61 (t, J=8.1 Hz, 2H), 6.97 (d, J=8.7 Hz, 4H), 4.66 (s, 4H), −2.77 (s, 2H); $^{13}$C NMR (CDCl$_3$, 75 MHz) δ 156.2, 141.0, 134.5, 131.2, 128.1, 126.9, 126.8, 121.3, 115.4, 107.9. UV-vis (CH$_2$Cl$_2$, λ$_{max}$, nm): 417, 513, 548, 588, 642. HRMS-EI ([M]$^+$): calcd for C$_{44}$H$_{30}$N$_4$O$_4$, 678.2267; found: 678.2257.

To a solution of 22-1b (or 22-2b) in anhydrous methylene in 0° C., pyridine (2.0 equiv per OH) and triflic anhydride (1.5 equiv per OH) was added dropwise succesively under 0° C. The mixture was stirred in 0° C. for 0.5 h and continued at room temperature for another 4-5 h. The solution was diluted with methylene chloride and washed with water to neutral. The methylene chloride solution was concentrated to dry and the residue was recrystallized in hexanes to give pure title compound as a purple solid (85-95% yield, in general). For 22-1c, $^1$H NMR (300 MHz, CDCl$_3$) δ 8.89 (d, J=4.8 Hz, 2H), 8.85 (m, 4H), 8.64 (d, J=4.8 Hz, 2H), 8.19-8.25 (m, 6H), 8.02 (t, J=8.1 Hz, 1H), 7.86 (d, J=8.1 Hz, 2H), 7.77 (m, 9H), −2.72 (s, 2H); $^{13}$C NMR (CDCl$_3$, 75 MHz) δ 150.2, 141.9, 141.8, 134.7, 134.5, 131.3, 131.0, 127.9, 127.8, 126.7, 122.1, 1201.3, 120.8, 107.7, 103.2. $^{14}$F NMR (CDCl$_3$, 75 MHz) 6-74.9. UV-vis (CH$_2$Cl$_2$, λ$_{max}$, nm): 417, 514, 548, 589, 643. HRMS-EI ([M]$^+$): calcd for C$_{46}$H$_{28}$F$_6$N$_4$O$_6$S$_2$, 910.1354; found: 910.1356. For 22-2c, $^1$H NMR (300 MHz, CDCl$_3$) δ 8.88 (d, J=4.8 Hz, 4H), 8.65 (d, J=4.8 Hz, 4H), 8.25 (m, 4H), 8.04 (t, J=8.1 Hz, 2H), 7.87 (m, 4H), 7.77 (m, 6H), −2.79 (s, 2H); $^{13}$C NMR (CDCl$_3$, 75 MHz) δ 150.2, 141.5, 134.9, 134.5, 131.5, 130.8, 127.9, 126.7, 121.5, 121.4, 121.2, 119.6, 115.4, 104.2. $^{14}$F NMR (CDCl$_3$, 75 MHz) δ −74.9. UV-vis (CH$_2$Cl$_2$, λ$_{max}$, nm): 416, 512, 546, 589, 644. HRMS-EI ([M]$^+$): calcd for C$_{48}$H$_{26}$F$_{12}$N$_4$O$_{12}$S$_4$, 1206.0238; found: 1206.0235.

Example 84

General Procedures for Synthesis of Chiralporphyrin via Palladium-catalyzed C—O-and C—N Bond Formation (Examples 85-95)

An oven-dried Schlenk tube equipped with a stirring bar was degassed on vacuum line and purged with nitrogen. The tube was then charged with palladium precursor (5 mol % per Br or triflate), phosphine ligand (10 mol % per Br or triflate), chiral building block (2-4 equiv per Br or triflate), bromoporphyrin or porphyrin triflate (0.05 mmol) and base (2.0-4.0 equiv per Br). The tube was capped with a Teflon screwcap, evacuated and backfilled with nitrogen. After the Teflon screwcap was replaced with a rubber septum, solvent (5 mL) was added. The tube was purged with nitrogen (1-2 min) and the septum was then replaced with the Teflon screwcap and sealed. The reaction mixture was heated in an oil bath with stirring and monitored by TLC. After cooling to room temperature, the reaction mixture was diluted with ethyl acetate, washed with water (3×) and concentrated to dryness. The solid residue was purified by flash chromatography.

Example 85

(R)-(+)-4-Benzyl-3-(10',20'-diphenyl-porphyrin-5'-yl)-oxazolidin-2-one

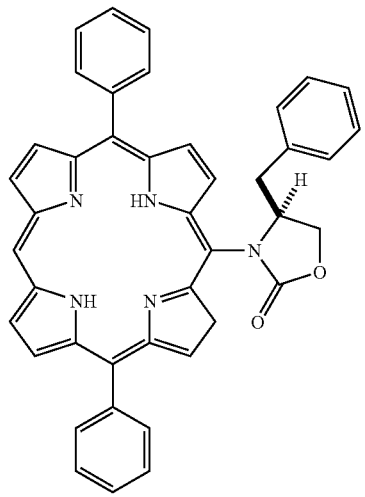

The general procedure was used to couple 5-bromo-10,20-diphenylporphin (27.1 mg, 0.05 mmol) with (R)-(+)-4-benzyl-2-oxazolidinone (35.4 mg, 0.2 mmol), using $Pd_2(dba)_3$ (2.3 mg, 0.0025 mmol) and Xantphos (5.78 mg, 0.01 mmol) in the presence of $Cs_2CO_3$ (37.6 mg, 0.1 mmol). The reaction was conducted in THF at 80° C. for 19 h. The title compound was isolated by flash chromatography (silica gel, ethyl acetate:hexanes (v/v)=4:6) as a purple-red solid (19 mg, 60%). $^1$H NMR (300 MHz, $CDCl_3$) δ 10.26 (s, 1H), 9.48 (d, J=5.4 Hz, 1H), 9.35 (d, J=4.5 Hz, 1H), 9.32 (d, J=4.8 Hz, 1H), 9.28 (d, J=4.8 Hz, 1H), 9.01-9.06 (m, 3H), 8.98 (d, J=5.2 Hz, 1H), 8.29 (t, bro., 2H), 8.17 (d, J=5.1 Hz, 2H), 7.79 (s, bro., 6H), 7.06 (s, bro., 3H), 6.82 (d, bro., 2H), 5.30 (m, bro., 1H), 5.00 (t, J=8.1 Hz, 1H), 4.84 (t, J=9.0 Hz, 1H), 3.21 (t, J=11.7 Hz, 2H), 3.21 (t, J=11.7 Hz, 2H), 2.80 (d, J=13.2 Hz, 1H), −3.03 (s, 2H); $^{13}$C NMR ($CDCl_3$, 75 MHz) δ 146.4, 141.2, 135.2, 134.7, 132.0, 131.0, 128.8, 128.7, 128.0, 127.0, 126.9, 106.7, 68.9, 66.5, 40.4. UV-vis (THF, $\lambda_{max}$, nm): 417, 476, 506, 539, 582, 638. HRMS-MALDI ($[M+H]^+$): calcd for $C_{42}H_{32}N_5O_2$, 638.2551; found: 638.2544.

Example 86

10-[17-(1,5-Dimethyl-hexyl)-10,13-dimethyl-hexadecahydro cyclopenta[a]phenanthren-3-yloxy]-5,15-diphenyl-porphyrin

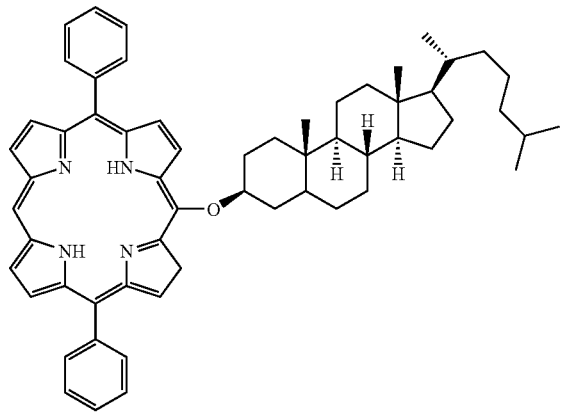

The general procedure was used to couple 5-bromo-10,20-diphenylporphin (27.1 mg, 0.05 mmol) with (+)-dihydrocholesterol (38.9 mg, 0.1 mmol), using $Pd_2(dba)_3$ (2.3 mg, 0.0025 mmol) and DPEphos (5.38 mg, 0.01 mmol) in the presence of $Cs_2CO_3$ (37.6 mg, 0.1 mmol). The reaction was conducted in THF at 100° C. for 24 h. The title compound was isolated by flash chromatography (silica gel, methylene chloride: hexanes (v/v)=8:2) as a purple-red solid (24 mg, 56%). $^1$H NMR (300 MHz, $CDCl_3$) δ 10.01 (s, 1H), 9.56 (d, J=4.8 Hz, 1H), 9.21 (d, J=4.8 Hz, 1H), 8.94 (d, J=4.8 Hz, 1H), 8.88 (d, J=4.8 Hz, 1H), 8.23 (m, 4H), 7.76 (m, 6H), 5.05 (s, bro., 1H), 2.26 (m, bro., 2H), 2.08 (q, 1H), 1.69-1.88 (m, 5H), 0.61-1.52 (m, 44), −2.76 (s, 2H); $^{13}$C NMR ($CDCl_3$, 75 MHz) δ 146.4, 143.1, 141.6, 137.7, 134.7, 131.5, 131.1, 129.9, 127.8, 127.7, 126.9, 119.3, 103.4, 92.3, 56.3, 56.1, 54.2, 44.9, 42.5, 39.9, 39.5, 37.1, 36.1, 35.8, 35.7, 35.4, 31.9, 29.4, 28.7, 28.2, 27.9, 24.1, 23.8, 22.8, 22.5, 21.2, 18.6, 12.6, 12.0. UV-vis ($CH_2Cl_2$, $\lambda_{max}$, nm): 412, 511, 546, 587, 643. HRMS-MALDI ($[M+H]^+$): calcd for $C_{59}H_{69}N_4O$, 849.5466; found: 849.5470.

Example 87

2-(10,20-Diphenyl-porphyrin-5-ylamino)-3-phenyl-propionic acid methyl ester

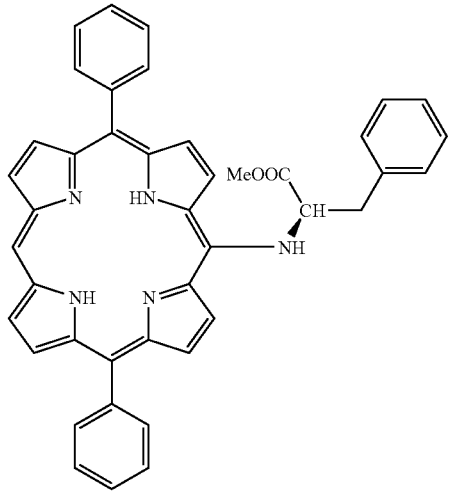

The general procedure was used to couple 5-bromo-10,20-diphenylporphin (27.1 mg, 0.05 mmol) with (L)-phenylalanine methyl ester hydrochloride (43 mg, 0.2 mmol), using Pd(OAc)$_2$ (1.12 mg, 0.005 mmol) and DPEphos (5.38 mg, 0.01 mmol) in the presence of $Cs_2CO_3$ (65.2 mg, 0.2 mmol). The reaction was conducted in THF at 100° C. for 24 h. The title compound was isolated by flash chromatography (silica gel, methylene chloride: hexanes (v/v)=8:2) as a purple-red solid (12 mg, 36%). $^1$H NMR (300 MHz, $CDCl_3$) δ 9.79 (s, 1H), 9.14 (d, J=4.8 Hz, 1H), 9.09 (d, J=4.8 Hz, 1H), 8.84 (d, J=4.8 Hz, 1H), 9.28 (d, J=4.8 Hz, 1H), 9.01-9.06 (m, 3H), 8.98 (d, J=4.8 Hz, 1H), 8.67 (d, J=4.8 Hz, 2H), 8.18 (m,4H), 7.77 (m, 6H), 7.49 (dd, J=1.5, 8.4 Hz, 2H), 7.34-7.43 (m, 3H), 6.60 (d, bro., 1H), 5.52 (d, bro, 1H), 3.63 (t, J=6.9 Hz, 1H), 3.32 (s, 3H), 2.16 (s, 2H), −2.32 (s, 2H); $^{13}$C NMR ($CDCl_3$, 75 MHz) δ 174.2, 141.7, 136.8, 134.5, 131.8, 130.8, 129.8, 128.8, 128.5, 127.6, 127.2, 126.8, 126.1, 119.4, 102.2, 72.1, 51.7, 40.8. UV-vis ($CH_2Cl_2$, $\lambda_{max}$, nm): 420, 521, 562, 660. HRMS-MALDI ($[M+H]^+$): calcd for $C_{42}H_{34}N_5O_2$, 640.2707; found: 640.2714.

Example 88

93-(10,20-Diphenyl-porphyrin-5-yloxy)-13-methyl-6,7,8,9,11,12,13,14,15,16-decahydro-cyclopenta[a]phenanthren-17-one

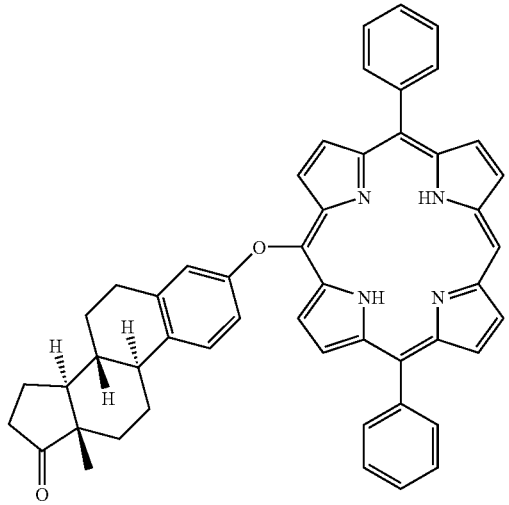

The general procedure was used to couple 5-bromo-10,20-diphenylporphin (27.1 mg, 0.05 mmol) with estrone (27 mg, 0.1 mmol), using Pd$_2$(dba)$_3$ (2.3 mg, 0.0025 mmol) and DPEphos (5.38 mg, 0.01 mmol) in the presence of Cs$_2$CO$_3$ (37.6 mg, 0.1 mmol). The reaction was conducted in THF at 100° C. for 24 h. The title compound was isolated by flash chromatography (silica gel, methylene chloride: hexanes (v/v)=8:2) as a purple-red solid (20 mg, 55%). $^1$H NMR (300 MHz, CDCl$_3$) δ 10.13 (s, 1H), 9.39 (d, J=4.8 Hz, 2H), 9.29 (d, J=4.8 Hz, 4H), 8.98 (d, J=4.8 Hz, 4H), 8.86 (d, J=4.8 Hz, 4H), 8.22 (m, 4H), 7.75 (m, 6H), 7.14 (d, J=9.0 Hz, 1H), 6.88 (d, J=8.4 Hz, 1H), 6.64 (d, J=1.8 Hz, 1H), 1.86-2.62 (m, H from estrone), 1.26-1.52 (m, H from estrone), 0.85 (s, 3H), −2.77 (s, 2H). $^{13}$C NMR (75 MHz, CDCl$_3$): δ 141.2, 138.1, 134.7, 133.0, 131.5, 130.8, 127.9, 127.8, 126.9, 126.5, 120.2, 119.7, 116.6, 114.1, 104.6, 50.3, 47.9, 44.0, 38.1, 35.8, 31.5, 29.4, 26.3, 25.8, 21.5, 13.8. UV-vis (CH$_2$Cl$_2$, λ$_{max}$, nm): 413, 510, 544, 585, 641. HRMS-EI ([M]$^+$): calcd for C$_{50}$H$_{42}$N$_4$O$_2$, 730.3308, found 730.3294.

Example 89

2'-(10,20-Diphenyl-porphyrin-5-yloxy)-[1,1']binaphthalenyl-2-ol

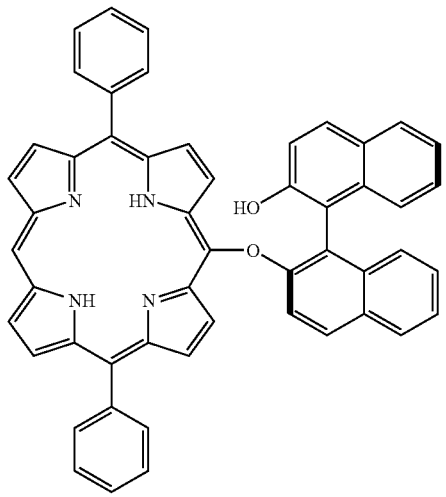

The general procedure was used to couple 5-bromo-10,20-diphenylporphin (54.2 mg, 0.1 mmol) with R-(+)-1,1'-Bi-2-naphthol (14.3 mg, 0.05 mmol), using Pd$_2$(dba)$_3$ (4.6 mg, 0.005 mmol) and DPEphos (10.8 mg, 0.02 mmol) in the presence of Cs$_2$CO$_3$ (37.6 mg, 0.1 mmol). The reaction was conducted in toluene at 100° C. for 24 h. The title compound was isolated by flash chromatography (silica gel, methylene chloride: hexanes (v/v)=8:2) as a purple-red solid (10 mg, 17%). $^1$H NMR (300 MHz, CDCl$_3$) δ 10.12 (s, 1H), 9.27 (d, J=4.8 Hz, 4H), 8.97 (d, J=4.8 Hz, 4H), 8.78 (d, J=4.8 Hz, 4H), 8.17 (m, 4H), 7.99 (d, J=9.0 Hz, 1H), 7.94 (d, J=7.5 Hz, 1H), 7.86 (d, J=8.7 Hz, 1H), 7.74 (m, 6H), 7.40-7.66 (m, 8H), 6.42 (d, J=9.6 Hz, 1H), −2.83 (s, 2H). $^{13}$C NMR (75 MHz, CDCl$_3$): δ 141.2, 134.7, 131.6, 131.0, 130.8, 130.4, 129.5, 128.6, 128.3, 127.9, 127.8, 127.6, 126.9, 125.2, 124.9, 124.6, 123.7, 119.8, 117.8, 117.2, 104.7, 88.5. UV-vis (CH$_2$Cl$_2$, λ$_{max}$, nm): 414, 511, 545, 586, 641. HRMS-EI ([M]$^+$): calcd for C$_{52}$H$_{34}$N$_4$O$_2$, 746.2682, found 746.2680.

Example 90

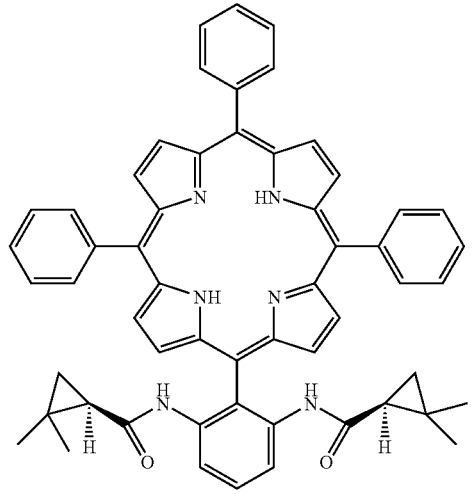

The general procedure was used to couple trifluoro-methanesulfonic acid 3-trifluoromethanesulfonyloxy-2-(10,15,20-triphenyl-porphyrin-5-yl)-phenyl ester (45.5 mg, 0.05 mmol) with (s)-(+)-2,2-dimethylcyclopropanecarboxamide (45.2 mg, 0.4 mmol), using Pd$_2$(OAc)$_2$ (2.2 mg, 0.01 mmol) and Xantphos (11.6 mg, 0.02 mmol) in the presence of Cs$_2$CO$_3$ (130.3 mg, 0.4 mmol). The reaction was conducted in THF at 100° C. for 20 h. The title compound was isolated by flash chromatography (silica gel, methylene chloride:ethyl acetate (v/v)=9:1) as a purple solid (14 mg, 34%). $^1$H NMR (300 MHz, CDCl$_3$) δ 8.89 (m, 6H), 8.81 (d, J=4.8 Hz, 2H), 8.45 (s,bro., 2H), 8.19 (d, J=6.6 Hz, 1H), 7.94 (d, J=7.5 Hz, 1H), 7.86 (d, J=8.7 Hz, 1H), 7.74 (m, 6H), 7.73-7.83 (m, 10H), 6.51 (s, 2H), 0.85 (s, 6H), 0.63 (s, 2H), 0.13 (s, 6H), 0.06 (s, 2H), −0.096 (s, 2H), −2.69 (s, 2H). $^{13}$C NMR (75 MHz, CDCl$_3$): δ 141.7, 141.4, 139.3, 134.5, 134.4, 130.2, 128.1, 126.9, 126.8, 122.0, 120.8, 29.0, 26.2, 22.3, 20.3, 18.3. UV-vis (CH$_2$Cl$_2$, λ$_{max}$, nm): 419, 515, 549, 590, 644. HRMS-EI ([M]$^+$): calcd for C$_{56}$H$_{48}$N$_6$O$_2$, 837.3839, found 837.3860.

Example 91

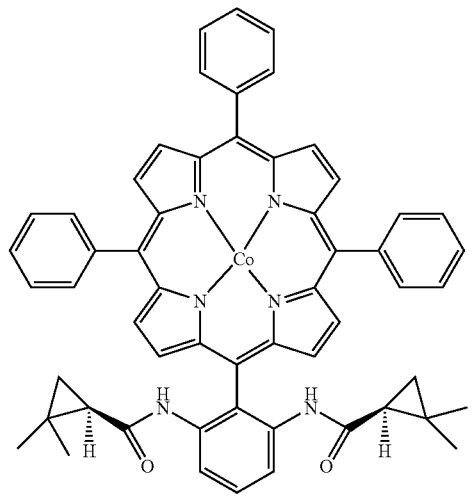

To the solution of free-base chiral porphyrin (Example 90, 21 mg, 0.0025 mmol) in 5 mL THF was added 2,6-dilutidine (8.6 µL, 0.073 mmol) and CoCl$_2$ (26 mg, 0.2 mmol). The mixture was refluxed 16 h, concentrated to dry, re-dissolved in methylene chloride and washed with water (3×), the organic layer was concentrated and the product was obtained after recrystallization in hexanes (22 mg, 98%). Since the integration of $^1$H NMR of cobalt complex was difficult to assign accurately, only the signals are provided herein. $^1$H NMR (300 MHz, CDCl$_3$) δ 15.7 (s, bro.), 12.8 (s, bro.), 10.5 (s, bro.), 9.74 (m, bro.), 7.76 (s, bro.), 1.43 (s, bro.), 1.25 (s, bro.), 0.86 (s), 0.20 (s), −1.35 (s, bro.), −3.8 (s, bro.), −5.34 (s, bro.), −6.25 (s, bro). UV-vis (CH$_2$Cl$_2$, λ$_{max}$, nm): 411, 440, 530, 554, 600. HRMS-EI ([M]$^+$): calcd for C$_{56}$H$_{46}$CoN$_6$O$_2$, 893.3014, found 893.3047.

Example 92

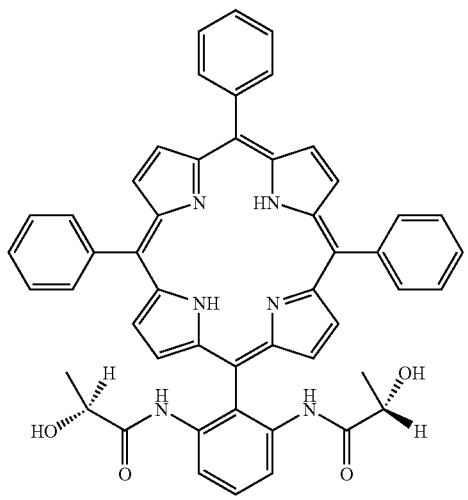

The general procedure was used to couple trifluoro-methanesulfonic acid 3-trifluoromethanesulfonyloxy-2-(10,15,20-triphenyl-porphyrin-5-yl)-phenyl ester (45.5 mg, 0.05 mmol) with L-(R)-lactamide (36 mg, 0.4 mmol), using Pd$_2$(OAc)$_2$ (2.2 mg, 0.01 mmol) and Xantphos (11.6 mg, 0.02 mmol) in the presence of Cs$_2$CO$_3$ (130.3 mg, 0.4 mmol). The reaction was conducted in THF at 100° C. for 21 h. The title compound was isolated by flash chromatography (silica gel, methylene chloride: THF (v/v)=9:1) as a purple solid (14 mg, 34%). $^1$H NMR (300 MHz, CDCl$_3$) δ 8.89 (m, 6H), 8.83 (m, 6H), 8.68 (d, J=4.8 Hz, 2H), 8.38 (d, J=8.7 Hz, 2H), 8.13 (m, 6H), 7.67-7.82 (m, 10H), 7.55 (s, 2H), 3.19 (q, J=6.0, 3.9 Hz, 2H), 0.40 (d, J=6.6 Hz 6H), 0.06 (s, 2H), −0.096 (s, 2H), −2.69 (s, 2H). $^{13}$C NMR (75 MHz, CDCl$_3$): δ 172.1, 141.3, 138.4, 134.6, 134.4, 130.4, 128.0, 126.9, 126.7, 120.9, 117.4, 67.7, 20.1. UV-vis (CH$_2$Cl$_2$, λ$_{max}$, nm): 418, 515, 550, 589, 644. HRMS-EI ([M]$^+$): calcd for C$_{50}$H$_{40}$N$_6$O$_4$, 788.3111, found 788.3127.

Example 93

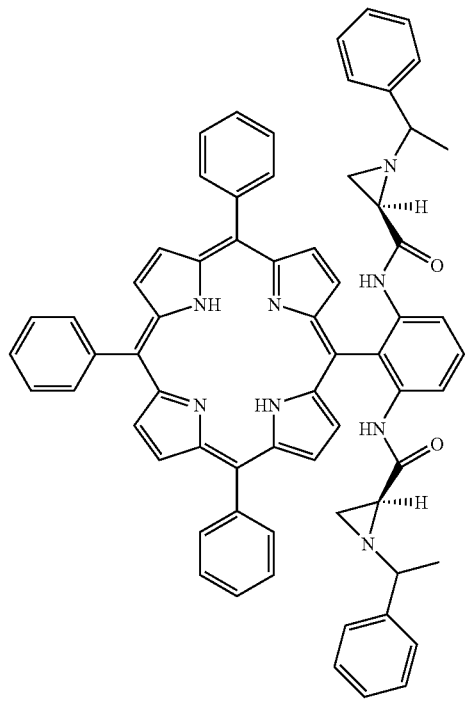

The general procedure was used to couple trifluoro-methanesulfonic acid 3-trifluoromethanesulfonyloxy-2-(10,15,20-triphenyl-porphyrin-5-yl)-phenyl ester (45.5 mg, 0.05 mmol) with 1-[1'-(R)-α-methylbenzyl]-aziridine-2(R)-carboxamide (64 mg, 0.4 mmol), using Pd$_2$(OAc)$_2$ (2.2 mg, 0.01 mmol) and Xantphos (11.6 mg, 0.02 mmol) in the presence of Cs$_2$CO$_3$ (130.3 mg, 0.4 mmol). The reaction was conducted in THF at 100° C. for 22 h. The title compound was isolated by flash chromatography (silica gel, methylene chloride:ethyl acetate (v/v)=9:1) as a purple solid (39 mg, 80%). $^1$H NMR (300 MHz, CDCl$_3$) δ 8.84 (t, J=4.8 Hz, 4H), 8.78 (d, J=4.8 Hz, 2H), 8.73 (d, J=4.8 Hz, 2H), 8.62 (d, J=8.1 Hz, 2H), 8.18-8.23 (m, 6H), 7.72-7.88 (m, 9H), 7.62-7.68 (m, 1H), 5.80 (t, J=7.5 Hz, 2H), 4.33 (t, J=7.5 Hz, 2H), 3.78 (d, J=7.2 Hz, 4H), 2.03 (s, 1H), 1.52 (dd, J=7.2, 3.0 Hz, 2H), 0.57 (d, J=6.3 Hz, 2H), 0.53 (dd, J=7.2, 3.0 Hz, 4H), −0.76 (d, J=5.7 Hz, 6H), −2.35 (s, 2H). $^{13}$C NMR (75 MHz, CDCl$_3$): δ 168.2, 142.0, 141.5, 140.9, 138.9, 134.3, 130.5, 127.8, 126.7, 125.9, 125.4, 124.2, 120.8, 120.7, 115.1, 106.2, 66.7, 39.4, 33.7, 20.4. UV-vis (CH$_2$Cl$_2$, λ$_{max}$, nm): 418, 513, 547, 588, 643. HRMS-EI ([M]$^+$): calcd for C$_{66}$H$_{54}$N$_8$O$_2$, 990.4370, found 990.4412.

Example 94

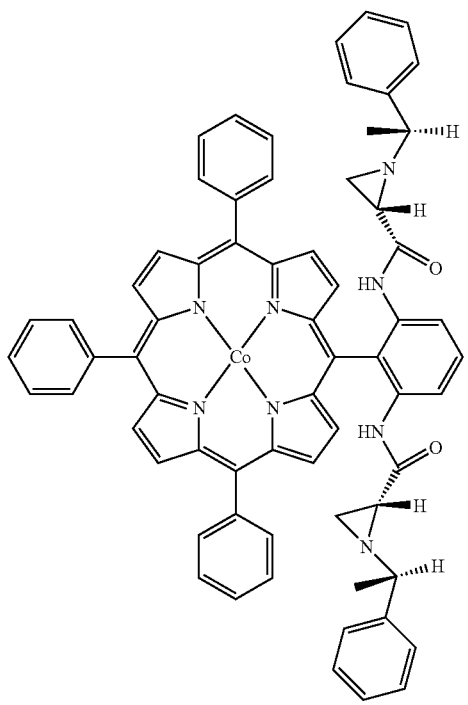

To the solution of free-base chiral porphyrin (Example 93, 12 mg, 0.0125 mmol) in 5 mL DMF was added Co(OAc)$_2$·4H$_2$O (25 mg, 0.1 mmol). The mixture was refluxed 2 h, concentrated to dry, re-dissolved in ethyl acetate and washed with water (3×), the organic layer was concentrated and the product was obtained after recrystallization in hexanes (10.7 mg, 82%). Since the integration of $^1$H NMR of cobalt complex was difficult to assign accurately, only the signals are provided herein. $^1$H NMR (300 MHz, CDCl$_3$) δ 17.0 (s, bro.), 14.2 (s, bro.), 11.2 (s, bro.), 10.19-10.40 (m), 8.74 (m, bro.), 7.76 (s, bro.), 1.25 (s, bro.), −0.61 (s, bro.), −1.98 (s, bro.), −5.89 (s, bro.), −6.09 (s, bro), −12.1 (s, bro). UV-vis (CH$_2$Cl$_2$, λ$_{max}$, nm): 409, 526. HRMS-EI ([M]$^+$): calcd for C$_{66}$H$_{52}$CoN$_8$O$_2$, 1047.3545, found 1047.3489.

Example 95

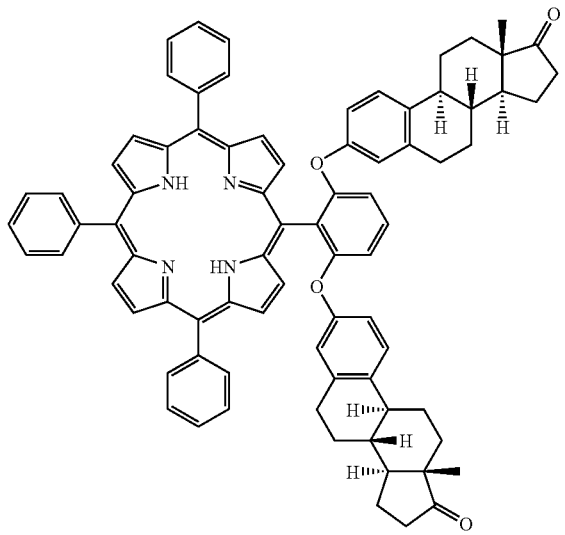

The general procedure was used to couple trifluoro-methanesulfonic acid 3-trifluoromethanesulfonyloxy-2-(10,15,20-triphenyl-porphyrin-5-yl)-phenyl ester (45.5 mg, 0.05 mmol) with estrone (54 mg, 0.2 mmol), using Pd$_2$(dba)$_3$ (4.6 mg, 0.005 mmol) and Xantphos (5.8 mg, 0.01 mmol) in the presence of Cs$_2$CO$_3$ (65.2 mg, 0.2 mmol). The reaction was conducted in toluene at 80° C. for 24 h. The title compound was isolated by flash chromatography (silica gel, methylene chloride) as a purple solid (39 mg, 67%). $^1$H NMR (300 MHz, CDCl$_3$) δ 8.85 (m, 8H), 8.28 (s, bro., 2H), 8.13 (m, 4H), 8.01 (s, bro, 1H), 7.62-7.82 (m, 11H), 7.56 (m, 2H), 7.38 (m, 4H), 2.78 (m, 1H), 2.13 (s, 6H), 0.08-1.76 (m, H from estrone), −2.75 (s, 2H). $^{13}$C NMR (75 MHz, CDCl$_3$): δ 157.7, 149.6, 143.3, 141.8, 134.6, 134.1, 131.1, 130.5, 128.9, 128.3, 127.9, 127.1, 126.8, 126.7, 125.2, 122.5, 122.0, 121.1, 120.8, 118.2, 115.7, 113.1, 102.8, 49.3, 47.2, 43.3, 37.1, 35.0, 30.9, 30.4, 29.7, 29.2, 25.5, 25.1, 21.0, 13.3. UV-vis (CH$_2$Cl$_2$, λ$_{max}$, nm): 421, 474, 513, 547, 5988, 643. MS-EI ([M-estrone-2]$^+$): 880.4.

Example 96

General Considerations for Bromoporphyrins as Versatile Synthons for Modular Construction of Chiral Porphyrins: Cobalt-Catalyzed Highly Enantioselective and Diastereoselective Cyclopropanation All cross-coupling reactions were carried out under a nitrogen atmosphere in oven-dried glassware following standard Schlenk techniques. Tetrahydrofuran (THF) and toluene were distilled under nitrogen from sodium benzophenone ketyl. Chiral amides were purchased from Aldrich Chemical Co. and Acros Organics, used without further purification. Anhydrous cobalt(II) chloride, cobalt acetate tetrahydrate, palladium(II) acetate, and 9,9-dimethyl-4,5-bis(diphenylphosphino)xanthene (Xantphos) were purchased from Strem Chemical Co. Cesium carbonate was obtained as a gift from Chemetall Chemical Products, Inc.

2,6-Dibromobenzaldehyde was synthesized according to the literature (Luliński et al., (2003) *J. Org. Chem.* 68: 5384). $^1$H NMR (300 MHz, CDCl$_3$): δ 10.24 (s, 1H), 7.63 (d, J=8.1 Hz, 2H), 7.20 (t, J=8.1 Hz, 1H).

2,6-Dibromo-4-trimethylsilylbenzaldehyde was synthesized according to the literature (*Luliński et al.,* (2003) *J. Org. Chem.* 68: 5384). $^1$H NMR (300 MHz, CDCl$_3$): δ 10.26 (s, 1H), 7.70 (s, 2H), 0.31 (s, 9H).

meso-(2,6-dibromophenyl)dipyrromethane was synthesized according to literature method (Naik et al., (2003) *Tetrahedron* 59: 2207) using Amberlyst 15 resin. $^1$H NMR (300 MHz, CDCl$_3$): δ 8.29 (s, 2H), 7.56 (d, J=8.1 Hz, 2H), 6.95 (t, J=8.1 Hz, 1H), 6.72 (s, 2H), 6.53 (s, 1H), 6.19 (m, 2H), 6.13 (s, 2H).

Example 97

General Procedures for Synthesis of Brominated Porphyrins

The brominated porphyrins were prepared according to the method described in literature. See Lindsey et al., (1989) *J.*

*Org. Chem.* 54: 828; Lindsey (2000) In *The Porphyrin Handbook*; Kadish, K. M., Smith, K. M., Guilard, R., Eds., Academic Press: San Diego, Calif., Vol. 1; pp 45-118. A mixture of meso-(2,6-dibromophenyl)dipyrromethane (1 mmol), aldehyde (1 mmol), and molecular sieves (4A, 0.300 g) in chloroform (150 mL) was purged with nitrogen for 10 min. Boron trifluoride diethyl etherate (0.1 mL) was added dropwise via a syringe and the flask was wrapped with aluminum foil to shield it from light. The solution was stirred under a nitrogen atmosphere at room temperature for 3 h, and 2,3-dichloro-5,6-dicyano-1,4-benzoquinone (DDQ) (1.2 mmol) was added as powder at one time. After 30 min, 1 mL of triethylamine was added. The reaction solution was then directly poured on the top of a silica gel column that was packed with dichloromethane. The column was eluted with dichloromethane. The fractions containing product were collected and concentrated on a rotary evaporator. The residue was washed several times with hexanes to afford the pure compound.

Example 98

5,15-Bis(2,6-dibromophenyl)-10,20-diphenylporphyrin 19a

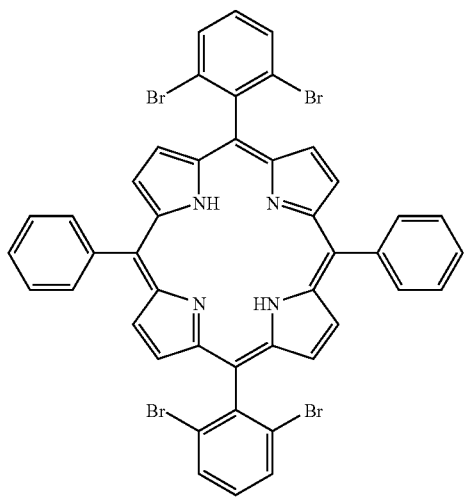

Purple solid. Yield: 41%. $^1$H NMR (300 MHz, CDCl$_3$): δ 8.84 (d, J=4.8 Hz, 4H), 8.63 (d, J=4.8 Hz, 4H), 8.22 (m, 4H), 8.01 (d, J=8.1 Hz, 4H), 7.73 (m, 6H), 7.52 (t, J=8.1 Hz, 2H), −2.61 (s, 2H). UV-vis (CH$_2$Cl$_2$), λ$_{max}$ nm (log ε): 419(5.65), 515(4.31), 548(3.76), 590(3.81), 646(3.41). HRMS-MALDI ([M+H]$^+$): calcd for C$_{44}$H$_{27}$Br$_4$N$_4$ 926.8964; found: 926.8992 with an isotope distribution pattern that is the same as the calculated one.

Example 99

5,15-Bis(2,6-dibromophenyl)-10,20-bis[4-(tert-butyl)phenyl]porphyrin 19b

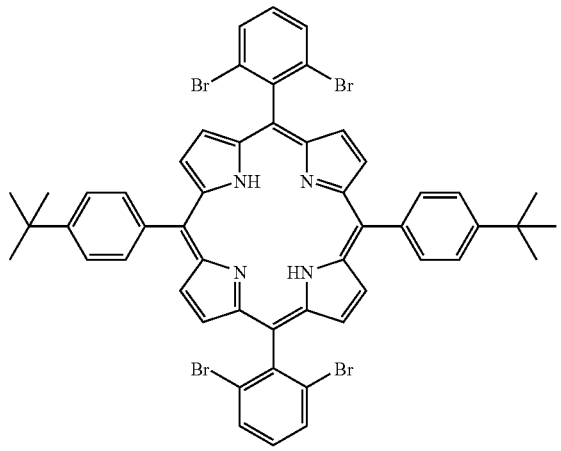

Purple solid. Yield: 61%. $^1$H NMR (300 MHz, CDCl$_3$): δ 8.88 (d, J=4.8 Hz, 4H), 8.61 (d, J=4.8 Hz, 4H), 8.14 (d, J=8.1 Hz, 4H), 8.01 (d, J=8.1 Hz, 4H), 7.73 (d, J=8.1 Hz, 4H), 7.52 (t, J=8.1 Hz, 2H), 1.52 (s, 18H), −2.57 (s, 2H). UV-vis (CH$_2$Cl$_2$), λ$_{max}$ nm (log ε): 421(5.68), 516(4.31), 551(3.82), 592(3.81), 647(3.47). HRMS-MALDI ([M+H]$^+$): calcd for C$_{52}$H$_{43}$Br$_4$N$_4$ 1039.0216; found: 1039.0236 with an isotope distribution pattern that is the same as the calculated one.

Example 100

5,15-Bis(2,6-dibromophenyl)-10,20-bis(4-trifluoromethylphenyl)porphyrin 19c

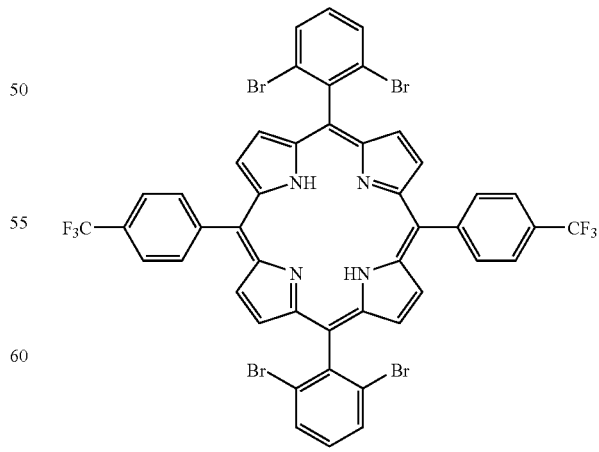

Purple solid. Yield: 45%. $^1$H NMR (300 MHz, CDCl$_3$): δ 8.77 (d, J=4.8 Hz, 4H), 8.66 (d, J=4.8 Hz, 4H), 8.36 (d, J=8.1

Hz, 4H), 8.03 (d, J=8.1 Hz, 4H), 8.01 (d, J=8.1 Hz, 4H), 7.54 (t, J=8.1 Hz, 2H), −2.63 (s, 2H). UV-vis (CH$_2$Cl$_2$), λ$_{max}$ nm (log ε): 419(5.65), 514(4.31), 547(3.67), 589(3.82), 644(3.20). HRMS-EI ([M]$^+$): calcd for C$_{46}$H$_{24}$Br$_4$F$_6$N$_4$ 1061.8639; found: 1061.8623 with an isotope distribution pattern that is the same as the calculated one.

Example 101

5,15-Bis(2,6-dibromophenyl)-10,20-bis(2,3,4,5,6-Pentafluorophenyl)porphyrin 19d

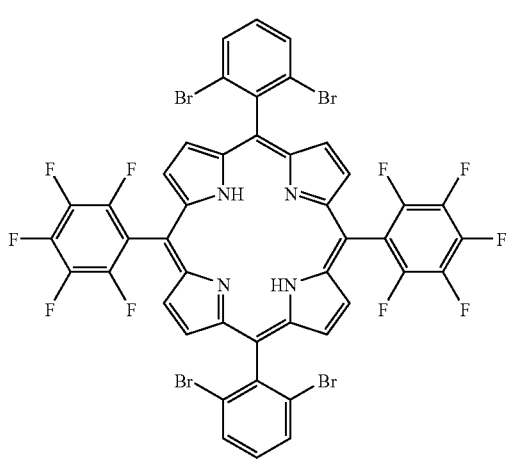

Purple solid. Yield: 19%. $^1$H NMR (300 MHz, CDCl$_3$): δ 8.78 (d, J=4.8 Hz, 4H), 8.73 (d, J=4.8 Hz, 4H), 8.04 (d, J=8.1 Hz, 4H), 7.57 (t, J=8.1 Hz, 2H), −2.68 (s, 2H). UV-vis (CH$_2$Cl$_2$), λ$_{max}$ nm (log ε): 416(5.62), 511(4.40), 547(3.72), 588(4.09), 643(3.35). HRMS-MALDI ([M+H]$^+$): calcd for C$_{44}$H$_{17}$Br$_4$F$_{10}$N$_4$ 1106.8022; found: 1106.8009 with an isotope distribution pattern that is the same as the calculated one.

Example 102

5,15-Bis(2,6-dibromophenyl)-10,20-bis(4-acetylphenyl)porphyrin 19e

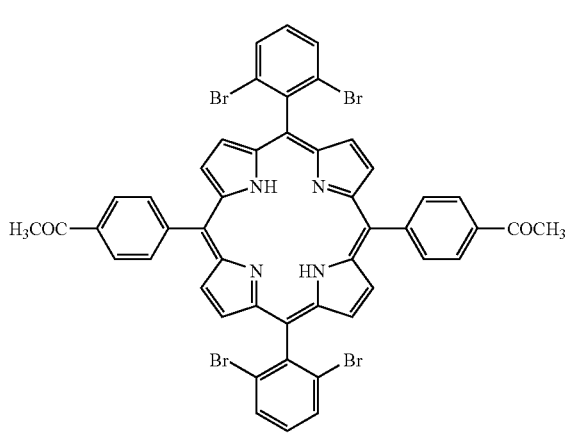

Purple solid. Yield: 45%. $^1$H NMR (300 MHz, CDCl$_3$): δ 8.79 (d, J=4.8 Hz, 4H), 8.66 (d, J=4.8 Hz, 4H), 8.35 (s, 8H), 8.02 (d, J=8.1 Hz, 4H), 7.54 (t, J=8.1 Hz, 2H), 2.89 (s, 6H), −2.61 (s, 2H). UV-vis (CH$_2$Cl$_2$), λ$_{max}$ nm (log ε): 421(5.59), 516(4.37), 549(3.79), 591(3.87), 646(3.44). HRMS-MALDI ([M+H]$^+$): calcd for C$_{48}$H$_{31}$Br$_4$N$_4$O$_2$ 1010.9175 found: 1010.9171 with an isotope distribution pattern that is the same as the calculated one.

Example 103

5,15-Bis(2,6-dibromophenyl)-10,20-dimesitylporphyrin 19f

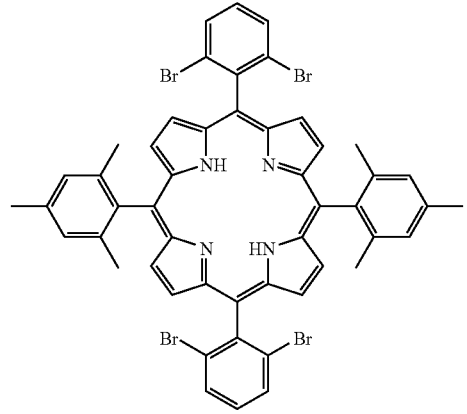

Purple solid. Yield: 41%. $^1$H NMR (300 MHz, CDCl$_3$): δ 8.66 (d, J=4.8 Hz, 4H), 8.53 (d, J=4.8 Hz, 4H), 8.00 (d, J=8.1 Hz, 4H), 7.50 (t, J=8.1 Hz, 2H), 7.25 (s, 4H), 2.60 (s, 6H), 1.84 (s, 12H), −2.49 (s, 2H). UV-vis (CH$_2$Cl$_2$), λ$_{max}$ nm (log ε): 419(5.75), 515(4.39), 547(3.79), 591(3.90), 647(3.46). HRMS-MALDI ([M+H]$^+$): calcd for C$_{50}$H$_{39}$Br$_4$N$_4$ 1010.9903; found: 1010.9907 with an isotope distribution pattern that is the same as the calculated one.

Example 104

5,15-Bis(2,6-dibromophenyl)-10,20-bis(2,6-dimethoxyphenyl)porphyrin 19g

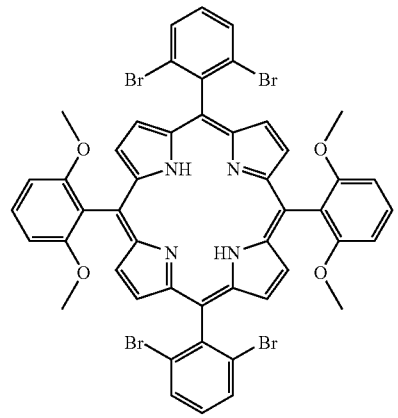

Purple solid. Yield: 69%. $^1$H NMR (300 MHz, CDCl$_3$): δ 8.73 (d, J=4.8 Hz, 4H), 8.53 (d, J=4.8 Hz, 4H), 7.98 (d, J=8.1 Hz, 4H), 7.69 (t, J=8.1 Hz, 2H), 7.48 (t, J=8.1 Hz, 2H), 6.97 (d, J=8.7 Hz, 4H), 3.51 (s, 12H), −2.49 (s, 2H). UV-vis (CH$_2$Cl$_2$), λ$_{max}$ nm (log ε): 420(5.79), 515(4.45), 545(3.72), 590(3.95), 644(3.26). HRMS-MALDI ([M+H]$^+$): calcd for C$_{48}$H$_{35}$Br$_4$N$_4$O$_4$ 1046.9386; found: 1046.9434 with an isotope distribution pattern that is the same as the calculated one.

Example 105

5,15-Bis(2,6-dibromophenyl)-10,20-bis(3,5-dimethoxyphenyl)porphyrin 19h

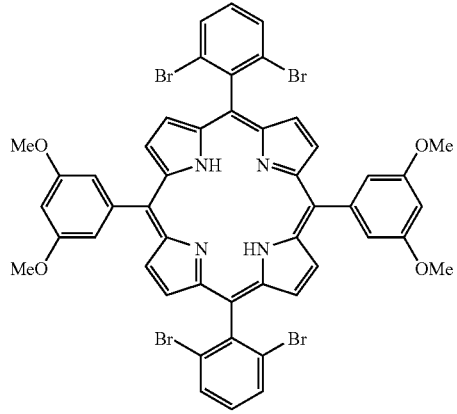

Purple solid. Yield: 55%. $^1$H NMR (300 MHz, CDCl$_3$): δ 8.92 (d, J=4.8 Hz, 4H), 8.61 (d, J=4.8 Hz, 4H), 8.01 (d, J=8.1 Hz, 4H), 7.52 (t, J=8.1 Hz, 2H), 7.40 (t, J=2.4 Hz, 4H), 6.87 (d, J=2.4 Hz, 2H), 3.94 (s, 12H), −2.65 (s, 2H). UV-vis (CH$_2$Cl$_2$), λ$_{max}$, nm (log ε): 421(5.79), 515(4.44), 548(3.80), 590(3.96), 645(3.50). HRMS-MALDI ([M+H]$^+$): calcd for C$_{48}$H$_{35}$Br$_4$N$_4$O$_4$ 1046.9386; found: 1046.9423 with an isotope distribution pattern that is the same as the calculated one.

Example 106

5,15-Bis(2,6-dibromophenyl)-10,20-bis[3.5-di(tert-butyl)phenylporphyrin 19i

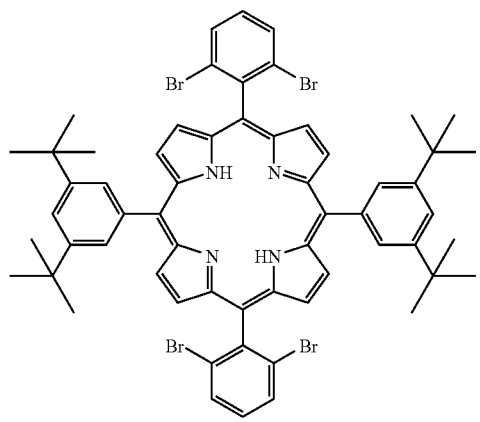

Purple solid. Yield: 69%. $^1$H NMR (300 MHz, CDCl$_3$): δ 8.90 (d, J=4.8 Hz, 4H), 8.65 (d, J=4.8 Hz, 4H), 8.11 (d, J=1.5 Hz, 4H), 8.01 (d, J=8.1 Hz, 4H), 7.79 (t, J=1.8 Hz, 2H), 7.51 (t, J=8.1 Hz, 2H), 1.53 (s, 36H), −2.52 (s, 2H). $^{13}$C NMR (75 MHz, CDCl$_3$): δ 148.8, 143.6, 140.6, 132.3, 131.4, 131.0, 129.9, 129.3, 128.5, 121.6, 121.1, 118.1, 35.1, 31.7. UV-vis (CH$_2$Cl$_2$), λ$_{max}$ nm (log ε): 421(5.69), 516(4.30), 551(3.79), 592(3.79), 648(3.50). HRMS-MALDI ([M+H]$^+$): calcd for C$_{60}$H$_{59}$Br$_4$N$_4$ 1151.1468; found: 1151.1459 with an isotope distribution pattern that is the same as the calculated one.

Example 107

5,15-Bis(2,6-dibromophenyl)-10,20-bisheptylporphyrin 19i

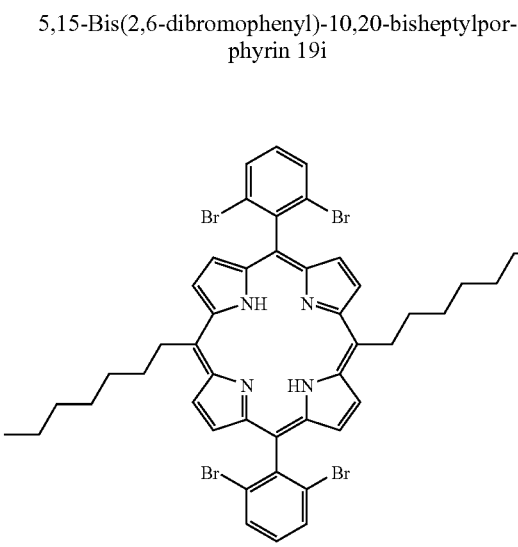

Purple solid. Yield: 53%. $^1$H NMR (300 MHz, CDCl$_3$): δ 9.40 (d, J=4.8 Hz, 4H), 8.66 (d, J=4.8 Hz, 4H), 8.03 (d, J=8.1 Hz, 4H), 7.54 (t, J=8.1 Hz, 2H), 4.89 t, J=7.8 Hz, 4H), 2.54 (m, 4H), 1.81 (m,4H), 1.52 (m, 4H), 1.33 (m, 8H), 0.90 (m, 6H), −2.45 (s, 2H). UV-vis (CH$_2$Cl$_2$), λ$_{max}$ nm (log ε): 419 (5.61), 518(4.31), 553(3.92), 596(3.80), 654(3.74). HRMS-MALDI ([M+H]$^+$): calcd for C$_{46}$H$_{47}$Br$_4$N$_4$, 971.0529; found: 971.0510 with an isotope distribution pattern that is the same as the calculated one.

Example 108

5,15-Bis(2.6-dibromophenyl)porphyrin 19k

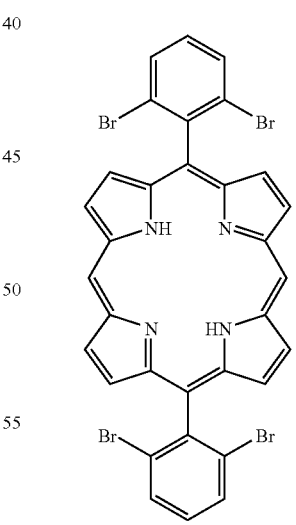

A mixture of dipyrromethane (0.146 g, 1 mmol), 2,6-dibromobenzaldehyde (0.264 g, 1 mmol) and molecular sieves (4A, 1.0 g) in chloroform (100 mL) was purged with nitrogen for 10 min. Boron trifluoride diethyl etherate (0.1 mL) was added dropwise via a syringe and the flask was wrapped with aluminum foil to shield it from light. The solution was stirred under a nitrogen atmosphere at room temperature for 16 h, and 2,3-dichloro-5,6-dicyano-1,4-benzoquinone (DDQ) (0.287 g, 1.2 mmol) was added as powder at one time. After 30 min, 1 mL of triethylamine was added. The reaction solution was then directly poured on the top of a silica gel column that was packed with dichloromethane. The column was eluted with dichloromethane. The fractions containing product were collected and concentrated on a rotary evaporator. The residue was washed several times with hexanes to afford the title compound as a purple solid. Yield: 0.055 g (14%). $^1$H NMR (300 MHz, CDCl$_3$): δ 10.26 (s, 2H), 9.36 (d, J=4.8 Hz, 4H), 8.84 (d, J=4.8 Hz, 4H), 8.01 (d, J=8.1 Hz, 4H), 7.57 (t, J=8.1 Hz, 2H), −3.07 (s, 2H). UV-vis (CH$_2$Cl$_2$), λ$_{max}$ nm (log ε): 407(5.73), 502(4.44), 534(3.95), 576(3.99), 630(3.53). HRMS-MALDI ([M+H]$^+$): calcd for C$_{32}$H$_{19}$Br$_4$N$_4$ 774.8338; found: 774.8476 with an isotope distribution pattern that is the same as the calculated one.

Example 109

General Procedures for Amidation of Bromoporphyrin

The general procedures for amidation of bromoporphyrin follow those described in Gao et al., (2004) *Org. Lett.* 6: 1837. The bromoporphyrin, chiral amide, Pd(OAc)$_2$, Xantphos, and Cs$_2$CO$_3$ were placed in an oven-dried, resealable Schlenk tube. The tube was capped with a Teflon screwcap, evacuated, and backfilled with nitrogen. The screwcap was replaced with a rubber septum, and THF was added via syringe. The tube was purged with nitrogen for 2 min, and then the septum was replaced with the Teflon screwcap. The tube was sealed, and its contents were heated with stirring. The resulting mixture was cooled to room temperature, taken up in ethyl acetate and concentrated in vacuo. The crude product was then purified by flash chromatography.

Example 110

Porphyrin 20a (Table 4, entry 1)

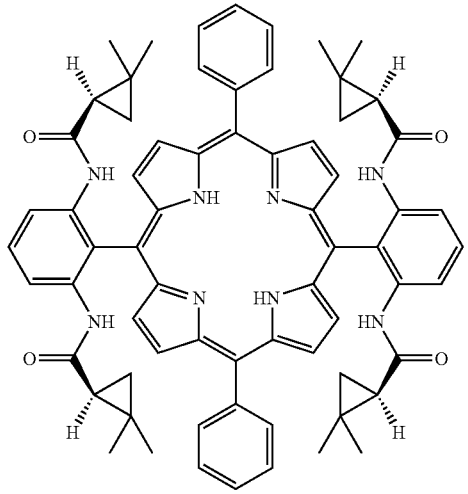

The general procedure was used to couple 5,15-bis(2,6-dibromophenyl)-10,20-diphenylporphyrin (0.093 g, 0.1 mmol) with (S)-(+)-2,2-dimethyl cyclopropanecarboxamide (0.362 g, 3.2 mmol), using Pd(OAc)$_2$ (0.009 g, 0.04 mmol), Xantphos (0.046 g, 0.08 mmol), and Cs$_2$CO$_3$ (0.522 g, 1.6 mmol). The reaction was conducted in THF (6 mL) at 100° C. for 60 h. The pure compound was isolated by flash column chromatography (silica gel, ethyl acetate:hexanes (v/v)=1:2) as purple solids (0.083 g, 78%). $^1$H NMR (300 MHz, CDCl$_3$): δ 8.95 (d, J=4.8 Hz, 4H), 8.87 (d, J=4.8 Hz, 4H), 8.44 (broad, 4H), 8.18 (d, J=6.0 Hz, 4H), 7.83 (m, 8H), 6.45 (broad, 4H), 0.87 (s, 12H), 0.69 (broad, 4H), −0.08-0.18 (m, 20H), −2.65 (s, 2H). $^{13}$C NMR (75 MHz, CDCl$_3$): δ 169.6, 140.7, 139.3, 134.4, 133.6, 130.4, 128.5, 127.1, 121.4, 117.8, 28.9, 26.3, 22.4, 20.4, 18.2. UV-vis (CH$_2$Cl$_2$), λ$_{max}$ nm (log ε): 420 (5.33), 516(4.09), 549(3.62), 589(3.59), 644(3.33). HRMS-EI ([M]$^+$): calcd for C$_{68}$H$_{66}$N$_8$O$_4$ 1058.5207, found 1058.5184 with an isotope distribution pattern that is the same as the calculated one.

Example 111

Porphyrin 20b (Table 4, entry 2)

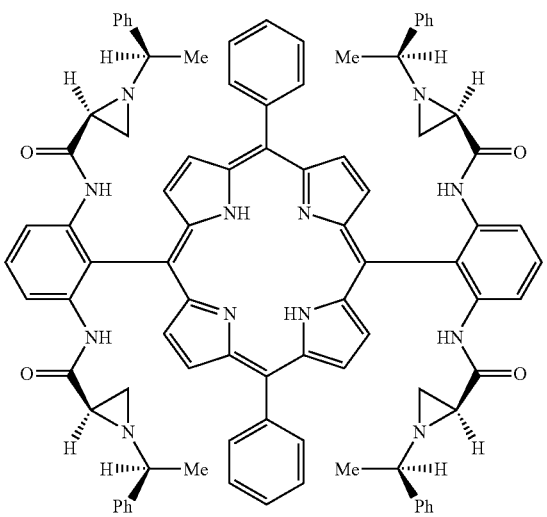

The general procedure was used to couple 5,15-bis(2,6-dibromophenyl)-10,20-diphenylporphyrin (0.023 g, 0.025 mmol) with 1-[1'(R)-a-methyl benzyl]-aziridine-2(R)-carboxamide (0.076 g, 0.4 mmol), using molecular sieves (4A, 0.05 g), Pd(OAc)$_2$ (0.002 g, 0.01 mmol), Xantphos (0.012 g, 0.02 mmol), and Cs$_2$CO$_3$ (0.130 g, 0.4 mmol). The reaction was conducted in THF (2 mL) at 100° C. for 60 h. The pure compound was isolated by flash column chromatography (silica gel, ethyl acetate:hexanes (v/v)=1:1) as purple solids (0.022 g, 64%). $^1$H NMR (300 MHz, CDCl$_3$): δ 8.89 (m, 8H), 8.58 (m, 8H), 7.93 (t, J=8.7 Hz, 2H), 7.55 (t, J=7.2 Hz, 2H), 7.34 (t, J=7.8 Hz, 4H), 6.75 (d, J=7.2 Hz, 4H), 5.87 (t, J=7.8 Hz, 4H), 4.59 (m, 16H), 1.63 (m, 8H), 0.53 (d, J=6.3 Hz, 12H), 0.27 (m, 8H), −2.08 (s, 2H). $^{13}$C NMR (75 MHz, CDCl$_3$): δ 168.7, 141.5, 140.6, 139.0, 133.2, 130.9, 127.7, 126.1, 125.3, 123.8, 121.8, 120.3, 116.0, 108.7, 66.6, 39.4, 34.0, 23.5. UV-vis (CH$_2$Cl$_2$), λ$_{max}$ nm (log ε): 421(5.60), 514(4.35), 548(3.92), 590(3.84), 646(3.73). HRMS-MALDI ([M]$^+$): calcd for C$_{88}$H$_{79}$N$_{12}$O$_4$ 1367.6342, found 1367.6343 with an isotope distribution pattern that is the same as the calculated one.

Example 112

Porphyrin 20c (Table 4, entry 3)

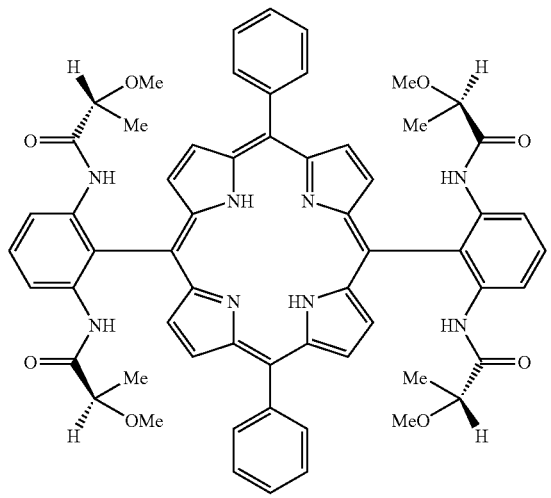

The general procedure was used to couple 5,15-bis(2,6-dibromophenyl)-10,20-diphenylporphyrin (0.046 g, 0.05 mmol) with (R)-(+)-2-methoxy propionamide (0.082 g, 0.8 mmol), using molecular sieves (4A, 0.100 g), Pd(OAc)$_2$ (0.004 g, 0.02 mmol), Xantphos (0.023 g, 0.04 mmol), and Cs$_2$CO$_3$ (0.261 g, 0.8 mmol). The reaction was conducted in THF (4 mL) at 100° C. for 64 h. The pure compound was isolated by flash column chromatography (silica gel, ethyl acetate:hexanes (v/v)=1:1) as purple solids (0.038 g, 75%). $^1$H NMR (300 MHz, CDCl$_3$): δ 8.86 (d, J=4.8 Hz, 4H), 8.79 (d, J=4.8 Hz, 4H), 8.53 (d, J=8.1 Hz, 4H), 8.09 (d, J=7.2 Hz, 4H), 7.88 (t, J=8.1 Hz, 2H), 7.77 (m, 10H), 3.03 (q, J=6.6 Hz, 4H), 1.22 (s, 12H), 0.62 (d, J=6.6 Hz, 12H), −2.56 (s, 2H). $^{13}$C NMR (75 MHz, CDCl$_3$): δ171.1, 140.9, 138.4, 134.4, 130.7, 128.3, 127.1, 122.4, 121.2, 117.2, 108.2, 78.0, 55.8, 17.7. UV-vis (CH$_2$Cl$_2$), λ$_{max}$, nm (log ε): 419(5.51), 514(4.24), 547(3.76), 589(3.72), 644(3.49). HRMS-MALDI ([M]$^+$): calcd for C$_{60}$H$_{59}$N$_8$O$_8$ 1019.4450, found 1019.4462 with an isotope distribution pattern that is the same as the calculated one.

Example 113

Porphyrin 20d (Table 4, entry 4)

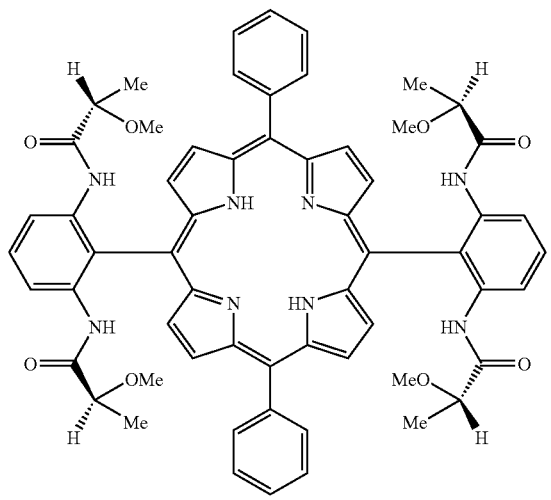

The general procedure was used to couple 5,15-bis(2,6-dibromophenyl)-10,20-diphenylporphyrin (0.046 g, 0.05 mmol) with (S)-(−)-2-methoxy propionamide (0.082 g, 0.8 mmol), using molecular sieves (4A, 0.1 g), Pd(OAc)$_2$ (0.004 g, 0.02 mmol), Xantphos (0.023 g, 0.04 mmol), and Cs$_2$CO$_3$ (0.261 g, 0.8 mmol). The reaction was conducted in THF (4 mL) at 80° C. for 62 h. The pure compound was isolated by flash column chromatography (silica gel, ethyl acetate:hexanes (v/v)=1:1) as purple solids (0.036 g, 71%). $^1$H NMR (300 MHz, CDCl$_3$): δ 8.86 (d, J=4.8 Hz, 4H), 8.79 (d, J=4.8 Hz, 4H), 8.53 (d, J=8.1 Hz, 4H), 8.09 (d, J=6.9 Hz, 4H), 7.88 (t, J=8.1 Hz, 2H), 7.77 (m, 10H), 3.03 (q, J=7.2 Hz, 4H), 1.22 (s, 12H), 0.62 (d, J=6.6 Hz, 12H), −2.57 (s, 2H). $^{13}$C NMR (75 MHz, CDCl$_3$): δ171.1, 140.9, 138.4, 134.4, 130.7, 128.3, 127.1, 122.3, 121.2, 117.1, 108.1, 78.0, 55.8, 17.7. UV-vis (CH$_2$Cl$_2$), λ$_{max}$, nm (log ε): 419(5.50), 514(4.23), 547(3.74), 587(3.70), 644(3.44). HRMS-MALDI ([M]$^+$): calcd for C$_{60}$H$_{59}$N$_8$O$_8$ 1019.4450, found 1019.4497 with an isotope distribution pattern that is the same as the calculated one.

Example 114

Porphyrin 20e (Table 4, entry 5)

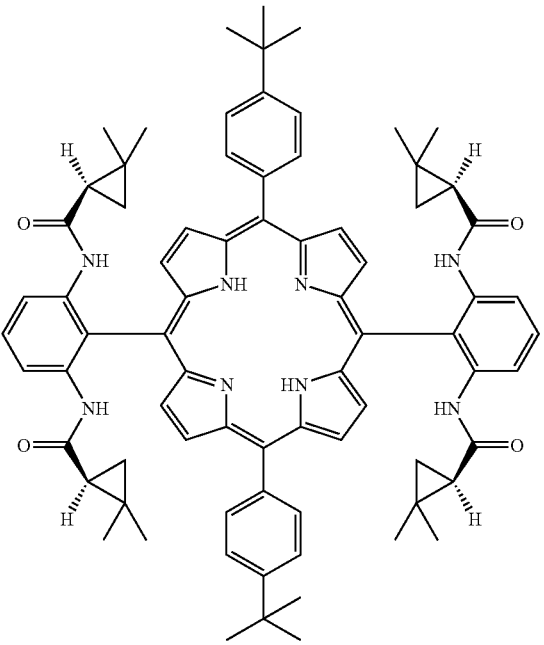

The general procedure was used to couple 5,15-bis(2,6-dibromophenyl)-10,20-bis[4-(tert-butyl)phenyl]porphyrin (0.078 g, 0.075 mmol) with (S)-(+)-2,2-dimethylcyclopropanecarboxamide (0.136 g, 1.2 mmol), using Pd(OAc)$_2$ (0.007 g, 0.03 mmol), Xantphos (0.035 g, 0.06 mmol), and Cs$_2$CO$_3$ (0.391 g, 1.2 mmol). The reaction was conducted in THF (6 mL) at 100° C. for 40 h. The pure compound was isolated by flash column chromatography (silica gel, ethyl acetate:hexanes (v/v)=1:4) as purple solids (0.076 g, 86%). $^1$H NMR (300 MHz, CDCl$_3$): δ 8.99 (d, J=4.8 Hz, 4H), 8.85 (d, J=4.8 Hz, 4H), 8.45 (broad, 4H), 8.10 (d, J=8.1 Hz, 4H), 7.81 (m, 6H), 6.46 (broad, 4H), 1.61 (s, 18H), 0.87 (s, 12H), 0.67 (broad, 4H), −0.11-0.17 (m, 20H), −2.63 (s, 2H). $^{13}$C NMR (75 MHz, CDCl$_3$): δ 169.7, 151.4, 139.3, 137.7, 134.0, 130.3, 124.1, 121.68, 117.5, 35.0, 31.6, 29.1, 26.3, 22.4, 20.4, 18.2. UV-vis (CH$_2$Cl$_2$), λ$_{max}$ nm (log ε): 421(5.38), 516(4.10), 552(3.69), 591(3.59), 648(3.49). HRMS-EI ([M]$^+$): calcd for C$_{76}$H$_{82}$N$_8$O$_4$ 1170.6459, found 1170.6451 with an isotope distribution pattern that is the same as the calculated one.

Example 115

Porphyrin 20f (Table 4, entry 6)

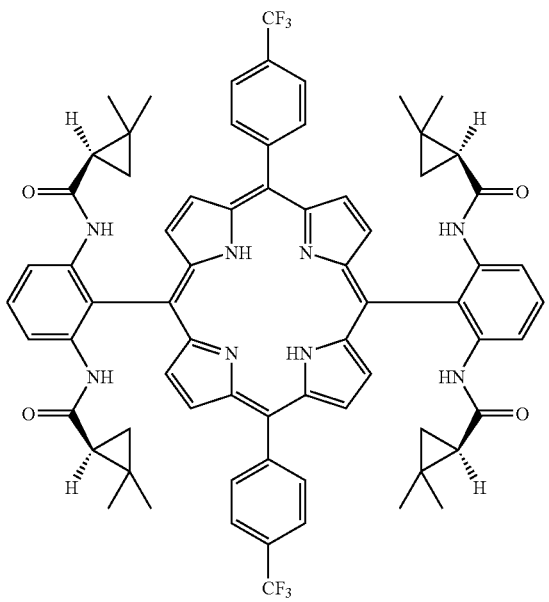

The general procedure was used to couple 5,15-bis(2,6-dibromophenyl)-10,20-bis(4-trifluoromethylphenyl)porphyrin (0.053 g, 0.05 mmol) with (S)-(+)-2,2-dimethylcyclopropanecarboxamide (0.184 g, 1.6 mmol), using Pd(OAc)$_2$ (0.004 g, 0.02 mmol), Xantphos (0.023 g, 0.04 mmol), and Cs$_2$CO$_3$ (0.261 g, 0.8 mmol). The reaction was conducted in THF (4 mL) at 100° C. for 60 h. The pure compound was isolated by flash column chromatography (silica gel, ethyl acetate:hexanes (v/v)=1:2) as purple solids (0.046 g, 77%). $^1$H NMR (300 MHz, CDCl$_3$): δ 8.89 (m, 8H), 8.41 (broad, 4H), 8.31 (d, J=8.1 Hz, 4H), 8.08 (d, J=8.1 Hz, 4H), 7.83 (t, J=8.1 Hz, 2H), 6.41 (broad, 4H), 0.85 (s, 12H), 0.69 (broad, 4H), −0.07-0.19 (m, 20H), −2.68 (s, 2H). $^{13}$C NMR (75 MHz, CDCl$_3$): δ 189.8, 170.2, 144.4, 139.3, 134.5, 130.6, 124.2, 119.6, 29.0, 26.3, 22.5, 20.4, 18.2. UV-vis (CH$_2$Cl$_2$), λ$_{max}$ nm (log ε): 420(5.53), 514(4.33), 547(3.77), 588(3.82), 643(3.43). HRMS-MALDI ([M+H]$^+$): calcd for C$_{70}$H$_{65}$F$_6$N$_8$O$_8$ 1195.5027, found 1195.5085 with an isotope distribution pattern that is the same as the calculated one.

Example 116

Porphyrin 20a (Table 4, entry 7)

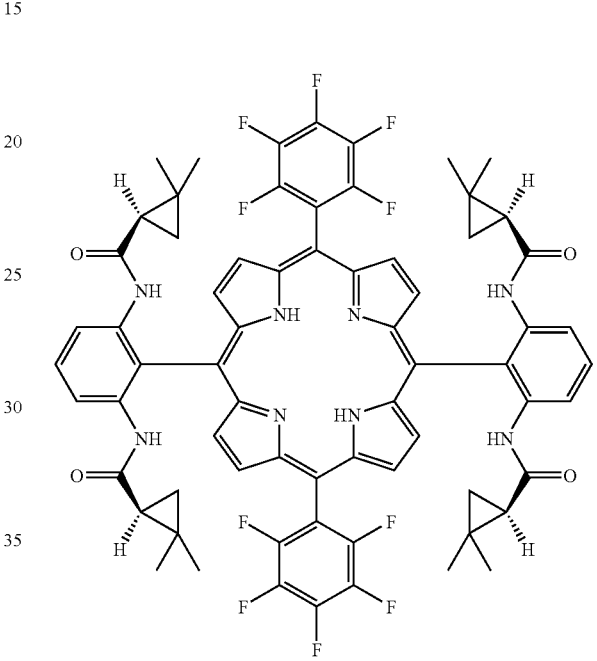

The general procedure was used to couple 5,15-bis(2,6-dibromophenyl)-10,20-bis(2,3,4,5,6-pentafluorophenyl)porphyrin (0.028 g, 0.025 mmol) with (S)-(+)-2,2-dimethylcyclopropanecarboxamide (0.091 g, 0.8 mmol), using Pd(OAc)$_2$ (0.002 g, 0.01 mmol), Xantphos (0.012 g, 0.02 mmol), and Cs$_2$CO$_3$ (0.130 g, 0.4 mmol). The reaction was conducted in THF (2 mL) at 100° C. for 60 h. The pure compound was isolated by flash column chromatography (silica gel, ethyl acetate:hexanes (v/v)=1:4) as purple solids (0.015 g, 46%). $^1$H NMR (300 MHz, CDCl$_3$): δ 8.99 (d, J=4.8 Hz, 4H), 8.91 (d, J=4.8 Hz, 4H), 8.36 (broad, 4H), 7.84 (t, J=8.1 Hz, 2H), 6.37 (broad, 4H), 0.81 (s, 12H), 0.69 (broad, 4H), −0.02-0.14 (m, 20H), −2.71 (s, 2H). $^{13}$C NMR (75 MHz, CDCl$_3$): δ 169.8, 139.1, 130.8, 118.7, 110.8, 103.5, 28.8, 26.1, 22.5, 20.4, 18.1. UV-vis (CH$_2$Cl$_2$), λ$_{max}$ nm (log ε): 419(5.54), 511(4.46), 544(3.64), 585(3.98), 639(3.15). HRMS-MALDI ([M+H]$^+$): calcd for C$_{68}$H$_{57}$F$_{10}$N$_8$O$_4$ 1239.4338, found 1239.4335 with an isotope distribution pattern that is the same as the calculated one.

Example 117

Porphyrin 20h (Table 4, entry 8)

Example 118

Porphyrin 20i (Table 4, entry 9)

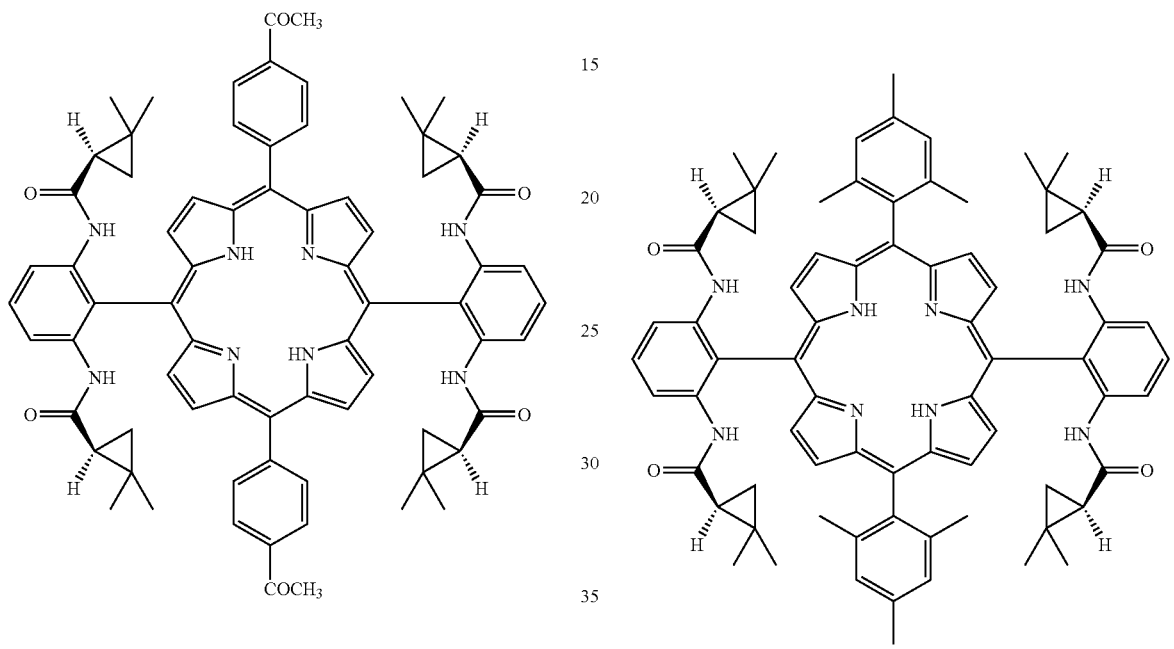

The general procedure was used to couple 5,15-bis(2,6-dibromophenyl)-10,20-bis(4-acetylphenyl)porphyrin (0.051 g, 0.05 mmol) with (S)-(+)-2,2-dimethylcyclopropanecarboxamide (0.184 g, 1.6 mmol), using Pd(OAc)$_2$ (0.004 g, 0.02 mmol), Xantphos (0.023 g, 0.04 mmol), and Cs$_2$CO$_3$ (0.261 g, 0.8 mmol). The reaction was conducted in THF (4 mL) at 100° C. for 60 h. The pure compound was isolated by flash column chromatography (silica gel, ethyl acetate:methylene chloride (v/v)=1:3) as purple solids (0.038 g, 66%). $^1$H NMR (300 MHz, CDCl$_3$): δ 8.92 (m, 8H), 8.30-8.42 (m, 12H), 7.83 (t, J=8.1 Hz, 2H), 6.46 (broad, 4H), 2.89 (s, 6H), 0.71-0.88 (m, 16H), −0.04-0.20 (m, 20H), −2.63 (s, 2H). $^{13}$C NMR (75 MHz, CDCl$_3$): δ 197.9, 171.0, 169.6, 145.5, 139.2, 136.8, 134.6, 130.5, 127.0, 118.0, 28.9, 27.0, 26.3, 22.4, 20.4, 18.2. UV-vis (CH$_2$Cl$_2$), λ$_{max}$ nm (log ϵ): 412(5.55), 516(4.32), 550(3.82), 589(3.79), 644(3.40). HRMS-MALDI ([M+H]$^+$): calcd for C$_{72}$H$_{71}$N$_8$O$_6$ 1143.5491, found 1143.5467 with an isotope distribution pattern that is the same as the calculated one.

The general procedure was used to couple 5,15-bis(2,6-dibromophenyl)-10,20-dimesitylporphyrin (0.051 g, 0.05 mmol) with (S)-(+)-2,2-dimethyl cyclopropanecarboxamide (0.181 g, 1.6 mmol), using Pd(OAc)$_2$ (0.004 g, 0.02 mmol), Xantphos (0.023 g, 0.04 mmol), and Cs$_2$CO$_3$ (0.261 g, 0.8 mmol). The reaction was conducted in THF (6 mL) at 100° C. for 56 h. The pure compound was isolated by flash column chromatography (silica gel, ethyl acetate:hexanes (v/v)=1:4) as purple solids (0.048 g, 84%). $^1$H NMR (300 MHz, CDCl$_3$): δ 8.80 (m, 8H), 8.42 (broad, 4H), 7.80 (t, J=8.1 Hz, 2H), 7.30 (s, 4H), 6.52 (broad, 4H), 2.63 (s, 6H), 1.82 (s, 12H), 0.86 (s, 12H), 0.68 (broad, 4H), −0.06-0.20 (m, 20H), −2.54 (s, 2H). $^{13}$C NMR (75 MHz, CDCl$_3$): δ 169.6, 147.3, 139.2, 138.9, 138.6, 136.9, 130.4, 128.2, 119.9, 117.6, 28.9, 26.4, 22.4, 21.7, 21.5, 20.5, 18.2. UV-vis (CH$_2$Cl$_2$), λ$_{max}$ nm (log ϵ): 421(5.42), 515(4.19), 549(3.68), 590(3.68), 645(3.48). HRMS-EI ([M]$^+$): calcd for C$_{74}$H$_{78}$N$_8$O$_4$ 1142.6146, found 1142.6115 with an isotope distribution pattern that is the same as the calculated one.

Example 119

Porphyrin 20j (Table 4, entry 10)

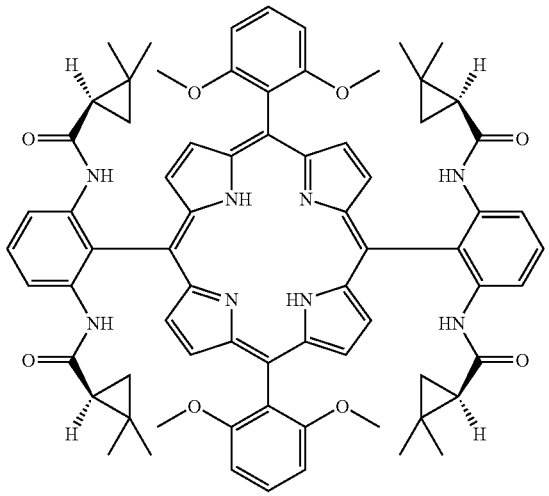

The general procedure was used to couple 5,15-bis(2,6-dibromophenyl)-10,20-bis(2,6-dimethoxyphenyl)porphyrin (0.105 g, 0.1 mmol) with (S)-(+)-2,2-dimethylcyclopropanecarboxamide (0.362 g, 3.2 mmol), using Pd(OAc)$_2$ (0.009 g, 0.04 mmol), Xantphos (0.046 g, 0.08 mmol), and Cs$_2$CO$_3$ (0.522 g, 1.6 mmol). The reaction was conducted in THF (6 mL) at 100° C. for 60 h. The pure compound was isolated by flash column chromatography (silica gel, ethyl acetate:hexanes (v/v)=1:2) as purple solids (0.069 g, 59%). $^1$H NMR (300 MHz, CDCl$_3$): δ 8.87 (d, J=4.8 Hz, 4H), 8.79 (d, J=4.8 Hz, 4H), 8.47 (broad, 4H), 7.81 (t, J=8.7 Hz, 4H), 7.06 (d, J=8.4 Hz, 4H), 6.58 (broad, 4H), 3.55 (s, 12H), 0.88 (s, 12H), 0.65 (broad, 4H), 0.04-0.21 (m, 20H), −2.47 (s, 2H). $^{13}$C NMR (75 MHz, CDCl$_3$): δ 169.6, 160.2, 139.2, 130.9, 130.1, 118.2, 117.0, 113.6, 107.1, 104.1, 55.9, 29.0, 26.2, 22.2, 20.1, 18.2. UV-vis (CH$_2$Cl$_2$), λ$_{max}$ nm (log ε): 412(5.50), 514(4.28), 547(3.67), 589(3.77), 643(3.38). HRMS-MALDI ([M+H]$^+$): calcd for C$_{72}$H$_{75}$N$_8$O$_8$ 1179.5702, found 1179.5758 with an isotope distribution pattern that is the same as the calculated one.

Example 120

Porphyrin 20k (Table 4, entry 11)

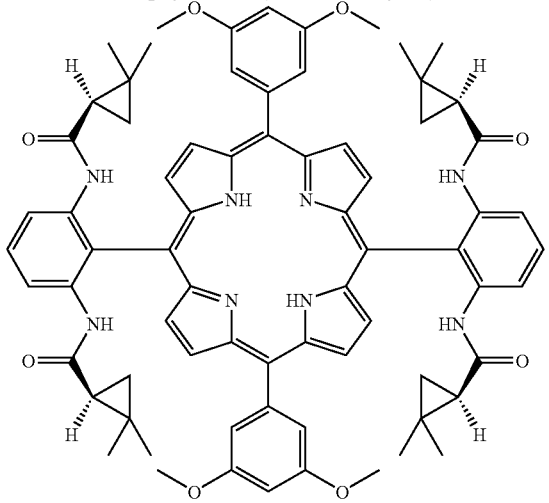

The general procedure was used to couple 5,15-bis(2,6-dibromophenyl)-10,20-bis(3,5-dimethoxyphenyl)porphyrin (0.053 g, 0.05 mmol) with (S)-(+)-2,2-dimethylcyclopropanecarboxamide (0.181 g, 1.6 mol), using Pd(OAc)$_2$ (0.004 g, 0.02 mmol), Xantphos (0.023 g, 0.04 mmol), and Cs$_2$CO$_3$ (0.261 g, 0.8 mmol). The reaction was conducted in THF (4 mL) at 100° C. for 48 h. The pure compound was isolated by flash column chromatography (silica gel, ethyl acetate:hexanes (v/v)=1:1) as purple solids (0.052 g, 88%). $^1$H NMR (300 MHz, CDCl$_3$): δ 9.04 (d, J=4.8 Hz, 4H), 8.84 (d, J=4.8 Hz, 4H), 8.44 (broad, 4H), 7.83 (t, J=8.7 Hz, 2H), 7.34 (d, J=1.8 Hz, 4H), 6.93 (t, J=1.8 Hz, 2H), 6.45 (broad, 4H), 3.98 (s, 12H), 0.88 (s, 12H), 0.69 (broad, 4H), −0.07-0.17 (m, 20H), −2.68 (s, 2H). $^{13}$C NMR (75 MHz, CDCl$_3$): δ 169.6, 159.1, 142.5, 139.3, 133.7, 130.4, 121.0, 117.7, 114.1, 100.1, 55.6, 29.0, 26.3, 22.4, 20.4, 18.3. UV-vis (CH$_2$Cl$_2$), λ$_{max}$ nm (log ε): 423(5.53), 515(4.34), 549(3.81), 589(3.85), 643(3.55). HRMS-MALDI ([M+H]$^+$): calcd for C$_{72}$H$_{75}$N$_8$O$_8$ 1179.5702, found 1179.5736 with an isotope distribution pattern that is the same as the calculated one.

Example 121

Porphyrin 20k (Table 4, entry 12)

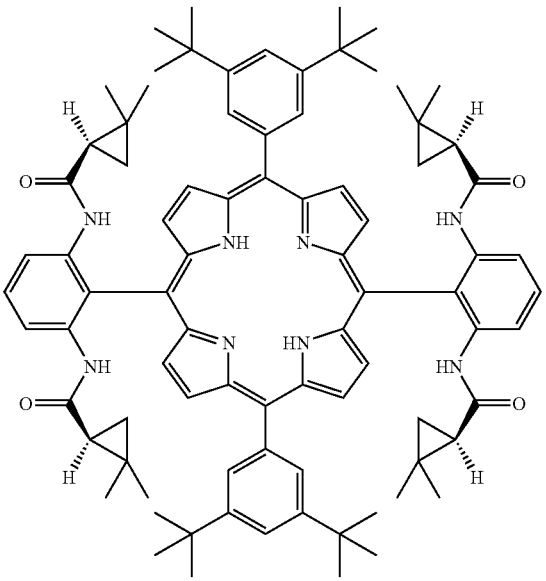

The general procedure was used to couple 5,15-bis(2,6-dibromophenyl)-10,20-bis[3,5-di(tert-butyl)phenyl]porphyrin (0.231 g, 0.2 mmol) with (S)-(+)-2,2-dimethylcyclopropanecarboxamide (0.362 g, 3.2 mmol), using Pd(OAc)$_2$ (0.018 g, 0.08 mmol), Xantphos (0.093 g, 0.16 mmol), and Cs$_2$CO$_3$ (1.045 g, 3.2 mmol). The reaction was conducted in THF (4 mL) at 100° C. for 48 h. The pure compound was isolated by flash column chromatography (silica gel, ethyl acetate:hexanes (v/v)=1:4) as purple solids (0.217 g, 85%). $^1$H NMR (300 MHz, CDCl$_3$): δ 8.99 (d, J=4.8 Hz, 4H), 8.87 (d, J=4.8 Hz, 4H), 8.44 (broad, 4H), 8.04 (d, J=1.5 Hz, 4H), 7.83 (m, 4H), 6.50 (broad, 4H), 1.53 (s, 36H), 0.87 (s, 12H), 0.69 (broad, 4H), −0.05-0.14 (m, 20H), −2.34 (s, 2H). $^{13}$C NMR (75 MHz, CDCl$_3$): δ 169.6, 149.3, 139.8, 139.2, 133.6, 130.3, 129.8, 122.7, 121.8, 117.4, 35.0, 31.7, 29.0, 26.3, 22.3, 20.2, 18.3. UV-vis (CH$_2$Cl$_2$), λ$_{max}$ nm (log ε): 422(5.46), 517(4.17), 552(3.77), 591(3.66), 646(3.53). HRMS-EI ([M]$^+$): calcd for C$_{84}$H$_{98}$N$_8$O$_4$ 1282.7711, found 1282.7715 with an isotope distribution pattern that is the same as the calculated one.

Example 122

Porphyrin 20m (Table 4, entry 13)

Example 123

Porphyrin 20n (Table 4, entry 14)

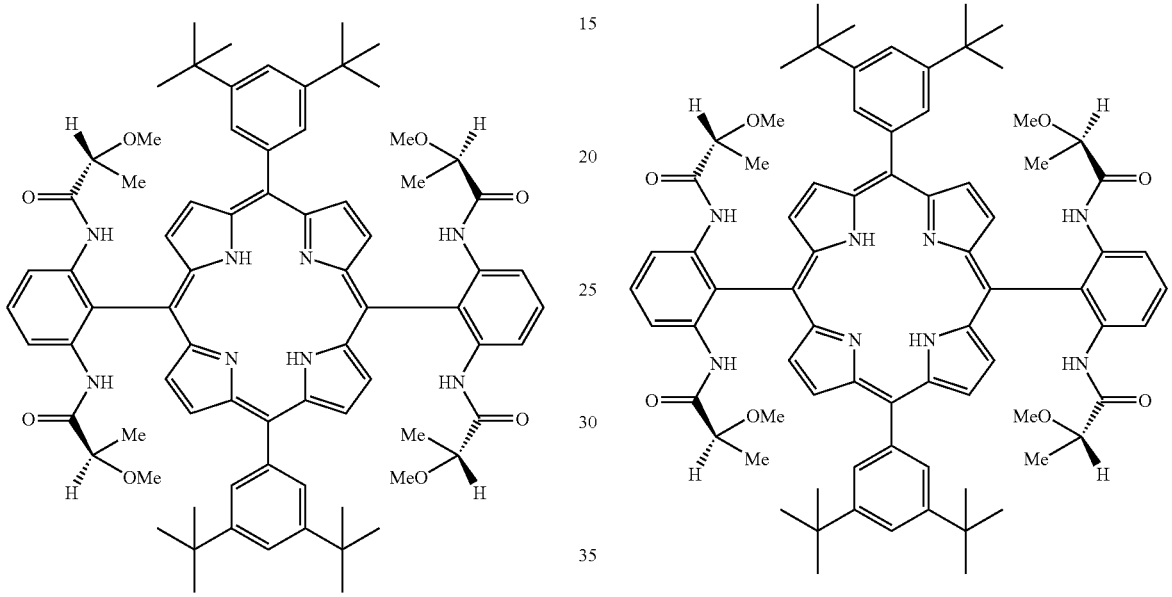

The general procedure was used to couple 5,15-bis(2,6-dibromophenyl)-10,20-bis[3,5-di(tert-butyl)phenyl]porphyrin (0.058 g, 0.05 mmol) with (R)-(+)-2-methoxypropionamide (0.082 g, 0.8 mmol), using molecular sieves (4A, 0.100 g), Pd(OAc)$_2$ (0.004 g, 0.02 mmol), Xantphos (0.023 g, 0.04 mmol), and Cs$_2$CO$_3$ (0.261 g, 0.8 mmol). The reaction was conducted in THF (4 mL) at 100° C. for 64 h. The pure compound was isolated by flash column chromatography (silica gel, ethyl acetate:hexanes (v/v)=1:2) as purple solids (0.049 g, 79%). $^1$H NMR (300 MHz, CDCl$_3$): δ 8.90 (d, J=4.8 Hz, 4H), 8.79 (d, J=4.8 Hz, 4H), 8.57 (d, J=8.7 Hz, 4H), 7.95 (s, 4H), 7.89 (t, J=8.7 Hz, 2H), 7.83 (s, 6H), 3.08 (q, J=6.6 Hz, 4H), 1.52 (s, 36H), 1.36 (s, 12H), 0.66 (d, J=6.6 Hz, 12H), −2.48 (s, 2H). $^{13}$C NMR (75 MHz, CDCl$_3$): δ 171.2, 149.2, 140.0, 138.5, 130.6, 129.8, 122.6, 122.3, 121.7, 117.0, 107.8, 78.1, 55.9, 35.0, 31.6, 17.7. UV-vis (CH$_2$Cl$_2$), λ$_{max}$ nm (log ε): 421(5.59), 516(4.29), 551(3.89), 592(3.76), 647(3.62). HRMS-MALDI ([M]$^+$): calcd for C$_{76}$H$_{91}$N$_8$O$_8$ 1243.6954, found 1243.6894 with an isotope distribution pattern that is the same as the calculated one.

The general procedure was used to couple 5,15-bis(2,6-dibromophenyl)-10,20-bis[3,5-di(tert-butyl)phenyl]porphyrin (0.058 g, 0.05 mmol) with (S)-(−)-2-methoxypropionamide (0.082 g, 0.8 mmol), using molecular sieves (4A, 0.1 g), Pd(OAc)$_2$ (0.004 g, 0.02 mmol), Xantphos (0.023 g, 0.04 mmol), and Cs$_2$CO$_3$ (0.261 g, 0.8 mmol). The reaction was conducted in THF (4 mL) at 100° C. for 48 h. The pure compound was isolated by flash column chromatography (silica gel, ethyl acetate:hexanes (v/v)=1:2) as purple solids (0.045 g, 72%). $^1$H NMR (300 MHz, CDCl$_3$): δ 8.90 (d, J=4.8 Hz, 4H), 8.79 (d, J=4.8 Hz, 4H), 8.57 (d, J=8.7 Hz, 4H), 7.94 (s, 4H), 7.88 (t, J=8.7 Hz, 2H), 7.82 (s, 6H), 3.08 (q, J=6.9 Hz, 4H), 1.52 (s, 36H), 1.35 (s, 12H), 0.65 (d, J=7.2 Hz, 12H), −2.48 (s, 2H). $^{13}$C NMR (75 MHz, CDCl$_3$): δ 171.2, 149.2, 140.0, 138.5, 130.6, 129.8, 122.6, 122.3, 121.7, 117.0, 107.8, 78.1, 55.9, 35.0, 31.6, 17.8. UV-vis (CH$_2$Cl$_2$), λ$_{max}$ nm (log ε): 421(5.61), 516(4.31), 551(3.91), 592(3.80), 648(3.68). HRMS-MALDI ([M]$^+$): calcd for C$_{76}$H$_{91}$N$_8$O$_8$ 1243.6954, found 1243.6991 with an isotope distribution pattern that is the same as the calculated one.

Example 124

Porphyrin 20o (Table 4, entry 15)

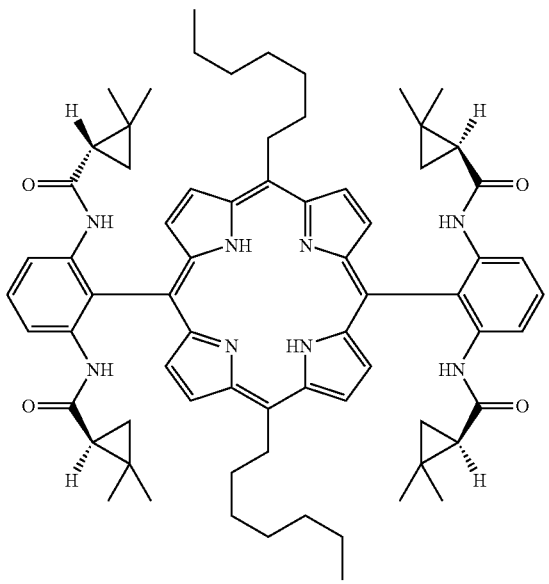

The general procedure was used to couple 5,15-bis(2,6-dibromophenyl)-10,20-bisheptylporphyrin (0.049 g, 0.05 mmol) with (S)-(+)-2,2-dimethylcyclopropanecarboxamide (0.184 g, 1.6 mmol), using Pd(OAc)$_2$ (0.004 g, 0.02 mmol), Xantphos (0.023 g, 0.04 mmol), and Cs$_2$CO$_3$ (0.261 g, 0.8 mmol). The reaction was conducted in THF (4 mL) at 100° C. for 60 h. The pure compound was isolated by flash column chromatography (silica gel, ethyl acetate:hexanes (v/v)=1:3) as purple solids (0.043 g, 74%). $^1$H NMR (300 MHz, CDCl$_3$): δ 9.56 (d, J=4.8 Hz, 4H), 8.95 (d, J=4.8 Hz, 4H), 8.51 (broad, 4H), 7.87 (t, J=8.1 Hz, 2H), 6.50 (broad, 4H), 5.03 (m, 4H), 2.55 (m, 4H), 1.86 (m, 4H), 1.37 (m, 6H), 0.91 (s, 12H), 0.70 (broad, 4H), −0.04-0.19 (m, 20H), −2.48 (s, 2H). $^{13}$C NMR (75 MHz, CDCl$_3$): δ 169.7, 139.3, 131.2, 130.3, 130.0, 121.4, 117.4, 107.5, 39.0, 35.2, 31.8, 30.5, 29.3, 28.9, 26.3, 22.7, 22.3, 20.4, 18.2, 14.1. UV-vis (CH$_2$Cl$_2$), λ$_{max}$ nm (log ε): 421(5.40), 517(4.16), 553(3.82), 594(3.62), 651(3.71). HRMS-MALDI ([M+H]$^+$): calcd for C$_{70}$H$_{87}$N$_8$O$_4$ 1103.6845, found 1103.6871 with an isotope distribution pattern that is the same as the calculated one.

Example 125

Porphyrin 20p (Table 4, entry 16)

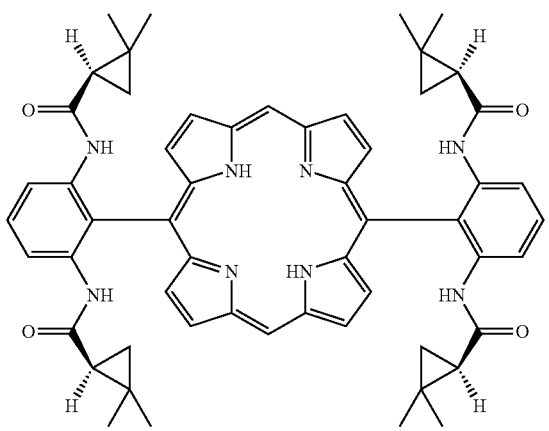

The general procedure was used to couple 5,15-bis(2,6-dibromophenyl)porphyrin (0.039 g, 0.05 mmol) with (S)-(+)-2,2-dimethylcyclopropane carboxamide (0.181 g, 1.6 mmol), using Pd(OAc)$_2$ (0.004 g, 0.02 mmol), Xantphos (0.023 g, 0.04 mmol), and Cs$_2$CO$_3$ (0.261 g, 0.8 mmol). The reaction was conducted in THF (6 mL) at 100° C. for 60 h. The pure compound was isolated by flash column chromatography (silica gel, ethyl acetate:hexanes (v/v)=1:1) as purple solids (0.036 g, 79%). $^1$H NMR (300 MHz, CDCl$_3$): δ 10.44 (s, 2H), 9.50 (d, J=4.8 Hz, 4H), 9.08 (d, J=4.8 Hz, 4H), 8.48 (broad, 4H), 7.86 (t, J=8.7 Hz, 2H), 6.47 (broad, 4H), 0.88 (s, 12H), 0.67 (broad, 4H), −0.14-0.13 (m, 20H), −3.05 (s, 2H). $^{13}$C NMR (75 MHz, CDCl$_3$): δ 169.7, 147.2, 146.4, 139.3, 133.7, 130.7, 130.5, 117.7, 108.0, 106.3, 28.9, 26.2, 22.4, 20.4, 18.2. UV-vis (CH$_2$Cl$_2$), λ$_{max}$ nm (log ε): 409(5.31), 503(4.12), 536(3.74), 575(3.67), 628(3.40). HRMS-MALDI ((M+H]$^+$): calcd for C$_{56}$H$_{59}$N$_8$O$_4$ 907.4654, found 907.4640 with an isotope distribution pattern that is the same as the calculated one.

Example 126

5,15-Bis(2,6-dibromo-4-trimethylsilanylphenyl)porphyrin

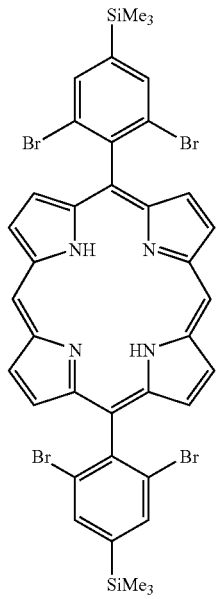

A mixture of dipyrromethane (0.146 g, 1 mmol), 2,6-dibromo-4-trimethylsilanyl-benzaldehyde (0.336 g, 1 mmol) and molecular sieves (4A, 0.3 g) in chloroform (150 mL) was purged with nitrogen for 10 min. Boron trifluoride diethyl etherate (0.1 mL) was added dropwise via a syringe and flask was wrapped with aluminum foil to shield it from light. The solution was stirred under nitrogen atmosphere at room temperature for 16 h, and 2,3-dichloro-5,6-dicyano-1,4-benzoquinone (DDQ) (0.287 g, 1.2 mmol) was added as powder at one time. After 30 min, 1 mL of triethylamine was added in. The reaction solution was then directly poured on the top of a silica gel column that was packed with dichloromethane. The column was eluted with dichloromethane. The fractions containing product were collected and concentrated on a rotary evaporator. The residue was washed several times with hexanes to afford the title compound as a purple solid. Yield: 0.058 g (14%). $^1$H NMR (300 MHz, CDCl$_3$): δ 10.25 (s, 2H), 9.35 (d, J=4.8 Hz, 4H), 8.85 (d, J=4.8 Hz, 4H), 8.11 (s, 4H), 0.54 (s, 18H), −3.09 (s, 2H). UV-vis (CH$_2$Cl$_2$): 407(5.62), 502(4.34), 534(3.88), 576(3.90), 630(3.45). HRMS-MALDI ([M+H]$^+$): calcd for $C_{38}H_{35}Br_4N_4Si_2$ 918.9128; found: 918.9124.

Example 127

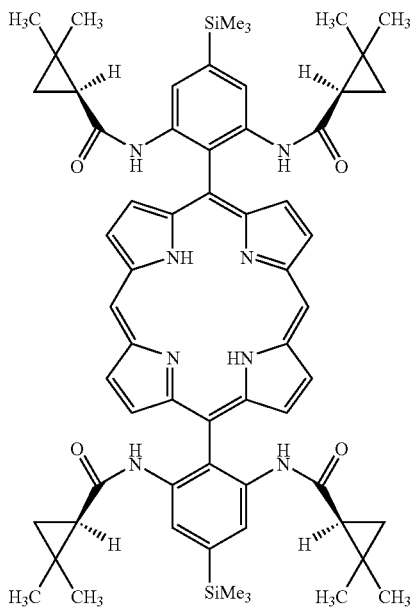

The general procedure was used to couple 5,15-bis(2,6-dibromo-4-trimethylsilanylphenyl)porphyrin (0.023 g, 0.025 mmol) with (S)-(+)-2,2-dimethylcyclopropanecarboxamide (0.091 g, 0.8 mmol), using Pd(OAc)$_2$ (0.002 g, 0.01 mmol), Xantphos (0.012 g, 0.02 mmol) and Cs$_2$CO$_3$ (0.130 g, 0.4 mmol). The reaction was conducted in THF (4 mL) at 100° C. for 41 h. The pure compound was isolated by flash column chromatography (silica gel, ethyl acetate:hexanes (v/v)=1:2) as purple solids (0.019 g, 72%). $^1$H NMR (300 MHz, CDCl$_3$): δ 10.44 (s, 2H), 9.50 (d, J=4.8 Hz, 4H), 9.12 (d, J=4.8 Hz, 4H), 8.66 (broad, 4H), 6.50 (broad, 4H), 0.86 (s, 12H), 0.69 (broad, 4H), 0.55 (s, 18H), −0.10-0.08 (m, 20H), −3.05 (s, 2H). $^{13}$C NMR (75 MHz, CDCl$_3$): δ 169.6, 147.0, 146.4, 138.3, 133.5, 130.7, 130.8, 122.3, 108.3, 106.2, 29.0, 26.3, 22.3, 20.3, 18.2, −0.87. UV-vis (CH$_2$Cl$_2$): 410(5.53), 503(4.33), 537(3.97), 575(3.88), 629(3.61). HRMS-MALDI ([M+H]$^+$): calcd for $C_{62}H_{75}N_8O_4Si_2$ 1051.5444, found 1051.5458.

Example 128

General Procedures for Synthesis of Cobalt Porphyrin Complex

The general procedures for the synthesis of cobalt porphyrin complex follow those described by Tsuchida et al., 1990 *Chem. Lett.* 3:389; Tsuchida et al., (1990) *J. Chem. Soc.-Dalton Trans.* 2713; Komatsu et al., (1990) *J. Chem. Soc.-Chem. Commun.* 66. Free base porphyrin and anhydrous CoCl$_2$ were placed in an oven-dried, resealable Schlenk tube. The tube was capped with a Teflon screwcap, evacuated, and backfilled with nitrogen. The screwcap was replaced with a rubber septum, 2,6-lutidine and dry THF were added via syringe. The tube was purged with nitrogen for 2 minutes, and then the septum was replaced with the Teflon screwcap. The tube was sealed, and its contents were heated with stirring. The resulting mixture was cooled to room temperature, taken up in ethyl acetate, and transferred to a separatory funnel. The mixture was washed with water 3 times and concentrated in vacuo.

Example 129

Cobalt Porphyrin 21a (Table 5, entry 1)

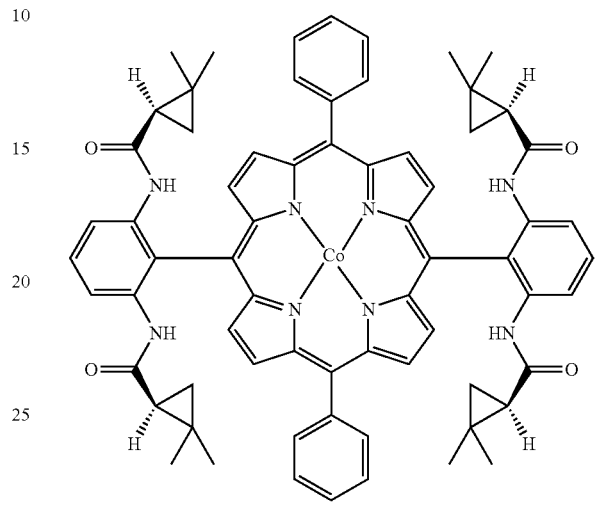

The general procedure was used for cobalt ion insertion. Free-base porphyrin (0.066 g), anhydrous CoCl$_2$ (0.073 g), 2,6-lutidine (0.025 mL), and dry THF (5 mL) were heated at 70° C. under N$_2$ for 16 hours. The resulting mixture was cooled to room temperature, taken up in ethyl acetate and transferred to a separatory funnel. The mixture was washed with water 3 times and concentrated in vacuo. The pure compound was obtained after flash column chromatography (silica gel, ethyl acetate:hexanes (v/v)=1:2) as a red solid (0.061 g, 88%). UV-vis (CH$_2$Cl$_2$), $\lambda_{max}$ nm (log ε): 412(5.29), 529(4.06), 556(3.71). HRMS-EI ([M]$^+$): calcd for $C_{68}H_{64}CoN_8O_4$, 1115.4383, found 1115.4376 with an isotope distribution pattern that is the same as the calculated one.

Example 130

Cobalt Porphyrin 21 b (Table 5, entry 2)

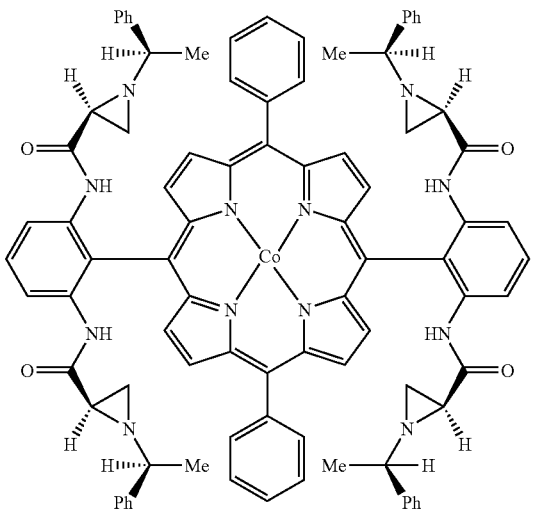

Free-base porphyrin (0.019 g), cobalt acetate tetrahydrate (0.028 g), and dry DMF (2 mL) were heated at 160° C. under $N_2$ for 3 hours. The resulting mixture was cooled to room temperature, taken up in ethyl acetate and transferred to a separatory funnel. The mixture was washed with water 3 times and concentrated in vacuo. The pure compound was obtained as a red solid (0.017 g, 86%). UV-vis ($CH_2Cl_2$), $\lambda_{max}$ nm (log $\epsilon$): 412(5.43), 528(4.30), 556(4.11), 615(3.71). HRMS-MALDI ([M+H]$^+$): calcd for $C_{80}H_{69}CoN_{12}O_4$ 1320.4891, found 1320.3267 with an isotope distribution pattern that is the same as the calculated one.

Example 131

Cobalt Porphyrin 21c (Table 5, entry 3)

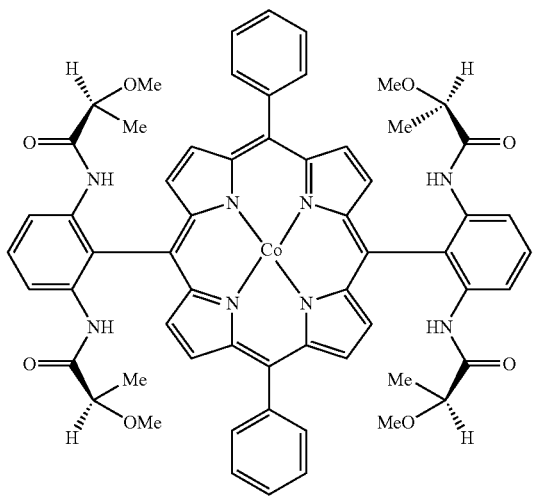

The general procedure was used for cobalt ion insertion. Free-base porphyrin (0.025 g), anhydrous $CoCl_2$ (0.029 g), 2,6-lutidine (0.010 mL), and dry THF (3 mL) were heated at 70° C. under $N_2$ for 15 hours. The resulting mixture was cooled to room temperature, taken up in ethyl acetate, and transferred to a separatory funnel. The mixture was washed with water 3 times and concentrated in vacuo. The pure compound was obtained as a red solid (0.025 g, 95%). UV-vis ($CH_2Cl_2$), $\lambda_{max}$ nm (log $\epsilon$): 412(5.49), 528(4.25), 556(3.91). HRMS-MALDI ([M]$^+$): calcd for $C_{60}H_{56}CoN_8O_8$ 1075.3548, found 1075.3518 with an isotope distribution pattern that is the same as the calculated one.

Example 132

Cobalt Porphyrin 21d (Table 5, entry 4)

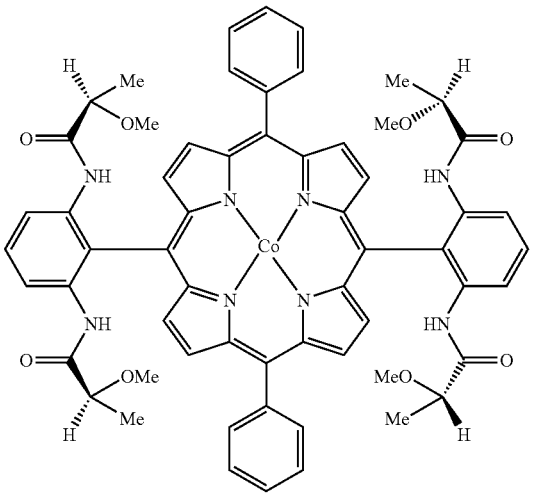

The general procedure was used for cobalt ion insertion. Free-base porphyrin (0.020 g), anhydrous $CoCl_2$ (0.023 g), 2,6-lutidine (0.008 mL), and dry THF (4 mL) were heated at 70° C. under $N_2$ for 14 hours. The resulting mixture was cooled to room temperature, taken up in ethyl acetate, and transferred to a separatory funnel. The mixture was washed with water 3 times and concentrated in vacuo. The pure compound was obtained as a red solid (0.020 g, 95%). UV-vis ($CH_2Cl_2$), $\lambda_{max}$ nm (log $\epsilon$): 412(5.65), 528(4.39), 556(3.85). HRMS-MALDI ([M]$^+$): calcd for $C_{60}H_{56}CoN_8O_8$ 1075.3548, found 1075.3544 with an isotope distribution pattern that is the same as the calculated one.

Example 133

Cobalt Porphyrin 21e (Table 5, entry 5)

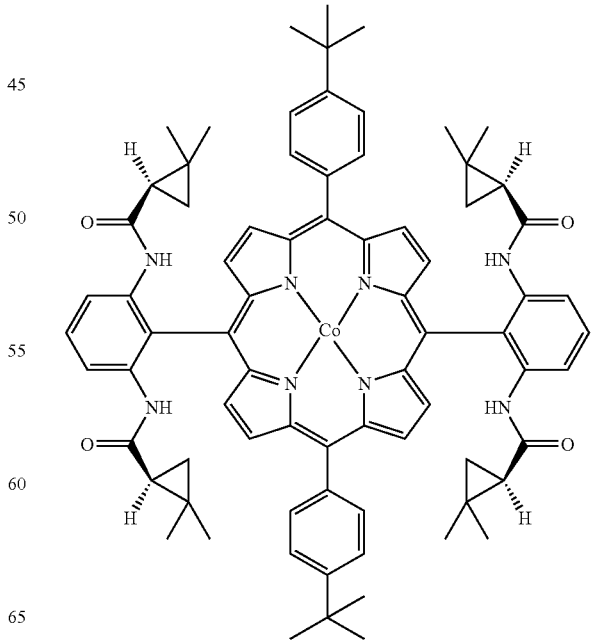

The general procedure was used for cobalt ion insertion. Free-base porphyrin (0.045 g), anhydrous $CoCl_2$ (0.045 g), 2,6-lutidine (0.014 mL), and dry THF (5 mL) were heated at 70° C. under $N_2$ for 12 hours. The resulting mixture was cooled to room temperature, taken up in ethyl acetate, and transferred to a separatory funnel. The mixture was washed with water 3 times and concentrated in vacuo. The pure compound was obtained after flash column chromatography (silica gel, ethyl acetate:hexanes (v/v)=1:4) as a red solid (0.034 g, 72%). UV-vis ($CH_2Cl_2$), $\lambda_{max}$ nm (log $\epsilon$): 413(5.48), 529(4.25), 554(3.92). HRMS-EI ($[M]^+$): calcd for $C_{76}H_{80}CoN_8O_4$ 1227.5635, found 1227.5593 with an isotope distribution pattern that is the same as the calculated one.

Example 134

Cobalt Porphyrin 21f (Table 5, entry 6)

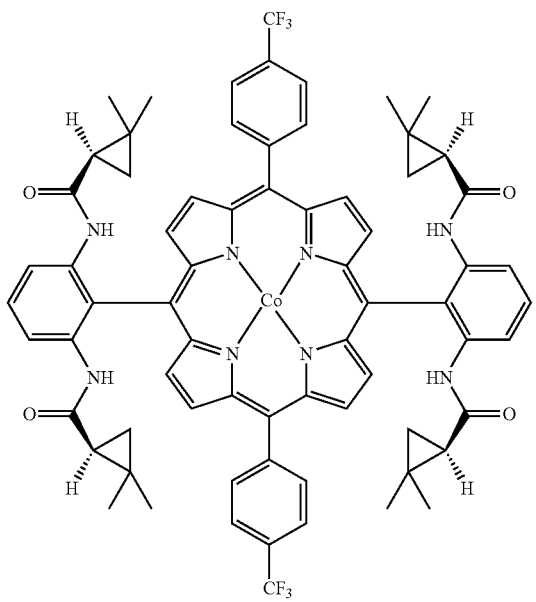

The general procedure was used for cobalt ion insertion. Free-base porphyrin (0.025 g), anhydrous $CoCl_2$ (0.022 g), 2,6-lutidine (0.008 mL), and dry THF (2 mL) were heated at 70° C. under $N_2$ for 17 hours. The resulting mixture was cooled to room temperature, taken up in ethyl acetate, and transferred to a separatory funnel. The mixture was washed with water 3 times and concentrated in vacuo. The pure compound was obtained as a red solid (0.025 g, 95%). UV-vis ($CH_2Cl_2$), $\lambda_{max}$ nm (log $\epsilon$): 420(4.85), 444(4.95), 523(4.11), 550(4.20). HRMS-EI ($[M]^+$): calcd for $C_{70}H_{62}CoF_6N_8O_4$ 1251.4125, found 1251.4085 with an isotope distribution pattern that is the same as the calculated one.

Example 135

Cobalt Porphyrin 21a (Table 5, entry 7)

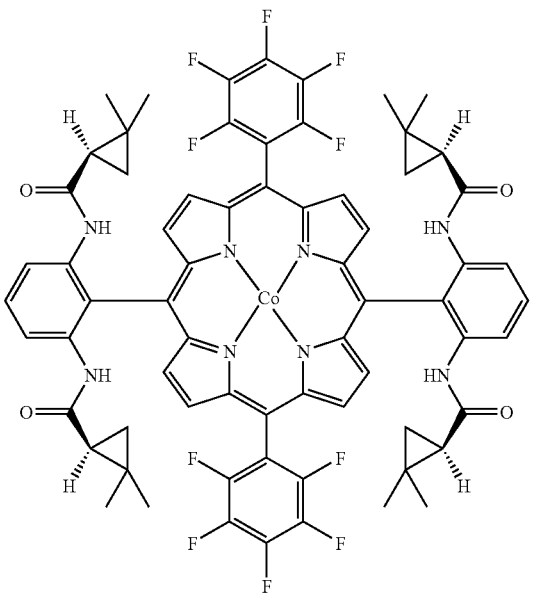

The general procedure was used for cobalt ion insertion. Free-base porphyrin (0.010 g), anhydrous $CoCl_2$ (0.009 g), 2,6-lutidine (0.005 mL), and dry THF (2 mL) were heated at 70° C. under $N_2$ for 14 hours. The resulting mixture was cooled to room temperature, taken up in ethyl acetate, and transferred to a separatory funnel. The mixture was washed with water 3 times and concentrated in vacuo. The pure compound was obtained as a red solid (0.009 g, 86%). UV-vis ($CH_2Cl_2$), $\lambda_{max}$ nm (log $\epsilon$): 410(5.57), 443(4.70), 527(4.41), 556(4.23). HRMS-MALDI ($[M]^+$): calcd for $C_{68}H_{54}CoF_{10}N_8O_4$ 1295.3435, found 1295.3459 with an isotope distribution pattern that is the same as the calculated one.

Example 136

Cobalt Porphyrin 21h (Table 5, entry 8)

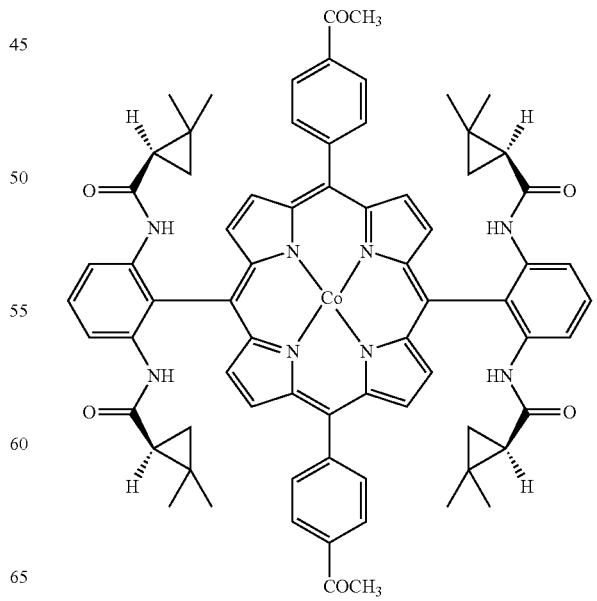

The general procedure was used for cobalt ion insertion. Free-base porphyrin (0.030 g), anhydrous $CoCl_2$ (0.031 g), 2,6-lutidine (0.010 mL), and dry THF (3 mL) were heated at 70° C. under $N_2$ for 12 hours. The resulting mixture was cooled to room temperature, taken up in ethyl acetate, and transferred to a separatory funnel. The mixture was washed with water 3 times and concentrated in vacuo. The pure compound was obtained after flash column chromatography (silica gel, ethyl acetate:hexanes (v/v)=1:1) as a red solid (0.026 g, 83%). UV-vis ($CH_2Cl_2$), $\lambda_{max}$ nm (log $\epsilon$): 413(5.53), 528(4.31), 553(3.98). HRMS-MALDI ($[M]^+$): calcd for $C_{72}H_{68}CoN_8O_6$ 1199.4588, found 1199.4572 with an isotope distribution pattern that is the same as the calculated one.

Example 137

Cobalt Porphyrin 21i (Table 5, entry 9)

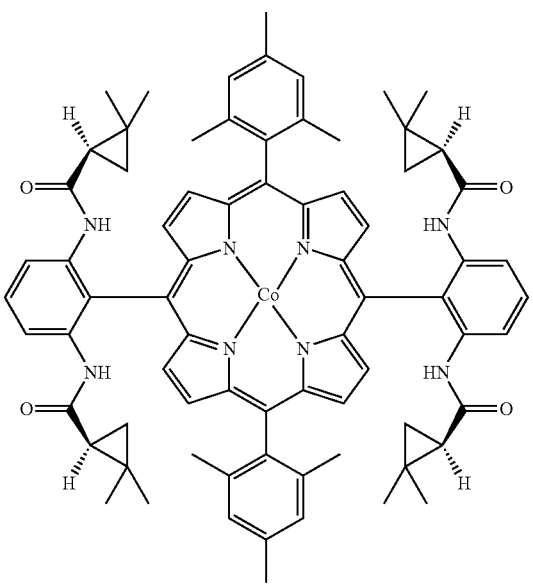

The general procedure was used for cobalt ion insertion. Free-base porphyrin (0.070 g), anhydrous $CoCl_2$ (0.071 g), 2,6-lutidine (0.024 mL), and dry THF (5 mL) were heated at 70° C. under $N_2$ for 16 hours. The resulting mixture was cooled to room temperature, taken up in ethyl acetate, and transferred to a separatory funnel. The mixture was washed with water 3 times and concentrated in vacuo. The pure compound was obtained after flash column chromatography (silica gel, ethyl acetate:hexanes (v/v)=1:3) as a red solid (0.067 g, 91%). UV-vis ($CH_2Cl_2$), $\lambda_{max}$ nm (log $\epsilon$): 413(5.33), 528(4.09), 558(3.73). HRMS-EI ($[M]^+$): calcd for $C_{74}H_{76}CoN_8O_4$, 1199.5322, found 1199.5320 with an isotope distribution pattern that is the same as the calculated one.

Example 138

Cobalt Porphyrin 21i (Table 5, entry 10)

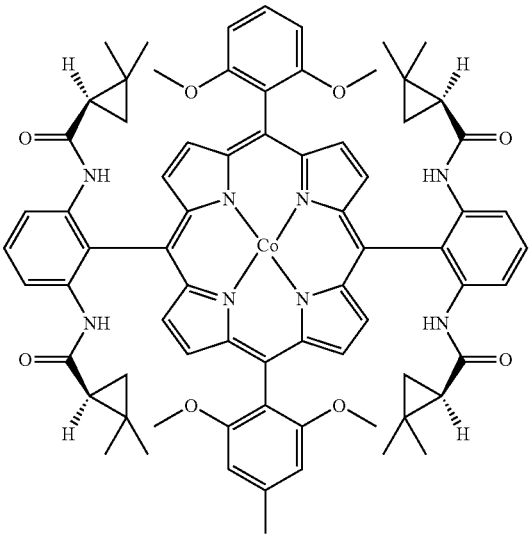

The general procedure was used for cobalt ion insertion. Free-base porphyrin (0.050 g), anhydrous $CoCl_2$ (0.044 g), 2,6-lutidine (0.015 mL), and dry THF (3 mL) were heated at 70° C. under $N_2$ for 19 hours. The resulting mixture was cooled to room temperature, taken up in ethyl acetate, and transferred to a separatory funnel. The mixture was washed with water 3 times and concentrated in vacuo. The pure compound was obtained as a red solid (0.050 g, 95%). UV-vis ($CH_2Cl_2$), $\lambda_{max}$ nm (log $\epsilon$): 413(5.18), 439(4.53), 532(4.09), 551(4.00). HRMS-EI ($[M]^+$): calcd for $C_{72}H_{72}CoN_8O_8$ 1235.4805, found 1235.4794 with an isotope distribution pattern that is the same as the calculated one.

Example 139

Cobalt Porphyrin 21k (Table 5, entry 11)

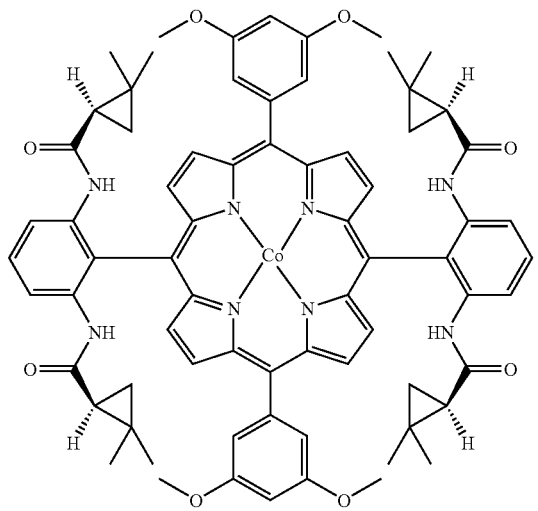

The general procedure was used for cobalt ion insertion. Free-base porphyrin (0.023 g), anhydrous CoCl$_2$ (0.022 g), 2,6-lutidine (0.007 mL), and dry THF (3 mL) were heated at 70° C. under N$_2$ for 15 hours. The resulting mixture was cooled to room temperature, taken up in ethyl acetate, and transferred to a separatory funnel. The mixture was washed with water 3 times and concentrated in vacuo. The pure compound was obtained as a red solid (0.023 g, 96%). UV-vis (CH$_2$Cl$_2$), $\lambda_{max}$ nm (log $\epsilon$): 414(4.92), 445(4.66), 530(4.13), 553(4.11). HRMS-MALDI ([M]$^+$): calcd for C$_{72}$H$_{72}$CoN$_8$O$_8$ 1235.4800, found 1235.4749 with an isotope distribution pattern that is the same as the calculated one.

Example 140

Cobalt Porphyrin 21l (Table 5, entry 12)

Example 141

Cobalt Porphyrin 21m (Table 5, entry 13)

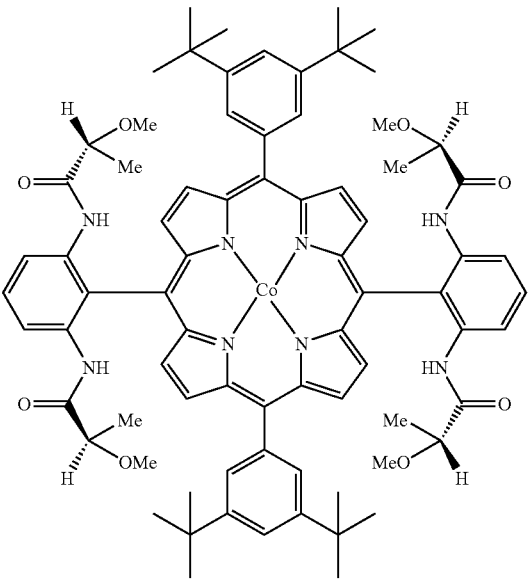

The general procedure was used for cobalt ion insertion. Free-base porphyrin (0.029 g), anhydrous CoCl$_2$ (0.026 g), 2,6-lutidine (0.010 mL), and dry THF (3 mL) were heated at 70° C. under N$_2$ for 15 hours. The resulting mixture was cooled to room temperature, taken up in ethyl acetate, and transferred to a separatory funnel. The mixture was washed with water 3 times and concentrated in vacuo. The pure compound was obtained as a red solid (0.029 g, 96%). UV-vis (CH$_2$Cl$_2$), $\lambda_{max}$ nm (log $\epsilon$): 414(5.52), 529(4.23), 558(3.96). HRMS-MALDI ([M]$^+$): calcd for C$_{76}$H$_{88}$CoN$_8$O$_8$ 1299.6052, found 1299.6082 with an isotope distribution pattern that is the same as the calculated one.

Example 142

Cobalt Porphyrin 21n (Table 5, entry 14)

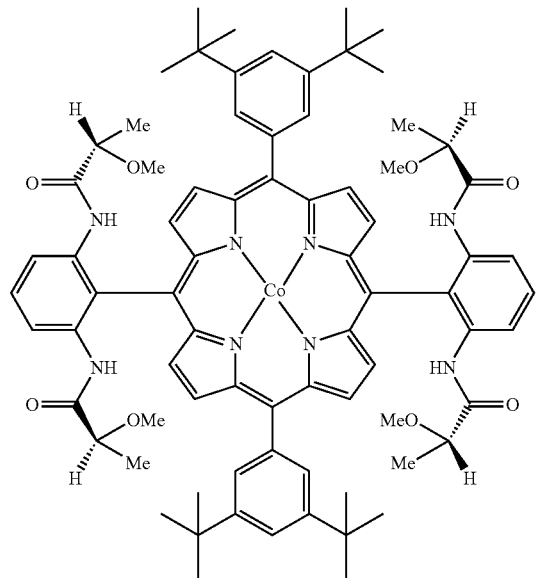

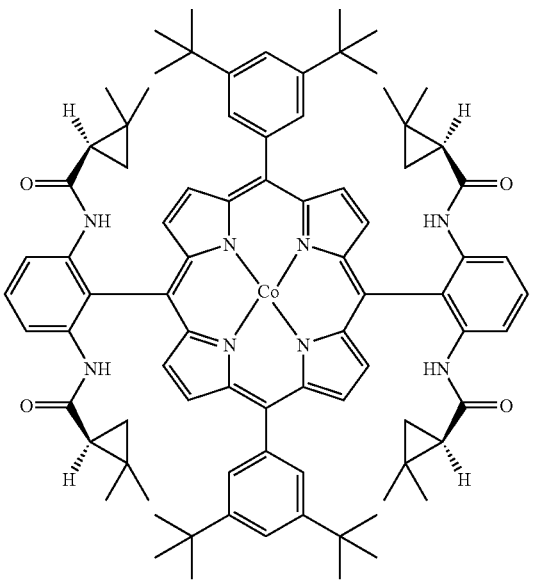

The general procedure was used for cobalt ion insertion. Free-base porphyrin (0.100 g), anhydrous CoCl$_2$ (0.080 g), 2,6-lutidine (0.027 mL), and dry THF (5 mL) were heated at 70° C. under N$_2$ for 9 hours. The resulting mixture was cooled to room temperature, taken up in ethyl acetate, and transferred to a separatory funnel. The mixture was washed with water 3 times and concentrated in vacuo. The pure compound was obtained after flash column chromatography (silica gel, ethyl acetate:hexanes (v/v)=1:4) as a red solid (0.099 g, 91%). UV-vis (CH$_2$Cl$_2$), $\lambda_{max}$ nm (log $\epsilon$): 414(5.37), 529(4.14), 549(3.84). HRMS-EI ([M]$^+$): calcd for C$_{84}$H$_{96}$CoN$_8$O$_4$ 1339.6887, found 1339.6909 with an isotope distribution pattern that is the same as the calculated one.

The general procedure was used for cobalt ion insertion. Free-base porphyrin (0.030 g), anhydrous $CoCl_2$ (0.028 g), 2,6-lutidine (0.010 mL), and dry THF (3 mL) were heated at 70° C. under $N_2$ for 15 hours. The resulting mixture was cooled to room temperature, taken up in ethyl acetate, and transferred to a separatory funnel. The mixture was washed with water 3 times and concentrated in vacuo. The pure compound was obtained as a red solid (0.029 g, 92%). UV-vis $(CH_2Cl_2)$, $\lambda_{max}$ nm (log $\epsilon$): 414(5.54), 529(4.29), 557(3.94). HRMS-MALDI ([M]$^+$): calcd for $C_{76}H_{88}CoN_8O_8$ 1299.6052, found 1299.6070 with an isotope distribution pattern that is the same as the calculated one.

Example 143

Cobalt Porphyrin 21o (Table 5, entry 15)

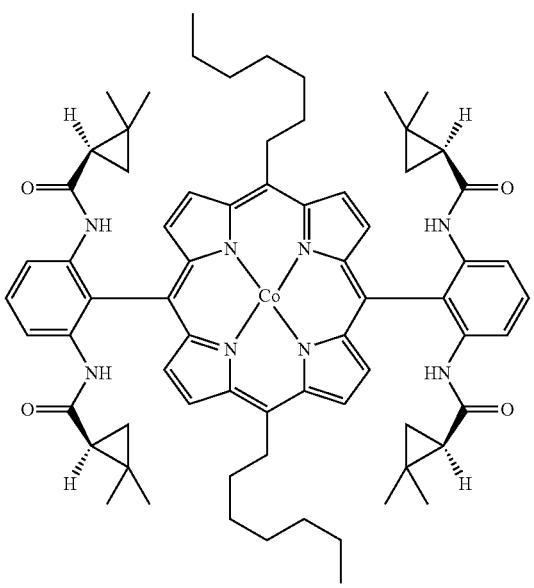

The general procedure was used for cobalt ion insertion. Free-base porphyrin (0.030 g), anhydrous $CoCl_2$ (0.030 g), 2,6-lutidine (0.009 mL), and dry THF (4 mL) were heated at 70° C. under $N_2$ for 16 hours. The resulting mixture was cooled to room temperature, taken up in ethyl acetate, and transferred to a separatory funnel. The mixture was washed with water 3 times and concentrated in vacuo. The pure compound was obtained as a red solid (0.030 g, 95%). UV-vis $(CH_2Cl_2)$, $\lambda^{max}$ nm (log $\epsilon$): 414(5.35), 443(4.37), 533(4.18), 560(3.89). HRMS-MALDI ([M]$^+$): calcd for $C_{70}H_{84}CoN_8O_4$ 1159.5942, found 1159.5927 with an isotope distribution pattern that is the same as the calculated one.

Example 144

Cobalt Porphyrin 21p (Table 5, entry 16)

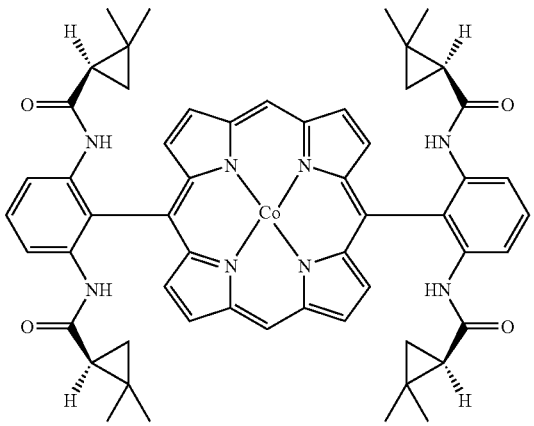

The general procedure was used for cobalt ion insertion. Free-base porphyrin (0.017 g), anhydrous $CoCl_2$ (0.022 g), 2,6-lutidine (0.007 mL), and dry THF (3 mL) were heated at 70° C. under $N_2$ for 15 hours. The resulting mixture was cooled to room temperature, taken up in ethyl acetate, and transferred to a separatory funnel. The mixture was washed with water 3 times and concentrated in vacuo. The pure compound was obtained as a red solid (0.017 g, 91%). UV-vis $(CH_2Cl_2)$, $\lambda_{max}$ nm (log $\epsilon$): 404(5.27), 428(4.93), 461(4.62), 521(4.39), 547(4.41). HRMS-MALDI ([M]$^+$): calcd for $C_{56}H_{56}CoN_8O_4$ 963.3751, found 963.3726 with an isotope distribution pattern that is the same as the calculated one.

Example 145

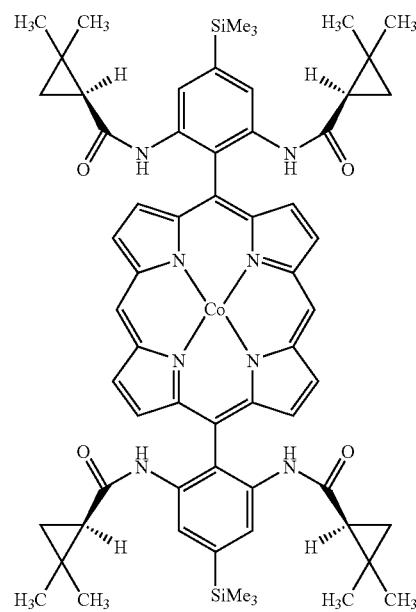

The general procedure was used for cobalt ion insertion. Free-base porphyrin (0.011 g), anhydrous $CoCl_2$ (0.012 g), 2,6-lutidine (0.004 mL) and dry THF (2 mL) were heated at 70° C. under $N_2$ for 16 hours. The resulting mixture was cooled to room temperature, taken up in ethyl acetate and transferred to a separatory funnel. The mixture was washed with water 3 times and concentrated in vacuo. The pure compound was obtained as a red solid (0.009 g, 78%). UV-vis ($CH_2Cl_2$): 404(5.51), 430(4.81), 454(4.39), 518(4.39), 549 (4.28). HRMS-MALDI ([M]$^+$): calcd for $C_{62}H_{72}CoN_8O_4Si_2$ 1107.4542, found 1107.4579.

Example 146

General Procedures for Cyclopropanation of Styrene

Catalyst (1 mol %) and DMAP were placed in an oven-dried, resealable Schlenk tube. The tube was capped with a Teflon screwcap, evacuated, and backfilled with nitrogen. The screwcap was replaced with a rubber septum, and 1.0 equivalent of styrene (0.25 mmol) was added via syringe, followed by toluene (0.5 mL), 1.2 equivalents of diazo compound and toluene again (0.5 mL). The tube was purged with nitrogen for 1 min and its contents were stirred at room temperature. After the reaction finished, the resulting mixture was concentrated and the residue was purified by flash silica gel chromatography to give the product.

Example 147

Ethyl 2-phenylcyclopropane-1-carboxylate $^1$H NMR (300 MHz, $CDCl_3$) trans-isomer: δ 7.09-7.31 (m, 5H), 4.17 (q, J=7.2 Hz, 2H), 2.52 (ddd, J=9.3, 6.6, 4.2 Hz, 1H), 1.90 (ddd, J=8.7, 5.4, 4.5 Hz, 1H), 1.60 (ddd, J=9.0, 5.1, 4.2 Hz, 1H), 1.30 (ddd, J=8.4, 6.6, 4.8 Hz, 1H), 1.28 (t, J=7.2 Hz, 3H). $^{13}$C NMR (75 MHz, $CDCl_3$) trans-isomer: δ 173.4, 140.1, 128.4, 126.4, 126.1, 60.7, 26.2, 24.2, 17.1, 14.3. $^1$H NMR (300 MHz, $CDCl_3$) cis-isomer: δ7.18-7.28 (m, 5H), 3.88 (q, J=7.2 Hz, 2H), 2.59 (m, 1H), 2.08 (ddd, J=9.0, 7.8, 5.6 Hz, 1H), 1.72 (ddd, J=6.3, 4.9, 4.4 Hz, 1H), 1.32 (ddd, J=8.9, 7.9, 5.0 Hz, 1H), 0.97 (t, J=7.2 Hz, 3H). $^{13}$C NMR (75 MHz, $CDCl_3$) cis-isomer: δ 170.9, 136.5, 129.2, 127.8, 126.6, 60.1, 25.4, 21.7, 14.0, 11.1.

Example 148 tert-Butyl 2-phenylcyclopropane-1-carboxylate $^1$H NMR (300 MHz, $CDCl_3$) trans-isomer: δ 7.07-7.29 (m, 5H), 2.44 (m, 1H), 1.82 (m, 1H), 1.53 (m, 1H), 1.46 (s, 9H), 1.21 (m, 1H). $^{13}$C NMR (75 MHz, $CDCl_3$) trans-isomer: δ 172.5, 140.5, 128.4, 126.3, 126.0, 80.5, 28.1, 26.0, 25.3, 17.0. $^1$H NMR (300 MHz, $CDCl_3$) cis-isomer: δ 7.17-7.27 (m, 5H), 2.52 (m, 1H), 1.99 (m, 1H), 1.65 (m, 1H), 1.24 (m, 1H), 1.13 (s, 9H). $^{13}$C NMR (75 MHz, $CDCl_3$) cis-isomer: δ 170.1, 136.8, 129.5, 127.8, 126.5, 80.0, 27.7, 25.0, 22.7, 10.5.

Results

1. Synthesis of Chiral Porphyrins

Figure 10:
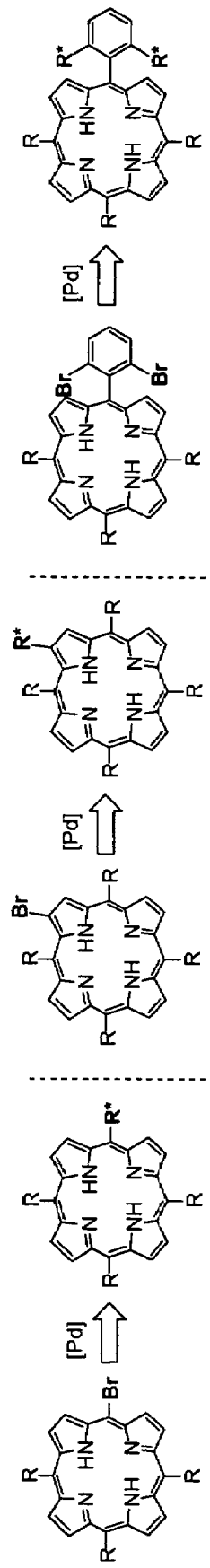
FIG. 10 illustrates generalized schemes A-F depicting the use of bromoporphyrins as synthons for the modular construction of chiral porphyrins of the presently disclosed subject matter.

A generalized schematic representation of the use of haloporphyrins, e.g., bromoporphyrins, as synthons for the modular construction of chiral porphyrins is provided in FIG. 10. More particularly, as shown in FIG. 11, in some embodiments, the presently disclosed subject matter describes the use of two types of brominated porphyrin synthons, e.g., 5,15-dibromoporphyrins (S1) and 5,15-bis(2,6-dibromophenyl)porphyrins (S2), which, in some embodiments, bear R substituents at the 10,20-positions, for the synthesis of chiral porphyrins.

Figure 11:
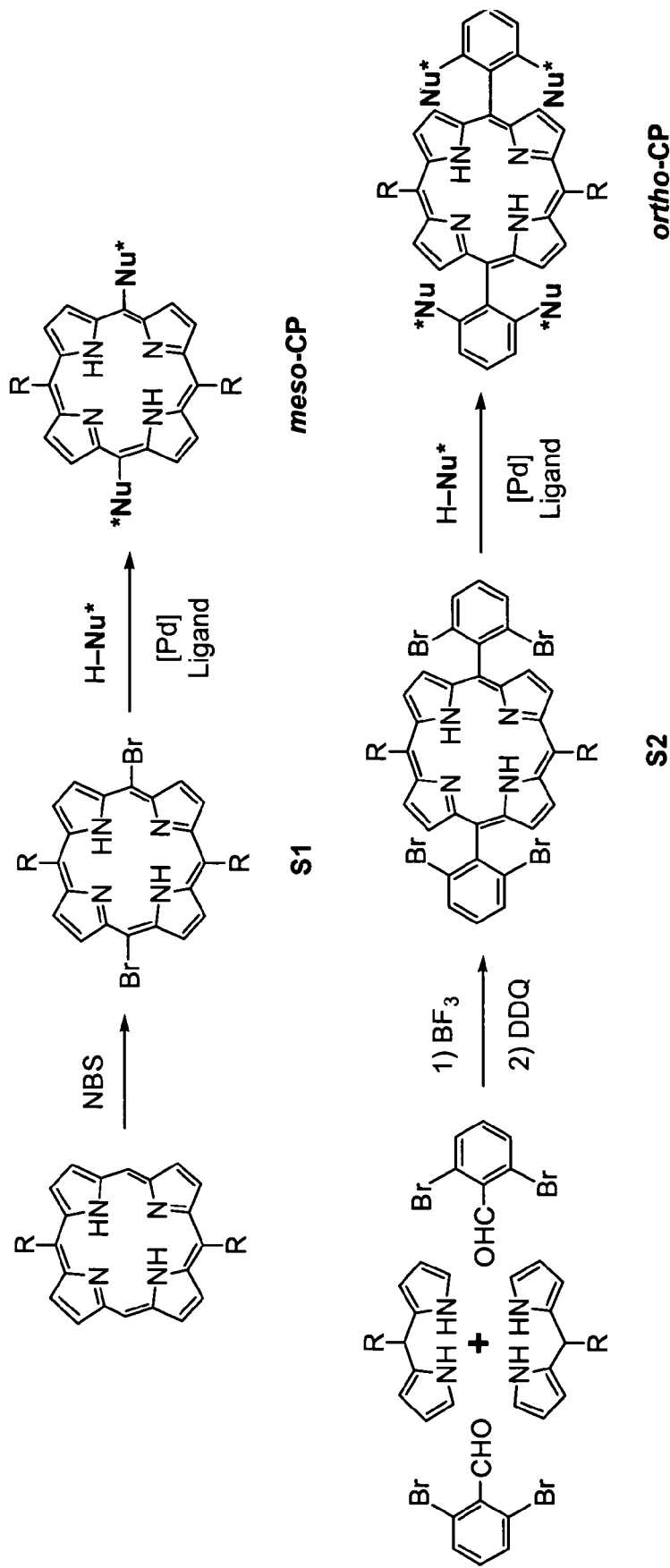
FIG. 11 illustrates generalized schemes for the preparation of bromoporphyrin synthons S1 and S2 and the synthesis of meso-chiral porphyrins (meso-CP), e.g., compounds 15a-15f and compounds 17a-17c, and ortho-chiral porphyrins (ortho-CP), e.g., compounds 20a-20p, which are representative, of the presently disclosed subject matter.

The bromoporphyrin synthons, e.g., bromoporphyrin synthons S1 and S2 as shown in FIG. 11, used in the presently disclosed subject matter are prepared by selective bromination of preformed porphyrins with N-bromosuccinimide (NBS) (first step in the upper reaction sequence of FIG. 11) and by MacDonald [2±2] porphyrin synthesis using Lindsey's condition, see Lindsey, (2000) in *The Porphyrin Handbook*; Kadish, K. M., Smith, K. M., Guilard, R., Eds., Academic Press: San Diego, Calif.; Vol. 1; pp 45-118 (first step in the lower reaction sequence of FIG. 11). Commercially available chiral building blocks are used as nucleophiles (designated as H-Nu* in FIG. 11) to couple with synthons S1 and S2 via palladium-mediated multiple crosscoupling reactions, yielding a series of $D_2$- or pseudo-$D_2$-symmetric meso-chiral porphyrins, e.g., compounds 15a-15f and compounds 17a-17c of FIG. 13, and ortho chiral porphyrins, e.g., compounds 20a-20d and compounds 20l-20o of FIG. 16, respectively. The R substituents at the 10,20-positions can be aromatic, substituted aromatic, aliphatic, substituted aliphatic, aralalkyl or heteroatom-containing groups, which allows fine-tuning of the electronic and steric environments and the manipulation of product solubility.

Figure 12:
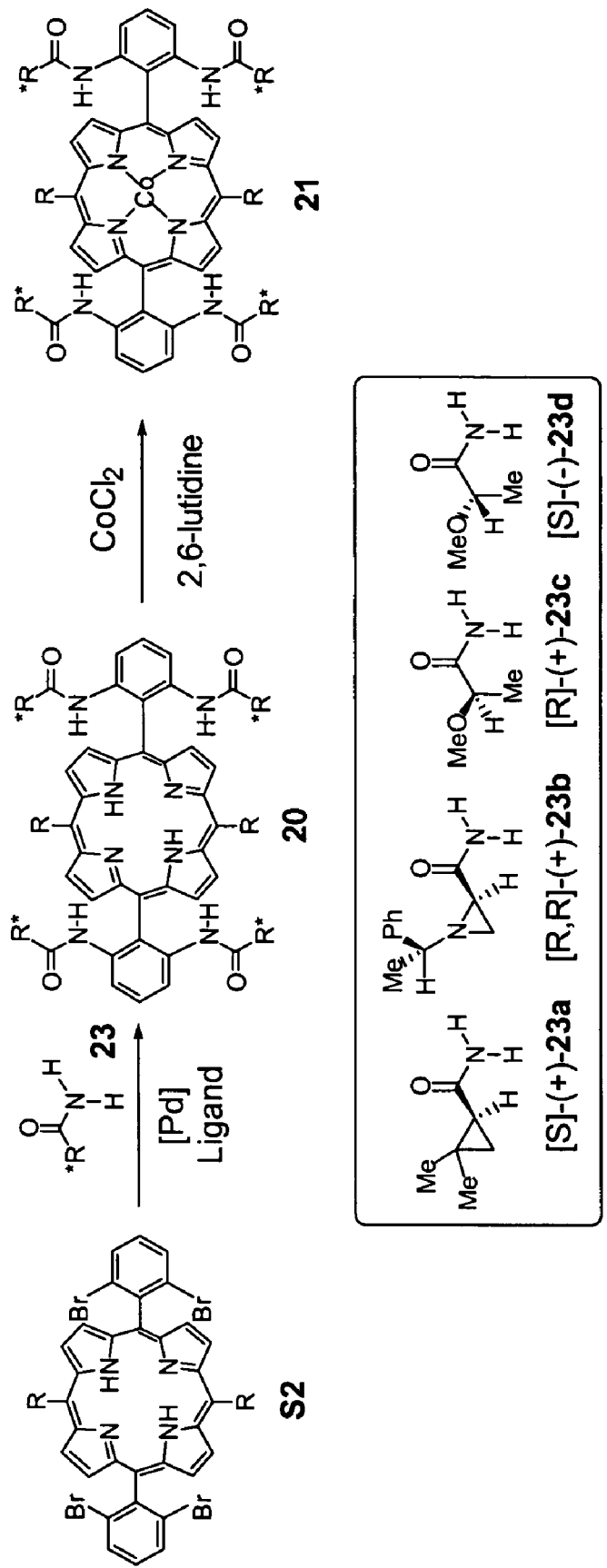
FIG. 12 illustrates generalized schemes for the synthesis of amido-substituted ortho chiral porphyrins 20, e.g., compounds 20a-20p, which are representative, but not inclusive, of the presently disclosed subject matter, via a palladium-catalyzed amidation reaction and cobalt complexes 21 thereof and the chemical structures of particular chiral amide reagents 23a, 23b, 23c, and 23d of the presently disclosed subject matter.

In some embodiments, the chiral nucleophile H-Nu* comprises a chiral amide. As shown in FIG. 12, the quadruple carbon-nitrogen bond formation reactions can be accomplished in high yields with different chiral amide building blocks, e.g., compounds 23a-23d, under mild conditions, forming a family of ortho-chiral porphyrins, e.g., compounds 20a-20p, and their corresponding Co complexes, e.g., compounds 21 a-21 p, of Table 4.

As summarized in Table 4, a series of 5,15-bis(2,6-dibromophenyl)porphyrins, 19a-19k, comprising different meso-aryl and meso-alkyl R groups at the 10,20-positions, were coupled with several optically pure amides 23a-23d under palladium-catalyzed amidation conditions. The combination of $Pd(OAc)_2$ and XantPhos mediates the quadruple amidation reactions of synthons 19a-19k with chiral amides 23a-23d to deliver a family of $D_2$-symmetric chiral porphyrins 20a-20p in high yields.

Without being bound to any particular theory, the near perpendicular arrangement between the meso-phenyl ring and the porphyrin plane, in combination with the trans-amide conformation, appears to direct the ortho-chiral R* units toward the center of porphyrins, as suggested from the observed large high-field NMR chemical shifts of the chiral R* units. As a result, as will be described in more detail herein below, high asymmetric induction can be achieved for catalytic reactions with metal complexes of these chiral porphyrins. Accordingly, through the combined use of the chiral R* and meso-R groups, it is possible to control diastereoselectivity as well as enantioselectivity in catalytic reactions with metal complexes of these chiral porphyrins.

TABLE 4

Synthesis of Chiral Porphyrins 20 and Cobalt Complexes 21.[a]

| Entry | R | 19 | 23 | 20: yield[a] | 21: yield[a] |
|---|---|---|---|---|---|
| 1 | Ph | 19a | 23a | 20a: 78% | 21a: 88% |
| 2 | Ph | 19a | 23b | 20b: 64% | 21b: 86% |
| 3 | Ph | 19a | 23c | 20c: 75% | 21c: 95% |
| 4 | Ph | 19a | 23d | 20d: 71% | 21d: 95% |
| 5 | 4-t-BuPh | 19b | 23a | 20e: 86% | 21e: 72% |
| 6 | 4-$CF_3$Ph | 19c | 23a | 20f: 77% | 21f: 95% |
| 7 | PentaFPh | 19d | 23a | 20g: 46% | 21g: 86% |

TABLE 4-continued

Synthesis of Chiral Porphyrins 20 and Cobalt Complexes 21.[a]

| Entry | R | 19 | 23 | 20: yield[a] | 21: yield[a] |
|---|---|---|---|---|---|
| 8 | 4-AcetylPh | 19e | 23a | 20h: 66% | 21h: 83% |
| 9 | 2,4,6-triMePh | 19f | 23a | 20i: 84% | 21i: 91% |
| 10 | 2,6-diMeOPh | 19g | 23a | 20j: 59% | 21j: 95% |
| 11 | 3,5-diMeOPh | 19h | 23a | 20k: 88% | 21k: 96% |
| 12 | 3,5-di-t-BuPh | 19i | 23a | 20l: 85% | 21l: 91% |
| 13 | 3,5-di-t-BuPh | 19i | 23c | 20m: 79% | 21m: 96% |
| 14 | 3,5-di-t-BuPh | 19i | 23d | 20n: 72% | 21n: 92% |
| 15 | 4-n-heptyl | 19j | 23a | 20o: 74% | 21o: 95% |
| 16 | H | 19k | 23a | 20p: 79% | 21p: 91% |

[a]Yields represent isolated yields of >95% purity as determined by $^1$H NMR.

As also will be described in more detail herein below cobalt complexes of chiral porphyrins 21a-21 p, which were prepared in high yields, were applied as catalysts for cyclopropanation using styrene as a model substrate (see Table 5).

Figure 13:
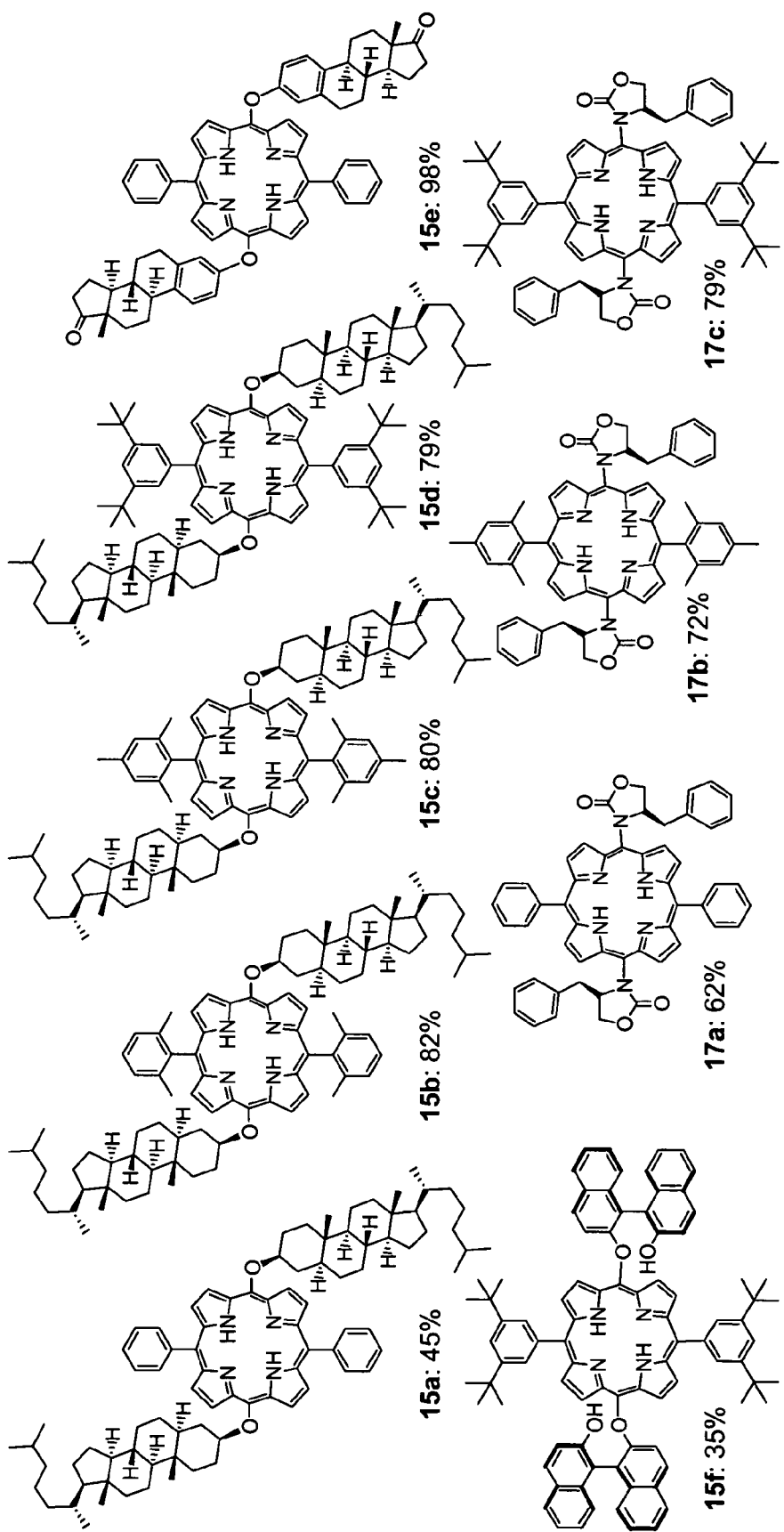
FIG. 13 provides the chemical structures and synthetic yields of meso-chiral porphyrins, e.g., compounds 15a-15f and compounds 17a-17c, which are representative, of the presently disclosed subject matter.

Representative meso-chiral porphyrins of the presently disclosed subject matter are provided in FIG. 13. By way of example, four meso-dibromoporphyrins S1 comprising different meso-aryl groups (e.g., R=phenyl; R=2,6-dimethylphenyl; R=2,4,6-trimethylphenyl; R=3,5-di-tert-butylphenyl), were prepared via selective bromination of the corresponding 5,15-diarylporphyrins. These meso-dibromoporphyrins were successfully coupled with chiral alcohols and chiral amides under palladium-catalyzed etheration and amidation conditions, affording a series of novel meso-chiral porphyrins 15a-15f and 17a-17c in 35-98% yields (see FIG. 13).

Figure 14:
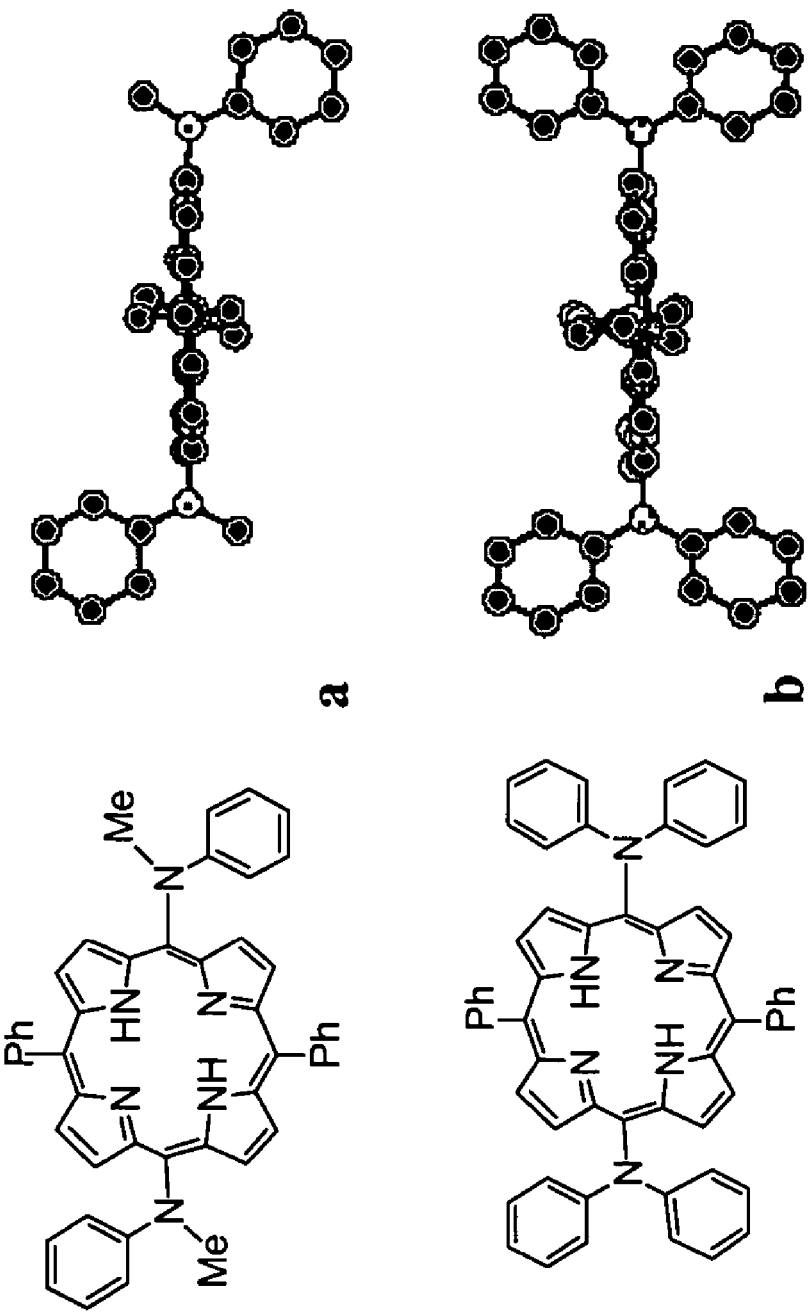
FIG. 14 represents the X-ray structures of exemplary meso-aminoporphyrins of the presently disclosed subject matter.

X-ray structural studies of several meso-aminoporphyrins (for example, see FIGS. 14a and 14b) revealed that all the amino nitrogen atoms adopt an almost perfect planar geometry to minimize steric interactions with the β-hydrogen atoms and that the plane is nearly perpendicular to the porphyrin ring. These data suggest that chiral secondary amines also could be suitable building blocks for the construction of meso-chiral porphyrins.

Figure 15:
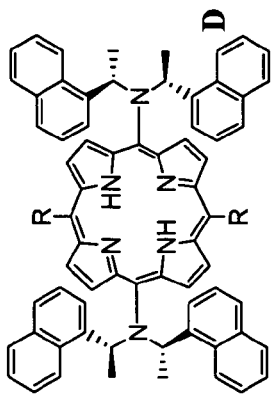
FIG. 15 provides the generalized chemical structures of meso-chiral porphyrins A, B, C, and D comprising $C_2$-symmetrical chiral secondary amine building blocks and which are representative of the presently disclosed subject matter.
Figure 15:
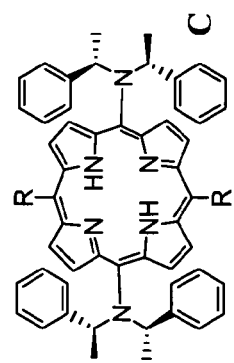
Figure 15:
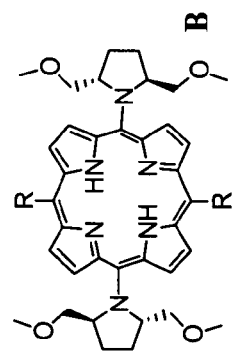
Figure 15:
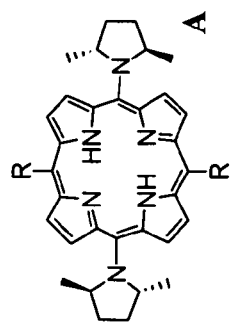

Accordingly, a series of meso-chiral porphyrins (represented generally as A, B, C, and D in FIG. 15) from reactions of synthon S1 with a selection of C2-symmetric chiral secondary amines via palladium-catalyzed double amination are provided by the presently disclosed subject matter. The meso-chiral porphyrins provided in FIG. 15 contain more rigid chiral appendages with desirable geometries and orientations and therefore also should be good ligands for asymmetric catalysis.

Figure 16:
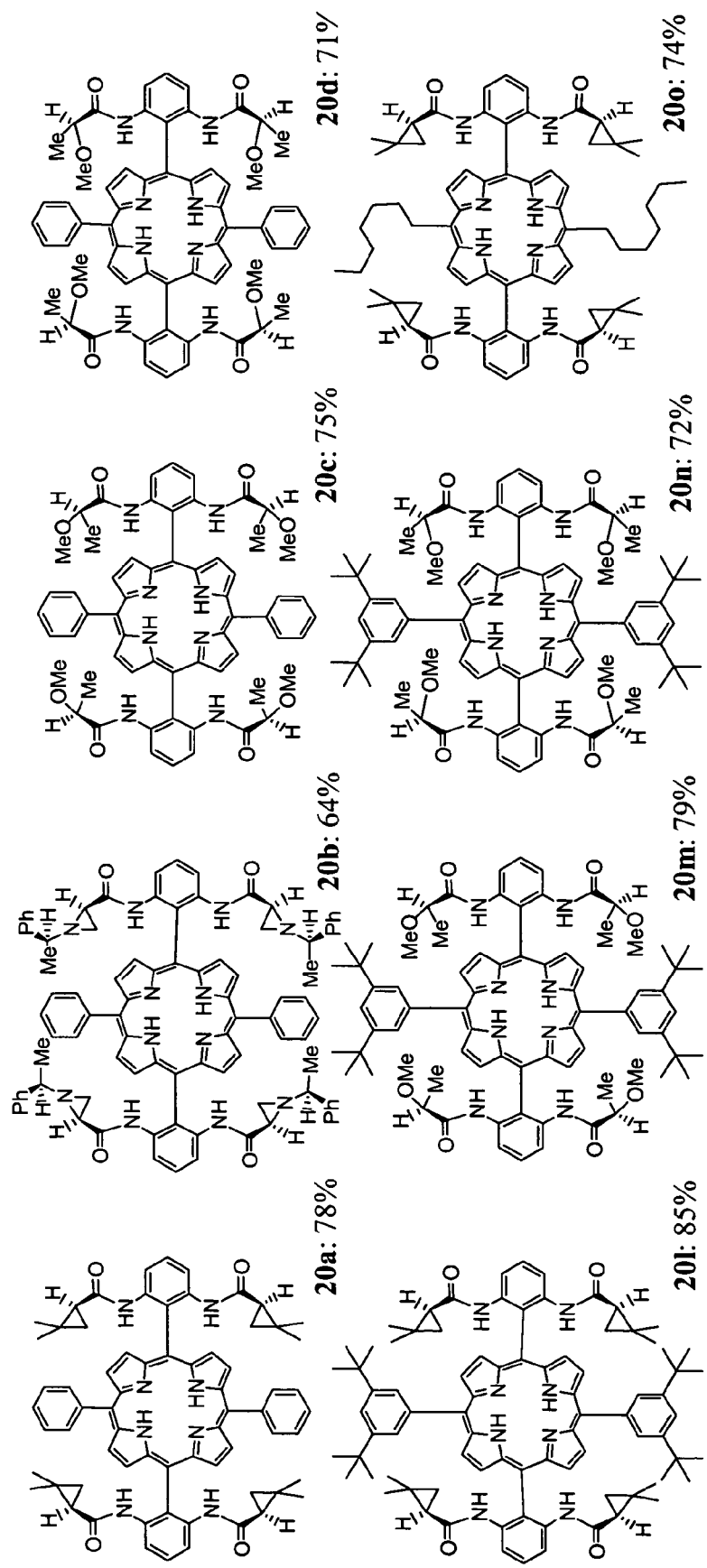
FIG. 16 provides the chemical structures and synthetic yields of $D_2$-symmetric ortho-chiral porphyrins, e.g., compounds 20a-20d and compounds 20l-20o, which are representative, of the presently disclosed subject matter.

Further, representative ortho-chiral porphyrins of the presently disclosed subject matter are provided in FIG. 16. By way of example, three 5,15-bis(2,6-dibromophenyl)porphyrins, S2, comprising different meso-aryl and meso-alkyl groups (e.g., R=phenyl; R=2,6-di-tert-butylphenyl; and R=n-heptyl), were prepared by MacDonald [2+2] porphyrin synthesis under Lindsey's condition from 2,6-dibromobenzaldhyde and corresponding dipyrromethanes. These dibromoporphyrins were coupled with chiral amides 23a-23d under palladium-catalyzed amidation conditions to produce ortho-chiral porphpyrins 20 (see, e.g., the reaction schemes provided in FIG. 12).

Accordingly, in some embodiments, the combination of the palladium catalyst Pd(OAc)$_2$ and the ligand XantPhos mediates the quadruple amidation reactions of synthons S2 with building blocks 23a-23d to yield a series of D$_2$-symmetric ortho-chiral porphyrins, e.g., compounds 20a-20d and 20l-20o, in 64-85% yields (see FIG. 16). Without being bound to any one particular theory, the near perpendicular arrangement between the meso-phenyl ring and the porphyrin plane, in combination with the trans-amide conformation, appears to direct the ortho-chiral units toward the center of the porphyrins. The observed large high-field NMR chemical shifts (Δδ~1.0-1.5 ppm) of the chiral units are consistent with this conclusion. As a result, high asymmetric induction can be achieved with these chiral porphyrins during catalysis. Using a variety of meso-R groups, it also is possible to control diastereoselectivity. As described in more detail herein below, the asymmetric cyclopropanation results demonstrate that both high enantioselectivity and high diastereoselectivity, as well as high chemical yields, can be achieved with an appropriate combination of chiral R* units and meso-R groups.

Further, the yields of the multiple amidation reactions can be improved by using different combinations of phosphine ligands and palladium precursors. Thus, syntheses using synthons S2 that bear a series of other aromatic and aliphatic groups, allowing finetuning of electronic and steric properties of the resulting chiral porphyrins, can be prepared by the method of the presently disclosed subject matter. Compared to carbon-based groups, heteroatom substituents are expected to have very different electronic and steric effects. Therefore, chiral porphyrins (represented by C in FIG. 17) bearing various meso-heteroatom substituents, including amino, amido, alkoxy/aryloxy, and alkylsulfanyl/arylsulfanyl groups are provided by the presently disclosed subject matter.

Figure 17:
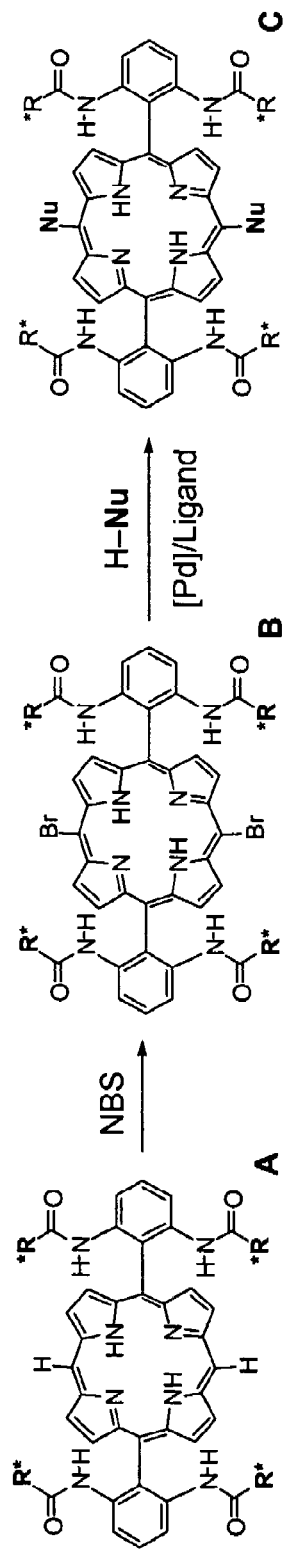
FIG. 17 is a generalized schematic representation of the synthesis of ortho-chiral porphyrins C comprising mesoheteroatom substituents, which are representative of the presently disclosed subject matter. More particularly.

Further, chiral porphyrins containing hydrogen atoms at meso-positions (represented by A in FIG. 17) can be prepared in a similar way as described for chiral porphyrins 15a-15f, 17a-17c, 20a-20d, and 20l-20o (see FIG. 11 and FIG. 12), and can be converted to meso-dibromoporphyrins (represented by B in FIG. 17) by selective bromination (see FIG. 17). The methods provided in FIG. 8 and described herein above allow the conversion of meso-dibromoporphyrins B to the desired meso heteroatom-substituted ortho-chiral porphyrins C. In addition to the achiral nucleophiles commonly employed, chiral nucleophiles can be attached in a similar manner in the construction, resulting in an array of meso-/ortho-heterochiral porphyrins, which provides a new dimension in the tuning of electronic, steric, and chiral environments.

Figure 18:
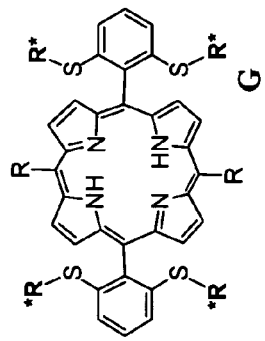
FIG. 18 provides the generalized chemical structures of ortho-chiral porphyrins D, E, F, and G, which are representative of the presently disclosed subject matter, and which can be prepared from various chiral building blocks.
Figure 18:
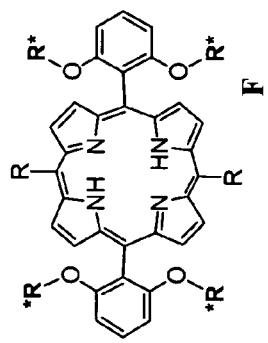
Figure 18:
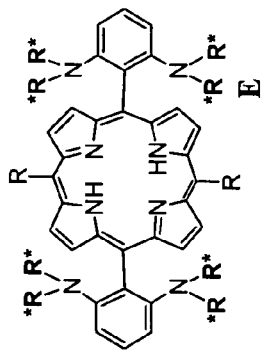
Figure 18:
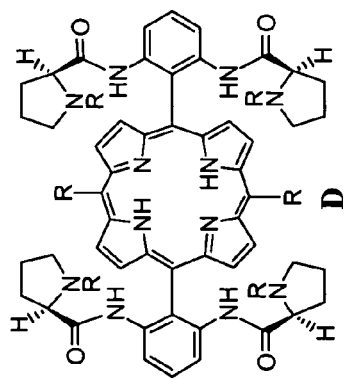

In addition to chiral amides 23a-23d, other primary and secondary chiral amides also can be employed in the construction of chiral porphyrins to produce diverse chiral environments. In particular, amides of natural α-amino acids and of short peptides can be attached to synthons S2. For example, primary amides of proline derivatives can be coupled with synthons S2 to afford chiral porphyrins of the presently disclosed subject matter (see, e.g., D of FIG. 18). Similarly, the strategy can be expanded to include chiral amines, chiral alcohols, and chiral thiols for the construction of ortho-chiral porphyrins E, F, and G of FIG. 18, respectively.

Figure 19:
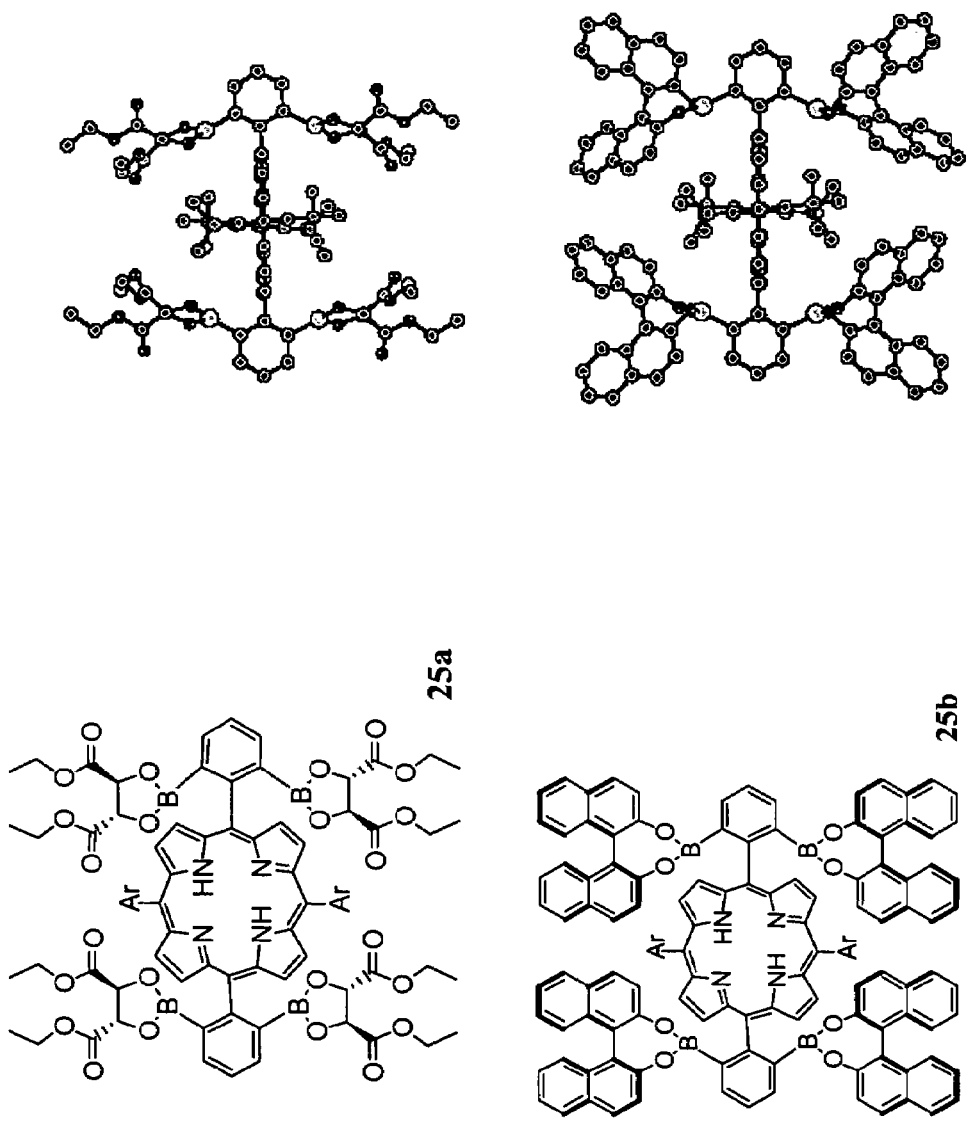
FIG. 19 represents the structures of borate ester-containing chiral porphyrins 25a and 25b, which are representative of the presently disclosed subject matter and computer generated 3D structures of the same.

Further, in view of the availability of chiral diborate esters, the palladium-mediated carbon-boron bond formation reactions can be employed to synthesize borate ester-containing chiral porphyrins. Two types of borate ester-containing chiral porphyrins 25a and 25b, along with their 3D structures generated from computer modeling, are shown in FIG. 19.

Further, in combination with computer modeling, the correlation between chiral porphyrin structure and observed catalytic activity in asymmetric cyclopropanation and aziridination can be used to guide the design and syntheses of new chiral porphyrins with improved reactivity and selectivity.

II. Asymmetric Cyclopropanation by Metalloporphyrins

Transition metal complex-mediated cyclopropanation of alkenes with diazo compounds as shown in Equation 1 is an efficient and selective method for constructing synthetically and biologically important cyclopropanes.

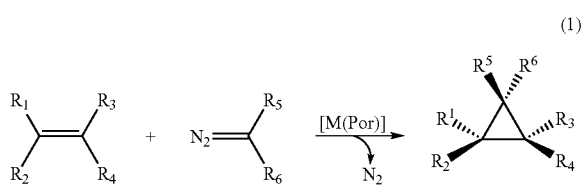

(1)

For representative examples of metal-catalyzed cyclopropanation, see Niimi et al., (2001) *Adv. Synth. Catal.* 343: 79; Ikeno et al., (2001) *Bull. Chem. Soc. Jpn.* 74: 2139; Che et al., (2002) *Coord. Chem. Rev.* 231: 151; Berkessel et al., (2003) *Chem Eur. J.* 9: 4746; Gross et al., (1999) *Tetrahedron Lett.* 40: 1571; Du et al., (2002) *Organometallics* 21: 4490; and Huang et al., (2003) *J. Org. Chem.* 68: 8179.

Among the various catalysts used in cyclopropanation reactions, metalloporphyrins are unique in their unusual selectivity and high catalytic turnover, as well as in their biological relevance. Several metalloporphyrins have been found to catalyze cyclopropanation, including Rh, Os, Fe, and Ru porphyrins. Despite the close periodic relationship of Co to Rh, until recently Co porphyrins had not been demonstrated to have catalytic carbene transfer activity. See Huang et al., (2003) *J. Org. Chem.*, 68: 8179; Penoni et al., (2003) *Eur. J. Inorg. Chem.* 1452; Niimi et al., *Adv. Synth. Catal.* (2001), 342: 79; and Ikeno et al., *Bull. Chem. Soc. Jpn.* (2001), 74: 2139. Although Co porphyrins have been shown to be better catalysts than previously known metalloporphyrins only moderate diastereoselectivity and enantioselectivity were achieved.

Figure 20:
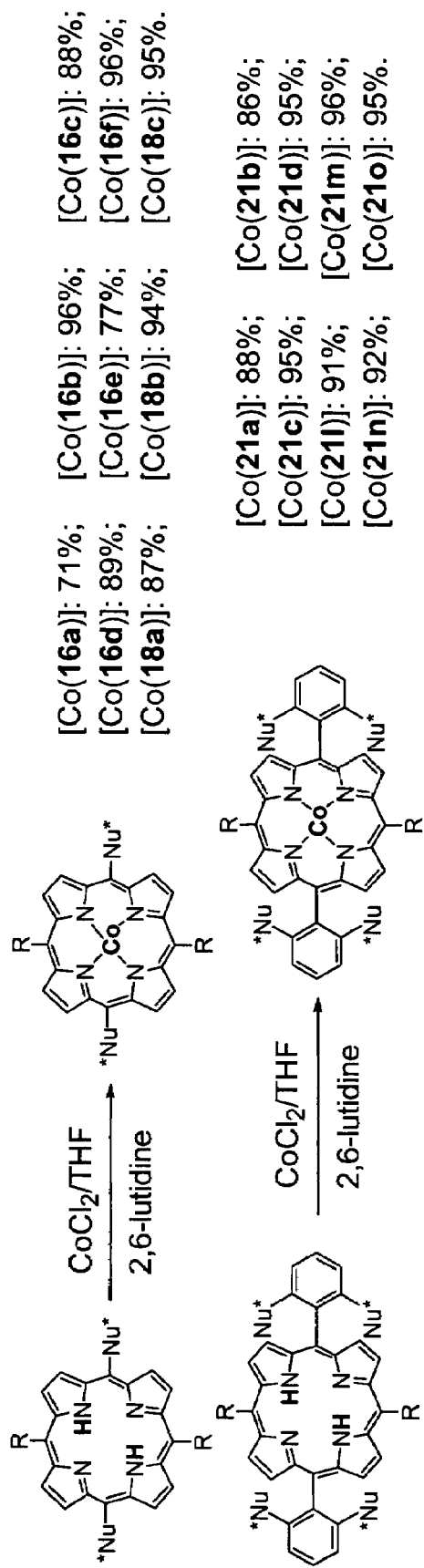
FIG. 20 is a schematic representation depicting the preparation of cobalt complexes of meso-chiral porphyrins, e.g., compounds 16a-16f and compounds 18a-18c, and ortho-chiral porphyrins, e.g., compounds 21a-21d and compounds 21l-21o, which are representative, of the presently disclosed subject matter.

The family of chiral porphyrins described by the presently disclosed subject matter improves cobalt-based, as well as other metal-based, catalytic systems for cyclopropanation. Accordingly, metal complexes, e.g., Co complexes, of meso-chiral and ortho-chiral porphyrins were prepared. By way of example, both meso-chiral porphyrins (e.g., compounds 15a-15f and compounds 17a-17c of FIG. 13) and ortho-chiral porphyrins (e.g., compounds 20a-20d and compounds 20i-20o of FIG. 16) were converted to their Co(II) complexes in high to excellent yields (see FIG. 20).

Figure 21:
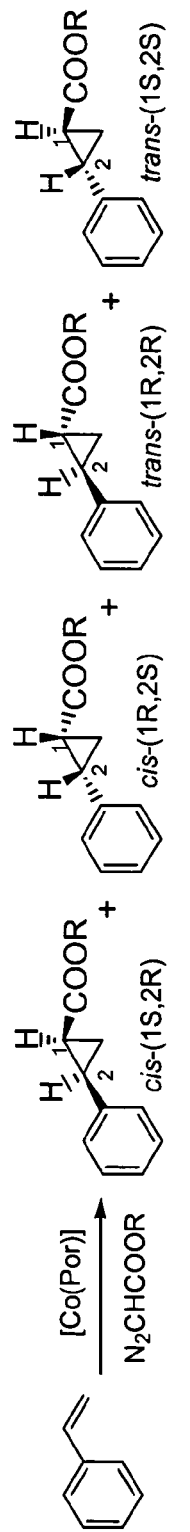
FIG. 21 is a generalized schematic representation of a cobalt-porphyrin complex catalyzed cyclopropanation reaction with styrene as the limiting reagent providing cis-(1S, 2R), cis-(1R,2S), trans-(1R,2R), and trans-(1S,2S) reaction products, which are representative of the presently disclosed subject matter.

Cobalt complexes of meso-chiral porphyrins, e.g., compounds 15a-15f and compounds 17a-17c, were found to be effective catalysts for the cyclopropanation of styrene as illustrated in FIG. 21. Using 2 mol % meso-chiral porphyrin catalysts, e.g., compounds 16a-16f and compounds 18a-18c, the reactions proceeded successfully at room temperature with styrene as the limiting reagent and did not require slow-addition of EDA, affording the desired product in up to 99% yield. While moderate trans selectivities (trans:cis ~70:30) were observed, the enantioselectivities (≦12% ee) were low. Without being bound to any particular theory, the orientation and flexibility of the chiral appendages (FIG. 13) are likely responsible for the low enantioselectivities.

Further, cobalt complexes of ortho-chiral porphyrins, e.g., compounds 21a-20d and compounds 21l-21o, also were examined as catalysts for the model cyclopropanation reaction provided in FIG. 21. Using 1 mol % ortho-chiral porphyrin catalyst, the reactions proceeded effectively at room temperature in a one-pot synthesis method with styrene as the limiting reagent, producing the desired cyclopropanes in high yields (see Table 5).

Each of the four possible stereoisomers (trans-(1R,2R), trans-(1S,2S), cis-(1S,2R), or cis-(1R,2S) as provided in FIG. 21) could be produced as the dominant product when Co(21a)], [Co(21b)], [Co(21c)] or [Co(21d)] was used as the catalyst, respectively, (Table 5, entries 1-4). This result indicates a high dependence of catalytic selectivity on the structure of the chiral R* units. The moderate enantioselectivities were doubled when 0.5 equivalents of 4-dimethylaminopyridine (DMAP) were added (Table 5, entries 5-7), suggesting significant trans influence of potential coordinate ligands on the metal center. The DMAP additive also boosted the production of the trans isomer (Table 5, entries 5-7). Further improvements in diastereoselectivity and enantioselectivity were observed when 21a was replaced with 21l wherein the two meso-groups are 3,5-di-tert-butylphenyl instead of phenyl (Table 5, entry 8). When t-BDA was used, the same catalyst produced trans-(1R,2R)-isomer as the only diastereomer in 95% ee, which was further improved to 98% ee at −20° C. (Table 5, entries 9 and 10). It is reasonable to expect that the same results would be obtained for trans-(1S,2S)-isomer if the enantiomer of 21l is employed as a catalyst.

TABLE 5

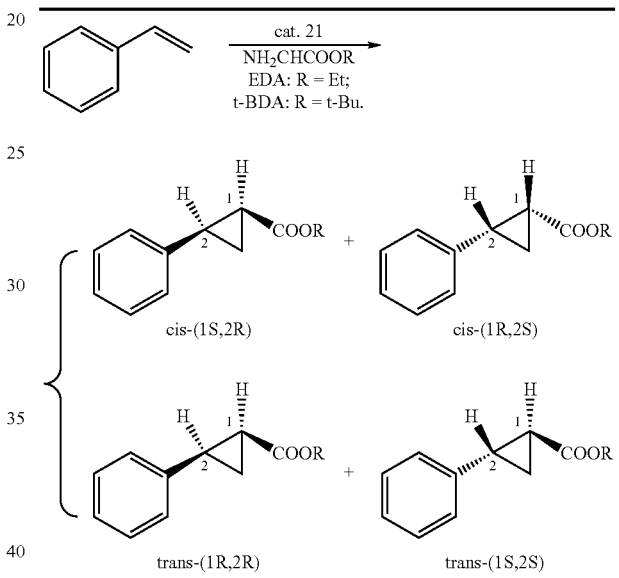

Asymmetric Cyclopropanation of Styrene Catalyzed by 21.[a]

| Entry | 21 | diazo | Additive | Yield (%)[b] | Trans:cis[b] | ee[c] | config[d] |
|---|---|---|---|---|---|---|---|
| 1 | 21a | EDA | — | 92 (—) | 87:13 | 31% | 1R,2R |
| 2 | 21b | EDA | — | 77 (—) | 66:34 | 35% | 1S,2S |
| 3 | 21c | EDA | — | 92 (—) | 32:68 | 48% | 1S,2R |
| 4 | 21d | EDA | — | 95 (—) | 32:68 | 51% | 1R,2S |
| 5 | 21a | EDA | DMAP | 91 (—) | 96:04 | 67% | 1R,2R |
| 6 | 21c | EDA | DMAP | 52 (—) | 44:56 | 88% | 1R,2R |
| 7 | 21d | EDA | DMAP | 57 (—) | 42:58 | 89% | 1R,2R |
| 8 | 21l | EDA | DMAP | 86 (82) | 97:03 | 78% | 1R,2R |
| 9 | 21l | t-BDA | DMAP | 88 (84) | >99:01 | 95% | 1R,2R |
| 10[e] | 21l | t-BDA | DMAP | 84 (85) | >99:01 | 98% | 1R,2R |
| 11 | 21m | EDA | DMAP | 65 (59) | 31:69 | 92% | 1S,2R |
| 12[f] | 21m | t-BDA | DMAP | 78 (75) | 37:63 | 96% | 1S,2R |
| 13 | 21n | EDA | DMAP | 68 (—) | 30:70 | 95% | 1R,2S |
| 14[f] | 21n | t-BDA | DMAP | 76 (—) | 38:62 | 95% | 1R,2S |
| 15 | 21o | EDA | DMAP | 80 (—) | 96:04 | 59% | 1R,2R |
| 16 | 21o | t-BDA | DMAP | 73 (—) | 99:01 | 78% | 1R,2R |

[a]Reactions were carried out at room temperature in toluene for 20 h under $N_2$ with 1.0 equiv of styrene, 1.2 equiv of diazo reagent and 1 mol % 21 in the presence of 0.5 equiv of additive. Concentration: 0.25 mmol styrene/1 mL toluene.
[b]Determined by GC. Yields in parentheses represent isolated yields.
[c]ee of major diastereomer determined by chiral GC.
[d]Absolute configuration of major enantiomer determined by optical rotation.
[e]Carried out at −20° C. for 8 h.
[f]5 mol % 21 was used.

The same structure modification resulted in 96% ee for cis-(1S,2R)-isomer with 21m and 95% ee for cis-(1R,2S)-isomer with 21 n (entries 12 and 14). The results obtained with 21o bearing meso-n-heptyl groups (Table 5, entries 15 and 16) further underline the importance of both R and R* groups of the chiral porphyrins (see, e.g., FIG. 18) in achieving high selectivities.

The prototypical cyclopropanation reaction (FIG. 21) also can be used to evaluate the catalytic activities of meso- and ortho-chiral porphyrins as provided in hereinabove. The C2-symmetric secondary chiral amine units of meso-chiral porphyrins as provided in FIG. 15 should avoid the unfavorable orientation and flexibility that are associated with the chiral alcohol and amide constituents of compounds 15a-15f and 17a-17c provided in FIG. 13, and should provide improved asymmetric induction. In combination with the tuning of the meso-R group, diastereomer differentiation also can be achieved. Given the results presented in Table 5, provided with cobalt complexes of ortho-chiral porphyrins 20a-21d and 20l-20o, systematic catalytic studies can be performed with ortho-chiral porphyrins (see, e.g., FIG. 16), C (FIG. 17) and D, E, F, and G (FIG. 18) that possess diverse electronic, steric, and chiral environments. In addition to DMAP, common nitrogen, phosphine, and sulfur coordinating ligands can be used as additives.

Figure 22:
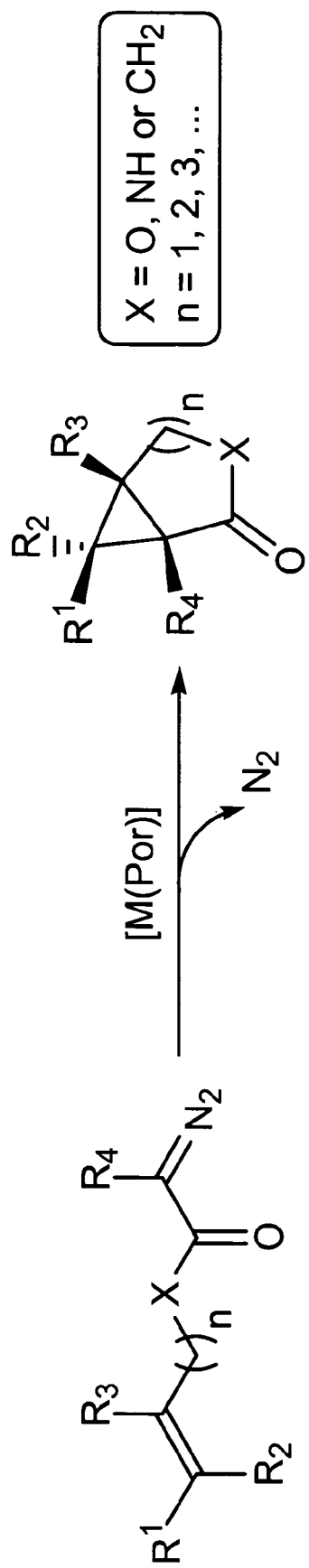
FIG. 22 is a generalized schematic representation of a metalloporphyrin catalyzed intramolecular asymmetric cyclopropanation reaction comprising diazo compounds bearing a pendant alkene C=C bond, the reaction and the diazo compounds being representative of the presently disclosed subject matter.

Efficient catalytic systems that allow exclusive formation of each one of the four possible isomers (FIG. 21) also can be developed, as achieved for the (1R,2R)-isomer with [Co(21l)] (Table 5, entry 10). Thus, the cobalt-based catalytic system can be applied to cyclopropanation reactions comprising a wide range of alkenes. In addition to styrene derivatives, substrates can include nonaromatic alkenes, including but not limited to di-, tri- and tetra-substituted alkenes; cis- and trans-alkenes; and cyclic and non-cyclic alkenes. In addition to EDA and t-BDA, other diazo reagents can be used as potential carbene sources to further expand the utility of the catalytic reaction, including, but not limited to 2,6-di-tert-butyl-4-methylphenyl diazoacetate, methyl phenyldiazoacetate, ethyl diazoacetacetate, diethyl diazomalonate, and trimethylsilyl-diazomethane. A series of diazo compounds bearing a pendant alkene C=C bond, including allylic diazoacetates (X=O, n=1), also can be employed for the development of intramolecular asymmetric cyclopropanation, leading to the construction of fused ring structures (see FIG. 22).

Thus, the presently disclosed subject matter demonstrates that chiral porphyrins with different electronic, steric, and chiral environments can be combined with different substrates to achieve high activity and selectivity. Accordingly, a chemical library or "toolbox" of effective chiral metalloporphyrins for the asymmetric cyclopropanation of a broad scope of substrates can be assembled.

In comparative studies of cobalt, iron, ruthenium and rhodium porphyrins for catalytic cyclopropanation of styrene, it was found that the catalytic conversion of styrene to the desired cyclopropane ester increased in the order of Ru(TPP)(CO), Fe(TPP)Cl, Rh(TPP)I and Co(TPP) (TPP: tetraphenylporphyrin) using a practical one-pot protocol (alkenes as limiting reagents and no slow addition of diazo reagents) because the formation of the dimerization products (ethyl maleate and ethyl fumarate) from EDA decreased in the same order. See Huang et al., supra. It was also observed that the trans:cis isomer ratios of the desired product increased from 64:34 with Rh(TPP)I to 75:25 with Co(TPP) to 88:12 with Fe(TPP)Cl to 94:06 with Ru(TPP)(CO). See Huang et al., supra. In addition to the foregoing ligand tuning, the observed metal ion effect should provide an additional element for controlling the catalytic activity and selectivity. In addition to cobalt, complexes of iron, ruthenium and rhodium with these chiral porphyrins can be prepared to further characterize the metal ion effect.

Accordingly, different metal complexes of ortho-chiral porphyrin 20l (see FIG. 23), the cobalt complex of which displayed remarkable diastereoselectivity and enantioselectivity (Table 5), can be used in the presently disclosed subject matter.

Figure 23:
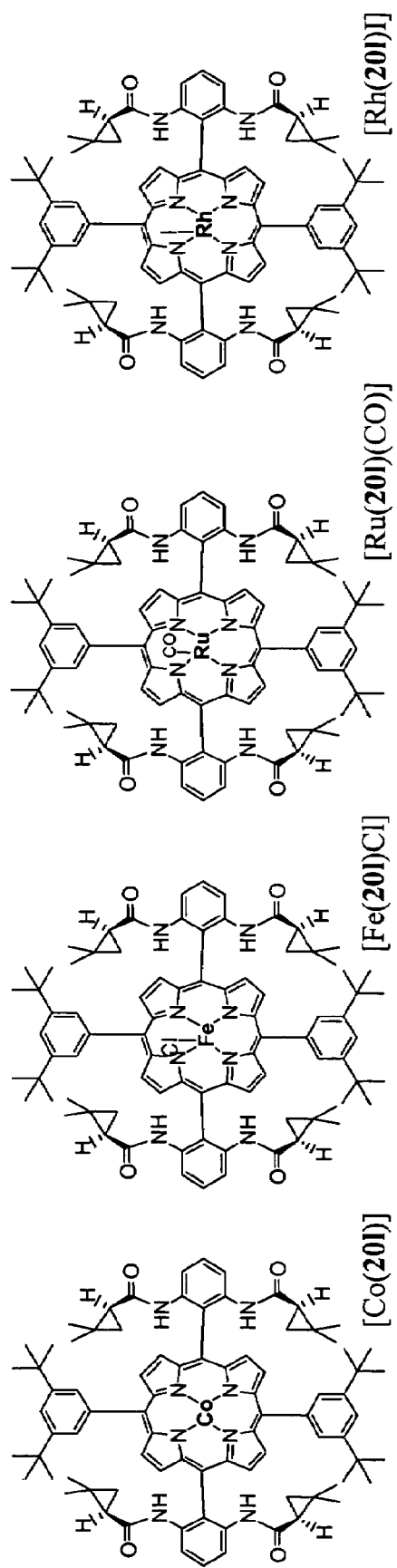
FIG. 23 provides the structures of the cobalt, iron, ruthenium, and rhodium complexes of $D_2$-symmetric meso-chiral porphyrin 20I, which are representative of the presently disclosed subject matter.

Given that the trans:cis isomer ratio was dramatically improved from 88:12 with Co(TPP) to >99:01 with [Co(20l)], it is of interest to determine the diastereoselectivities and enantioselectivities of [Fe(20l)Cl], [Ru(20l)(CO)], [Rh(20l)I] (see FIG. 23). Because Rh(TPP)I gave the highest cis:trans isomer ratio, [Rh(20f)I] and Rh(20gI] also can be prepared by the presently disclosed subject matter in an effort to further increase the cis-diastereoselectivity observed for [Co(20m)] and [Co(20n)] (see Table 5).

Figure 24:
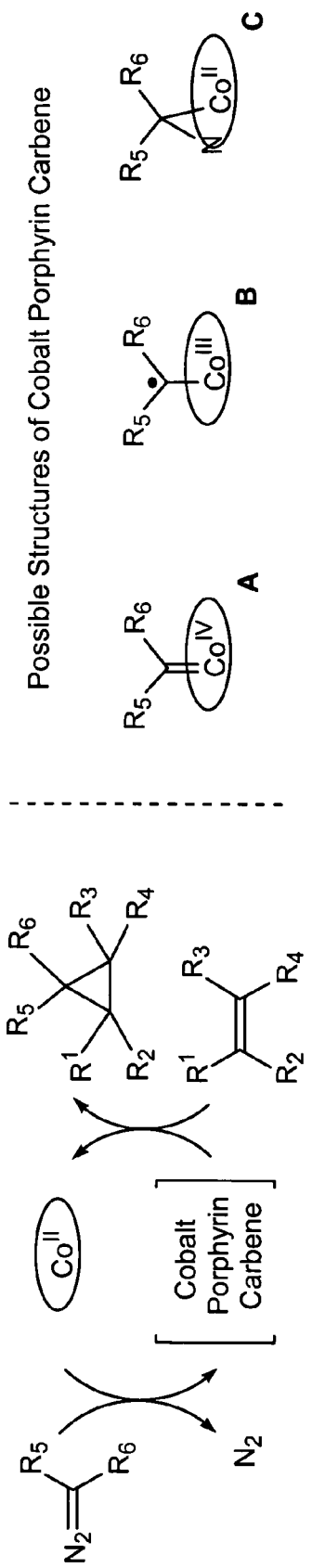
FIG. 24 is an illustration of a possible cyclopropanation mechanism by cobalt porphyrins, which is representative of the presently disclosed subject matter.

Understanding the reaction mechanism is of fundamental importance for the further improvement of the metalloporphyrin-catalyzed cyclopropanation systems. Without being bound to any particular theory, on the basis of the proposed mechanisms for other metalloporphyrin systems, it is reasonable to assume the catalytic cyclopropanation by cobalt porphyrins proceeds via a similar mechanism involving a metal-carbene intermediate, although a noncarbene mechanism cannot be excluded. As shown in FIG. 24, reaction of Co(II) porphyrin with the diazo reagent generates a cobalt porphyrin carbene intermediate with the expulsion of nitrogen.

Carbene transfer from the intermediate to the alkene substrate affords the cyclopropane product and regenerates Co(II) porphyrin which continues the catalytic cycle. Three possible structures could be proposed for the cobalt porphyrin carbene intermediate (FIG. 24). Structure A of FIG. 24 represents a normal metal-carbene complex with a Co—C double bond that requires an uncommon Co(IV) high oxidation state. Stable carbene complexes of rhodium, iron, ruthenium, and osmium porphyrins have been characterized. Structure B of FIG. 24 illustrates an unusual metal-carbene complex with a Co—C single bond between a Co(III) center and a carbon-based radical. A similar structure was recently proposed for 3-oxobutylideneaminato-cobalt and salen-cobalt-based cyclopropanation system. Structure C of FIG. 24 contains a carbene unit bridging a Co(II) center and one of the pyrrole nitrogen atoms. This bonding mode was previously observed in Co(III) porphyrins, but not in Co(II) porphyrins.

III. Asymmetric Aziridination by Metallolorphyrins

Aziridines are a class of synthetically and biologically important compounds that have found many applications. Among synthetic methodologies, transition metal complex-mediated aziridination represents a direct and powerful approach for the construction of the aziridine rings. In comparison to the considerable advances of analogous epoxidation and cyclopropanation, metal-catalyzed aziridination is much less developed.

[N-(p-toluenesulfonyl)imino]phenyliodinane (PhI=NTs) has been extensively used as a primary nitrene source for catalytic aziridination. While significant progress has been made with PhI=NTs in a number of metal-catalyzed systems, this nitrene source suffers from several drawbacks: commercial unavailability, high cost, insolubility, and the generation of PhI as a by-product. To overcome these limitations, it is desirable to develop catalytic systems capable of employing alternative nitrene sources.

Recently, there has been growing interest in using chloramine-T (CT), bromamine-T (BT) and organic azides as alternative nitrene sources for metal-catalyzed aziridination, because of their attractive properties. The commercially available CT is inexpensive and has excellent stability. The analogous BT, which can be easily prepared from CT, has the same characteristics but exhibits different reactivity. Organic azides represent a class of compounds with diverse structures that can be synthesized in straightforward reactions of the corresponding halides with sodium azide. Many low cost organic azides are also commercially available. Furthermore, catalytic aziridination processes with these nitrene sources would generate more environmentally benign by-products (sodium halides or dinitrogen).

Owing to their unusual selectivity and excellent stability, as well as their biological relevance, metalloporphyrins have played a pivotal role in the development of several important catalytic atom/group transfer reactions, including aziridination. In fact, metalloporphyrins were the first transition metal complexes that demonstrated catalytic aziridination activity. Following this breakthrough, porphyrin complexes of several metal ions (Mn, Fe, and Ru) were reported to be effective with PhI=NTs. While CT, BT, and organic azides have been pursued using several transition metal complex systems, the catalytic activity of metalloporphyrins with these attractive nitrene sources has not been explored.

Accordingly, the presently disclosed subject matter identifies suitable alternative nitrene sources for catalytic aziridination by metalloporphyrins. Employing the family of new chiral porphyrins described hereinabove asymmetric versions of the aziridination processes shown in Equations 4 and 5 are possible.

Figure 25:
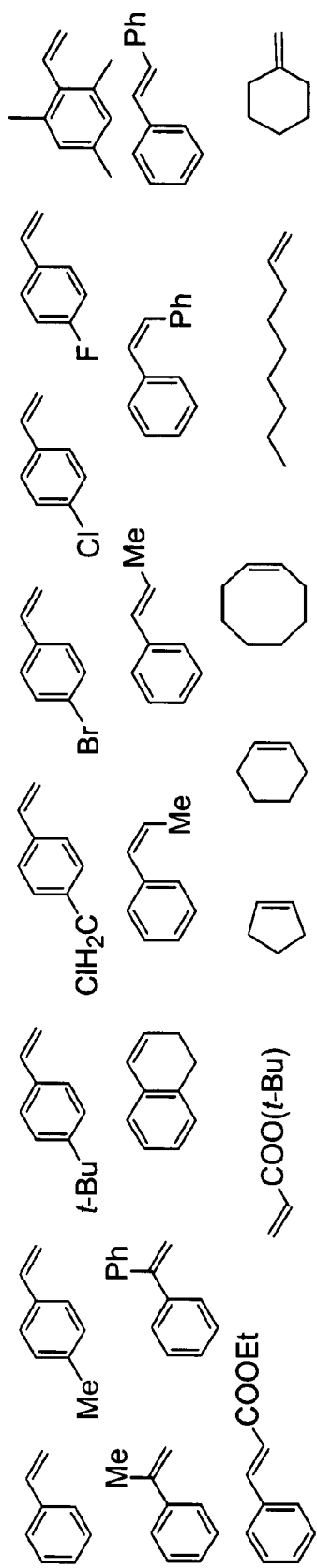
FIG. 25 provides the chemical structures of alkene substrates, which are representative of the presently disclosed subject matter, for the aziridination by Fe(TPP)Cl with bromamine-T.

Further, Bromamine-T is an effective nitrene source for aziridination of alkenes by metalloporphyrins (see Equation 4).

esters (see FIG. 25), producing the corresponding N-sulfonylated aziridines. The isolated yields ranged from 35% for aliphatic alkenes to 80% for styrene derivatives.

For 1,2-disubstituted alkenes, only moderate stereospecificities were achieved. A notable porphyrin ligand dependence was uncovered for the Fe(Por)Cl/BT catalytic system. While no catalytic activity was observed with Fe(OEP)Cl (OEP: octaethylporphyrin), the electron deficient Fe(TPFPP)Cl (TPFPP: tetrakis(pentafluorophenyl)porphyrin) improved the yield of styrene reaction significantly. It is also worth pointing out that other metalloporphyrins could aziridinate styrene with BT, including Mn(TPP)Cl, Ru(TPP)(CO), and Co(TPP), albeit at lower yields.

Figure 26:
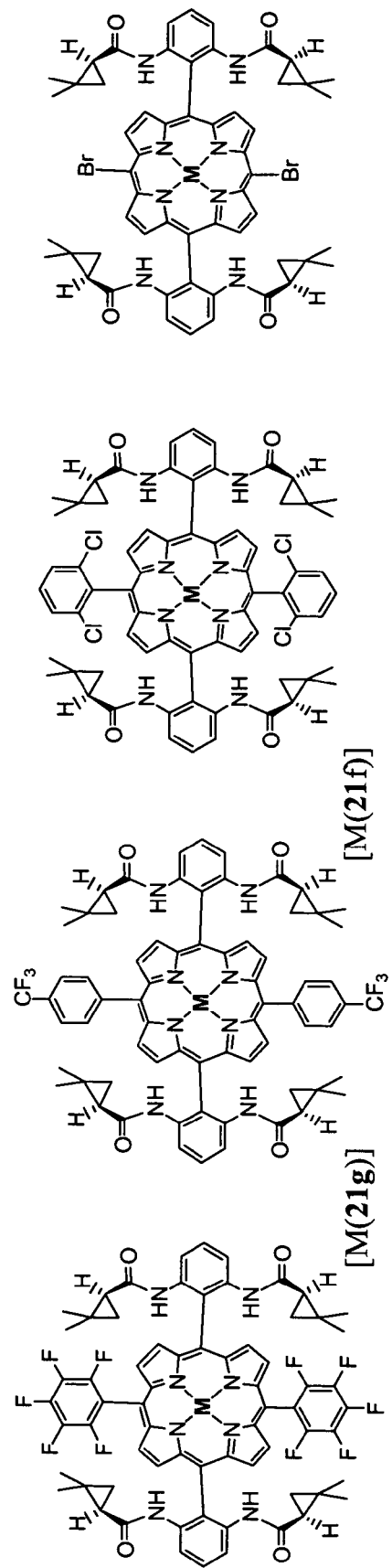
FIG. 26 provides the chemical structures of metal complexes of $D_2$-symmetric meso-chiral porphyrins, e.g., [M(21g)] and [M(21f)], bearing electron-withdrawing groups, which are representative of the presently disclosed subject matter.

While iron, manganese, and ruthenium porphyrins were previously known to catalyze aziridination with PhI=NTs, cobalt porphyrins have not been demonstrated to have aziridination activity. Accordingly, a series of achiral porphyrins with varied electronic and steric properties including porphyrins with various heteroatom substituents, can be used to improve the yields and stereospecificity of the Fe/BT aziridination system. More particularly, cobalt porphyrins, along with manganese and ruthenium porphyrins, can be used as catalysts for aziridination with BT. In addition to the asymmetric aziridination activities of the meso- and ortho-chiral porphyrins, $D_2$-symmetric meso-chiral porphyrins that bear electron-withdrawing groups can be prepared, along with their iron, cobalt, manganese, and ruthenium complexes (FIG. 26).

These electron-deficient chiral metalloporphyrins may have enhanced catalytic activity and allow asymmetric induction for aziridination of alkenes with BT. Similar approaches to those outlined hereinabove involving asymmetric cyclopropanation can be applied to gain a mechanistic understanding of asymmetric aziridination catalyzed by metalloporphyrins with BT, including the characterization of potential metalloporphyrin nitrene intermediates.

In comparison with N-sulfonylated aziridines, N-phosphorylated and N-phosphinylated aziridines have been shown to be advantageous as synthetic building blocks, since the phosphoryl and phosphinyl groups bring suitable activation to the aziridine ring and can be easily deprotected. Although methods are available for the preparation of N-phosphorous-substituted aziridines, their direct synthesis via metal-mediated aziridination of alkenes has not been developed. To this end, the presently disclosed subject matter provides the application of diphenylphosphoryl azide (DPPA) as a new nitrene source for aziridination by metalloporphyrins (Equation 5).

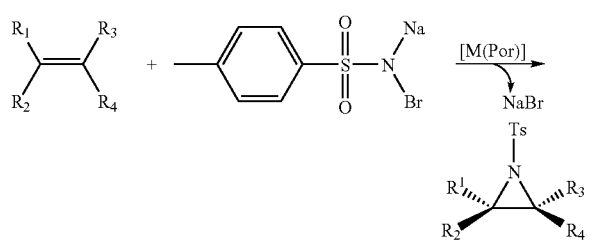

(4)

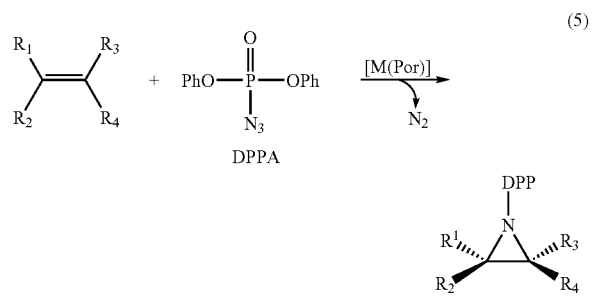

(5)

The combination of Fe(TPP)Cl and BT can effect aziridination reactions under mild and practical conditions with alkenes as limiting agents. The catalytic system is general and suitable for a wide range of substrates, including aromatic, aliphatic, cyclic, and acyclic alkenes, and α,β-unsaturated The results of the catalytic aziridination of styrene with DPPA by metal complexes of the common TPP under different conditions are provided in Table 6.

TABLE 6

Aziridination of Styene with DPPA Catalzyed by Metalloporphyrins.

| Entry | Catalyst | Loading (mol %) | S:A | Solvent | Temp (° C.) | Time (h) | Yield (%) |
|---|---|---|---|---|---|---|---|
| 1 | Co(TPP) | 5 | 5:1 | Dichloromethane | 40 | 12 | 0 |
| 2 | Co(TPP) | 5 | 5:1 | Tetrahydrofuran | 65 | 12 | 0 |
| 3 | Co(TPP) | 5 | 5:1 | Toluene | 110 | 12 | 32 |
| 4 | Co(TPP) | 5 | 5:1 | Dimethylformamide | 150 | 12 | 0 |
| 5 | Co(TPP) | 5 | 5:1 | Chlorobenzene | 120 | 12 | 74 |
| 7 | Co(TPP) | 5 | 5:1 | Chlorobenzene | 120 | 6 | 60 |
| 8 | Co(TPP) | 10 | 5:1 | Chlorobenzene | 120 | 12 | 76 |
| 9 | Co(TPP) | 5 | 2:1 | Chlorobenzene | 120 | 12 | 54 |
| 10 | Co(TPP) | 5 | 1:2 | Chlorobenzene | 120 | 12 | 0 |
| 11 | Mn(TPP)Cl | 5 | 5:1 | Chlorobenzene | 120 | 12 | 0 |
| 12 | Fe(TPP)Cl | 5 | 5:1 | Chlorobenzene | 120 | 12 | 0 |
| 13 | Ru(TPP)(CO) | 5 | 5:1 | Chlorobenzene | 120 | 12 | 5 |

For example, the reaction in chlorobenzene afforded the desired N-phosphorylated aziridine in good yield. Decreasing the styrene/DPPA ratio reduced the yield. No aziridine was observed when styrene was used as the limiting reagent. Without being bound to any particular theory, cobalt appears to be essential to the catalytic process; none or only a trace of the desired product was formed with other metalloporphyrins or without a catalyst.

Figure 27:
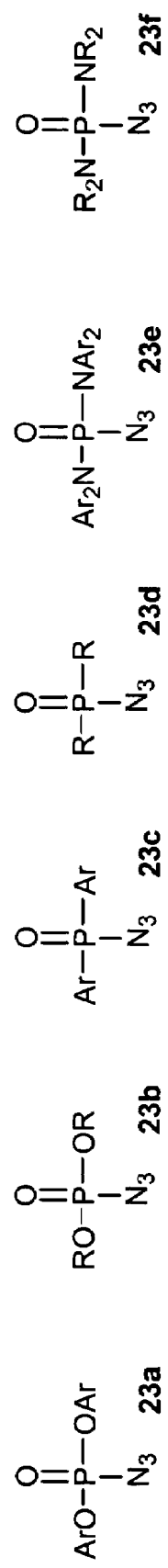
FIG. 27 provides the chemical structures of phosphoryl (24a & 24b), phosphinyl (24c & 24d), and phosphorodiamidic (24e & 24f) azidees for use with the presently disclosed subject matter.

Cobalt porphyrins are capable of catalyzing aziridination with DPPA, forming synthetically useful N-phosphorylated aziridines. These results, together with the results of Co(TPP)/BT mediated aziridination, represents the first examples of cobalt-catalyzed aziridination and one of only a few catalytic aziridination systems that employs azides as nitrene sources. In addition to the further optimization of various reaction parameters, including the examination of possible trans effects of potential coordinating ligands, porphyrins containing different electronic and steric substituents can be employed to improve the catalytic efficiency, to expand the substrate scope, and to achieve high stereospecificity. Meanwhile, known derivatives of phosphoryl azides and related phosphinyl and phosphorodiamidic azides, e.g., compounds 24a-24f of FIG. 27, also can be employed as potential nitrene sources.

IV. Asymmetric Epoxidation by Metalloporphyrins

The chiral porphyrins of the presently disclosed subject matter also can be used as catalysts in asymmetric epoxidation reactions (see Equation 3).

(3)

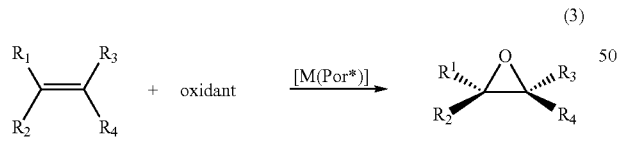

For representative metal-catalzyed epoxidation reactions, see Boschi, (1994) "Asymmetric Syntheses" In *Metalloporphyrins Catalyzed Oxidations*; Montanari, F., Casella, L., Eds.; Kluwer Academic Publishers: Boston, 1994; pp 239-267; Naruta, (1994) "Asymmetric Oxidation with Chiral Porphyrin Catalysts" In *Metalloporphyrins in Catalytic Oxidations*; Sheldon, R. A., Ed.; Marcel Dekker: New York, 1994; pp 241-259; Groves et al., (1983) *J. Am. Chem. Soc.* 105: 5791; Marchon et al., (2003) "Chiral Metalloporphyrins and Their Use in Enantiocontrol" in *The Porphyrin Handbook*; Kadish, K. M., Smith, K. M., Guilard, R., Eds.; Academic Press: San Diego, Calif., Vol. 11; pp 75-132; Rose et al., (2000) *Polyhedron* 19: 581; and Collman et al., (1993) *Science* 261: 1404-1411.

In some embodiments, the oxidant is selected from the group consisting of sodium hypochlorite, potassium monopersulfate, hydrogen peroxide, alkylhydroperoxides, m-chloroperbenzoic acid, amines N-oxides, iodosylbenzene, and dioxygen.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A chiral porphyrin compound having the structure of Formula (I):

(I)

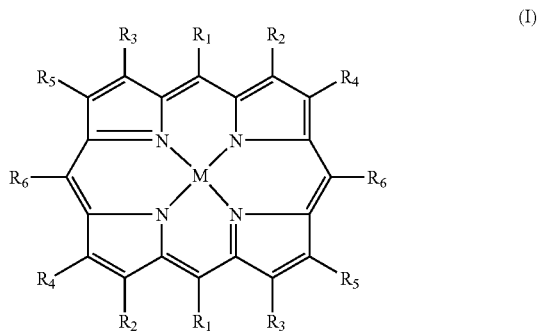

wherein:

M is present or absent and when present is $H_2$ or a transition metal;

$R_1$, $R_2$, $R_3$, $R_4$, $R_5$ and $R_6$ are each independently selected from the group consisting of a heteroatom-containing chiral moiety, H, alkyl, substituted alkyl, arylalkyl, aryl, and substituted aryl; and at least one of $R_1$, $R_2$, $R_3$, $R_4$, $R_5$ and $R_6$ is a heteroatom-containing chiral moiety selected from the group consisting of (+)-estrone, (+)-dihydrocholesterol, R-(+)-1,1'-bi-2-naphthol, (R)-(+)-4-benzyl-2-oxazolidinone, (L)-phenylalanine methyl ester, 1-[1'-(R)-α-methylbenzyl]-aziridine-2(R)-carboxamide, (R)-(−)-2-methoxypropionamide, (S)-(+)-2-methoxypropionamide, (S)-(+)-2,2-dimethylcyclopropanecarboxamide, and L-(R)-lactamide; or at least one of $R_1$ and $R_6$ is a group having the structure:

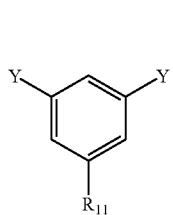

wherein:

$R_{11}$ is selected from the group consisting of H, alkyl, substituted alkyl, alkoxy, substituted alkoxy, halogen, arylalkyl, aryl, and substituted aryl and wherein Y is selected from the group consisting of (+)-estrone, (+)-dihydrocholesterol, R-(+)-1,1'-bi-2-naphthol, (R)-(+)-4-benzyl-2-oxazolidinone, (L)-phenylalanine methyl ester, 1-[1'-(R)-α-methylbenzyl]-aziridine-2(R)-carboxamide, (R)-(−)-2-methoxypropionamide, (S)-(+)-2,2-dimethylcyclopropanecarboxamide, and L-(R)-lactamide.

2. The compound according to claim 1, wherein M is selected from the group consisting of $H_2$, Zn, Fe, Ni, Co, Mn, Ru, and Rh.

3. The compound according to claim 1, wherein M is Co.

4. The compound according to claim 1, wherein at least one of $R_1$ and $R_6$ is H.

5. The compound according to claim 1, wherein at least one of $R_1$ and $R_6$ is alkyl.

6. The compound according to claim 5, wherein at least one of $R_1$ and $R_6$ is n-heptyl.

7. The compound according to claim 1, wherein at least one of $R_1$ and $R_6$ is aryl.

8. The compound according to claim 7, wherein at least one of $R_1$ and $R_6$ is phenyl.

9. The compound according to claim 1, wherein at least one of $R_1$ and $R_6$ is substituted aryl.

10. The compound according to claim 9, wherein at least one of $R_1$ and $R_6$ is selected from the group consisting of 2,6-dimethylphenyl, 2,4,6-trimethylphenyl, 3,5-di-tert-butylphenyl, 2,6-dimethoxyphenyl, 3,5-dimethoxyphenyl, 4-t-butylphenyl, 4-acetylphenyl, 4-trifluoromethylphenyl, and pentafluorophenyl.

11. The compound according to claim 1, wherein at least one of $R_1$ and $R_6$ is selected from the group consisting of (+)-estrone; (+)-dihydrocholesterol; R-(+)-1,1'-bi-2-naphthol; (R)-(+)-4-benzyl-2-oxazolidinone; (L)-phenylalanine methyl ester; 1-[1'-(R)-α-methylbenzyl]-aziridine-2(R)-carboxamide; (R)-(−)-2-methoxypropionamide; (S)-(+)-2-methoxypropionamide; (S)-(+)-2,2-dimethylcyclopropanecarboxamide; and L-(R)-lactamide.

12. The compound according to claim 1, wherein each $R_6$ is selected from the group consisting of (+)-estrone; (+)-dihydrocholesterol; R-(+)-1,1'-bi-2-naphthol; (R)-(+)-4-benzyl-2-oxazolidinone; (L)-phenylalanine methyl ester; 1-[1'-(R)-α-methylbenzyl]-aziridine-2(R)-carboxamide; (R)-(−)-2-methoxypropionamide; (S)-(+)-2-methoxypropionamide; (S)-(+)-2,2- dimethylcyclopropanecarboxamide; and L-(R)-lactamide.

13. The chiral porphyrin of claim 1, wherein the chiral porphyrin has a structure selected from the group consisting of:

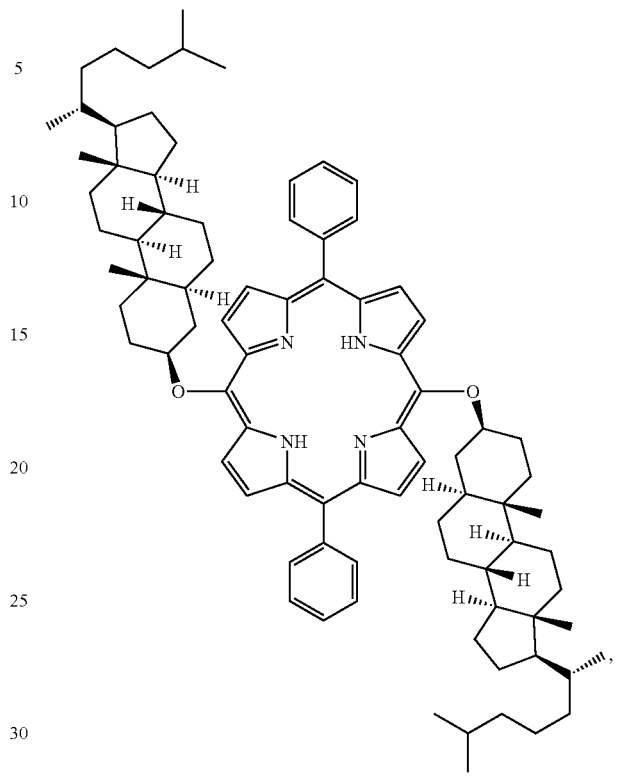

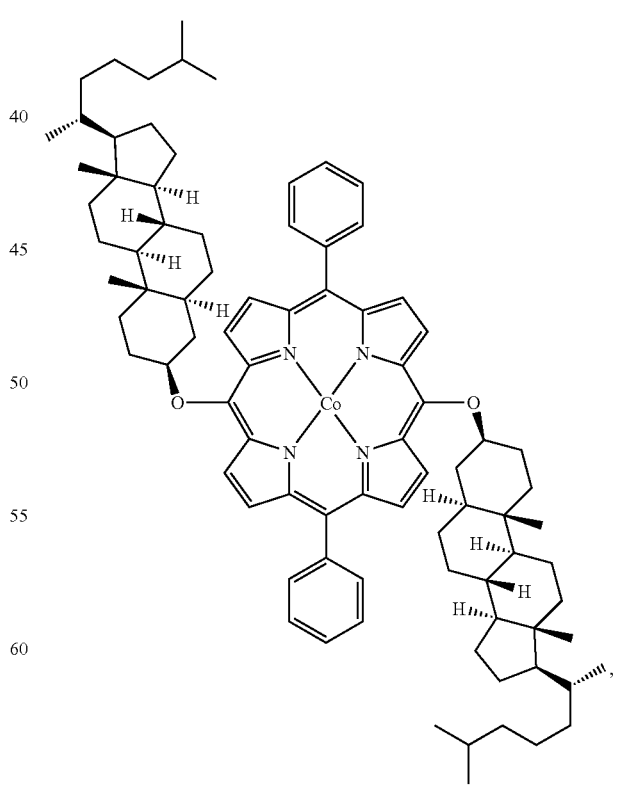

123
-continued
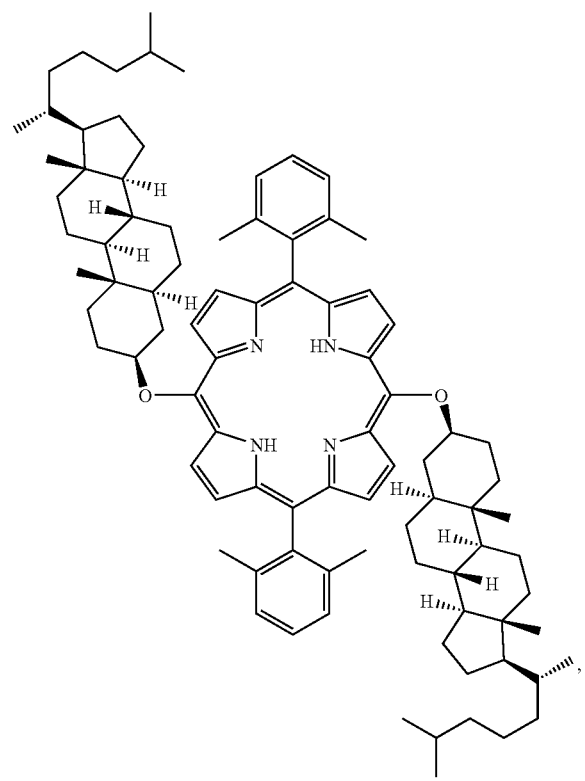
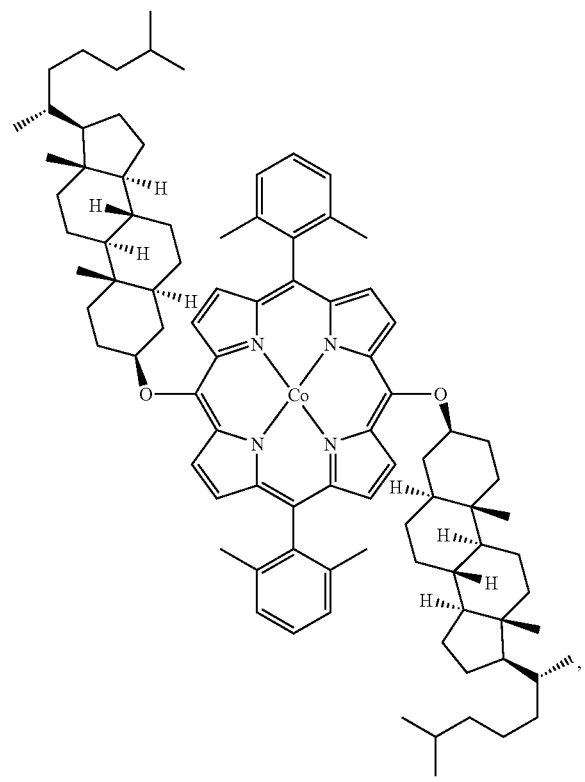
124
-continued
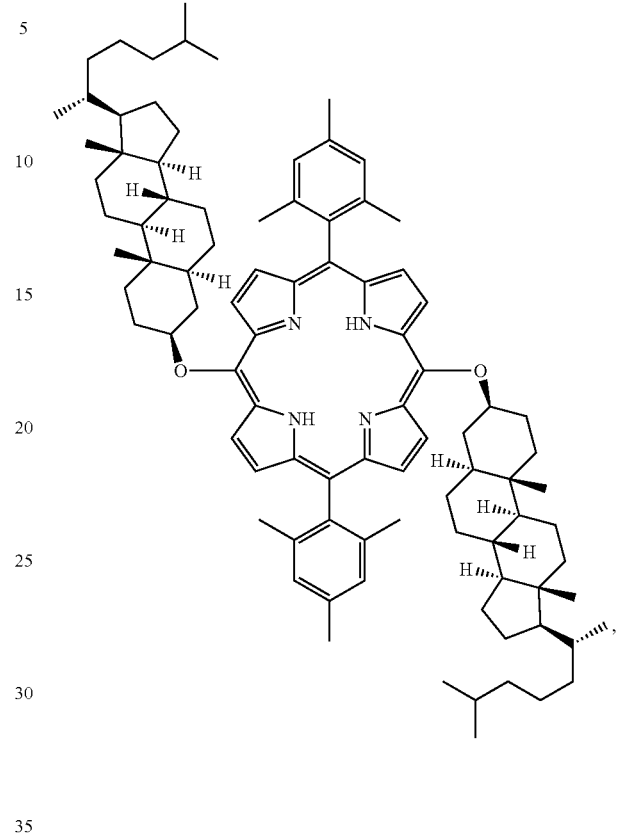
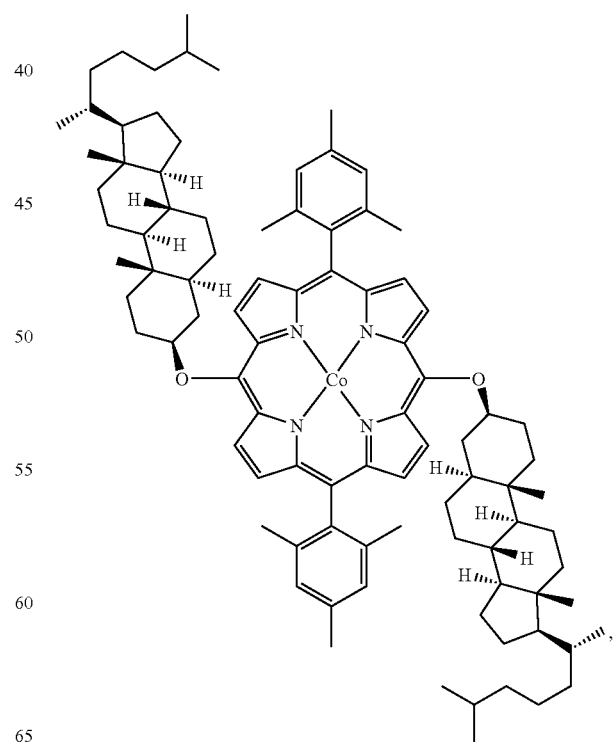

125
-continued
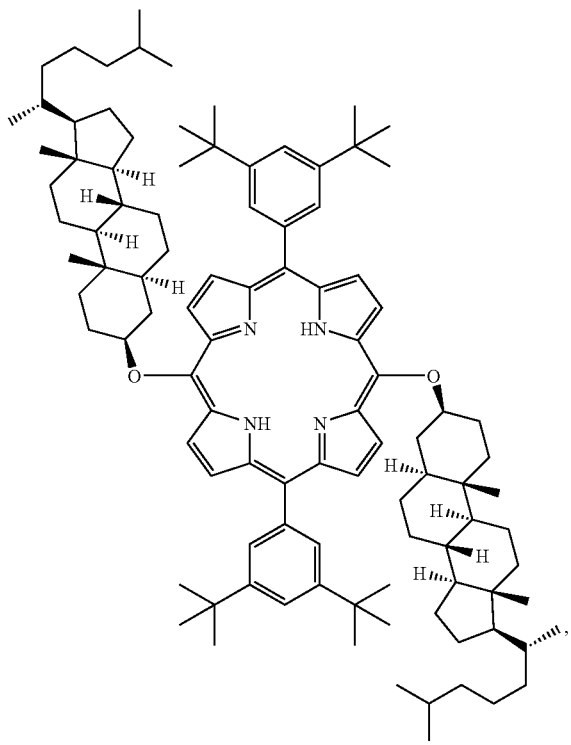
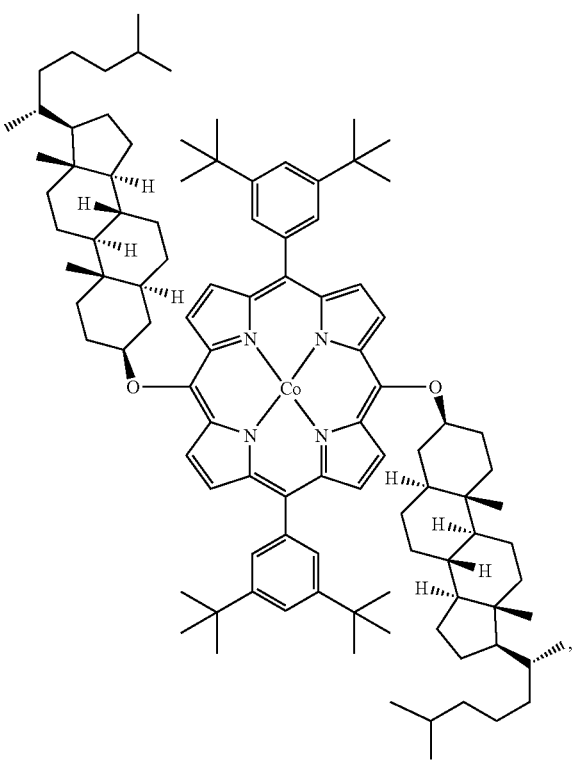
126
-continued
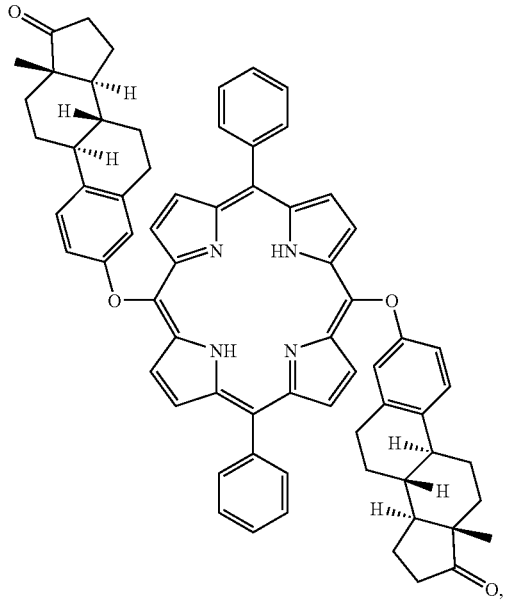
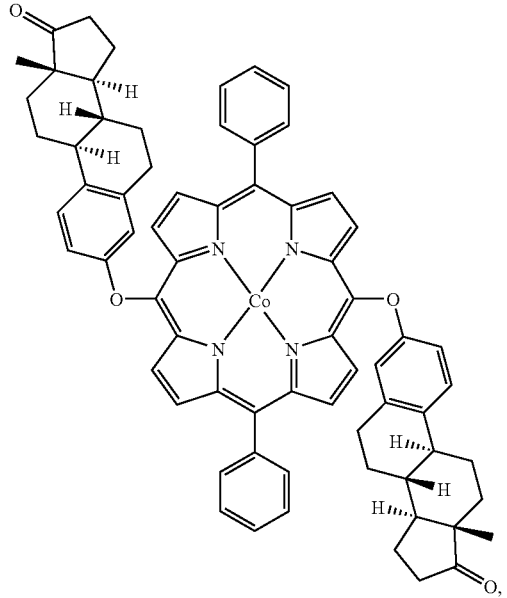

127
-continued
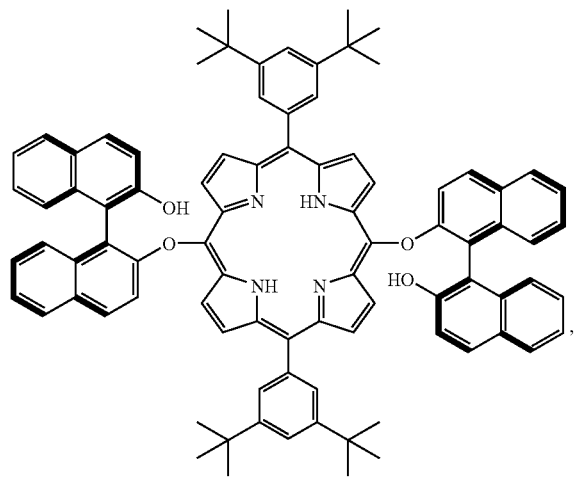
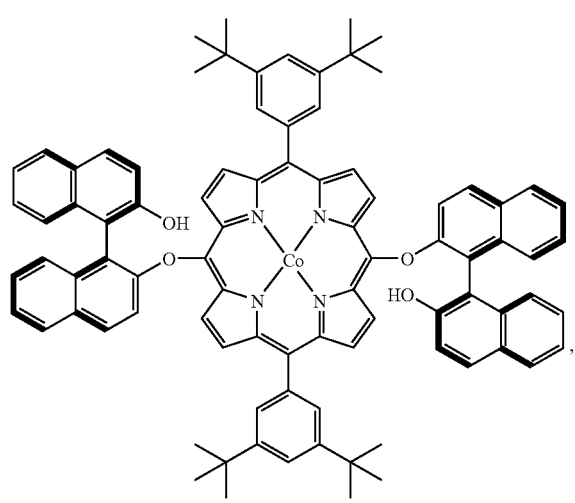
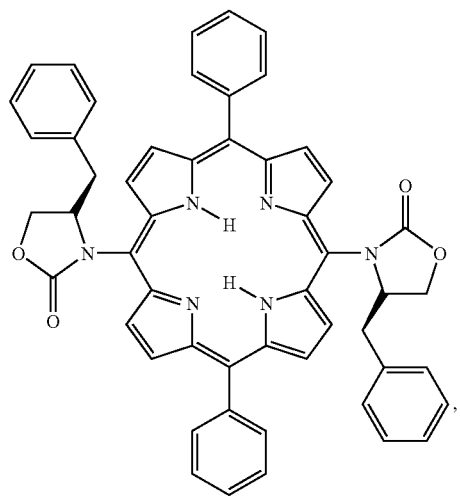
128
-continued
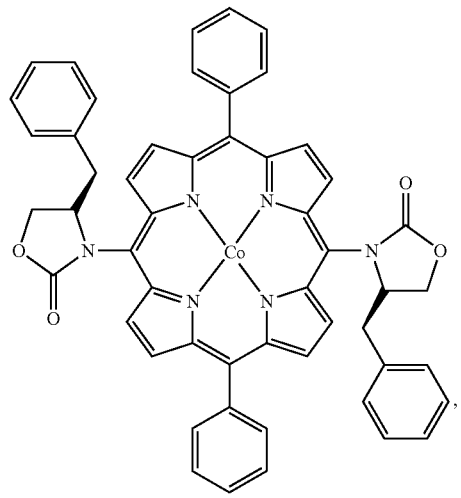
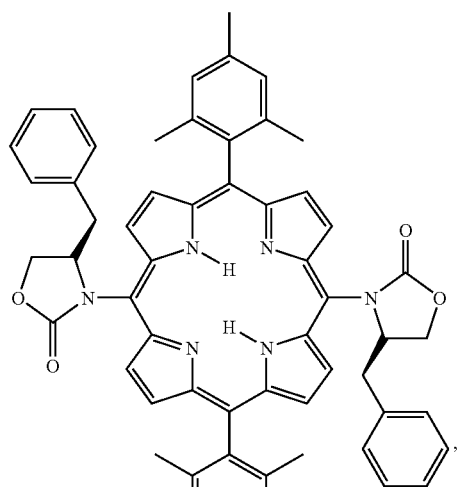
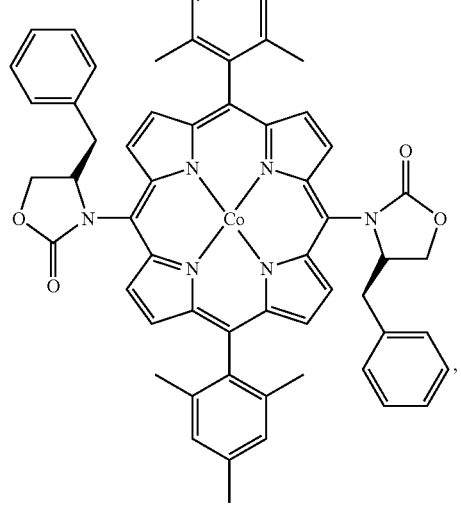

129
-continued
130
-continued
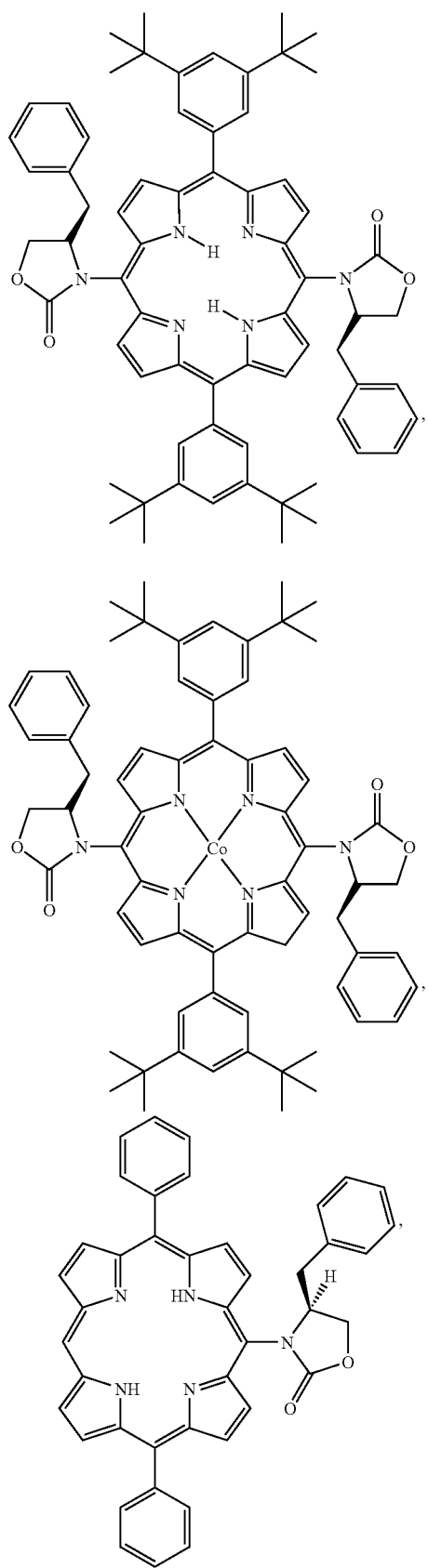
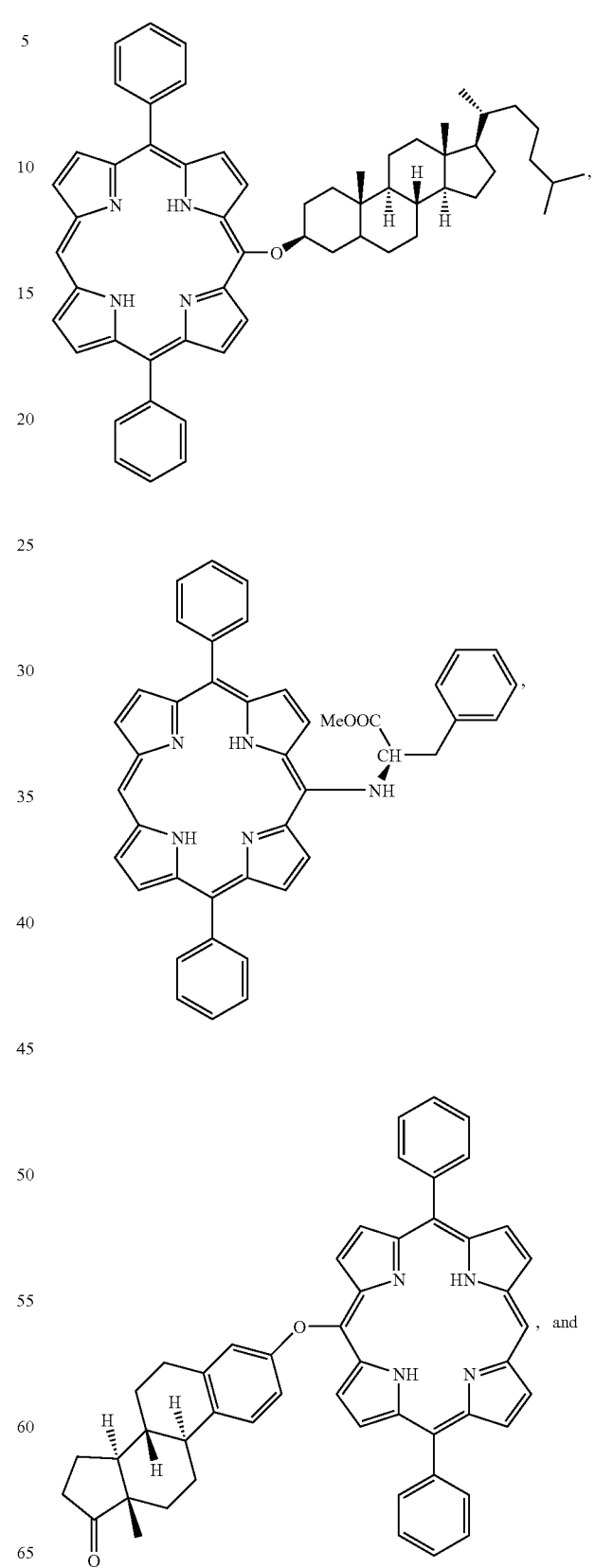

-continued

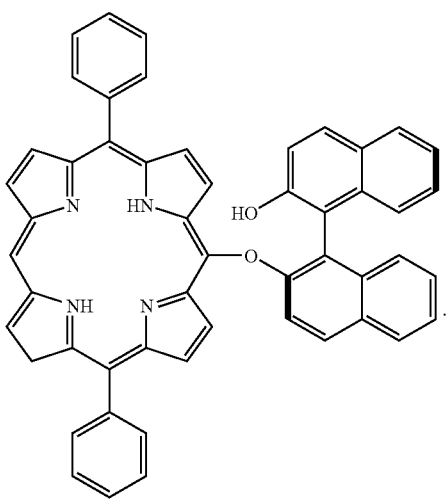

14. A chiral porphyrin compound having the structure:

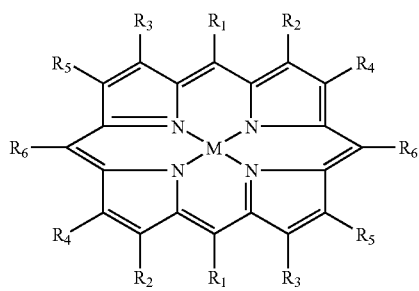

wherein:
M is present or absent and when present is H₂ or a transition metal;
R₁, R₂, R₃, R₄, R₅, and R₆ are each independently selected from the group consisting of H, alkyl, substituted alkyl, arylalkyl, aryl, and substituted aryl; and
wherein at least one of R₁ and R₆ has the structure:

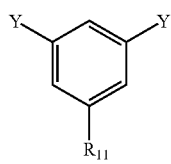

wherein R₁₁ is selected from the group consisting of H, alkyl, substituted alkyl, alkoxy, substituted alkoxy, halogen, arylalkyl, aryl, and substituted aryl, and Y is selected from the group consisting of (+)-estrone; (+)-dihydrocholesterol; R-(+)-1,1'-bi-2-naphthol; (R)-(+)-4-benzyl-2-oxazolidinone; (L)-phenylalanine methyl ester; 1-[1'-(R)- α-methylbenzyl]-aziridine-2(R)-carboxamide; (R)-(−)-2-methoxypropionamide; (S)-(+)-2-methoxypropionamide; (S)-(+)-2,2-dimethylcyclopropanecarboxamide; and L-(R)-lactamide.

15. The chiral porphyrin of claim 14, wherein the chiral porphyrin has a structure selected from the group consisting of:

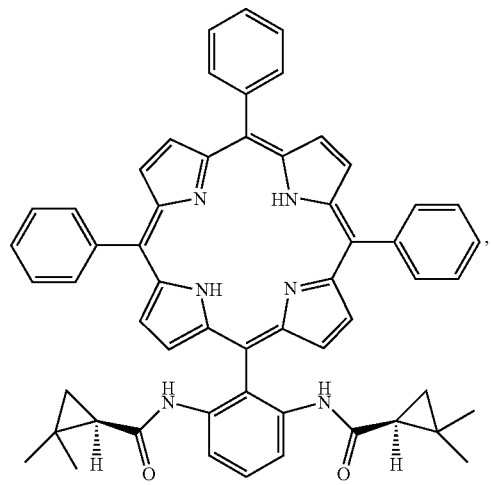

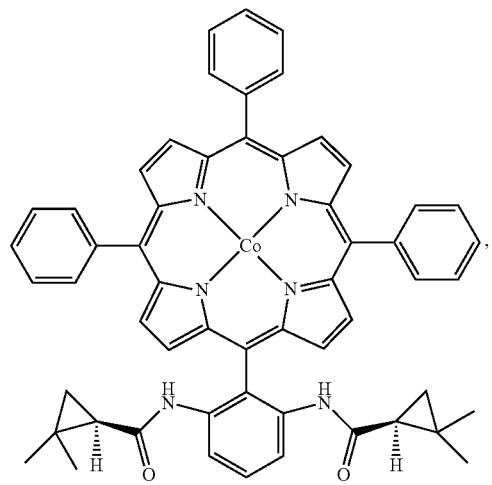

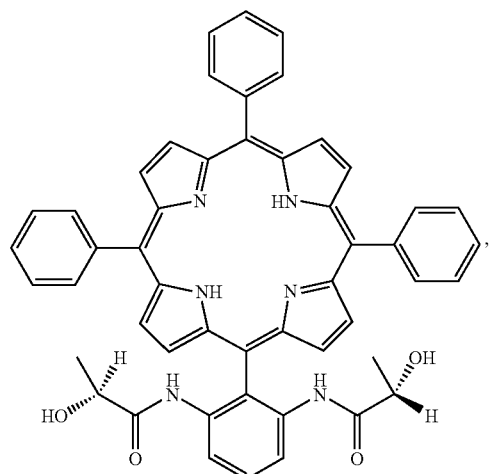

133
-continued
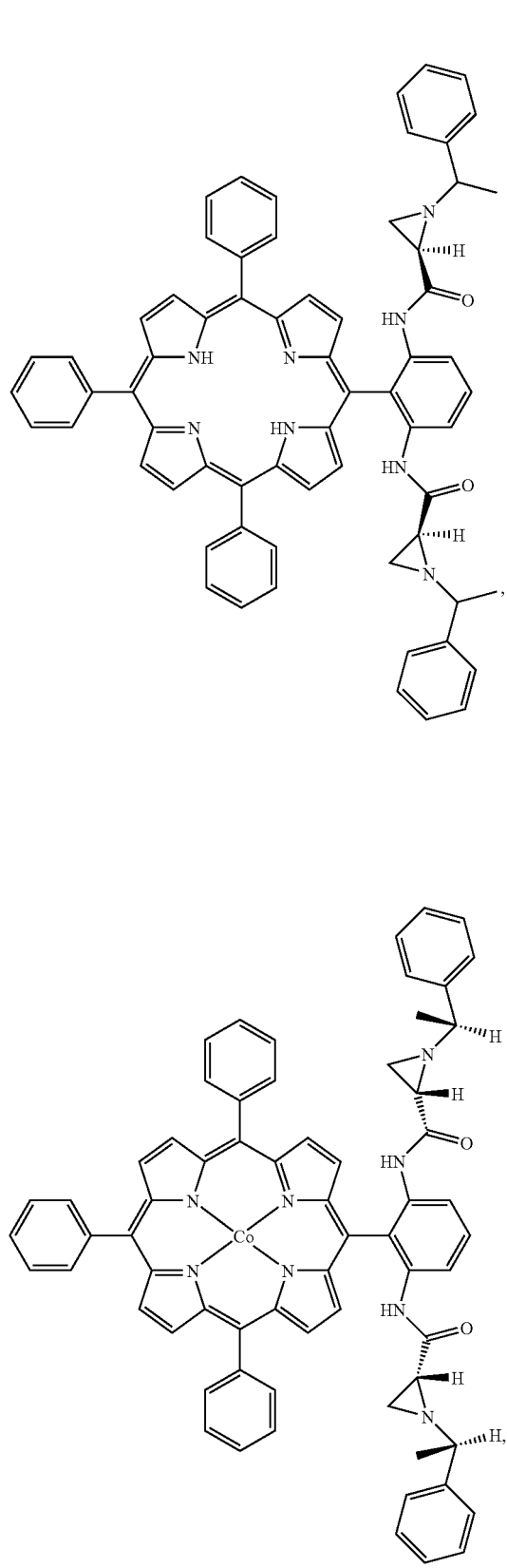
134
-continued
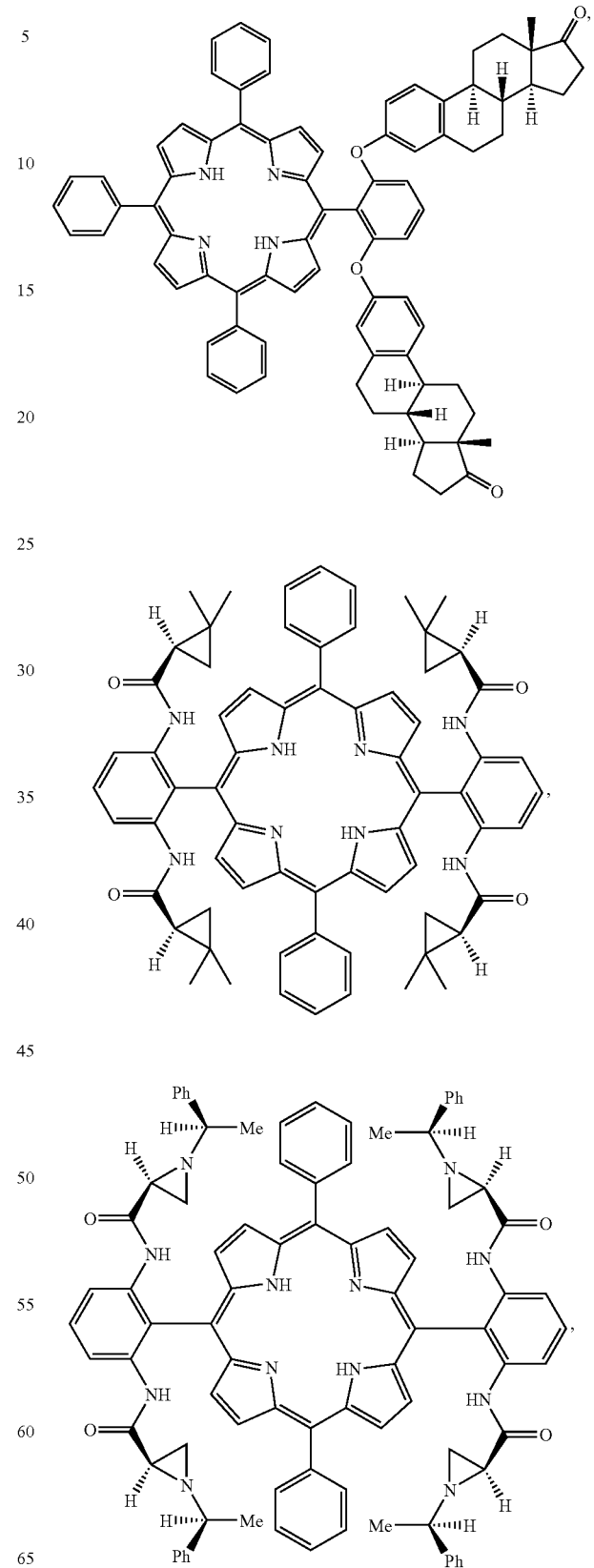

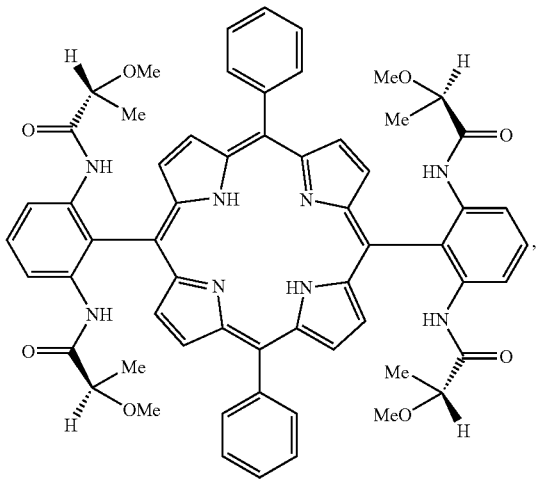
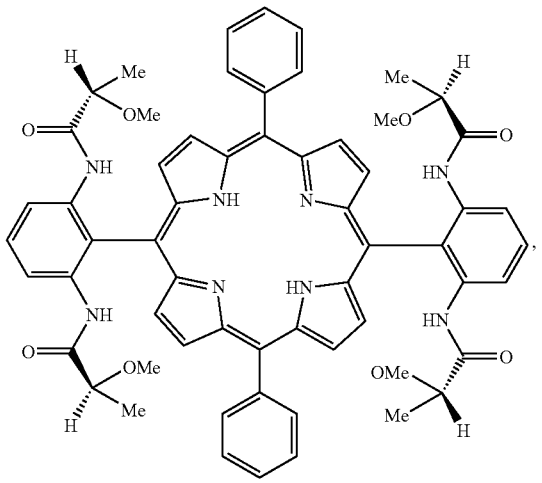
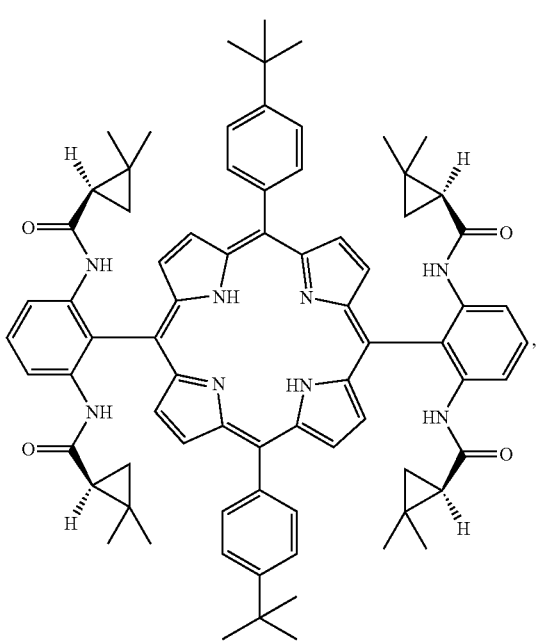
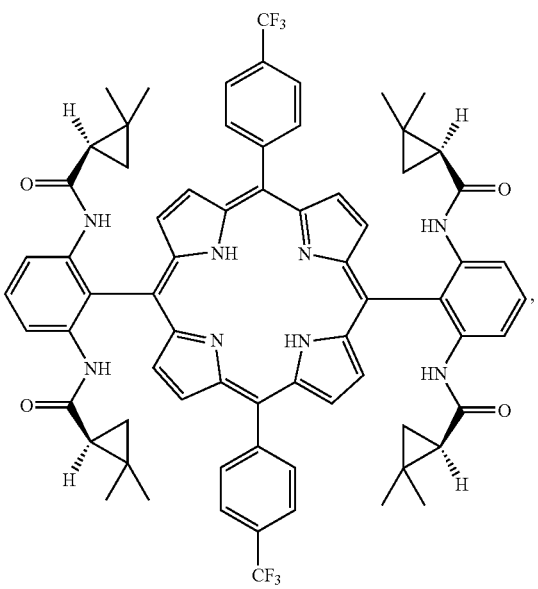
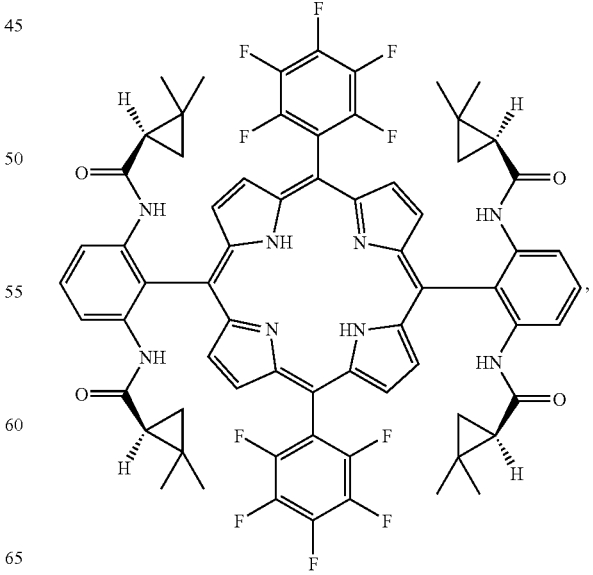

137
-continued
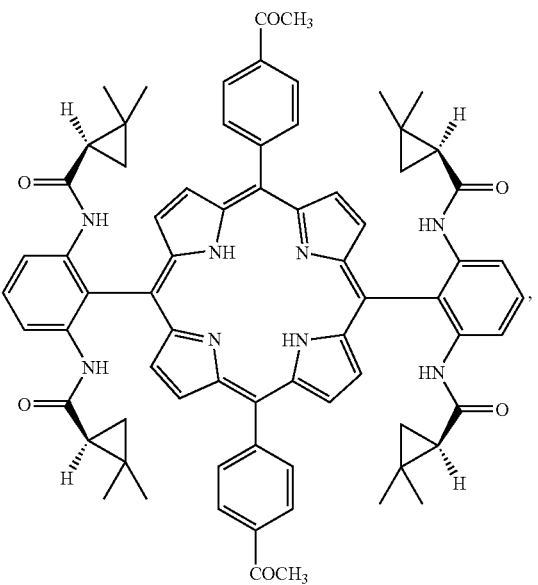
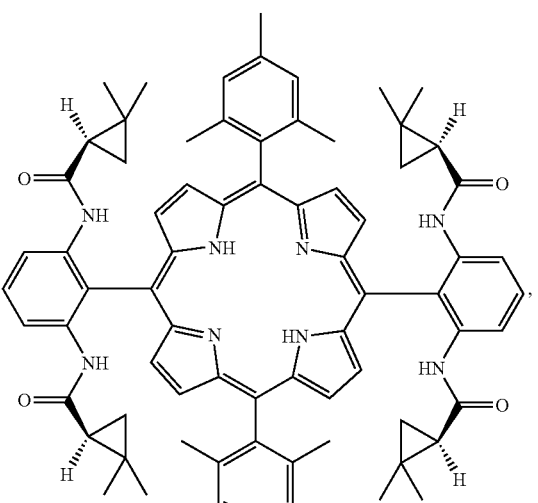
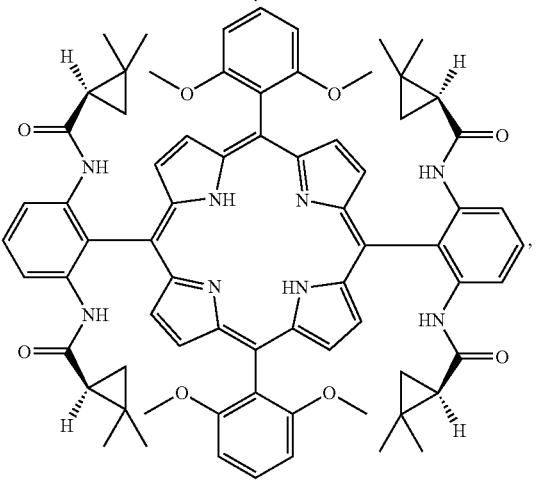
138
-continued
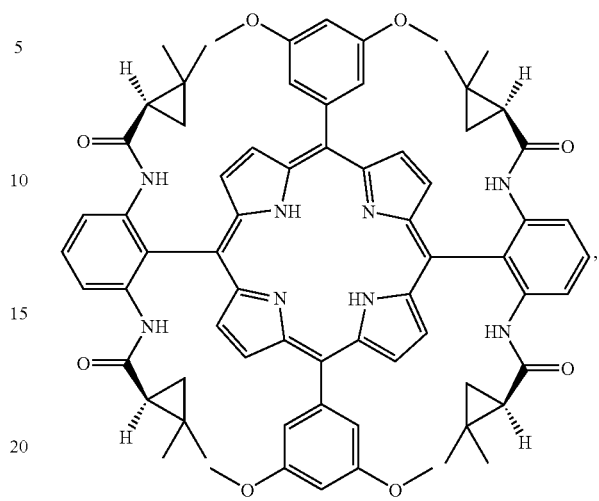
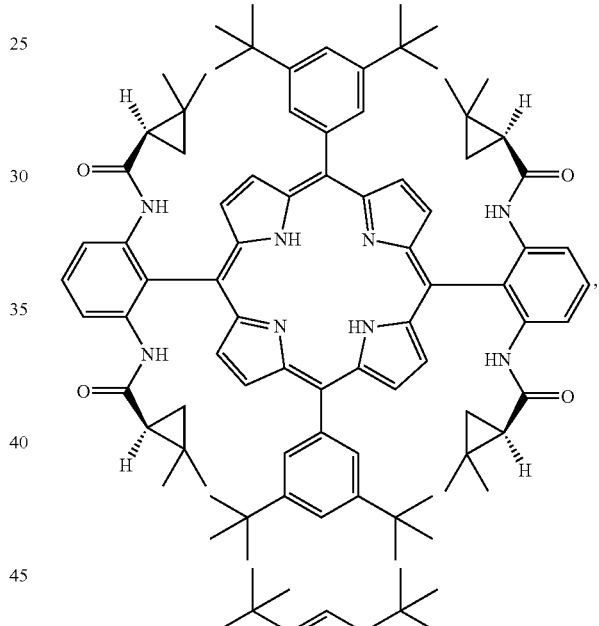
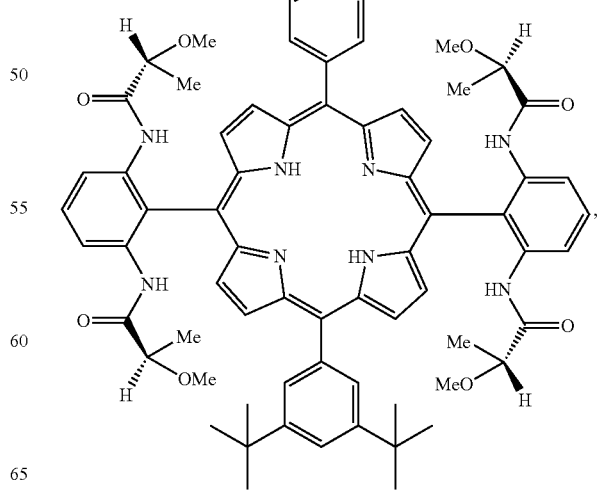

139
-continued
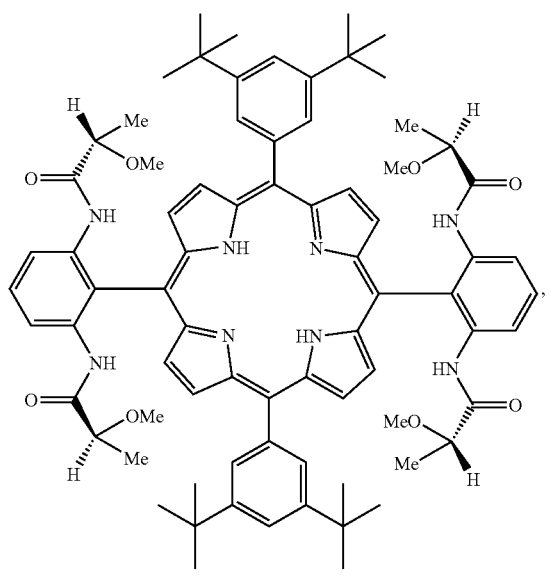
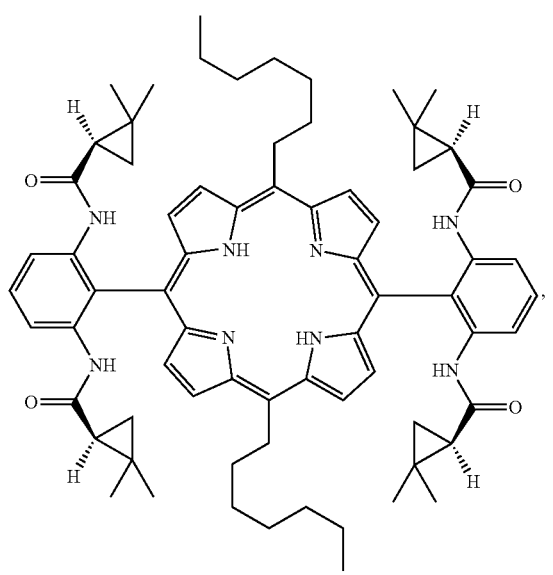
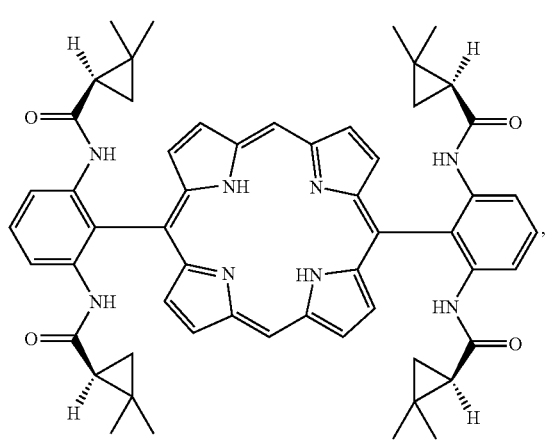
140
-continued
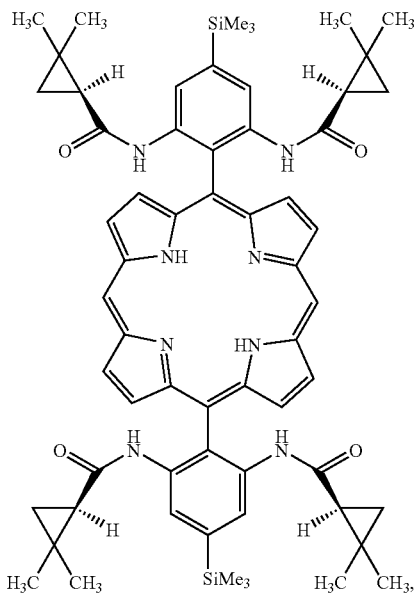
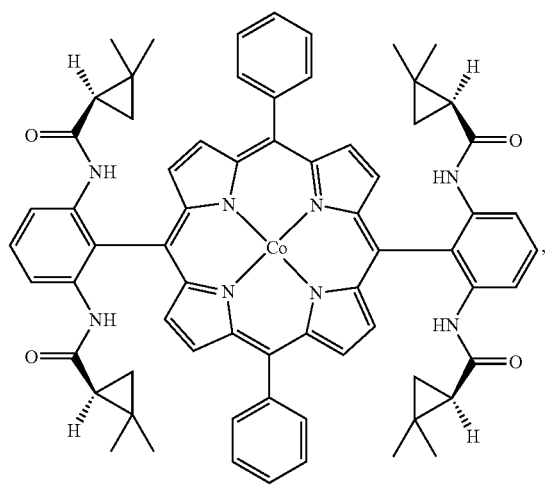
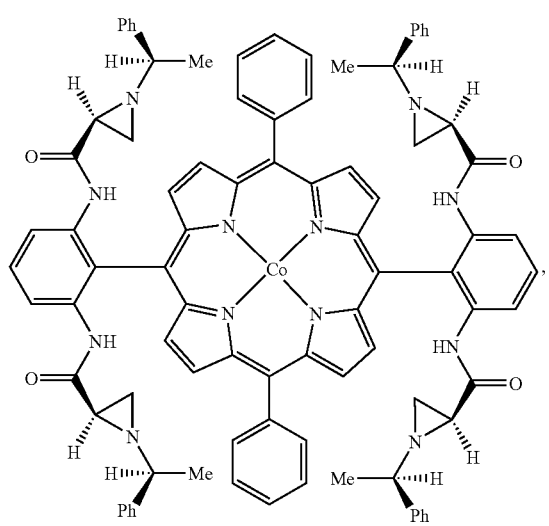

141
-continued
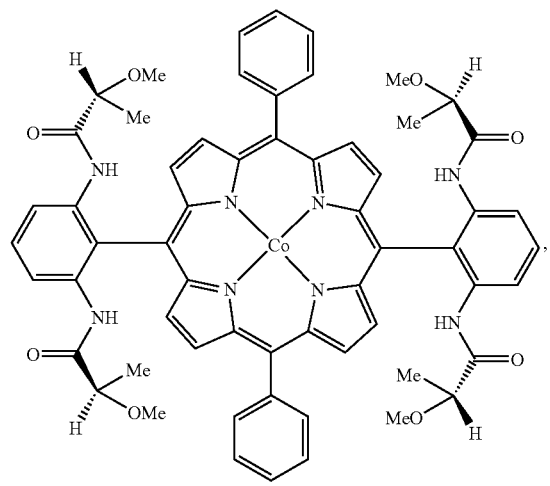
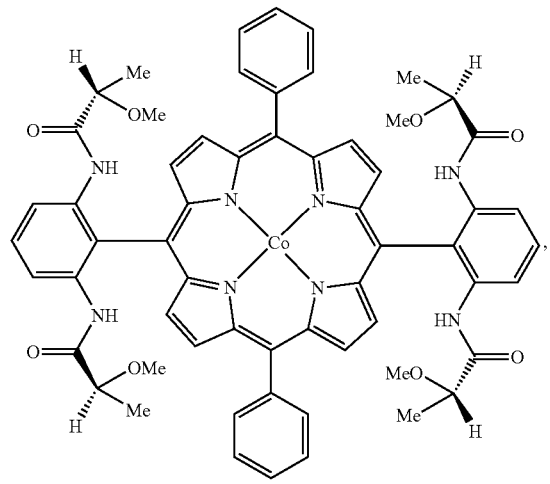
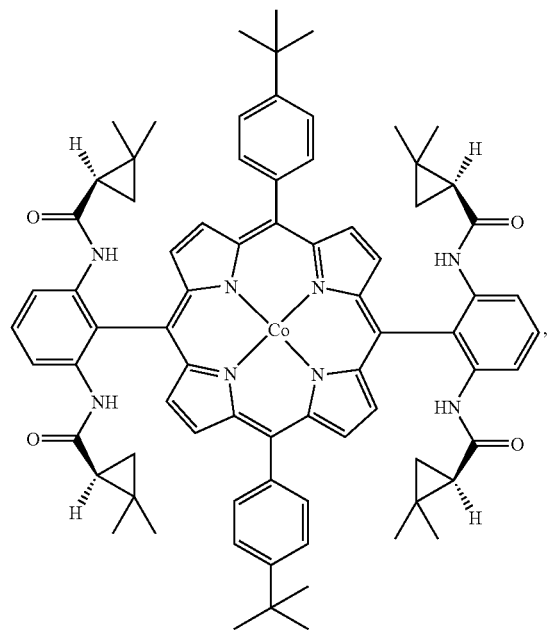
142
-continued
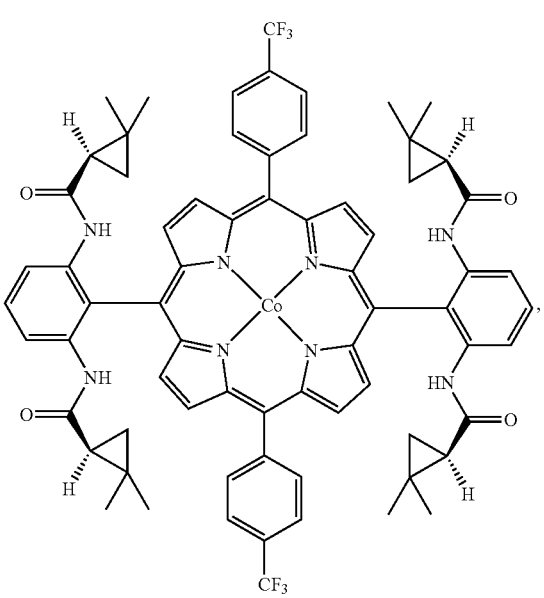
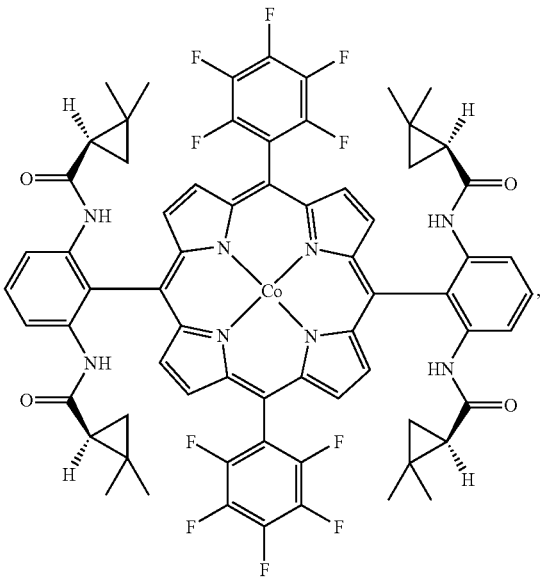

143
-continued
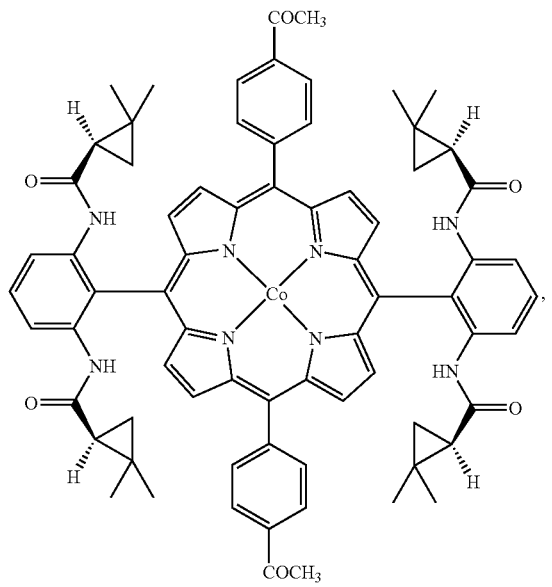
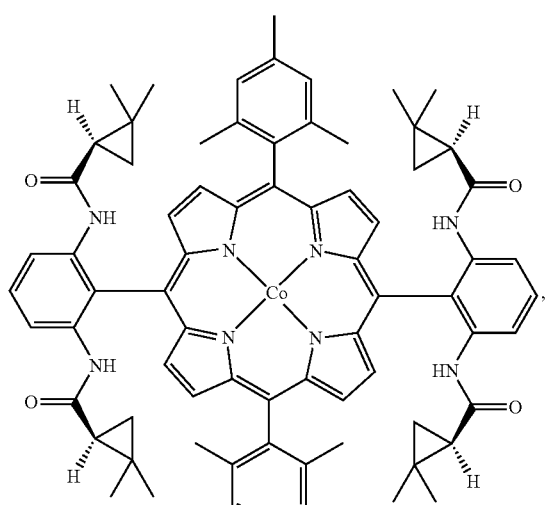
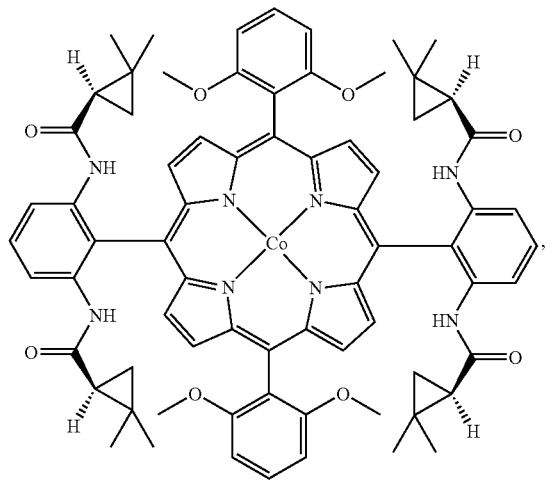
144
-continued
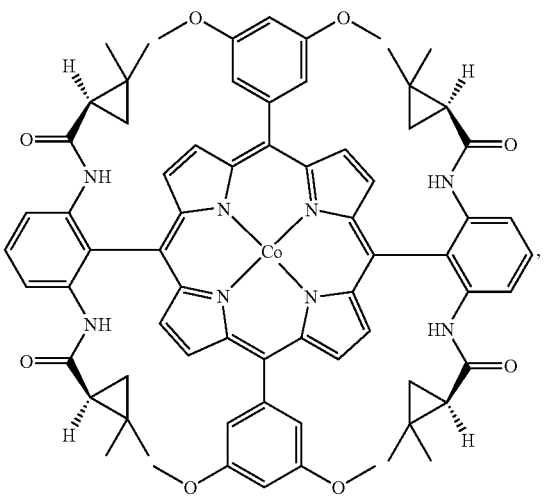
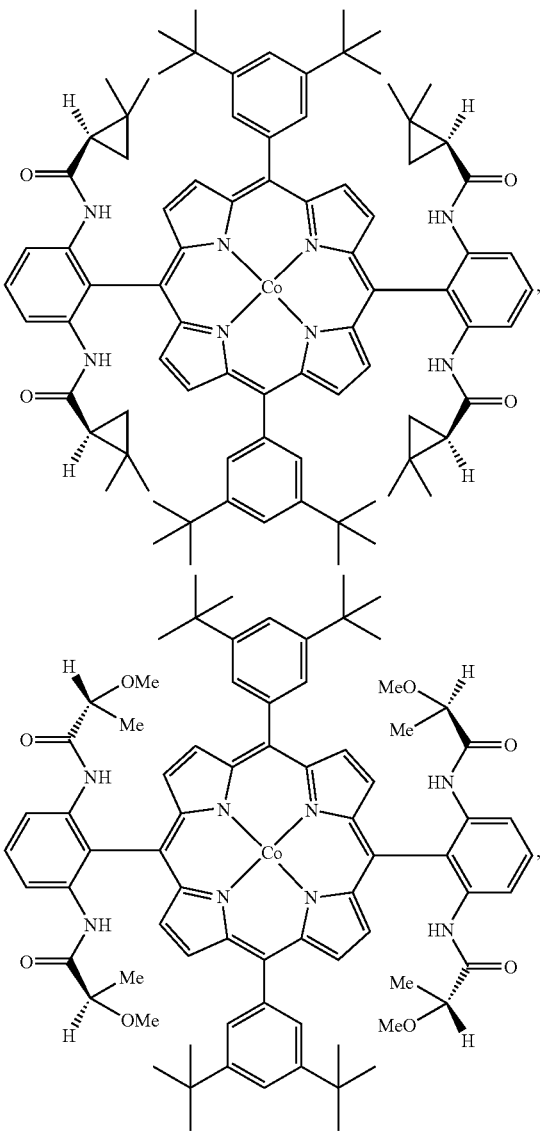

-continued

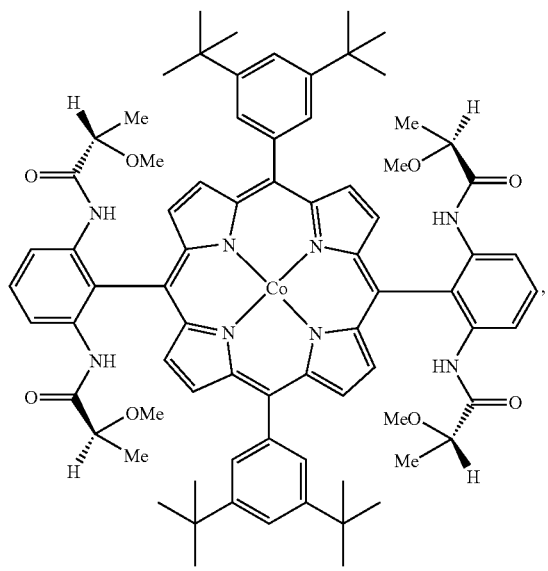

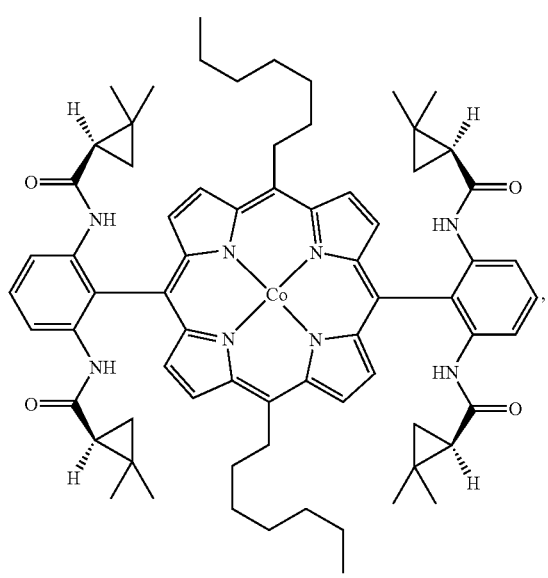

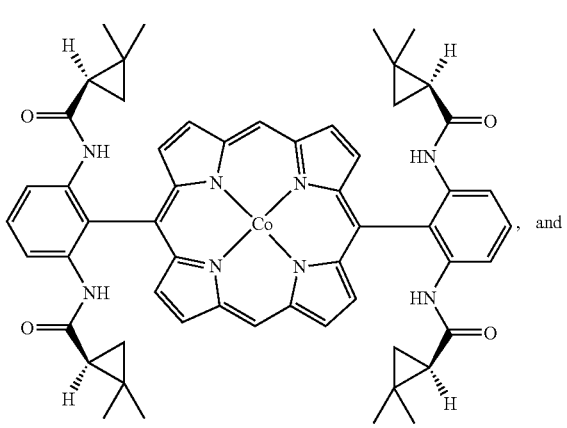

-continued

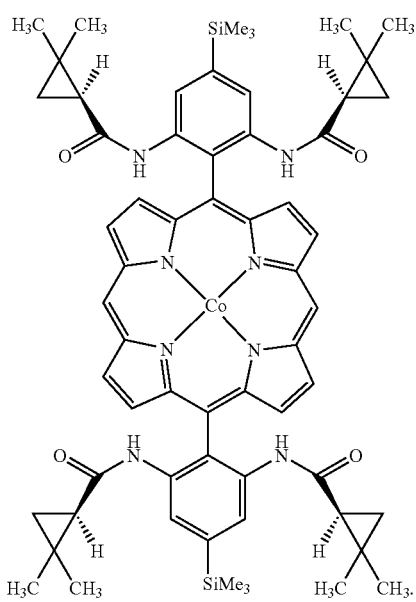

16. A method of synthesizing a heteroatom-substituted chiral porphyrin compound of claim 1, comprising reacting a porphyrin precursor with a chiral reagent comprising a heteroatom, the porphyrin precursor having a structure of Formula II:

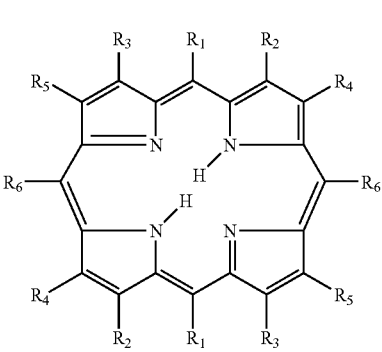

wherein:
$R_1$, $R_2$, $R_3$, $R_4$, $R_5$ and $R_6$ are each independently selected from the group consisting of X, H, alkyl, substituted alkyl, arylalkyl, aryl, and substituted aryl;
X is selected from the group consisting of halogen, trifluoromethanesulfonate (OTf), OTf-substituted aryl, haloaryl and haloalkyl, and at least one of $R_1$, $R_2$, $R_3$, $R_4$, $R_5$ and $R_6$ is X;
wherein the chiral reagent comprising a heteroatom has the structure H-Y and Y is a heteroatom-containing chiral moiety comprising at least one of N, O, S, and B; and
wherein the porphyrin precursor and chiral reagent comprising a heteroatom are reacted in the presence of a metal compound, a ligand, and a base to produce a heteroatom-substituted chiral porphyrin.

17. The method according to claim 16, wherein X is a halogen selected from the group consisting of Br, Cl, I and F.

18. The method according to claim 17, wherein X is Br.

19. The method according to claim 16, wherein at least one meso-position of the porphyrin precursor of Formula I is halogenated.

20. The method according to claim 16, wherein X is haloaryl.

21. The method according to claim 20, wherein the haloaryl is 2,6-dibromophenyl.

22. The method of claim 16, wherein the metal compound comprises a metal selected from the group consisting of Pd, Pt, Ni, or Cu.

23. The method according to claim 16, wherein the metal compound is a metal precursor compound selected from the group consisting of $Pd(dba)_2$, $Pd_2(dba)_3$, $Pd(OAc)_2$, $PdCl_2$, $Pd(TFA)_2$, and $(CH_3CN)_2PdCl_2$.

24. The method of claim 16, wherein the base is selected from the group consisting of n-BuLi, LDA, $NaNH_2$, NaOH, $Et_3N$, NaOAc, KOt-Bu, NaOt-Bu, $Cs_2CO_3$, $K_2CO_3$, and $K_3PO_4$.

25. The method according to claim 16, wherein the ligand is selected from the group of ligands consisting of:

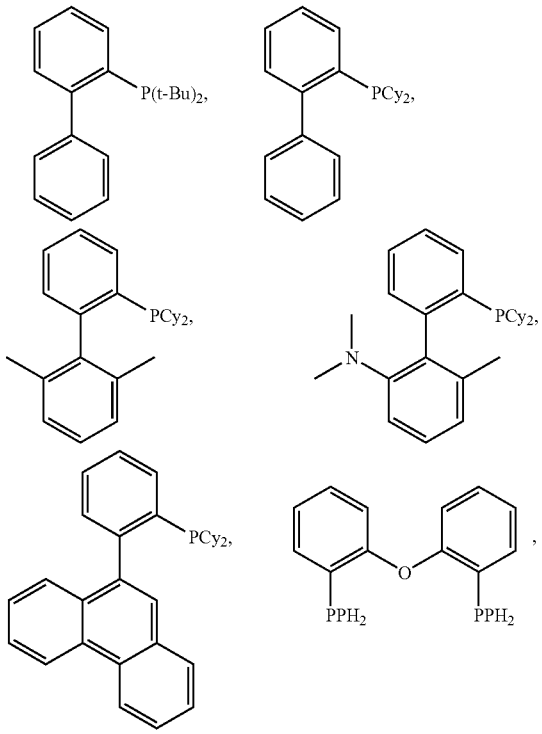

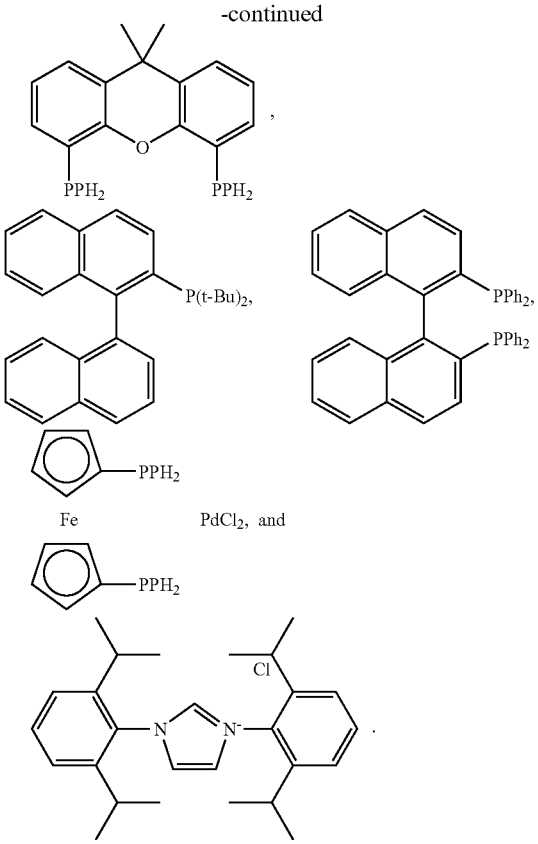

26. The method according to claim 16, wherein Y comprises a heteroatom-containing chiral moiety selected from the group consisting of $NR_7R_8$, $OR_9$, $SR_{10}$, and $BR_{10}$ wherein $R_7$, $R_8$, $R_9$, and $R_{10}$ are each independently selected from the group consisting of H, alkyl, substituted alkyl, arylalkyl, alkoxyl, carboxyl, aryl, and substituted aryl.

27. The method according to claim 16, wherein Y is a selected from the group consisting of chiral amino, substituted chiral amino, chiral amido, substituted chiral amido, chiral alkoxy, substituted chiral alkoxy, chiral thio, substituted chiral thio, and chiral borate ester moieties.

28. The method according to claim 16, wherein Y is selected from the group consisting of (+)-estrone; (+)-dihydrocholesterol; R-(+)-1,1'-bi-2-naphthol; (R)-(+)-4-benzyl-2-oxazolidinone; (L)-phenylalanine methyl ester; 1-[1'-(R)-α-methylbenzyl]-aziridine-2(R)-carboxamide; (R)-(−)-2-methoxypropionamide; (S)-(+)-2-methoxypropionamide; (S)-(+)-2,2-dimethylcyclopropanecarboxamide; and L-(R)-lactamide.

* * * * *